US009587249B2

(12) United States Patent
Schwarz et al.

(10) Patent No.: US 9,587,249 B2
(45) Date of Patent: Mar. 7, 2017

(54) MODELS OF THROMBOTIC THROMBOCYTOPENIC PURPURA AND METHODS OF USE THEREOF

(75) Inventors: Hans-Peter Schwarz, Vienna (AT); Eva-Maria Muchitsch, Vienna (AT); Peter Turecek, Klosterneuburg (AT)

(73) Assignees: BAXALTA GMBH, Opfikon (CH); BAXALTA INCORPORATED, Bannockburn, IL (US)

( * ) Notice: Subject to any disclaimer, the term of this patent is extended or adjusted under 35 U.S.C. 154(b) by 95 days.

(21) Appl. No.: 12/606,884

(22) Filed: Oct. 27, 2009

(65) Prior Publication Data

US 2010/0115637 A1 May 6, 2010

Related U.S. Application Data

(60) Provisional application No. 61/108,781, filed on Oct. 27, 2008, provisional application No. 61/156,768, filed on Mar. 2, 2009.

(51) Int. Cl.
*A01K 67/027* (2006.01)
*C12N 15/85* (2006.01)

(52) U.S. Cl.
CPC ........ *C12N 15/8509* (2013.01); *A01K 67/027* (2013.01); *A01K 67/0275* (2013.01); *A01K 2217/052* (2013.01); *A01K 2217/054* (2013.01); *A01K 2217/075* (2013.01); *A01K 2227/105* (2013.01); *A01K 2267/03* (2013.01); *A01K 2267/0306* (2013.01); *A01K 2267/0325* (2013.01); *A01K 2267/0381* (2013.01)

(58) Field of Classification Search
CPC .......... A01K 67/0275; A01K 2217/052; A01K 2217/054; A01K 2267/0381; A01K 2267/0306; A01K 67/027
See application file for complete search history.

(56) References Cited

U.S. PATENT DOCUMENTS

| | | | |
|---|---|---|---|
| 4,736,866 A | 4/1988 | Leder et al. |
| 4,757,006 A | 7/1988 | Toole, Jr. et al. |
| 5,175,384 A | 12/1992 | Krimpenfort et al. |
| 5,175,385 A | 12/1992 | Wagner et al. |
| 5,446,143 A | 8/1995 | Simpson et al. |
| 6,447,796 B1 | 9/2002 | Vook et al. |
| 6,492,575 B1 | 12/2002 | Wagner et al. |
| 6,802,849 B2 | 10/2004 | Blaeser et al. |
| 6,802,856 B2 | 10/2004 | Wilson |
| 6,802,857 B1 | 10/2004 | Walsh et al. |
| 6,802,859 B1 | 10/2004 | Pazienza et al. |
| 6,805,704 B1 | 10/2004 | Hoyns |
| 6,805,705 B2 | 10/2004 | Hong et al. |
| 6,805,707 B1 | 10/2004 | Hong et al. |
| 6,805,709 B1 | 10/2004 | Schaldach et al. |
| 6,811,566 B1 | 11/2004 | Penn et al. |
| 6,814,749 B2 | 11/2004 | Cox et al. |
| 6,818,013 B2 | 11/2004 | Mitelberg et al. |
| 6,818,014 B2 | 11/2004 | Brown et al. |
| 6,818,016 B1 | 11/2004 | Nabel et al. |
| 6,818,247 B1 | 11/2004 | Chen et al. |
| 6,819,951 B2 | 11/2004 | Patel et al. |
| 6,821,291 B2 | 11/2004 | Bolea et al. |
| 6,821,296 B2 | 11/2004 | Brauckman et al. |
| 6,821,549 B2 | 11/2004 | Jayaraman |
| 6,824,532 B2 | 11/2004 | Gillis et al. |
| 6,824,551 B2 | 11/2004 | Trerotola |
| 6,824,553 B1 | 11/2004 | Samson et al. |
| 6,824,554 B1 | 11/2004 | Jang |
| 6,824,561 B2 | 11/2004 | Soykan et al. |
| 6,827,703 B1 | 12/2004 | Ackerman |
| 6,827,730 B1 | 12/2004 | Leschinsky |
| 6,827,732 B2 | 12/2004 | Thompson |
| 6,827,735 B2 | 12/2004 | Greenberg |
| 6,827,798 B1 | 12/2004 | Ichikawa et al. |
| 6,829,497 B2 | 12/2004 | Mogul |
| 2004/0204377 A1 | 10/2004 | Rana |
| 2005/0222064 A1 | 10/2005 | Vargeese et al. |
| 2005/0239687 A1 | 10/2005 | Divita et al. |
| 2006/0014289 A1 | 1/2006 | Ahmadian et al. |
| 2006/0019912 A1 | 1/2006 | Burkoth et al. |

FOREIGN PATENT DOCUMENTS

| | | |
|---|---|---|
| WO | WO-00/53722 | 9/2000 |
| WO | WO-03/046185 | 6/2003 |
| WO | WO-03/047518 | 6/2003 |
| WO | WO-2008/005290 | 1/2008 |

OTHER PUBLICATIONS

Roussi et al Blood Coagul Fibrinolysis. Jun. 1998;9(4):361-72.*
Chauhan et al Blood, 2007, vol. 3, No. 7, 3452-3457.*
Wolfer et al Trends in Neuroscience, 2002, 25 (7): 336-340.*
Vardi et al , Journal of Thrombosis and Haemostasis, 7: 1134-1142.*
Gitten et al (Thrombotic Thrombocytopenic Purpura or Disseminated Intravascular Coagulation? Diagnostic Dilemma in the ICU, 2012, Anesthesiology Publications and Presentations. 120, http://escholarship.umassmed.edu/anesthesiology_pubs/120).*
Muchitsch et al Semin Thromb Hemost. Jul. 2010;36(5):522-8, abstract, p. 1-2.*
Motto et al Journal of Clinical Investigation, 2005, 115, 2752-2761.*
Swartz et al Semin Thromb Hemost. Apr. 2002;28(2):215-26.*
Pergolizzi et al Blood. Aug. 1, 2006;108(3):862-9.*
Muchitsch et al Semin Thromb Hemost. Jul. 2010;36(5):522-8.*

(Continued)

*Primary Examiner* — Anoop Singh
(74) *Attorney, Agent, or Firm* — Troutman Sanders LLP

(57) ABSTRACT

The invention relates to the development of an animal model for testing various agents in the treatment of a clotting disorder. More specifically, the invention relates to the use of ultra-large molecular weight multimers of von Willebrand factor (VWF) in various mouse strains to induce thrombotic thrombocytopenic purpura (TTP)-like symptoms for the development of a mouse model of TTP. The invention also provides methods for generating such animal disease models and screening methods for identifying biologically active compounds which are effective in the treatment of TTP.

10 Claims, 32 Drawing Sheets

(56) References Cited

OTHER PUBLICATIONS

Antoine et al., ADAMTS13 gene defects in two brothers with constitutional thrombotic thrombocytopenic purpura and normalization of von Willebrand factor-cleaving protease activity by recombinant human ADAMTS13. *British J. Haematol.* 120(5): 821-4 (2003).

Banno et al., Complete deficiency in ADAMTS13 is prothrombotic, but it alone is not sufficient to cause thrombotic thrombocytopenic purpura. *Blood* 107:3161-66 (2007).

Banno et al., Identification of strain-specific variants of mouse Adamts13 gene encoding von Willebrand factor-cleaving protease. *J. Biol. Chem.* 279(29): 30896-903 (2004).

Banno et al., The function of ADAMTS13 in thrombogenesis in vivo: Insights from mutant mice. *Int. J. Hematol.* 91(5): 30-5 (2010).

Batzer et al., Enhanced evolutionary PCR using oligonucleotides with inosine at the 3'-terminus. *Nucleic Acid Res.* 19: 5081 (1991).

Bodine et al., Combination of interleukins 3 and 6 preserves stem cell function in culture and enhances retrovirus-mediated gene transfer into hematopoietic stem cells. *Proc. Natl. Acad. Sci.* 86: 8897-901 (1989).

Bodine et al., Introduction and expression of human beta globin genes into primitive murine hematopoietic progenitor cells by retrovirus mediated gene transfer. *Prog. Clin. Biol. Res.* 319: 589-600 (1989).

Brinkhous et al., Von Willebrand Factor and animal models: Contributions to gene therapy, thrombotic thrombocytopenic purpura, and coronary artery thrombosis. *Mayo Clin. Proc.* 66:733-42 (1991).

Capecchi et al., Altering the genome by homologous recombination. *Science* 244:1288-92 (1989).

Capecchi, The new mouse genetics: Altering the genome by gene targeting. *Trends Genet.* 5: 70-6 (1989).

Chauhan et al., ADAMTS13: a new link between thrombosis and inflammation. *J. Exp. Med.* 205: 2065-74 (2008).

Chauhan et al., Systemic antithrombotic effects of ADAMTS13. *J. Exp. Med.* 203: 767-76 (2006).

Chauhan et al., The combined roles of ADAMTS13 and VWF in murine models of TTP, endotoxemia, and thrombosis. *Blood* 111:3452-57 (2008).

Chauhan et al., the metalloprotease ADAMTS13 is a natural antithrombotic. Abstract 409: *Blood* 106(11): 123A (2005).

Desch et al., Thrombotic thrombocytopenic purpura in humans and mice. *Arterioscler. Thromb. Vasc. Biol.* 27:1901-8 (2007).

Diaz et al., Exchange of viral promoter/enhancer elements with heterologous regulatory sequences generates targeted hybrid long terminal repeat vectors for gene therapy of melanoma. *J. Virol.* 72:789-95 (1998).

Dick et al., Transcriptional targeting of herpes simplex virus for cell-specific replication. *Trends Genet.* 2:165-70 (1986).

Doetschman et al., Targetted correction of a mutant HPRT gene in mouse embryonic stem cells. *Nature* 330: 576-8 (1987).

Eglitis et al., Retroviral-meditated gene transfer into hemopoietic cells. *Adv. Exp. Med Biol.* 241: 19-27 (1988).

Ezov et al., A chemically induced rat model of hemolysis with disseminated thrombosis. *Cardiovasc. Toxicol.* 2:181-93 (2002).

Fix, Strategies for delivery of peptides utilizing absorption-enhancing agents. *J. Pharm. Sci.* 85: 1282-5 (1996).

Gilboa, Retroviral gene transfer: Application to human therapy. *Adv. Exp. Med. Biol.* 241: 29-33 (1988).

Gilmore et al., Delivery strategies for siRNA-mediated gene silencing. *Curr. Drug Delivery* 3:147-5 (2006).

Gonzalez et al., New class of polymers for the delivery of macromolecular therapeutics. *Bioconjugate Chem.* 10: 1068-74 (1999).

Gordon, Transgenic animals. *Int. Rev. Cytol.* 115:171-229 (1989).

Griedley et al., Insertional mutagenesis in mice. *Trends Genet.* 3:162 (1987).

Hallet et al., Transposition and site-specific recombination: adapting DNA cut-and-paste mechanisms to a variety of genetic rearrangements. *FEMS Microbiol. Rev.* 21:157-78 (1997).

Haren et al, Integrating DNA: Transposases and retroviral integrases. *Annu. Rev. Microbiol.* 53:245-81 (1999).

Herbert et al., A large-scale process to produce microencapsulated proteins. *Pharmaceut. Res.* 15:357 (1998).

Hu et al., Development of an adenovirus vector with tetracycline-regulatable human tumor necrosis factor {alpha} gene expression. *Cancer Res.* 57:3339-43 (1997).

Ivics et al, Genetic radiotherapy overcomes tumor resistance to cytotoxic agents. *Methods Cell Biol.* 60: 99-131 (1999).

Johnson et al., A month-long effect from a single injection of microencapsulated humand growth hormone. *Nature Med.* 2:795-9 (1996).

Keiding et al., A month-long effect from a single injection of microencapsulated human growth hormone. *Scand. J. Clin Lab. Invest.* 33:291-306 (1974).

Kim et al., Transcriptional targeting of replication-defective adenovirus transgene expression to smooth muscle cells in vivo. *J. Clin. Invest.* 100:1006-14 (1997).

Kozak et al., Ping-pong amplification of a retroviral vector achieves high-level gene expression: human growth hormone production. *J. Virol.* 64: 3500-8 (1990).

Kruszyna et al. Method for measuring increased plasma hemoglobin in the presence of erythrocytes. *Clin. Chem.* 23: 2156-9 (1977).

Lachin, Worst-rank score analysis with informatively missing observations in clinical trials. *Controlled Clinical Trials* 20: 408-22 (1999).

Laje et al., Correction of murine ADAMTS13 deficiency by hematopoietic progenitor cell-mediated gene therapy. *Blood* 113: 2172-80 (2009).

Lemischka et al., Developmental potential and dynamic behavior of hematopoietic stem cells. *Cell* 45:917-27 (1986).

Levy et al., ADAMTS13 turns 3. *Blood* 106:11-17 (2005).

Mahendroo et al., Tissue-specific and hormonally controlled alternative promoters regulate aromatase cytochrome P450 gene expression in human adipose tissue. *J. Biol. Chem.* 268: 19463-70 (1993).

Mimuro et al., Unbalanced expression of ADAMTS13 and von Willebrand factor in mouse endotoxinemia. *Thromb. Res.* 122:91-7 (2008).

Miyata et al., ADAMTS13 assays and ADAMTS13-deficient mice. *Curr. Opin. Hematol.* 14:277-83 (2007).

Miyata et al., Measurement of ADAMTS13 activity and inhibitors. *Curr. Opin. Hematol.* 12:384-9 (2005).

Miyatake et al., Transcriptional targeting of herpes simplex virus for cell-specific replication. *J. Virol.* 1: 5124-32 (1997).

Moake, Studies on the pathophysiology of thrombotic thrombocytopenic purpura. *Semin. Hematol.* 34:83-9 (1997).

Moake, Von Willebrand factor, ADAMTS-13, and thrombotic thrombocytopenic purpura. *Semin. Hematol.* 41:4-14 (2004).

Mori et al., Total body irradiation as a method of preparation for bone marrow transplantation: A new technique and review. *Japan. J. Clin. Oncol.* 14(Suppl.1): 457-63 (1984).

Mosbach et al., Formation of proinsulin by immobilized Bacillus subtilis. *Nature* 302:543-5 (1983).

Motto et al., Shigatoxin triggers thrombotic thrombocytopenic purpura in genetically susceptible ADAMTS13-deficient mice. *J. Clin. Invest.* 115:2752-61 (2005).

Niiya et al., Correction of ADAMTS13 deficiency by in utero gene transfer of lentiviral vector encoding ADAMTS13 genes. *Mol. Ther.* 17:34-41 (2009).

Niiya et al., Phenotypic correction of Adamts13-deficient mice by early intra-amniotic gene transfer of lentiviral vector encoding ADAMTS13 genes. *Blood* 110: 66A (2007).

Ohtsuka et al., An alternative approach to deoxyoligonucleotides as hybridization probes by insertion of deoxyinosine at ambiguous codon positions. *J. Biol. Chem.* 260:2605-8 (1985).

Oliyai et al., Prodrugs of peptides and proteins for improved formulation and delivery. *Ann. Rev. Pharmacol. Toxicol.* 32: 521-44 (1993).

(56) References Cited

OTHER PUBLICATIONS

Ozaki et al., Use of von Willebrand factor promoter to transduce suicidal gene to human endothelial cells, HUVEC. *Hum. Gene Ther.* 7:1483-90 (1996).
Palva et al., Secretion of interferon by *Bacillus subtilis*. Gene 22:229-35 (1983).
Patil et al., DNA-based therapeutics and DNA delivery systems: A comprehensive review. *AAPS Journal* 7:E61-77 (2005).
Pergolizzi et al., Correction of a murine model of von Willebrand disease by gene transfer. *Blood* 108:862-9 (2006).
Plaimauer et al., Clonding, expression, and functional characterization of the von Willebrand factor-cleaving protease (ADAMTS13). *Blood* 100:3626-32 (2002).
Queen et al., Cell-type specific regulation of a K immunoglobulin gene by promoter and enhancer elements. *Immunol. Rev.* 89:49-68 (1986).
Reznikoff et al., Tn5: A molecular window on transposition. *Biochem. Biophys. Res. Commun.* 266:729-34 (1999).
Rossolini et al., Use of deoxyinosine-containing primers vs degenerate primers for polymerase chain reaction based on ambiguous sequence information. *Mol. Cell. Probes* 8:91-8 (1994).
Sanders et al., Thrombotic thrombocytopenia induced in dogs and pigs : The role of plasma and platelet vWF in animal models of thrombotic thrombocytopenic purpura. *Arterioscler. Thromb. Vasc. Biol.* 15:793-800 (2005).
Seung et al., Genetic radiotherapy overcomes tumor resistance to cytotoxic agents. *Cancer Res.* 55:5561-5 (1995).
Shi et al., Modulation of the specificity and activity of a cellular promoter in an adenoviral vector. *Hum. Gene Ther.* 8:403-10 (1997).
Simpson et al., Tissue-specific promoters regulate aromatase cytochrome P450 expression. *Clin. Chem.* 39:317-24 (1993).
Suzuki et al., Regulatable promoters for use in gene therapy applications: Modification of the 5'-flanking region of the CFTR gene with multiple cAMP response elements to support basal, low-level gene expression that can be upregulated by exogenous agents that raise intracellular levels of cAMP. *Hum. Gene Ther.* 7:1883-93 (1996).
Tracy, Development and scale-up of a microsphere protein delivery system. *Biotechnol. Prog.* 14:108 (1998).
Wagner et al., Transfer of genes into embryonal carcinoma cells by retrovirus infection: efficient expression from an internal promoter. *EMBO J.* 4:663 (1985).
Wood et al, Expression of active human factor VIII from recombinant DNA clones. *Nature* 312:330-7 (1984).
Yagi et al., A novel ES cell line, TT2, with high germline-differentiating potency. *Anal. Biochem.* 14:70-6 (1993).
Zhou et al., An IAP retrotransposon in the mouse ADAMTS13 gene creates ADAMTS13 variant proteins that are less effective in cleaving von Willebrand factor multimers. *Blood* 110:886-93 (2007).
International Search Report, PCT/US2009/062228, European Patent Office, dated May 26, 2010.
Schwarz et al., Involvement of low-density lipoprotein receptor-related protein (LRP) in the clearance of factor VIII in von Willebrand factor-deficient mice. *Blood* 95(5): 1703-8 (2000).
Schiviz et al., A new mouse mimicking thrombotic thrombocytopenic purpura: Correction of symptoms by recombinant human ADAMTS13. *Blood* 119(25): 6128-35 (2012).

\* cited by examiner 1 2 3 4 5 6

MODELS OF THROMBOTIC THROMBOCYTOPENIC PURPURA AND METHODS OF USE THEREOF

RELATED APPLICATIONS

This application claims benefit of U.S. Provisional Patent Application Ser. No. 61/108,781, filed Oct. 27, 2008, and U.S. Provisional Patent Application Ser. No. 61/156,768, filed Mar. 2, 2009, each of which is incorporated herein by reference in its entirety.

FIELD OF THE INVENTION

The invention generally relates to the development of a thrombotic thrombocytopenic purpura (TTP) mouse model. More specifically, the invention relates to the use of ultra-large molecular weight multimers of von Willebrand factor (VWF) in various mouse strains to induce TTP-like symptoms for the development of a mouse model of TTP. The invention also provides methods for generating such animal disease models and screening methods for identifying biologically active compounds which are effective in the treatment of TTP.

BACKGROUND OF THE INVENTION

Thrombotic thrombocytopenic purpura ("TTP" or Moschcowitz disease) is a severe and rare disorder of the blood-coagulation system, causing extensive microscopic blood clots to form in the small blood vessels throughout the body. Most cases of TTP arise from deficiency or inhibition of the enzyme ADAMTS13 (a disintegrin and metalloprotease with thrombospondin type 1 domains 13). ADAMTS13 is the proteolytic enzyme responsible for cleaving large multimers of von Willebrand factor (VWF) and is also known as VWF cleaving protease. Thus, there is a relationship between the biological function of ADAMTS13 and the existence of ultra-large molecular weight multimers of VWF and the occurrence of TTP or TTP-like clinical symptoms. TTP also may be related to cancer, chemotherapy, HIV infection, hormone replacement therapy and estrogens, and a number of commonly used medications (including ticlopidine, clopidogrel, and cyclosporine A).

A low level of ADAMTS13 causes clotting substances (platelets) in the blood to clump. As the platelets clump together, there are fewer platelets available in the bloodstream. This clumping, or aggregation, can lead to bleeding under the skin and purple-colored spots called purpura. It also can cause red blood cells to break apart (undergo hemolysis) as they are subjected to shear stress as they pass the microscopic platelet clots. Red blood cells are thus destroyed prematurely. Reduced blood flow and cellular injury results in end organ damage. Current therapy is based on support and plasmapheresis to reduce circulating antibodies against ADAMTS13 and replenish blood levels of ADAMTS13.

Development of antibodies to protein therapeutics is a persistent problem when biopharmaceuticals are used for treatment of disorders like TTP and hemophilia. These antibodies often inhibit the activity of the protein therapeutic thereby reducing the efficacy of the treatment or requiring increasing doses of drug to maintain therapeutic levels. Because these blood disorders are often lifelong conditions, the appearance of antibodies specific for therapeutic blood clotting factors is particularly trying for patients receiving the treatment and challenging for doctors treating these patients.

The role that preclinical models play in the evaluation of drug efficacy and optimization of lead compounds is an essential one in pharmaceutical companies. Without a robust, dependable animal model of human disease, the design of better molecules becomes a daunting task. For this objective, transgenic and knockout mouse and rat models have held great promise, but yet have been underutilized in the pharmaceutical industry. The limited use of such models is likely due in part to the failure of many current transgenic and knockout models to exhibit essential qualities of preclinical screening models; validity, reliability, and utility.

In an effort to better understand TTP and the potential for therapy, an animal model for the disorder has been sought. Early attempts to recreate a TTP model relied on chemical induction using, e.g., venom factor botrocetin or 2-butoxyethanol (BE). Botrocetin acts by binding and multimerizing VWF, resulting in platelet aggregation. Animals treated with the factor exhibit transient thrombocytopenia, but not all of the symptoms associated with TTP (Sanders et al., *Arterioscler. Thromb. Vasc. Biol.* 15:793-800, 2005; Brinkhous et al., *Mayo Clin. Proc.* 66:733-42, 1991). Similarly, BE-treated animals developed certain symptoms of TTP, including hemolysis and thrombosis (Ezov et al., *Cardiovasc. Toxicol.* 2:181-93, 2002). However, the model fails to exhibit all of the hallmark symptoms of TTP. Later attempts involved generation of ADAMTS13 deficient mice. In most genetic backgrounds, however, the phenotype is minimal, indicating that ADAMTS13 deficiency is not sufficient to cause TTP (Banno et al., *Blood* 107:3161-66, 2006; Desch et al., *Arterioscler. Thromb. Vasc. Biol.* 27:1901-08, 2007).

Currently, no valid animal model is available to test therapies for the treatment of TTP. Therapies are limited, and include such procedures as plasma treatment, plasma exchange, and splenectomy. Thus, there exists a need in the art to develop such a model and to develop methods to study the effects of various TTP therapies in vivo without study on human patients. Further, there remains a need in the art to determine if administration of exogenous therapeutic protein to a patient will result in production of antigen-specific antibodies which inhibit protein activity in vivo.

SUMMARY OF THE INVENTION

The invention addresses one or more needs in the art relating to treatment of blood clotting disorders by providing various animal models, wherein recombinant human VWF, which contains ultra-large and high molecular weight multimers, is administered to mice to induce clinical symptoms of TTP and is associated with thrombocytopenia and microthrombosis.

In one aspect, the invention includes normal mice, mice deficient in VWF, and ADAMTS13 knock-out mice. Thus, the invention provides a variety of animal models that can be used to test the in vivo efficacy of drugs to treat TTP. The invention contemplates that combination therapies are used by administering an agent of interest with a compound such as, but not limited to, preparations containing purified or recombinant ADAMTS13.

In one embodiment, the invention includes animal models for testing the efficacy of a therapeutic agent in the treatment of a blood clotting disorder. Such animal models generally comprise an inability to breakdown recombinant VWF polypeptide. Such clotting disorders are generally characterized by the presence of one or more blood clots in said animal model(s). In one aspect, the disorder is thrombotic thrombocytopenic purpura. In another aspect, the recombinant VWF polypeptide is human. In an additional aspect, the model is a mouse. In a further aspect, the mouse is deficient in ADAMTS13 polypeptide. In yet another aspect, the mouse is deficient in VWF polypeptide. In yet another aspect, the mouse model is of a C57BL/6J strain.

In another embodiment, the invention includes methods of testing an agent for its ability to reduce blood clotting in a mammal administered recombinant von Willebrand factor in an amount effective to cause mortality. Such methods generally comprise comparing mortality rates in an animal model in the presence and absence of a test agent wherein decreased mortality in the presence of the test agent indicates that the test agent has the ability to reduce blood clotting. In one aspect, the animal model is deficient in ADAMTS13 polypeptide. In various aspects, the amount of recombinant VWF is greater than 1000 RCoU/kg, greater than 2000 RCoU/kg, or greater than 4000 RCoU/kg.

In still another embodiment, the invention includes methods of testing an agent for its ability to reduce blood clotting in a mammal administered recombinant VWF polypeptide in an amount effective to cause a pathology. Such methods generally comprise comparing the pathology in an animal model in the presence and absence of a test agent wherein decreased incidence or severity of the pathology in the presence of the test agent indicates that the test agent has the ability to reduce blood clotting. In various aspects, the methods of the invention further comprise administering the test agent over a range of dosages. In some aspects, the recombinant VWF polypeptide is human. In various aspects, the amount of recombinant VWF polypeptide is greater than 250 RCoU/kg, greater than 500 RCoU/kg, greater than 1000 RCoU/kg, greater than 2000 RCoU/kg, or greater than 4000 RCoU/kg. In various aspects, the animal model is deficient in a ADAMTS13 polypeptide or a VWF polypeptide. In some aspects, the animal model is a mouse. In further aspects, the mouse is of a C57BL/6J strain.

In various aspects, the pathology is a clinical, histological, or behavioral pathology. Such clinical pathology may be evident by one or more changes in lactate dehydrogenase level, creatinine kinase level, hematocrit, hemoglobulin concentration, erythrocyte count, reticulocyte count, total leukocyte count, differential leukocyte count, blood morphology abnormality, platelet count, mean cell volume, mean cell hemoglobulin concentration, or blood cell level in the urine. In other aspects, the pathology is a histological pathology. Such histological pathology may be evident by one or more of the following manifestations including, but not limited to, microthrombi, myocardial necrosis, increased coronary perivasculitis, myocardial degeneration, myocardial infarction, myocardial reparation, glia cell foci, cortical necrosis, hemorrhage, increased incidence or mean severity of a microthrombi, a disseminated intravascular coagulopathy (DIC), thrombotic thrombocytopenic purpura (TTP), ischemic heart disease, a thromboembolic change, reactive coronary perivasculitis, inflammation, fibrosis, necrosis, hemosiderin deposition, calcification, renal infarction, or a reduction in body mass. Such behavioral pathology may be evident by one or more of the following manifestations including, but not limited to, behavioral depression, a prone body position, a side body position, an abnormal body position, dyspnea, ataxia, immobility, convulsions, cramps, or piloerection.

This invention is based on the finding that recombinant human VWF (rVWF), which comprises ultra-large and high molecular weight multimers, can induce clinical symptoms of TTP in mice. It was observed that administration of rVWF causes thrombocytopenia and micro-thrombosis in mice. The mouse model described herein can be used to design prophylactic and ameliorating therapies for TTP.

The invention provides methods of inducing symptoms of TTP in a mammal, said method comprising the step of administering to the mammal a composition comprising recombinant human VWF (rVWF), wherein the rVWF composition forms high molecular weight multimers, and wherein the administration results in at least one symptom of TTP in the mammal. In some embodiments, the rVWF is not significantly cleaved by ADAMTS13. In some embodiments, the mammal is selected from the group consisting of a mouse, a rat, a rabbit, a rodent, and a non-human primate. In some embodiments, the symptom of TTP is selected from the group consisting of: reduced platelet levels, anemia, histopathological effects, increased blood creatinine kinase levels, increased blood creatinine levels, increased microthombi, and increased blood lactate dehydrogenase levels.

In some embodiments, the mammal is a mouse or other rodent, and has normal endogenous VWF levels. In some embodiments, the mouse or other rodent has deficient levels of endogenous VWF (e.g., a VWF knockout mouse). In some embodiments, the mouse or other rodent has deficient levels of endogenous ADAMTS13 (e.g., an ADAMTS13 knockout mouse). In some embodiments, the mouse or other rodent lacks both endogenous ADAMTS13 and VWF. In some embodiments, the mouse or other rodent is humanized. In some embodiments, the mouse or other rodent is immunodeficient.

In some embodiments, rVWF is administered once, e.g., to effect an acute response in the mammal. In some embodiments, rVWF is administered at a dose of at least about 1000 RCoU/kg body weight of the mammal. In some embodiments, the dose is at least about 1500 RCoU/kg, e.g., 2000, 2500, 3000, 4000, or 5000 RCoU/kg body weight of the mammal.

In some embodiments, rVWF is administered more than once, e.g., chronically, to effect a lower-level response in the mammal. In some embodiments, the rVWF is administered periodically, e.g., once per about 24, 48, or 72 hours, or weekly. In some embodiments, periodic administration lasts for at least one week, one month, or over two or three months. In such embodiments, rVWF is generally administered at a lower dose than for the acute model, e.g., at least about 250 RCoU/kg body weight. In some embodiments, rVWF is administered at about 300, 400, 500, 600, 700, 800, or 1000 RCoU/kg body weight of the mammal.

In some embodiments, recombinant Factor VIII (rFVIII) is further administered to the mammal. In some embodiments, the rFVIII is administered at the same time, e.g., in a single composition with, rVWF. In some embodiments, the rVWF and rFVIII are administered separately, e.g., consecutively. In some embodiments, rVWF and rFVIII are administered in a dose ratio that is similar to the ratio found in normal plasma. In some embodiments, rFVIII is administered at a dose of at least about 500 IU/kg body weight of the mammal, e.g., at least 750, 1000, 1500, 2000, 2500, 3000, 3500, 4000, or 5000 IU/kg body weight.

In some embodiments, rVWF is administered intravenously. In some embodiments, rVWF is administered via injection, e.g., subcutaneously, intraperitoneally, intramuscularly, and the like. In some embodiments, rVWF is administered by inhalation.

In some embodiments, the invention provides a mammalian model of TTP, said model comprising a mammal injected with a composition comprising rVWF, wherein the rVWF composition forms high molecular weight multimers, and wherein the administration results in at least on symptom of TTP in the mammal. In some embodiments, the mammal is selected from the group consisting of: a mouse, rat, rabbit, a rodent, or non-human primate. In some embodiments, the symptom of TTP is selected from the group of: reduced platelet levels, anemia, histopathological effects, increased blood creatinine kinase levels, increased blood creatinine levels, increased microthombi, and increased blood lactate dehydrogenase levels.

In some embodiments, the invention provides a mammalian model of TTP comprising a transgenic mammal, wherein the transgenic mammal expresses recombinant human von Willebrand factor (rVWF) from a transgene comprising a polynucleotide encoding rVWF, wherein said rVWF forms high molecular weight multimers, and wherein the injection results in formation of at least one symptom of TTP. In some embodiments, the mammal is selected from the group consisting of a mouse, rat, rabbit, a rodent, or non-human primate. In some embodiments, the symptom of TTP is selected from the group consisting of: reduced platelet levels, anemia, histopathological effects, increased blood creatinine kinase levels, increased blood creatinine levels, increased microthombi, and increased blood lactate dehydrogenase levels.

In some embodiments, the mammalian model is a model for acute TTP. In some embodiments, rVWF is administered only once. In such embodiments, rVWF is injected at a dose of at least 1000 RCoU/kg body weight of the mammal. In some embodiments, the dose is at least 1500 RCoU/kg, e.g., 2000, 2500, 3000, 4000, or 5000 RCoU/kg body weight of the mammal.

In some embodiments, the mammalian model is a model for chronic TTP. In some embodiments, rVWF is administered more than once. For example, rVWF can be administered periodically, e.g., every 24, 48, or 72 hours, or weekly. In some embodiments, rVWF is administered at a dose of, e.g., at least 250 RCoU/kg body weight. In some embodiments, rVWF is administered at 300, 400, 500, 600, 700, 800, or 1000 RCoU/kg body weight of the mammal.

In some embodiments, the invention provides methods for assessing the effect of a test composition on symptoms of TTP, the method comprising the steps of: (a) administering to a mammal a composition comprising rVWF, wherein the rVWF forms high molecular weight multimers, and wherein the administration results in formation of at least one symptom of TTP; (b) administering the test composition to the mammal; and (c) determining the effects of the test composition on at least one symptom of TTP.

In some embodiments, the mammal is selected from the group consisting of: a mouse, rat, rabbit, a rodent, or non-human primate. In some embodiments, the symptom of TTP is selected from the group consisting of: reduced platelet levels, anemia, histopathological effects, increased blood creatinine kinase levels, increased blood creatinine levels, increased microthombi, and increased blood lactate dehydrogenase levels.

In some embodiments, the effect of the test composition is assessed in an acute mammalian model for TTP. In some embodiments, the effect of the test composition is assessed in a chronic mammalian model for TTP.

In some embodiments, the test composition and the composition comprising rVWF are administered at the same time. In some embodiments, the test composition is administered before the composition comprising rVWF, e.g., to prevent, delay the onset, or reduce the severity of at least one symptom of TTP.

In some embodiments, the test composition is administered at least one hour after administration of the rVWF composition. In some embodiments, the test composition is administered at least 3 hours after administration of the rVWF composition, e.g., at least 5, 6, 8, 12, 18, 24, or 48 hours after administration of the rVWF composition. In some embodiments, the test composition is administered at least 1 or 2 weeks after administration of the rVWF composition.

In some embodiments, the effect of the test composition is assessed by comparison to a control mammal that does not receive the test composition, and/or one that does not receive the composition comprising rVWF. In some embodiments, the effect of the test composition is assessed by comparison to the same mammal before administration of the composition comprising rVWF.

In some embodiments, the test composition is a recombinant protease, e.g., recombinant ADAMTS13. In other embodiments the test composition is a plasma derived product, e.g., fresh frozen plasma or a purified fraction of plasma. In other embodiments, the test composition is a non-proteinaceous therapeutic. In some embodiments the non-proteinaceous therapeutic is a small molecule therapeutic. In some of these embodiments, the small molecule is a glucocorticoid; in others a antiplatelet medication (e.g., aspirin, dipyridamole) in others azothiprin, cyclophosphamide, prostacyclin, or the like.

Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

DETAILED DESCRIPTION OF THE INVENTION

Figure 1:
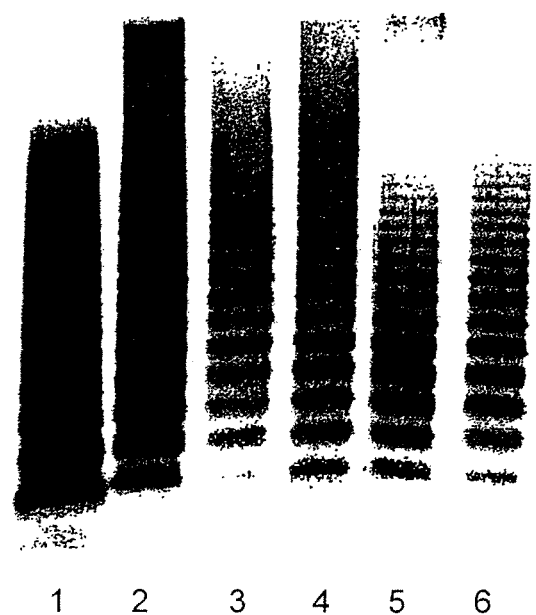
FIG. 1 is a gel electrophoresis of VWF from various sources demonstrating the sizes of VWF forms in each milieu. Lane 1 is normal human plasma; lane 2 is C57BL/6J mouse plasma; lanes 5 and 6 are also from C57BL/6J mice; lanes 3 and 4 are from ADAMTS13 deficient mice.

The present invention provides a model of TTP, based on the finding that a recombinant human VWF (referred to as "rVWF"), which contains ultra-large and high molecular weight multimers, can induce clinical symptoms of TTP and is associated with thrombocytopenia and micro-thrombosis when administered to mice. These effects were seen in normal mice, VWF-deficient mice, and most prominently in ADAMTS13 deficient mice also lacking human ADAMTS13. In control experiments, the data demonstrated that human VWF lacking ultra-large molecular weight multimers, as can be purified from human plasma, was not able to induce the TTP-like symptoms. The data also demonstrated that ADAMTS13 treatment of mice with TTP-like symptoms induced by application of rVWF would prevent the occurrence of TTP-like symptoms otherwise induced by rVWF. The invention therefore provides a model which can be used to test the in vivo efficacy of various agents in the treatment of TTP. The methods provided address the need in the art for improved methods to test the effectiveness of new therapies in the treatment of TTP.

Accordingly, animal models are provided for testing the efficacy of a therapeutic agent in the treatment of a blood clotting disorder, wherein the disorder is characterized by the presence of blood clots in blood vessels throughout the body.

In one aspect, methods are provided for testing an agent for its ability to reduce blood clotting in a mammal comprising the steps of: administering to an animal model an amount of recombinant VWF effective to cause mortality in combination with varying amounts of the agent; examining the model for a reduction in mortality compared to the model not exposed to the agent; and selecting the agent for its ability to reduce mortality in the model. More simply stated, methods are provided for testing an agent for its ability to reduce blood clotting in a mammal administered recombinant VWF in an amount effective to cause mortality comprising comparing mortality rates in an animal model in the presence and absence of a test agent, wherein decreased mortality in the presence of the test agent indicates that the test agent has the ability to reduce blood clotting.

Methods are also provided for testing an agent for its ability to reduce blood clotting in a mammal comprising the steps of: administering to an animal model an amount of recombinant VWF effective to cause a pathology in the animal model in combination with various amounts of the agent; examining the model for an improvement in the pathology compared to the model not exposed to the agent; and selecting the agent for its ability to improve the pathology in the model. Here again and more simply stated, methods are provided for testing an agent for its ability to reduce blood clotting in a mammal administered recombinant von Willebrand factor in an amount effective to cause a pathology comprising comparing the pathology in an animal model in the presence and absence of a test agent, wherein decreased incidence or severity of the pathology in the presence of the test agent indicates that the test agent has the ability to reduce blood clotting.

In various embodiments, recombinant VWF is administered to the animal model at a dose of at least about 10 RCoU/kg BW, of at least about 20 RCoU/kg BW, of at least about 30 RCoU/kg BW, of at least about 40 RCoU/kg BW, of at least about 50 RCoU/kg BW, of at least about 60 RCoU/kg BW, of at least about 70 RCoU/kg BW, of at least about 80 RCoU/kg BW, of at least about 90 RCoU/kg BW, of at least about 100 RCoU/kg BW, of at least about 150 RCoU/kg BW, of at least about 200 RCoU/kg BW, of at least about 250 RCoU/kg BW, of at least about 300 RCoU/kg BW, of at least about 350 RCoU/kg BW, of at least about 400 RCoU/kg BW, of at least about 450 RCoU/kg BW, of at least about 500 RCoU/kg BW, of at least about 550 RCoU/kg BW, of at least about 600 RCoU/kg BW, of at least about 650 RCoU/kg BW, of at least about 700 RCoU/kg BW, of at least about 750 RCoU/kg BW, of at least about 800 RCoU/kg BW, of at least about 850 RCoU/kg BW, of at least about 900 RCoU/kg BW, of at least about 950 RCoU/kg BW, of at least about 1000 RCoU/kg BW, of at least about 1200 RCoU/kg BW, of at least about 1400 RCoU/kg BW, of at least about 1600 RCoU/kg BW, of at least about 1800 RCoU/kg BW, of at least about 2000 RCoU/kg BW, of at least about 2500 RCoU/kg BW, of at least about 3000 RCoU/kg BW, of at least about 3500 RCoU/kg BW, of at least about 4000 RCoU/kg BW, of at least about 4500 RCoU/kg BW, of at least about 5000 RCoU/kg BW, of at least about 6000 RCoU/kg BW, of at least about 7000 RCoU/kg BW, of at least about 8000 RCoU/kg BW, of at least about 9000 RCoU/kg BW, of at least about 10000 RCoU/kg BW, of at least about 20000 RCoU/kg BW, of at least about 50000 RCoU/kg BW, and of at least about 100000 RCoU/kg BW, and up to more than 100000 RCoU/kg BW.

In certain aspects of the methods provided, recombinant FVIII is optionally administered to the animal model at a dose of at least about 10 IU/kg BW, of at least about 20 IU/kg BW, of at least about 30 IU/kg BW, of at least about 40 IU/kg BW, of at least about 50 IU/kg BW, of at least about 60 IU/kg BW, of at least about 70 IU/kg BW, of at least about 80 IU/kg BW, of at least about 90 IU/kg BW, of at least about 100 IU/kg BW, of at least about 150 IU/kg BW, of at least about 200 IU/kg BW, of at least about 250 IU/kg BW, of at least about 300 IU/kg BW, of at least about 350 IU/kg BW, of at least about 400 IU/kg BW, of at least about 450 IU/kg BW, of at least about 500 IU/kg BW, of at least about 550 IU/kg BW, of at least about 600 IU/kg BW, of at least about 650 IU/kg BW, of at least about 700 IU/kg BW, of at least about 750 IU/kg BW, of at least about 800 IU/kg BW, of at least about 850 IU/kg BW, of at least about 900 IU/kg BW, of at least about 950 IU/kg BW, of at least about 1000 IU/kg BW, of at least about 1200 IU/kg BW, of at least about 1400 IU/kg BW, of at least about 1600 IU/kg BW, of at least about 1800 IU/kg BW, of at least about 2000 IU/kg BW, of at least about 2500 IU/kg BW, of at least about 3000 IU/kg BW, of at least about 3500 IU/kg BW, of at least about 4000 IU/kg BW, of at least about 4500 IU/kg BW, of at least about 5000 IU/kg BW, of at least about 6000 IU/kg BW, of at least about 7000 IU/kg BW, of at least about 8000 IU/kg BW, of at least about 9000 IU/kg BW, of at least about 10000 IU/kg BW, of at least about 20000 IU/kg BW, of at least about 50000 IU/kg BW, and of at least about 100000 IU/kg BW, and up to more than 100000 IU/kg BW.

In the methods provided, the test agent is administered to the animal model at any dose, including a variety of doses. The dosage may be based on body weight, activity of the agent, route of administration, condition of the animal recipient, and various factors as known to one of skill in the art.

Definitions

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

The following abbreviations are used throughout.

| | |
|---|---|
| ADAMTS13 | a disintegrin and metalloprotease with thrombospondin type 1 domains - 13 |
| BW | body weight |
| IU | international units |
| n.a. | not applicable |
| IV | intravenous |
| CV | Coefficient of variation |
| NOAEL | No Observed Adverse Effect Level |
| SEM | Standard Error of Mean |
| SOP | Standard Operating Procedure |
| mEq | milli equivalent |
| RCo | ristocetin cofactor |
| VWF | von Willebrand factor |
| rVWF | recombinant von Willebrand factor |
| rFVIII | recombinant factor eight |
| WFI | water for injection |
| STADS | short-term analysis data set |
| LTADS | long-term analysis data set |

It is noted here that, as used in this specification and the appended claims, the singular forms "a," "an," and "the" include plural reference unless the context clearly dictates otherwise.

As used herein, the following terms have the meanings ascribed to them unless specified otherwise.

The term "gene" refers to a DNA sequence that encodes or a particular sequence of amino acids which comprise all or part of one or more polypeptides, proteins or enzymes, and may or may not include introns, and regulatory DNA sequences, such as promoter or enhancer sequences, 5'-untranslated region, or 3'-untranslated region which affect, for example, the conditions under which the gene is expressed. Some genes, which are not structural genes, may be transcribed from DNA to RNA, but are not translated into an amino acid sequence. Other genes may function as regulators of structural genes or as regulators of DNA transcription.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues linked via peptide bonds. The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "protein" typically refers to large polypeptides. The term "peptide" typically refers to short polypeptides. Synthetic polypeptides can be synthesized, for example, using an automated polypeptide synthesizer.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same when compared and aligned for maximum correspondence over a comparison window, or designated region as measured using one of the following sequence comparison algorithms or by manual alignment and visual inspection. "Substantial identity" refers to sequences with at least 80%, 85%, 90%, 95%, 98%, or 99% identity over a specified sequence. The identity generally exists over a region that is at least about 50-100 amino acids or nucleotides in length.

The term "endogenous" refers to a polypeptide or polynucleotide or other compound that is expressed naturally in the host organism, or originates within a cell, tissue or organism. "Exogenous" refers to a polypeptide, polynucleotide or other compound that originates outside a cell, tissue or organism.

The term "agent" or "compound" describes any molecule, e.g. protein or pharmaceutical, with the capability of affecting blood clotting or other biological parameter in the animal model of the invention.

The term "NOAEL" or "no observable adverse effect level" denotes the level of exposure of an organism, found by experiment or observation, at which there is no biologically or statistically significant (e.g. alteration of morphology, functional capacity, growth, development or life span) increase in the frequency or severity of any adverse effects in the exposed population when compared to its appropriate control. In toxicology, NOAEL is specifically the highest tested dose or concentration of a substance (i.e. a chemical) or agent (e.g. radiation), at which no such adverse effect is found in exposed test organisms where higher doses or concentrations resulted in an adverse effect. This level may be used in the process of establishing a dose-response relationship, a fundamental step in most risk assessment methodologies.

As used herein, TTP or Moschcowitz disease, refers to microangiopathic hemolytic anemia and associated symptoms. Symptoms of TTP include: neurological symptoms (behavioral changes, altered mental status, stroke, headaches); kidney failure; fever; thrombocytopenia (low platelet count); bruising; purpura; anemia; and jaundice. TTP is characterized by abnormally high levels of platelet aggregation and blood coagulation, which results in shearing of red blood cells. Additional symptoms are described herein.

TTP is generally caused by a deficiency in ADAMTS13. The syndrome can be broadly divided into two categories, acquired and familial. In the former, TTP symptoms result because of auto-antibodies directed against ADAMTS13. Familial TTP is generally caused by a mutation (e.g., nonsense, frameshift, or missense) in the ADAMTS13 gene (see, e.g., Desch et al., *Arterioscler. Thromb. Vasc. Biol.* 27:1901-08, 2007).

As used herein, "histopathological effects" generally include effects observed in tissue structure, either micro- or macro-scopically. Histopathological effects of TTP include microthrombosis (especially in the heart and other organs), myocardial necrosis, myocardial degeneration, and increased coronary perivasculitis. Additional TTP histopathological effects are described in the Examples section.

Likewise, the term "pathology" refers to an abnormal physiological condition. As used herein, the pathology can be clinical, histological, or behavioral, and it refers to a deviation from an assumed normal state. If the pathology is a "clinical pathology," it reflects an abnormality in a bodily fluid, such as, but not limited to, blood and urine. The clinical pathology can be observed using chemistry, microbiology, hematology or molecular pathology. If the pathology is a "histological pathology," it can be observed using gross, microscopic, or molecular examination of organs, tissues, or whole bodies (autopsy or necropsy), including measuring differences in body mass. If the pathology is a "behavioral pathology," it can be observed by monitoring changes in the animal's appearance and behavior.

von Willebrand factor, or VWF, is a large, multimeric glycoprotein that binds to Factor VIII (FVIII) to aid in blood coagulation. Thrombin releases FVIII from VWF, which leads to rapid degradation of FVIII. Under normal conditions, the VWF monomer is assembled into multimers in the endoplasmic reticulum and golgi before secretion. Multimers of VWF can be extremely large, >20,000 kD, and consist of over 80 monomer subunits of 250 kD each. ADAMTS13 (A Disintegrin-like And Metalloprotease with Thrombospondin type 1 motif 13) cleaves VWF between Y1605 and M1606, which leads to its degradation by other proteases.

Human recombinant VWF, or "rVWF," as used herein, refers to recombinant VWF that forms high molecular weight multimers. Unlike plasma-derived VWF, rVWF has not been exposed to endogenous ADAMTS13 and therefore has not been cleaved at Y1605-M1606. Unless stated otherwise "rVWF" refers to the human sequence and substantially identical variants thereof.

"Factor VIII" (FVIII) refers to a blood clotting factor that associates with VWF in circulation. This association prevents degradation of FVIII. Upon activation by thrombin, FVIII dissociates and enters the coagulation cascade.

"ADAMTS13" (A Disintegrin-like And Metalloprotease with ThromboSpondin type 1 motif no. 13) refers to a metalloprotease that cleaves VWF in the blood, and reduces its activity (e.g., as an adhesive link between platelets and the subendothelium). For a review of the role of ADAMTS13 in TTP, see Levy et al., Blood 106:11-17, 2005.

A "control," as used herein, can refer to an active, positive, negative or vehicle control. As will be understood by those of skill in the art, controls are used to establish the relevance of experimental results, and provide a comparison for the condition being tested. For example, a negative control generally refers to a sample that represents an untreated, or "normal," state. Negative controls can also include samples treated with, e.g., inactive components. A non-limiting set of exemplary controls are shown in the Examples.

As used herein, an "acute" model of TTP or an "acute" response, indicates that the mammal experiences severe symptoms of TTP, including organ damage. In some cases, the mammal is unable to recover fully. Such acute models can be indicative of the conditions observed in human patients with severe TTP, e.g., those with genetic defects in ADAMTS13. In some embodiments of the invention, an acute model of TTP is created by administering a high dose of rVWF, e.g., in a single bolus.

As used herein, a "chronic" model of TTP or a "chronic" response, indicates that the mammal experiences long-term, less sever symptoms of TTP. Such chronic models can be indicative of the condition found in some human patients of TTP that experience less severe symptoms, such as those without severe ADAMTS13 deficiency. In some embodiments of the invention, a chronic model of TTP is created by administering lower doses of rVWF, e.g., in multiple administrations over a period of time.

The term "reduces the severity," when referring to a symptom of TTP, means that the symptom has delayed onset, reduced severity, or causes less damage to the animal. Generally, severity of a symptom is compared to a control, e.g., that does not receive an active prophylactic or therapeutic composition. In that case, a composition can be said to reduce the severity of a symptom of TTP if the symptom is reduced by 10%, 25%, 30%, 50%, 80%, or 100% (i.e., essentially eliminated), as compared to the control level of the symptom.

Blood Clotting Factors and Blood Enzymes

As mentioned above, methods provided optionally include use of Factor VIII. Factor VIII (FVIII) is a blood plasma glycoprotein of about 260 kDa molecular mass produced in the liver of mammals. It is a critical component of the cascade of coagulation reactions that lead to blood clotting. Within this cascade is a step in which Factor IXa, in conjunction with FVIII, converts Factor X to an activated form, Factor Xa. FVIII acts as a cofactor at this step, being required with calcium ions and phospholipid for the activity of Factor IXa. The two most common hemophilic disorders are caused by a deficiency of functional FVIII (Hemophilia A, about 80% of all cases) or functional Factor IXa (Hemophilia B or Christmas Factor disease).

Until recently, the standard treatment of Hemophilia A involved frequent infusion of preparations of FVIII concentrates derived from the plasmas of human donors. While this replacement therapy is generally effective, such treatment puts patients at risk for virus-transmissible diseases such as hepatitis and AIDS. Although this risk has been reduced by further purification of FVIII from plasma by immunopurification using monoclonal antibodies, and by inactivating viruses by treatment with either an organic solvent or heat, such preparations have greatly increased the cost of treatment and are not without risk. For these reasons, patients have been treated episodically, rather than prophylactically. A further complication is that about 15% of patients develop inhibitory antibodies to plasma-derived FVIII.

An important advance in the treatment of Hemophilia A has been the isolation of cDNA clones encoding the complete 2,351 amino acid sequence of human FVIII (see, Wood et al, Nature, 312: 330 (1984) and U.S. Pat. No. 4,757,006, Jul. 12, 1988) and the provision of the human FVIII gene DNA sequence and recombinant methods for its production. However, patients receiving recombinant FVIII may still develop FVIII-specific antibodies which interfere with treatment of the disease. Factor VIII products for the treatment of Hemophilia A include, but are not limited to: ADVATE® (Antihemophilic Factor (Recombinant), Plasma/Albumin-Free Method, rAHF-PFM, Baxter), recombinant Antihemophilic Factor (BIOCLATE™, GENARC®, HELIXATE FS®, KOATE®, KOGENATE FS®, RECOMBINATE®): MONOCLATE-P®, purified preparation of Factor VIII:C, Antihemophilic Factor/von Willebrand factor Complex (Human) HUMATE-P® and ALPHANATE®, Anti-hemophilic Factor/von Willebrand factor Complex (Human); and HYATE C®, purified pig Factor VIII.

Accordingly, methods provided include use of HAEMATE® P (ZLB Behring GmbH, Marburg, Germany) as a positive control. HAEMATE® P as used in the working examples of the invention contains the active ingredients VWF and FVIII (114.34 IU VWF:RCo/mL, 77 IU FVIII/mL) and is produced by extractions from blood plasma from screened blood donors. However, other forms and concentrations of HAEMATE® P are also contemplated for use in the methods.

Methods provided also include, in various aspects, use of VWF. VWF is an adhesive complex glycoprotein with a molecular mass of the monomer of about 260 kDa. VWF circulates in human plasma both as a dimer and as oligomers ranging in molecular mass from 450 kDa to 20,000 kDa. The precursor polypeptide, pre-pro-VWF, is synthesized in endothelial cells and megakaryocytes, and consists of a 22-amino acid residue signal peptide, a 741-residue propeptide and a 2050-residue polypeptide. After in vivo removal of the signal peptide, two pro-VWF units are linked via disulfide bonds forming dimers, the building blocks for mature VWF multimers. Further polymers of VWF with increasing molecular weights, up to 20 million Dalton, are formed from the VWF dimers by linking. It is presumed that particularly the high-molecular weight VWF multimers have an essential importance in blood coagulation.

VWF syndrome manifests clinically when there is either an underproduction or an overproduction of VWF. Overproduction of VWF causes increased thrombosis (formation of a clot or thrombus inside a blood vessel, obstructing the flow of blood) while reduced levels of, or lack of, high-molecular forms of VWF causes increased bleeding and an increased bleeding time due to inhibition of platelet aggregation and wound closure.

A VWF deficiency may also cause a phenotypic Hemophilia A since VWF is an essential component of functional FVIII. In these instances, the half-life of Factor VIII is reduced to such an extent that its function in the blood coagulation cascade is impaired. Patients suffering from von Willebrand disease (VWD) or VWF syndrome frequently exhibit an FVIII deficiency. In these patients, the reduced FVIII activity is not the consequence of a defect of the X chromosomal gene, but an indirect consequence of the quantitative and qualitative change of VWF in plasma. The differentiation between Hemophilia A and VWD may normally be effected by measuring the VWF antigen or by determining the ristocetin-cofactor activity. Ristocetin cofactor activity is measured by adding ristocetin and a platelet substrate to the patient's plasma. Ristocetin enhances binding of VWF to the platelet glycoprotein lb receptor, resulting in agglutination. The patient's VWF will support the platelet agglutination induced by the ristocetin as measured by a change in light transmission. Therefore, this is an in vitro measurement of the functional activity of the patient's VWF, and is the most sensitive assay for diagnosing VWD. Both the VWF antigen content and the ristocetin cofactor activity are lowered in most VWD patients, whereas they are normal in Hemophilia A patients. VWF products for the treatment of VWF syndrome include, but are not limited to: HUMATE-P®; and, IMMUNATE®, INNOBRAND®, and 8Y®, which therapies comprise FVIII/VWF concentrate from plasma.

Human rVWF is resistant to the proteolytic activity of murine ADAMTS13 present in murine plasma. This observation has been demonstrated in vitro by exposing human rVWF to plasmas of various species, including mice, and either measuring residual VWF activity or visualizing the multimeric composition. The resistance of human VWF to murine ADAMTS13 was also demonstrated ex vivo after infusion of rVWF into mice. Plasma samples obtained at various time points after infusion did not show any VWF fragments derived from the action of ADAMTS13 after cleavage at $Tyr^{1605}$-$MET^{1606}$ (the C-terminal 176 kDa and the N-terminal 140 kDa), consistent with the resistance of rVWF to murine ADAMTS13 in vivo. In contrast, administration of rVWF into a rabbit resulted in the expected cleavage pattern of the VWF subunit with the appearance of the fragments on immunoblots that used monoclonal antibodies.

Recombinant VWF consists of intact VWF subunits because rVWF has never been exposed to ADAMTS13-specific proteolysis. Plasma-derived VWF consists of subunits which are cleaved at $Tyr^{1605}$-$MET^{1606}$ in the A2 domain of VWF. Normal C57BL/6J mice have murine ADAMTS13 that is unable to cleave human rVWF with intact subunits. Therefore, administering rVWF into C57BL/6J mice results in ultra-large VWF multimers and impaired metabolism of rVWF.

ADAMTS13 (a disintegrin and metalloproteinase with a thrombospondin type 1 motif, member 13)—also known as VWF-cleaving protease (VWFCP)—is a zinc-containing metalloprotease enzyme that cleaves VWF. ADAMTS13 is secreted in blood and degrades large VWF multimers, decreasing their activity. ADAMTS13 is a metalloprotease consisting of multiple structural and functional domains, and these domains may participate in the recognition and binding of ADAMTS13 to VWF. The ULVWF multimers are cleaved by ADAMTS13 as they are secreted from endothelial cells.

It has been found that patients with congenital TTP or acquired TTP are severely deficient in ADAMTS13. Congenital ADAMTS13 deficiency is caused by mutations of the ADAMTS13 gene. Patients with the familial form have severe protease deficiency. ADAMTS13 gene mutation in familial TTP causes inactivity or decreased activity of ADAMTS13. Acquired deficiency occurs with the production of autoantibodies inhibiting ADAMTS13 activity. Acquired TTP is idiopathic secondary complications of autoimmune disease, malignancy, stem cell transplantation, pregnancy (especially the third trimester), certain drugs (including ticlopidine, mitomycin, clopidogrel, and cyclosporine) or infection.

Thrombotic Thrombocytopenic Purpura (TTP) and Other Blood Clotting Disorders

The invention provides animal models and methods of testing an agent for its ability to reduce blood clotting disorders (thrombophilia) including, but not limited to, thrombotic thrombocytopenic purpura (TTP) and other thrombotic microangiopathies. TTP is a life-threatening multisystem disorder that was first described by Moschcowitz in 1924 when he observed that a 16 year-old girl had anemia, petechiae, and microscopic hematuria. The girl died of multiorgan failure, and, at autopsy, disseminated microvascular thrombi were prevalent. These thrombi remain the hallmark of the pathologic diagnosis.

The TTP syndrome is characterized by microangiopathic hemolysis and platelet aggregation/hyaline thrombi whose formation is unrelated to coagulation system activity. Platelet microthrombi predominate; they form in the microcirculation (i.e., arterioles, capillaries) throughout the body causing partial occlusion of vessels. Organ ischemia, thrombocytopenia, and erythrocyte fragmentation (i.e., schistocytes) occur. The thrombi partially occlude the vascular lumina with overlying proliferative endothelial cells. The endothelia of the kidneys, brain, heart, pancreas, spleen, and adrenal glands are particularly vulnerable to TTP. The liver, lungs, gastrointestinal tract, gallbladder, skeletal muscles, retina, pituitary gland, ovaries, uterus, and testes are also affected to a lesser extent. No inflammatory changes occur.

In 1982, Moake and his colleagues observed ultralarge von Willebrand factor (ULVWF) multimers in the plasma of four patients with relapsing TTP (Moake, Semin. Hematol. 34:83-89, 1997; Moake, Semin. Hematol. 41:4-14, 2004). These multimers were the same size as those noted in the endothelial cells. The plasma of normal individuals has much smaller VWF. Moake suggested that there was a deficiency in an enzyme that reduces the large VWF to its normal size in plasma in patients with TTP. Also noted was that this large VWF has a greater ability to adhere with platelets mediating a thrombus formation.

The agitated endothelial cells are the main source of ULVWF multimers in the bloodstream where they bind to specific surface platelet receptors. The ULVWF multimers entangled with platelets adhering to the subendothelium. The pathogenesis of TTP is due to the platelet clumping in the microvasculature. There is an increased adherence of the ULVWF and lack of a functioning proteolytic enzyme to normalize this multimer. The sheer stress of fluid and platelet thrombi in the microcirculation does not enhance proteolysis of ULVWF. How the adhesive bond opposes shear stress in the microangiopathic causing platelet initiating thrombus formation and contributes to platelet activity is yet to be solved.

Plasma exchange has been the first-line therapy for TTP since 1991. Congenital deficiency can replace the deficiency and mutations in the ADAMTS13 gene by plasma infusion. Acquired deficiency can remove the inhibitor of ADAMTS13 by plasmapheresis. However, plasma exchange is more effective treatment than plasma infusion.

ADAMTS13 multimers are abundant and fibrinogen/fibrin is minimal in TTP, whereas fibrinogen is abundant in disseminated intravascular coagulation (DIC). The ULVWF, that is, ADAMTS13 multimer, is a marker found in the plasma of patients most likely to have a recurrence of TTP.

This life-threatening condition may have a positive outcome if recognized early and medical intervention is initiated early. Thus, the present invention provides animal models to be used in the development of new therapies in the treatment of TTP.

Design of a Murine Model for TTP

Recombinant VWF consists of intact VWF subunits because it has never been exposed to proteolysis by endogenous circulating ADAMTS13. Plasma-derived VWF consists of subunits which are cleaved by ADAMTS13 at $Tyr^{1605}$-$MET^{1606}$ in the A2 domain of VWF. Thus, plasma-derived VWF preparations, such as HAEMATE® P, provide a useful control for the present invention.

Ultra-large molecular-weight multimers are physiological in humans under special circumstances, e.g., upon stimulation of endothelial cells with DDAVP (DDAVP is a treatment for mild hemophilia A and von Willebrand's disease). Upon stimulation of endothelial cells, stored VWF is released into the circulation from Weibel-Palade bodies in the form of ultra-large VWF. These ultra-large VWF multimers disappear within 2 hours, accompanied by increased proteolysis of VWF by human ADAMTS13. Plasma concentrations of VWF after DDAVP administration return to baseline over about 24 hours.

Murine ADAMTS13 does not sufficiently cleave human rVWF to decrease the ultra-large molecular weight multimers of rVWF, as the human factor is resistant to murine ADAMTS13. In addition, normal mice have ultra-large molecular weight multimers of VWF in circulation because murine ADAMTS13 has a decreased activity even for endogenous murine VWF.

In ADAMTS13 deficient mice, endogenous murine VWF consists of ultra-large molecular-weight multimers because of the absence of ADAMTS13. Administration of human rVWF, either directly or through expression of a transgene, therefore results in supraphysiological circulating levels of VWF and a substantial increase in ultra-large VWF multimers.

Recombinant Protein Expression

Recombinant VWF to be used according to the invention includes human forms of VWF and polymorphic and allelic variants thereof, e.g., polypeptides with substantial identity to the sequence of Genpept accession number P04275.1. Similarly, recombinant Factor VIII includes human forms of the coagulation factor, including various isoforms, alleles, and polymorphic variants. Generally, Factor VIII will have a sequence substantially identical to that of Genpept accession number P00451.1. Human FVIII is also commercially available. Recombinant ADAMTS13 includes human forms of the protease and polymorphic and allelic variants thereof, e.g., polypeptides with substantial identity to the sequence of Genpept accession number Q3SYG5.

Recombinant techniques that can be used to express and obtain rVWF, rFVIII, or rADAMTS13 polypeptides and complexes are routine in the field. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

In general, the nucleic acid sequence encoding the protein of interest (e.g., VWF, FVIII, and ADAMTS13) is cloned from cDNA or a genomic DNA library, or isolated using amplification techniques with oligonucleotide primers. For example, the coding sequence can be isolated from a human nucleic acid (genomic or cDNA) library by hybridizing with a nucleic acid probe. Amplification techniques using primers can be used to amplify and isolate a polynucleotide sequence encoding the protein of interest from cDNA or RNA (see, e.g., Dieffenfach & Dveksler, *PCR Primer: A Laboratory Manual* (1995)).

One of skill will appreciate that any particular polypeptide sequence can include polymorphic or allelic variations that will not affect the activity of the polypeptide or its use according to the invention.

To obtain high level expression of the protein of interest (e.g., VWF, FVIII, ADAMTS13), one typically subclones a sequence encoding the factor into an expression vector that contains a strong promoter to direct transcription. Such techniques are well known in the art, and are generally described, e.g., in Ausubel et al., *Current Protocols in Molecular Biology* (1995 supplement); and Sambrook et al., *Molecular Cloning: a Laboratory Manual*, 2nd Ed., (1989).

The protein can be expressed in any kind of cell. Suitable bacterial promoters are well known in the art and described, e.g., in Sambrook et al. and Ausubel et al. Bacterial expression systems for expressing proteins are available in, e.g., *E. coli, Bacillus* sp., and *Salmonella* (Palva et al., *Gene* 22:229-235, 1983); Mosbach et al., *Nature* 302:543-545, 1983). Kits for such expression systems are commercially available.

Other microbes, such as yeast (e.g., *Saccharomyces*), can also be used for expression. Yeast have a host of suitable vectors with expression control sequences, such as promoters, including 3-phosphoglycerate kinase or other glycolytic enzymes, and an origin of replication, termination sequences and the like as desired.

Mammalian cell culture can also be used to express and produce recombinant polypeptides (see Winnacker, "From Genes to Clones", VCH Publishers, New York (1987)). Mammalian cells include HEK-293 cells, HUVECs, EA.hy926, CMK cells, the CHO cell lines, various COS cell lines, HeLa cells, myeloma cell lines, etc. Expression vectors for these cells can include expression control sequences, such as an origin of replication, a promoter, an enhancer (Queen et al., *Immunol. Rev.* 89:49-68, 1986), and necessary processing information sites, such as ribosome binding sites, RNA splice sites, polyadenylation sites, and transcriptional terminator sequences. Expression control sequences include promoters derived from SV40, adenovirus, bovine papilloma virus, cytomegalovirus and the like. A selectable marker, such as a neo expression cassette, can also be included in the expression vector.

The protein of interest (e.g., VWF, FVIII, or ADAMTS13) can then be isolated from other contaminating proteins and substances using common methods. Protein purification techniques include, for example, methods utilizing solubility (such as salt precipitation and solvent precipitation), methods utilizing the difference in molecular weight (such as dialysis, ultra-filtration, gel-filtration, and SDS-polyacrylamide gel electrophoresis), methods utilizing a difference in electric charge (such as ion-exchange column chromatography), methods utilizing specific interaction (such as affinity chromatography), methods utilizing a difference in hydrophobicity (such as reversed-phase high performance liquid chromatography) and methods utilizing a difference in isoelectric point (such as isoelectric focusing electrophoresis). Reference resources include: Scopes, Protein Purification: Principles and Practice, Springer Press, 3d edition (1994) and Abelson et al., *Methods in Enzymology*, Volume 182: Guide to Protein Purification, Academic Press (1990).

Administration of rVWF Compositions

The rVWF compositions of the invention can be administered by different routes, including intravenous, intraperitoneal, subcutaneous, intramuscular, transmucosal, or inhalant.

The composition is generally injected intravenously, e.g., via tail vein, as is common in the art. For injection, the composition is formulated in sterile, physiologically compatible buffers or solutions, such as saline solution, Hank's solution, or Ringer's solution. In addition, the compounds may be formulated in solid form and redissolved or suspended immediately prior to use. Lyophilized forms can also be produced.

For transmucosal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration can be via spray, pump, atomizer, or nebulizer.

Transgenic Expression of rVWF in Animals

In some embodiments, the present invention provides a non-human animal expressing recombinant VWF as a model for TTP. The transgenic animal can be used for developing a biologically active agent effective to prevent or reduce TTP symptoms. In one aspect, the subject transgenic animal carries a nucleotide sequence encoding VWF stably integrated into the genome of the animal, wherein the VWF forms high molecular weight multimers. Typically, the VWF transgene is from an exogenous source, i.e., from a different animal than that expressing the transgene. In some embodiments, the VWF is recombinant human VWF.

A "transgenic animal" refers to any non-human animal (e.g. mouse, rat, other rodent, pig, or primate) in which one or more cells contain a heterologous nucleic acid introduced using common transgenic techniques. The nucleic acid is introduced into the cell, directly or indirectly, by introduction into a precursor of the cell, by way of deliberate genetic manipulation, such as by microinjection, or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

The present invention contemplates transgenic animals that carries the desired transgene in all their cells, as well as animals which carry the transgenes in some, but not all their cells, i.e., mosaic animals. The transgene can be integrated as a single copy or in concatamers, e.g., head-to-head tandems or head-to-tail tandems. The transgene can also be selectively introduced into or selectively activated in a particular tissue or cell type (e.g., endothelial cells, megakaryocytes, subendothelial cells). The regulatory sequences required for such cell-type specific activation will be apparent to those of skill in the art.

The transgene can be integrated into the chromosomal site of the endogenous counterpart using gene targeting. Briefly, when such a technique is to be utilized, vectors containing some nucleotide sequences homologous to the endogenous counterpart are designed for the purpose of integrating, via homologous recombination with chromosomal sequences, into and disrupting the function of the nucleotide sequence of the endogenous gene.

Advances in technologies for embryo micromanipulation now permit introduction of heterologous DNA into fertilized mammalian ova as well. For instance, totipotent or pluripotent stem cells can be transformed by microinjection, calcium phosphate mediated precipitation, liposome fusion, retroviral infection or other means. The transformed cells are then introduced into the embryo, and the embryo will then develop into a transgenic animal. In some embodiments, developing embryos are infected with a viral vector containing the VWF transgene so that transgenic animals expressing the transgene can be produced from the infected embryo. In some embodiments, the VWF transgene is injected into the pronucleus or cytoplasm of the embryo, preferably at the single cell stage, and the embryo is allowed to develop into a mature transgenic animal. These and other variant methods for generating transgenic animals are well established in the art (see, e.g., U.S. Pat. Nos. 5,175,385 and 5,175,384).

Transgenic animals include "knockouts" and "knockins". A "knockout" has an alteration in the target gene via the introduction of transgenic sequences that results in a decrease of function of the target gene, typically such that target gene expression is insignificant or undetectable. A "knockin" is a transgenic animal having an alteration in a host cell genome that results in an augmented expression of a target gene, e.g., by introduction of an additional copy of the target gene, or by operatively inserting a regulatory sequence that provides for enhanced expression of an endogenous copy of the target gene. The knock-in or knock-out transgenic animals can be heterozygous or homozygous with respect to the target genes. Both knockouts and knockins can be "bigenic," i.e., having at least two altered genes. For example, a bigenic animal can include a rVWF knock-in and an ADAMTS13 knock-out.

Transgenic mice can be derived using methodology known to those of skill in the art, see, e.g., Hogan et al., Manipulating the Mouse Embryo: A Laboratory Manual, 1988; Teratocarcinomas and Embryonic Stem Cells: A Practical Approach, Robertson, ed., 1987; and Capecchi et al., *Science* 244:1288, 1989.

Animals of the Invention

The invention includes animal models of TTP that can be established by administration of recombinant VWF, either directly or via transgenic expression. Mice are commonly used, as rodents are inexpensive, reproduce quickly, and may be housed in large numbers in a fairly small facility. Other rodents, such as rats, hamsters, gerbils, guinea pigs, and the like, may also be used according to the invention. Experiments may be set up with a large number of replicates.

Mice that can be used according to the invention include common laboratory strains, such as C57BL/6J, Balb-c, and FVB strains. Such mice are readily available from Jackson Labs, Bar Harbor, Me.

Immunodeficient mice and other rodents can be used according to the invention. These mice or rodents lack a functional immune system, and include, e.g., SCID, RAG 1 or 2 knock-outs, and Nude mice. Such mice or rodents can be useful, e.g., for ruling out the inflammatory or immune effects of introducing an exogenous substance into the mouse or rodent. Again, such mice are readily available from commercial sources.

In addition, humanized rodents, such as humanized mice, rats, hamsters, gerbils, guinea pigs, and the like, can be used. Humanized rodents, such as mice, carry functioning human genes, cells, tissues, and/or organs that are initially transplanted and grown in the animal. Humanized rodents, such as mice, are often generated to have an immune system that is essentially human. Such mice are useful, e.g., for determining human responses to therapeutic substances. For example, in the bone marrow/liver/thymus, or "BLT" mouse, non-obese diabetic (NOD)/SCID mice (which lack endogenous T and B cells) are surgically implanted with fetal thymes and liver or ganoids, as in the SCID-hub system. The mice are then sub lethally irradiated and transplanted with autologous CD34+ stem cells obtained from fetal liver. These cells then take up residence in the murine bone marrow. Thus, the mice undergo a bone marrow transplant, receiving human stem cells that are autologous to their human thymus and liver implants. Rodents, such as mice, prepared in this way show an impressive range of human cells in peripheral blood, including mature T and B lymphocytes, monocytes, macrophages, and dendritic cells. Equally importantly, they show extensive infiltration of organs and tissues with human cells, including liver, lung, and gastrointestinal tract. Humanized rodents, such as mice, are known in the art, and are commercially available (see, e.g., Gonzales and Cheung (Aug. 5, 2008) *J. Pharmacol. Exp. Ther.*; Ito et al. (2008) Current Topics in Microbiology and Immunology, Springer-Verlag, Berlin and Heidelberg, p. 53-76; Schmidt et al. (2008) PLoS ONE 3:e3192).

As explained above, such rodents can be genetically altered to express a transgene or disrupt an endogenous gene. For example, in some embodiments of the invention, ADAMTS13 deficient mice, or other rodent, (e.g., ADAMTS13 knockout mice) are used. In some embodiments, mice, or other rodents, lacking endogenous VWF (VWF knock-outs) are used. Double knockouts (ADAMTS13−/− and VWF−/−) can be ADAMTS13 knockout mice were initially generated using gene targeting (Banno et al., *Blood* 107:3161-66, 2006; Desch et al., *Arterioscler. Thromb. Vasc. Biol.* 27:1901-08, 2007). They have been characterized extensively, and are publicly available (see, e.g., Miyata et al., *Curr. Opin. Hematol.* 14:277-83, 2007; Chauhan et al., *Blood* 111:3452-57, 2008; Chauhan et al., *J. Exp. Med.* 205:2065-74, 2008). ADAMTS13 deficient mice are viable and fertile, but are susceptible to thrombosis. However, spontaneous thrombocytopenia, hemolytic anemia, and microvascular thrombosis are generally not observed. Some of these symptoms can be induced, e.g., by administering $FeCl_3$ or Shigatoxin to the knockout mice (Chauhan et al., *Blood* 111:3452-57, 2008).

VWF knockout mice are also known in the art and commercially available (see, e.g., Pergolizzi et al., *Blood* 108:862-69, 2006). VWF knockout mice are viable and fertile, and do not display any gross physical or behavioral abnormalities. However, they exhibit defects in hemostasis characterized by prolonged bleeding times and occasional spontaneous bleeding. The knockouts also lack thrombus formation following vascular injury, and FVIII levels are reduced.

Test Agents or Compounds

The agents or compounds (or "compositions) to be tested on the animal models of the invention can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (e.g., DMSO-based) solutions are used.

Exemplary test agents or compounds (or "compositions) include proteases that target high molecular weight complexes of VWF, including ADAMTS13, ADAMTS13 variants that retain activity, and species homologs. Such polypeptide compositions can be designed using a polynucleotide vector that encodes the polypeptide sequence of interest (e.g., in an adenoviral vector). Test compositions also include peptides, antibody fragments, and small molecules that interfere with aggregation of VWF. Additional compositions include compounds that interfere with expression of VWF polypeptides and polynucleotides (e.g., antisense RNA, siRNA, etc.). Other examples are small molecules which may be used to treat TTP such as glucocorticoids, antiplatelet medication (e.g., aspirin, dipyridamole,) azothiprin, cyclophosphamide, prostacyclin, or the like.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Efficacy assays, e.g., for binding of a test compound to VWF polypeptides or polynucleotides, can designed so that large chemical libraries are screened with automated assay steps, typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In some embodiments, high throughput screening methods are used which involve providing a combinatorial chemical or peptide library containing a large number of test compounds. Such "combinatorial chemical libraries" are then screened in one or more assays to identify those library members (particular chemical species or subclasses) that display a desired characteristic activity. In this instance, such compounds are screened for their ability to reduce expression or aggregation of VWF.

Methods of the invention utilize compositions comprising test agents. To administer compositions comprising test agents (including polypeptides, fragments, and analogs or variants thereof) described herein to test subjects, the test agents are formulated in a composition comprising one or more pharmaceutically acceptable carriers. The phrase "pharmaceutically or pharmacologically acceptable" refers to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds that are test agents, in certain instances, form solvates with water or common organic solvents. Such solvates are contemplated as well.

The compositions are administered, for example and without limitation, orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. In certain aspects, compositions are essentially free of pyrogens, as well as other impurities that could be harmful to the recipient.

Formulation of the pharmaceutical composition vary according to the route of administration selected (e.g., solution, emulsion). An appropriate composition comprising the composition to be administered can be prepared in a physiologically acceptable vehicle or carrier. For solutions or emulsions, suitable carriers include, for example and without limitation, aqueous or alcoholic/aqueous solutions, emulsions or suspensions, including saline and buffered media. Parenteral vehicles include, for example and without limitation, sodium chloride solution, Ringer's dextrose, dextrose and sodium chloride, lactated Ringer's or fixed oils. Intravenous vehicles include, for example and without limitation, various additives, preservatives, or fluid, nutrient or electrolyte replenishers.

Compositions, including pharmaceutical compositions, useful in the methods of the invention containing a test agent as an active ingredient contain in certain aspects pharmaceutically acceptable carriers or additives depending on the route of administration. Examples of such carriers or additives include without limitation, water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

A variety of aqueous carriers, e.g., water, buffered water, 0.4% saline, 0.3% glycine, or aqueous suspensions contain, in certain aspects, the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The compositions are, in various embodiments, lyophilized for storage and reconstituted in a suitable carrier prior to use. This technique has been shown to be effective with conventional immunoglobulins. Any suitable lyophilization and reconstitution techniques is employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of test agent in these formulations varies widely, for example from less than about 0.5%, usually at or at least about 1% to as much as 15 or 20% by weight and will be selected primarily based on fluid volumes, viscosities, etc., in accordance with the particular mode of administration selected. Thus, for example, a typical pharmaceutical composition for parenteral injection is made up to contain 1 ml sterile buffered water, and 50 mg of a test agent. A typical composition for intravenous infusion is made up to contain 250 ml of sterile Ringer's solution, and 150 mg of blood clotting factor. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of bispecific antibody is within the range of 0.01 mg to 1000 mg per kg of body weight per administration.

The pharmaceutical compositions are in certain aspects in the form of a sterile injectable aqueous, oleaginous suspension, dispersions or sterile powders for the extemporaneous preparation of sterile injectable solutions or dispersions. The suspension are formulated according to the known art using those suitable dispersing or wetting agents and suspending agents which have been mentioned above. The sterile injectable preparation include sterile injectable solutions or suspensions in a non-toxic parenterally-acceptable diluent or solvent, for example as a solution in 1,3-butane diol. The carrier is in certain aspects a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose, any bland fixed oil is employed including synthetic mono- or diglycerides. In addition, fatty acids such as oleic acid find use in the preparation of injectables.

In all cases, the form must be sterile and must be fluid to the extent that easy syringability exists if administration by injection is employed. The proper fluidity is maintained, for example, by the use of a coating, such as lecithin or other coating well known in the art, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms is brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions is brought about by the use in the compositions of agents delaying absorption, for example, aluminum monostearate and gelatin.

Compositions useful for administration are, for example and without limitation, formulated with uptake or absorption enhancers to increase their efficacy. Such enhancers, include, for example, salicylate, glycocholate/linoleate, glycholate, aprotinin, bacitracin, SDS, caprate and the like. See, e.g., Fix (J. Pharm. Sci., 85:1282-1285, 1996) and Oliyai et al. (Ann. Rev. Pharmacol. Toxicol., 32:521-544, 1993).

In addition, the properties of hydrophilicity and hydrophobicity of the compositions contemplated for use in the methods of the invention are well balanced, thereby enhancing their utility for both in vitro and especially in vivo uses, while other compositions lacking such balance are of substantially less utility. Specifically, compositions contemplated for use in the invention have an appropriate degree of solubility in aqueous media which permits absorption and bioavailability in the body, while also having a degree of solubility in lipids which permits the compounds to traverse the cell membrane to a putative site of action.

Physiologically Acceptable Compositions

The present invention provides the first valid animal model for TTP, creating the opportunity for well-controlled testing of compositions for TTP prevention and amelioration. Accordingly, physiologically (or pharmaceutically) acceptable compositions comprising, e.g., rVWF, FVIII, or compositions for the prevention or amelioration of TTP, are included in the invention.

In some embodiments, physiologically acceptable compositions can be formulated for administration by oral, intraperitoneal, transdermal, subcutaneous, intravenous or intramuscular injection, inhalation, topical, intralesional, infusion; liposome-mediated delivery; topical, rectal, intrabronchial, nasal, transmucosal, intestinal, or other common means. The physiologically acceptable compositions can be administered in a variety of unit dosage forms depending upon the method/mode of administration. Suitable unit dosage forms include, but are not limited to, powders, tablets, pills, capsules, lozenges, suppositories, patches, nasal sprays, injectibles, implantable sustained-release formulations, etc.

As such, in another aspect, the present invention provides physiologically acceptable compositions comprising an effective amount of a test composition and an acceptable carrier and/or excipients. A physiologically (or pharmaceutically) acceptable carrier includes any solvents, dispersion media, or coatings that are physiologically compatible and that preferably does not interfere with or otherwise inhibit the activity of the polypeptide or peptidomimetic. The carrier is generally suitable for intravenous, intramuscular, oral, intraperitoneal, transdermal, topical, or subcutaneous administration.

Physiologically acceptable carriers can contain one or more physiologically acceptable compound(s) that act, for example, to stabilize the composition or to increase or decrease the absorption of the test agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

In some embodiments, the pharmaceutically acceptable carrier is physiological saline. Other physiologically acceptable carriers and their formulations are well-known and generally described in, for example, Remington's Pharmaceutical Science (18th Ed., ed. Gennaro, Mack Publishing Co., Easton, Pa., 1990). Various pharmaceutically acceptable excipients are well-known in the art and can be found in, for example, Handbook of Pharmaceutical Excipients (4th ed., Ed. Rowe et al., Pharmaceutical Press, Washington, D.C.). Again, the pharmaceutical composition can be formulated as a solution, microemulsion, liposome, capsule, tablet, or other suitable form. The active component may be coated in a material to protect it from inactivation by the environment prior to reaching the target site of action.

In some embodiments, implanted devices (e.g., arterial and intravenous stents, including eluting stents, and catheters) are used to deliver physiologically acceptable compositions. For example, aqueous solutions comprising a physiologically acceptable composition administered directly through the stents and catheters. Suitable stents are described in, e.g., U.S. Pat. Nos. 6,827,735; 6,827,735; 6,827,732; 6,824,561; 6,821,549; 6,821,296; 6,821,291; 6,818,247; 6,818,016; 6,818,014; 6,818,013; 6,814,749; 6,811,566; 6,805,709; 6,805,707; 6,805,705; 6,805,704; 6,802,859; 6,802,857; 6,802,856; and 49 6,802,849. Suitable catheters are described in, e.g., U.S. Pat. Nos. 6,829, 497; 6,827,798; 6,827,730; 6,827,703; 6,824,554; 6,824, 553; 6,824,551; 6,824,532; and 6,819,951.

Elevated serum half-life can be maintained by the use of sustained-release polypeptide "packaging" systems. Such sustained release systems are well known to those of skill in the art. In one preferred embodiment, the ProLease biodegradable microsphere delivery system for proteins and polypeptides is used (Tracy, Biotechnol. Prog., 14:108 (1998); Johnson et al., Nature Med., 2:795 (1996); Herbert et al., Pharmaceut. Res., 15:357 (1998)), which involves the use of a dry powder composed of biodegradable polymeric microspheres containing the polypeptide in a polymer matrix that can be compounded as a dry formulation with or without other agents.

Oligonucleotides (e.g., protein-encoding or inhibitory) can be delivered by direct transfection or transfection and expression via an expression vector. Appropriate expression vectors include mammalian expression vectors and viral vectors, into which has been cloned an oligonucleotide with the appropriate regulatory sequences including a promoter to result in expression in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to an animal, carriers and diluents and their salts, and/or can be present in pharmaceutically acceptable formulations. Methods for the delivery of nucleic acid molecules are described, for example, in Gilmore, et al., Curr. Drug Delivery (2006) 3:147-5 and Patil, et al., AAPS Journal (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, e.g., Gonzalez et al., 1999, *Bioconjugate Chem.*, 10:1068-1074; Wang et al., International PCT publication Nos. WO03/47518 and WO03/46185), poly(lactic-co-glycolic) acid (PLGA) and PLCA microspheres (see, e.g., U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In some embodiments, oligonucleotide sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

Methods of Determining the Effect of a Test Composition on Symptoms of TTP

The present invention provides the first animal model for TTP, creating the opportunity for well-controlled testing of compositions for TTP prevention and amelioration. The following disclosure describes a few of the observations and assays that can be applied in the animal models of the invention.

TTP symptoms that can be observed in the present animal model include behavioral symptoms, such as confusion, piloerection, behavioral depression, and ataxia. Hematological and serochemical symptoms of TTP include reduced platelet count, reduced hematocrit, and increased creatinine kinase, creatinine, and lactate dehydrogenase. The terms "increase" and "decrease" are determined relative to a non-TTP control, e.g., an animal under normal conditions. Histopathological symptoms that can be observed include microthrombi or necrosis in various organs and tissues, especially the heart. Additional microscopic and macroscopic TTP symptoms are described in the Examples section.

The amount of hemolysis can be determined by measuring the level of hemoglobin in the plasma. A higher than normal level indicates RBC lysis, such as that associated with TTP. Thus, a decrease in plasma hemoglobin, relative to that observed in the mouse, or other rodent, model of the invention, indicates that a test compound effectively ameliorates TTP.

Plasma hemoglobin levels can be measured visually, e.g., after separating cellular blood components by gentle centrifugation. Traditional methods also include the Benzidine technique, as described, e.g., by Crosby and Furth (1956) *Blood* 11:380. Plasma hemoglobin can also be measured specifically in rodents (where separation of cellular components can be more challenging than in humans) using the methods described by Kruszyna et al. (1977) *Clin. Chem.* 23:2156-59. Briefly, ferricyanide is added to the plasma portion of blood and the absorbance measured at 540 nm. Cyanide is then added to the solution and A540 remeasured. A1 is then subtracted from A2 to determine the amount of free hemoglobin. Additional methods are known in the art.

Hematocrit is a measure of the proportion of blood volume occupied by red blood cells (RBCs), expressed as a percentage of total blood volume. It can be measured relatively simply, e.g., by gently centrifuging blood in a tube with volume indications. The bottom (heaviest) layer is composed of RBCs, followed by a smaller layer of white blood cells, topped by the cell-free plasma component. Automated hematocrit analyzers are commercially available, and often offer a more accurate reading. Hematocrit in mice is generally in the range of about 38-45. A lower than normal hematocrit is indicative of RBC lysis and is associated with TTP.

A platelet count can be accomplished using common laboratory techniques, such as counting on a hemacytometer. Alternatively, electronic blood analyzers can be used. There are two types of electronic counting, voltage-pulse and electro-optical counting systems. In both systems, the collected blood is diluted and counted by passing the blood through an electronic counter. The instruments are set to count only particles within the proper size range for platelets. The upper and lower levels of the size range are called size exclusion limits. Any cells or material larger or smaller than the size exclusion limits will not be counted. A normal range is generally between 150,000-450,000 per µl of blood. While high platelet counts are normally associated with thrombocytic conditions, TTP is generally characterized by low platelet counts.

Creatinine levels are generally detected to determine kidney function. A normal range is usually between about 50 and 120 µmol/liter of blood, but is generally elevated in TTP. As the kidney is a highly vascularized organ, a significant number of TTP patients experience kidney failure. Creatinine kinase (CK) is an enzyme primarily found in heart and skeletal muscle and the brain. As CK is primarily intracellular, higher than normal CK levels are indicative of tissue and cellular damage, such as that associated with TTP. Blood creatinine kinase is generally present at about 15-180 Units per liter of blood. Both creatinine and CK levels are typically measured using automated blood analysis equipment.

Lactose dehydrogenase levels are another indicator of hemolysis, and are generally extremely high in TTP patients. Elevated LDH levels and hemolysis are also associated with hyperbilirubinemia (bile in blood) and low haptoglobulin levels. LDH can be measured using an indirect enzymatic spectroscopic method as described, e.g., in J. Clin Lab. Invest. 33: 291-306 (1974). LDH catalyses the lactate to pyruvate reaction at pH8.8-9.8 with the concomitant production of NADH. NADH is then measured spectrophotometrically at 340 nm, and LDH calculated proportionally. LDH levels are normally in the range of about 100-250 U/liter of blood.

Additional symptoms that can be include fever, kidney failure, signs of jaundice (yellowish eyes or skin), and signs of anemia, such as low hemoglobin levels and dark urine. Seizures can occur, as can heart arrhythmias or heart failure.

In some embodiments the test composition results a reduction in the severity of at least one TTP symptom observed in a TTP animal model, or a delay in the onset of the symptom. In some embodiments, the severity of the TTP symptom is reduced by at least 5%, e.g., 10%, 20%, 30%, or more. In some embodiments, the test composition will eliminate the symptom, i.e., reduce the severity of symptom to statistical insignificance as compared to an appropriate control.

Generally, studies of particular test compositions include appropriate controls, to rule out background effects, e.g., of a buffer used for administration. Examples of appropriate controls are described in the Examples section. For example, a test composition study can include a condition with the test composition compared to a condition with the test composition buffer alone. These conditions can be tested on any of the animal models described herein.

Animal Models

In general, animals of the invention include any species except humans. Of particular interest are mammals, including species such as mouse, rat, rabbit, sheep, hamsters, gerbils, guinea pig, and pig, and others, as methods are developed, including bovine and non-human primates. In one aspect, the animal is a mouse. In a further aspect, the mouse is of the strain C57BL/6J.

In an even further aspect, the animals of the invention are genetically modified animals in which at least one foreign gene has been inserted into the genome or knocked out of the genome. Such transgenic animals allow regulatory processes on the cellular level to be examined and influenced in a systematic and specific manner not achievable with other test systems. Transgenic animals of the type described are useful for analyzing in vivo effects of administration of a therapeutic test agent. In one aspect, a transgenic animal of the invention includes a VWF-deficient animal. In another aspect, a transgenic animal of the invention includes an ADAMTS13-deficient animal.

Transgenic animals also serve as models for evaluating the effect of test agents on causing the development of anti-self antibodies in context of a putative tolerant host immune system. Such understanding is essential to the design and testing of agents for treatment of blood clotting disorders including, but not limited to, TTP, VWD, and the like.

The transgenes herein comprise a coding sequence (e.g., cDNA, a synthetic coding sequence, or genomic DNA) for a human blood clotting factor or other protein flanked by natural regulatory (expression control) sequences, or associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The coding sequence is, in certain aspects, modified by many means known in the art. Non-limiting examples of such modifications include methylation, "caps," substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides contain, for example and without limitation one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides are, in certain aspects derivatized by formation of a methyl or ethyl phosphotriester or an alkyl phosphoramidate linkage. Furthermore, the polynucleotides herein are, again, in certain aspects modified with a label capable of providing a detectable signal, either directly or indirectly. Exemplary labels include radioisotopes, fluorescent molecules, biotin, and the like.

The control of gene expression is accomplished by a variety of means well-known in the art. Expression of a transgene is alternatively constitutive or regulated to be inducible or repressible by known means, typically by choosing a promoter that is responsive to a given set of conditions, e.g., presence of a given compound, or a specified substance, or change in an environmental condition such as tissue type or temperature. The term "inducible expression" extends to any means for causing gene expression to take place under defined conditions, the choice of means and conditions being chosen on the basis of convenience and appropriateness for the host organism.

Transformation is carried out by a variety of known techniques, depending on the organism, on characteristics of the organism's cells and of its biology. Stable transformation involves DNA entry into cells and into the cell nucleus. For organisms that can be regenerated from single cells (which includes some mammals), transformation is, for example, carried out in in vitro culture, followed by selection for transformants and regeneration of the transformants. Methods often used for transferring DNA or RNA into cells include micro-injection, particle gun bombardment, forming DNA or RNA complexes with cationic lipids, liposomes or other carrier materials, electroporation, and incorporating transforming DNA or RNA into virus vectors. Other techniques are known in the art. DNA transfer into the cell nucleus occurs by cellular processes, and is, in certain aspects, aided by choice of an appropriate vector, by including integration site sequences which are acted upon by an intracellular transposase or recombinase (see e.g., [Craig, Ann. Rev. Genet. 1988, 22:77; Cox. In Genetic Recombination (R. Kucherlapati and G. R. Smith, eds.) 1988, American Society for Microbiology, Washington, D.C., pages 429-493; Hoess. In Nucleic Acid and Molecular Biology (F. Eckstein and D. M. J. Lilley eds.) Vol. 4, 1990, Springer-Verlag, Berlin, pages 99-109.

As set out above, in one aspect, the animal model of the invention is a mouse. The genetic background of mouse strains from which the various embryonic stem (ES) cells are derived are known in the art, including ES cells originating from mouse strain C57BL/6J or 129: R1 cells originate from a mouse blastocyst from a cross between the sub-strains 129/Sv and 129/Sv-CP (Nagy et al., Proc. Natl. Acad. Sci. USA 90:8424-8, 1993); GS1 cells originate from 129/Sv/Ev. D3-cells (Doetschman et al., Nature 330:576-8, 1987) and J1 cells originate from 129/Sv or 129/terSv. TT2 cells which also yielded ES mice originated from an F1 hybrid strain (C57BL/6×CBA) (Yagi et al., Anal. Biochem. 14:70-6, 1993). In a particular aspect, the invention includes C57BL/6J mice and knockout mice derived from C57BL/6J mice.

Expression vectors and nucleic acids used to express a protein of interest in the invention contain in various embodiments a tissue-specific promoter. Such promoters are known in the art and include, but are not limited to liver-specific promoters (e.g., albumin; Miyatake et al., J. Virol. 1:5124-32, 1997; α-fetoprotein), muscle-specific promoters (e.g., myosin light chain 1 (Shi et al., Hum. Gene Ther. 8:403-10, 1997, α-actin), pancreatic-specific promoter (e.g., insulin or glucagon promoters), neural-specific promoters (e.g., the tyrosine hydroxylase promoter or the neuron-specific enolase promoter), endothelial cell-specific promoters (e.g., von Willebrand factor; Ozaki et al., Hum. Gene Ther. 7:1483-90, 1996), and smooth muscle-cells specific promoters (e.g., 22a; Kim et al., *J. Clin. Invest.* 100:1006-14, 1997). Other tissue specific promoters include promoters are also being used in developing cancer therapies, including tyrosinase-specific promoters (Diaz et al., J. Virol. 72:789-95, 1998), an adipose tissue promoter derived from human aromatase cytochrome p450 (p450arom) (see U.S. Pat. No. 5,446,143; Mahendroo et al., *J. Biol. Chem.* 268:19463 19470, 1993; and Simpson et al., *Clin. Chem.* 39:317 324, 1993). The vectors and other nucleic acid molecules useful in the methods of the invention can also include sequences that limit the temporal expression of the transgene. For example, the transgene can be controlled by drug inducible promoters by, for example including cAMP response element enhancers in a promoter and treating the transfected or infected cell with a cAMP modulating drug (Suzuki et al., *Hum. Gene Ther.* 7:1883-93, 1996). Alternatively, repressor elements prevent transcription in the presence of the drug (Hu et al., *Cancer Res.* 57:3339-43, 1997). Spatial control of expression has also been achieved by using ionizing radiation (radiotherapy) in conjunction with the erg gene promoter (Sung et al., Cancer Res. 55:5561-5, 1995).

The recombinant nucleic acid constructs encoding the proteins of interest are, for example, inserted into any suitable plasmid, bacteriophage, or viral vector for amplification, and are propagated using methods known in the art, such as those described in Molecular Cloning A Laboratory Manual, 2nd Ed., ed. by Sambrook, Fritsch and Maniatis (Cold Spring Harbor Laboratory Press: 1989). In one embodiment, expression vectors compatible with eukaryotic cells, such as vertebrate cells, are used. Eukaryotic cell expression vectors are well known in the art and are available from commercial sources. Contemplated expression vectors contain both prokaryotic sequences (to facilitate the propagation of the vector in bacteria), and one or more eukaryotic transcription units that are functional in swine cells. Typically, such vectors provide convenient restriction sites for insertion of the desired recombinant DNA molecule. The pcDNAI, pSV2, pSVK, pMSG, pSVL, pPVV-1/PML2d and pTDT1 (ATCC No. 31255) derived vectors are examples of mammalian expression vectors suitable for transfection of non-human cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for expression of proteins in swine cells. The various methods employed in the preparation of the plasmids and transformation of host cells are well known in the art. For other suitable expression systems for useful in the present invention, as well as general recombinant procedures, see Molecular Cloning A Laboratory Manual, 2nd Ed., ed. by Sambrook, Fritsch and Maniatis (Cold Spring Harbor Laboratory Press: 1989).

Techniques for creating a transgenic animal, particularly a mouse or rat are well known (Gordon, *International Rev. Cytol.* 115:171-229, 1989). Various approaches to introducing transgenes are available, including microinjection of nucleic acids into cells, retrovirus vector methods, and gene transfer into embryonic stem (ES) cells. Genes are, in certain aspects, interrupted to produce transgenic knock-out animals.

Any method for generating knock-out animals is contemplated by the invention. In some embodiments, the VWF gene is disrupted by homologous recombination between the endogenous allele and a mutant VWF gene or appropriate sequence to delete the endogenous allele, or a portion thereof, which has been introduced into an embryonic stem cell precursor of the animal. The embryonic stem cell precursor is then allowed to develop, resulting in an animal having a functionally disrupted VWF gene. The animal may have one VWF gene allele functionally disrupted (i.e., the animal may be heterozygous for the null mutation), or in another aspect, the animal has both VWF gene alleles functionally disrupted (i.e., the animal can be homozygous for the mutation). In one embodiment of the invention, functional disruption of both VWF gene alleles produces animals in which expression of the VWF gene product in cells of the animal is substantially or completely absent relative to non-mutant animals. In another embodiment, the VWF gene alleles are disrupted such that an altered (i.e., mutant) VWF gene product is produced in cells of the animal. Such animal can be deficient in VWF or be lacking VWF altogether, In one aspect, a nonhuman animal of the invention having a functionally disrupted VWF gene is a mouse.

In a further embodiment, the invention includes the use of an animal with a disrupted ADAMTS13 gene. In one aspect, a nonhuman animal having a functionally disrupted ADAMTS13 gene is a mouse. ADAMTS13-deficient mice are used in the invention because this transgenic strain mimics the condition in patients who lack the ADAMTS13-cleavage protease for VWF. Additionally, these mice are used in the invention because mice are widely used in acute toxicity studies and are generally recognized as suitable for such toxicity studies by regulatory authorities. In a further aspect, the ADAMTS13-deficient and VWF-deficient mice of the invention are derived from the C57BL/6J strain. In an even further aspect, C57BL/6J mice are used as additional controls and are used as a model of the invention.

If fertilized oocytes are used for generating a transgenic, desired foreign DNA or transgene is incorporated into the oocytes. Incorporation of the transgene into the oocyte is carried out by several methods such as via an appropriate retroviral vector, or by microinjection. Transgenic mice are generated routinely in the art by microinjection of DNA into blastocysts isolated from pregnant mice, as described in U.S. Pat. No. 4,736,866, and as provided by B. Hogan et al. entitled "Manipulating the Mouse Embryo: A Laboratory Manual", Cold Spring Harbor Laboratory, Cold Spring Harbor, N.Y., U.S.A. (1986). See also, e.g., Haren et al, *Annu. Rev. Microbiol.* 53:245-281, 1999; Reznikoff et al., *Biochem. Biophys. Res. Commun.* 266(3):729-734, 1999; Ivics et al, *Methods Cell Bid.,* 60:99-131, 1999; Hall et al., *FEMS Microbiol. Rev.* 21:157-178 1997. U.S. Pat. No. 6,492,575 describes a method to of making transgenic mice by transforming ES cells and inject the transformed cells into a tetrapliod blastocyst. By interbreeding heterozygous siblings, homozygous animals carrying the desired gene can be obtained.

Additionally, Capecchi et al. describe a method by which transgenes can be incorporated into embryonic, fetal or adult pluripotent stem cells (Science 244:1288-1292, 1991). In this method, embryonic stem cells are isolated from blastocysts cultivated in vitro. These embryonic stem cells can be kept stable in culture over many cell generations without differentiation. The transgene is then incorporated into the embryonic stem cells by electroporation or other methods of transformation. Stem cells carrying the transgene are selected for and injected into the inner cell mass of blastocysts. The blastocysts are then implanted into pseudopregnant females. Since not all the cells of the inner cell mass of the blastocysts carry the transgenes, the animals are chimeric with respect to the transgenes. Crossbreeding of the chimeric animals allows for the production of animals which carry the transgene. An overview of the process is provided by Capecchi, Trends in Genetics 1989, 5:70-76.

Delivery of the transgene is in one aspect accomplished by a retroviral delivery system, see e.g., Eglitis et al., *Adv. Exp. Med. Biol.* 241:19, 1988. In one embodiment, a retroviral construct is one in which the structural genes of the virus are replaced by a single gene which is then transcribed under the control of regulatory elements contained in the viral long terminal repeat (LTR). A variety of single-gene-vector backbones have been used, including the Moloney murine leukemia virus (MoMuLV). Retroviral vectors which permit multiple insertions of different genes such as a gene for a selectable marker and a second gene of interest, under the control of an internal promoter can be derived from this type of backbone, see e.g., Gilboa, *Adv. Exp. Med. Biol.* 241:29, 1988.

The elements of the construction of vectors for the expression of a protein product are known to those skilled in the art. Efficient expression from retroviral vectors is observed when "strong" promoters are used to control transcription, such as the SV 40 promoter or LTR promoters, reviewed in Chang et al., *Int. J. Cell Cloning* 7:264, 1989. These promoters are constitutive and do not generally permit tissue-specific expression. Other suitable promoters are discussed herein.

The use of packaging cell lines increases the efficiency and the infectivity of the produced recombinant virions, see Miller, 1990, *Human Gene Therapy* 1:5. Murine retroviral vectors have been useful for transferring genes efficiently into murine embryonic, see e.g., Wagner et al., 1985, EMBO J. 4:663; Griedley et al., *Trends Genet.* 3:162, 1987, and hematopoietic stem cells, see e.g., Lemischka et al., *Cell* 45:917-927, 1986; Dick et al., *Trends Genet.* 2:165-170, 1986.

An additional retroviral technology which permits attainment of much higher viral titers than were previously possible involves amplification by consecutive transfer between ecotropic and amphotropic packaging cell lines, the so-called "ping-pong" method, see e.g., Kozak et al., *J. Virol.* 64:3500-3508, 1990; Bodine et al., *Prog. Clin. Biol. Res.* 319: 589-600, 1989. In addition, a techniques for increasing viral titers permit the use of virus-containing supernatants rather than direct incubation with virus-producing cell lines to attain efficient transduction, see e.g., Bodine et al., *Prog. Clin. Biol. Res.* 319:589-600, 1989. Because replication of cellular DNA is required for integration of retroviral vectors into the host genome, it may be desirable to increase the frequency at which target stem cells which are actively cycling e.g., by inducing target cells to divide by treatment in vitro with growth factors, see e.g., Lemischka et al., *Cell* 45:917-927, 1986; Bodine et al., *Proc. Natl. Acad. Sci.* 86:8897-8901, 1989, or to expose the recipient to 5-fluorouracil, see e.g., Mori et al., *Japan. J. Clin. Oncol.* 14 Suppl. 1:457-463, 1984.

In certain embodiments, the present invention provides methods of generating a transgenic animal, comprising crossing the knockout animal of the present invention (e.g. a mouse) with a second animal (e.g. a second mouse).

In some embodiments, the present invention provides methods of screening a compound (agent), comprising: a) exposing the animal to a compound; and b) determining a response of the animal to the compound. In certain embodiments, a change in response compared to a control animal not exposed to the compound, indicates the response to the compound. In other embodiments, the animals (cells, tissue or organs of the animal) are examined directly without comparison to a wild-type animal.

In some embodiments, in determining the response the animal has to the compound, the blood and urine from the animal is examined. In other embodiments, an organ or tissue from the animal is examined. Such organs and tissues include, but are not limited to, eye, eye tissue, retina, retinal tissue, kidney, kidney tissue, pancreas pancreatic tissue, prostate, prostatic tissue, bladder, bladder tissue, heart, heart tissue, brain, brain tissue, adrenals, adrenal tissue, liver, liver tissue, lungs, lung tissue, spleen, spleen tissue, or combinations thereof, are examined. Compounds that, for example, reduce or prevent blood clotting in these organs or tissues may be considered potentially beneficial in the treatment of TTP.

In some embodiments, the compound tested is a candidate anti-clotting agent or an agent that increases ADAMTS13 expression or activity. While not limited to any mechanism, it is believed that the animal models of the invention have an increased susceptibility to blood clotting. As such, the animal models of the invention allow the anti-clotting potential of candidate compounds to be readily evaluated.

As set out herein above, the terms "agent" and "compound" are used interchangeably to describe any molecule, e.g. protein or pharmaceutical, with the capability of affecting blood clotting in the animal model of the invention. In one aspect, the agent reduces blood clotting in the animal model. In another aspect, the agent reduces mortality in the animal model. In a further aspect, the agent improves a pathology in the animal model. Generally, a plurality of assay mixtures is run in parallel with different agent concentrations to obtain a differential response to the various concentrations. Typically, one of these concentrations serves as a negative control, i.e. at zero concentration or below the level of detection.

Candidate agents (compounds) encompass numerous chemical classes and are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Screening may be directed to known pharmacologically active compounds and chemical analogs thereof.

Clinical Evaluation of the Animals

Thrombotic thrombocytopenic purpura (TTP) is a clinical diagnosis with no pathognomonic laboratory test findings. In the past, a pentad of signs and symptoms (i.e., pathologies) was associated with TTP: thrombocytopenia, microangiopathic hemolytic anemia, neurologic abnormalities, renal failure, and fever. The invention includes monitoring these pathologies for agents that decrease these and other clinically, behaviorally, and histologically relevant pathologies.

Current clinical practice diagnostic criteria include thrombocytopenia, schistocytosis, and significant elevations in serum LDH levels to suggest the diagnosis of TTP. The absence of in vitro tests capable of detecting abnormalities in all the molecular interactions required for the cleavage of ULVWF multimers by ADAMTS13 in vivo is a limitation. Thus, the invention includes the pathological examination of the blood, the urine, and various organs of the body of the animal model. Necropsy is performed on animals at various time points and tissues including, but not limited to, adrenal glands, brain, heart, kidneys, liver, lungs, spleen, and eyes, are collected for histopathological examination.

Hematological investigation comprises analysis of hematocrit, hemoglobulin concentration, erythrocyte count, reticulocytes, total leukocyte count, differential leukocyte count, abnormalities of the blood morphology, platelet count, mean cell hemoglobulin, mean cell volume and mean cell hemoglobulin concentration.

Although a primary endpoint in testing the effect of various agents on the animal models is mortality, the invention includes the monitoring of activity level and physical conditions of the animals after treatment. Animals are also weighed at various time points (for example, days 0, 1, 7, 14, and the like) as animal weight provides an indication of general health. Long-term studies are also contemplated in the invention so that time points may extend for weeks, months, and the like.

The invention includes the use of laboratory tests that are often used in making the diagnosis of TTP. Such test include blood tests. Blood and/or urine is drawn under anesthesia (when appropriate) and includes, but is not limited to, the following tests: (1) Complete blood count (CBC)—Thrombocytopenia and anemia are noted. Evidence of thrombocytopenia may precede the appearance of fragmented RBCs and LDH elevation by several days. (2) Peripheral blood smear—Fragmented RBCs (i.e., schistocytes) are consistent with hemolysis. Schistocytes on a blood smear is the morphologic hallmark of the disease, but no guidelines exist as to the number of schistocytes required to differentiate TTP from other thrombotic microangiopathies. (3) Lactate dehydrogenase (LDH) level—Extremely elevated, mostly as a consequence of LDH from ischemic or necrotic tissue cells rather than due to hemolysis. (4) Indirect bilirubin level—Elevated. (5) Reticulocyte count—Elevated. (6) Prothrombin time (PT) and activated partial thromboplastin time (aPTT)—Normal. (6) DIC panel (eg, fibrinogen, D-dimer)—The results are usually normal. Increasing D-dimer levels are the most specific DIC parameter and reflect fibrinolysis of cross-linked fibrin. (7) Creatinine level—Mildly elevated (46%). (8) Urinalysis—Proteinuria and microscopic hematuria.

Statistical Methods, Calculations, Comparisons

The invention includes the use of any statistical methods, calculations, and comparisons, known to one of skill in the art. Some statistical methods, calculations, and comparisons that are discussed in the Examples infra are described herein. However, they are not in any way meant to be exclusive or limiting, as one of skill in the art may use any acceptable methods known to one of skill in the art. In one aspect, for example, the invention includes the monitoring of the minimum detectable dose (MDD) in body mass development. MDD is defined as the minimum dose which is shifted from the corresponding buffer. In the working examples of the invention, the MDD was estimated for rVWF+rFVIII as well as for rVWF by using contrasts that were tested in a step-down manner. Different doses of rVWF+rFVIII and rVWF were also compared with the corresponding buffer for mortality and body mass development. Additionally, HAEMATE® P at a dose of 2000 RCoU/kg VWF+1664 IU/kg FVIII was compared with rVWF+rFVIII at a dose of 2000 RCoU/kg rVWF+1538 IU/kg rFVIII. This comparison was made for mortality and body mass development.

All statistical calculations discussed in the Examples infra were, for example, performed with SAS version 8.2 for Linux. The level of statistical significance was set to 5%. The null hypotheses of no differences were tested against their two-sided alternatives. The short-term analysis data set (STADS) consisted of animals that received treatment at study day 0 and were killed at study day 1. The long-term analysis data set (LTADS) consisted of animals that received treatment at study day 0 and were killed on study day 14.

In certain aspects of the invention, any endpoint is considered in evaluating the effectiveness of a test agent in the animal model. In one aspect, the primary endpoint for statistical evaluation is mortality. In a further aspect, secondary endpoints for statistical evaluations was body mass development (as a percentage of body mass at day 0) and changes in hematological and serological variables. Changes in hematological and serological variables are analyzed using descriptive statistics. An additional analysis is performed to test the null hypothesis of no trend in mortality with increasing doses of rVWF+rFVIII as well as with rVWF alone against the two-sided alternative using the Cochran-Armitage trend test as an exact test [by SAS procedure PROC FREQ, statement=EXACT TREND].

In one aspect of the invention, studies are carried out with different doses of rVWF alone, or in combination with different doses of rFVIII. In such studies, the minimum detectable dose (MDD) in body mass development, defined as the minimum dose which is shifted from the corresponding buffer, is estimated in a step-down manner using contrasts. Modifications of studies are carried out based on the toxicity of various reagents used in the methods of the invention. For example, a comparison of HAEMATE® P with rVWF+rFVIII at a dose of 4000 RCoU/kg had been planned in initial experiments, but this dose proved not to be feasible with HAEMATE® P (citrate toxicity) and a dose of 2000 RCoU/kg of HAEMATE® P was included. Therefore, rVWF+rFVIII at a dose of 2000 RCoU/kg+1538 IU/kg was compared with HAEMATE® P at a dose of 2000 RCoU/kg VWF (see Examples).

In one aspect, hematological and serological variables grouped by compound and study day are summarized using means and coefficient of variations instead of medians and ranges. This is done because coefficients of variations are scale independent and allow assessment of differences in variability of doses in laboratory variables.

Analysis of Mortality

The invention includes the analysis of mortality. Any statistical methods known in the art are contemplated for use in the invention. The invention includes, but is not limited to, the following statistical methods. The proportion of animals that die during the observational period and corresponding two-sided 95% confidence intervals may be calculated per compound and dose. Two-sided 95% confidence intervals may be calculated by the Wilson score method (Altman et al., Statistics with Confidence. Brit. Med. J. Books, 2nd ed., J W Arrowsmith Ltd., Bristol, pages 46-48, 2000). These analyses may be performed for the STADS, LTADS and for the pooled STADS and LTADS separately. These analyses may also be provided for male and female animals separately and for male and female animals combined.

Differences in mortality between different doses of rVWF and rVWF+rFVIII with the corresponding buffer may be assessed for male and female animals combined by the two-sided Fisher exact test [by SAS procedure PROC MULTTEST]. This analysis may be performed for the pooled STADS and LTADS. Adjustment for multiplicity for comparison of five dose groups with the corresponding buffer simultaneously may be applied using the Holm method (Scandinavian J. Stat. 6:65-70, 1979). Unadjusted and multiplicity adjusted two-sided p-values are presented. No adjustment for multiplicity is applied for investigation of different compounds.

An additional analysis is performed to test the null hypothesis of no trend in mortality with increasing doses of rVWF+rFVIII as well as of rVWF alone against the two-sided alternative using the Cochran-Armitage trend test as an exact test [by SAS procedure PROC FREQ, statement=EXACT TREND]. This analysis may be performed for the pooled STADS and LTADS and for male and females combined.

Analysis of Body Mass Development

The change in body mass between study day 0 and study days 1, 7 and 14 (as a percentage of body mass at day 0) is another point of evaluation and, in certain aspects, is visualized using box plots grouped by compound and dose. Male and female animals are, in certain aspects, combined for these box plots. The treatment arm of HAEMATE® P administered with a dose of 4000 RCoU/kg was not included in box plots in the instant Examples as only data from 2 animals were available.

The lower edge of the box represented the 25th percentile (or 1st quartile), the upper edge of the box represented the 75th percentile (or 3rd quartile) and the line within the lower edge and the upper edge of the box indicated the median. The plus indicated the mean. The distance from the lower edge to the upper edge of the box represented the inter-quartile range (IQR). A whisker was drawn above the 75th percentile to the largest data value that was less or equal to the value that was 1.5*IQR above the 75th percentile. Any data value larger than that was marked. A whisker was drawn below the 25th percentile to the smallest data value that was less or equal to the value that was 1.5*IQR below the 25th percentile. Any data value smaller than that was marked.

Means and corresponding two-sided 95% bootstrap-t confidence intervals (Efron et al., "An Introduction to the Bootstrap." Chapman and Hall/CRC, Boca Raton, London, N.Y., Washington D.C., 1993) were presented for changes in body mass between study day 0 and study days 1, 7 and 14 (as A % of body mass at day 0) grouped by compound and dose. These analyses were performed for changes from day 0 to day 1 (STADS), for changes from day 0 to day 7 (LTADS) and for changes from day 0 to day 14 (LTADS) for male and female animals separately as well as for male and female animals combined. Bootstrap-t confidence intervals were calculated based on 10,000 bootstrap replications stratified by sex. Two-sided 95% bootstrap-t confidence intervals for means were provided for a sample size greater than 3 animals.

Box plots, means and corresponding two-sided 95% confidence intervals for means of body mass development have to be interpreted with great caution because they did not incorporate animals that died before the planned date of killing. Animals that die before the planned date receive the lowest rank (Lachin, Controlled Clinical Trials 20: 408-422, 1999) for calculation of two-sided p-values. Two-sided p-values are therefore appropriate to assess effects in body mass development between compounds than means and corresponding two-sided 95% confidence intervals of body mass development.

Differences in body mass development between different doses of rVWF and rVWF+rFVIII with the corresponding buffer are assessed, for example, for changes from day 0 to day 1 (STADS) and for changes from day 0 to day 14 (LTADS) separately.

Body mass development is compared for the contrasts specified by a two-sided permutation test [by SAS procedure PROC MULTTEST, option=PERMUTATION, statement=TEST MEAN] stratified by sex with 1,000,000 permutation replications.

Adjustment for multiplicity for comparison of five dose groups with the corresponding buffer simultaneously is, for example, applied using the Holm method (Scandinavian J. Stat. 6:65-70, 1979). In the Examples herein, unadjusted and multiplicity adjusted two-sided p-values are presented. No adjustment for multiplicity is applied for investigation of different compounds or for investigation of different study days.

Differences in body mass development between HAEMATE® P and the corresponding dose of rVWF+rFVIII are, for example, assessed for changes from day 0 to day 1 (STADS) and for changes from day 0 to day 14 (LTADS) separately. Two-sided p-values are calculated by permutation tests [by SAS procedure PROC MULTTEST, option=PERMUTATION, statement=TEST MEAN] stratified by sex with 1,000,000 permutation replications. No adjustment for multiplicity is applied for investigation of two different study days.

The minimum detectable dose (MDD), defined as the minimum dose which is shifted from the corresponding buffer, is in one aspect estimated using contrasts which are tested in a step-down manner as suggested by Tamhane at al. (Biometrics 52:21-37, 1996; procedure SD2). As this analysis is exploratory, linear and reverse helmert contrasts are considered for estimation where the contrast that resulted in the lowest MDD was reported.

The minimum detectable dose so determined is one dose level higher than the no observed adverse effect level dose (NOAEL). The minimum detectable dose is, for example, estimated for rVWF+rFVIII and for rVWF for changes in body mass from day 0 to day 1 (STADS) as well as for changes in body mass from day 0 to day 14 (LTADS) separately.

Two-sided p-values for linear contrasts are, for example, calculated using permutation tests [by SAS procedure PROC MULTTEST, option=PERMUTATION, statement=TEST MEAN] stratified by sex with 1,000,000 permutation replications. No adjustment for multiplicity is applied for investigation of different compounds or for investigation of different study days.

Hematological and serological variables at, for example, study day 1 and study day 14 are visualized using box plots grouped by compound and dose. Male and female animals are optionally combined for these figures. The treatment arm of HAEMATE® P administered with a dose of 4000 RCoU/kg was not included in box plots as only data from 2 animals are available.

Hematological and serological variables at, for example, study day 1 and study day 14 are summarized using means and coefficient of variations (CV) grouped by compound and dose. These statistics are provided for male and female animals separately as well as for male and female animals combined.

Body mass development is, for example, ranked over all compounds investigated per study day. Animals that die before the planned killing date received the lowest rank. The ranks of body mass development is used for the contrasts investigated. The missing values are not replaced for the calculation of means and corresponding confidence intervals or for generation of box plots.

The missing values are not replaced for hematological and serological variables of animals that before the planned killing date.

Examination of Various Pathologies

The invention includes the monitoring and/or measuring of various pathologies, which refer to a deviation from an assumed normal state. Such pathologies include, but are not limited to, clinical, behavioral, and histological pathologies.

If the pathology is a "clinical pathology," it reflects an abnormality in a bodily fluid, such as, but not limited to, blood and urine. The clinical pathology is observed, for example, using chemistry, microbiology, hematology or molecular pathology. For example, hematological investigation is used to detect an abnormality in hematocrit, hemoglobulin concentration, erythrocyte count, reticulocytes, total leukocyte count, differential leukocyte count, abnormalities of the blood morphology, platelet count, mean cell hemoglobulin, mean cell volume and mean cell hemoglobulin concentration. Blood chemistry investigation is used to detect an abnormality in lactate dehydrogenase (LDH) and/or creatinine kinase (CK) levels. Urine is examined for copper-colored urine, bloody urine, and other urine abnormalities.

If the pathology is a "behavioral pathology," it is observed in one aspect by monitoring changes in the animal's appearance and behavior. For example, behavioral pathologies include, but are not limited to, behavioral depression, changes in body position (such as prone or side), dyspnea, ataxia, immobility, convulsions, dyspnea, cramps, and piloerection.

If the pathology is a "histological pathology," it is observed in one aspect using gross, microscopic, or molecular examination of organs, tissues, or whole bodies (autopsy or necropsy), including measuring differences in body mass.

Histological preparation of the tissues is performed. Slides of all tissue samples are collected at necropsy from every animal in the test-compound-treated high-dose groups, the reference-compound-treated groups, the control groups as well as tissue samples of all macroscopic findings are processed, embedded in paraffin, cut at a nominal thickness of 2 to 4 micrometers, stained with hematoxylin and eosin (H&E) and examined by light microscope by the study pathologist. The same process applies to tissue samples from several organs (heart, brain, eyes, kidneys, adrenals, and lungs) of every animal in all other test-compound-treated groups.

The microscopic findings are recorded by the pathologist during histopathological examination. The slides are evaluated and histological changes are described, wherever possible, according to distribution, severity and morphologic character. Such histopathologies include, but are not limited to, microthrombi, myocardial necrosis, increased coronary perivasculitis, myocardial degeneration/reparation, glia cell foci, cortical necrosis, hemorrhage, increased incidence or mean severity of a microthrombi, a disseminated intravascular coagulopathy (DIC), thrombotic thrombocytopenic purpura (TTP), ischemic heart disease, thromboembolic changes, necrosis, reactive coronary perivasculitis, inflammation, fibrosis, hemosiderin deposition, calcification, renal infarction, and a reduction in body mass.

Each publication, patent application, patent, and other reference cited herein is incorporated by reference in its entirety to the extent that it is not inconsistent with the present disclosure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Additional aspects and details of the invention will be apparent from the following examples, which are intended to be illustrative rather than limiting. Example 1 describes the acute toxicity of human rVWF alone or in combination with human rFVIII in C57BL/6J mice. Example 2 describes the acute toxicity of human rVWF alone or in combination with human rFVIII in VWF-deficient mice. Example 3 describes the acute toxicity of human rVWF alone or in combination with human rFVIII in ADAMTS13-deficient mice. Example 4 shows that the acute toxicity of human rVWF in ADAMTS13-deficient mice can be attenuated with the co-administration of human rADAMTS13. Example 5 shows that murine ADAMTS13 does not react with rVWF. Example 6 describes the intravenous application of human rVWF alone or in combination with human rFVIII in C57Bl/6J mice. Example 7 describes the intravenous application of human rVWF alone or in combination with human rFVIII in VWF-deficient mice. Example 8 describes the intravenous application of human rVWF alone or in combination with human rFVIII in ADAMTS13-deficient mice. Example 9 describes the coadministration of human rADAMTS13 with human rVWF in ADAMTS13 deficient mice.

Example 1

Acute Toxicity of Human Recombinant Von Willebrand Factor (RVWF) Alone or in Combination with Human Recombinant Factor VIII (RFVIII) in C57BL/6J Mice The aim of the study was to determine the acute toxicity profile of recombinant VWF (rVWF) alone or in combination with recombinant factor VIII (rFVIII) (ADVATE®, Baxter) after a single intravenous injection (clinical application route) in C57BL/6J mice. The study was carried out to determine if thrombotic events, especially microvascular, could occur after the administration of the test agents. Mice of the C57BL/6J strain were chosen for this study because they are the genetic background strain to VWF-deficient and ADAMTS13-deficient mice used in parallel acute toxicity studies (see Examples 2 and 3).

Recombinant VWF, administered alone or in combination with rFVIII, was compared with a human plasma-derived VWF-FVIII preparation (HAEMATE® P), the corresponding solution buffers (vehicle control), and isotonic saline (negative control).

Recombinant VWF was tested alone at five dose levels: 4000, 2000, 1000, 500, and 250 ristocetin cofactor (RCo) U/kg body weight (BW), and in combination with rFVIII also at five doses. In the combined administration, the doses of rVWF were the same as in the single administration and those of rFVIII were 3077, 1538, 769, 385, and 192 IU/kg rFVIII in descending order, i.e., 4000 RCoU/kg BW rVWF was co-administered with 3077 IU/kg rFVIII, 2000 RCoU/kg BW rVWF was co-administered with 1538 IU/kg rFVIII, and the like. HAEMATE® P was tested at 2000 RCoU/kg BW (+1347 IU/kg BW FVIII). The corresponding buffers for rVWF alone, the mixed buffer, and isotonic saline were administered according to the highest dose volume given (i.e., 31.7 mL/kg, 49.3 mL/kg, and 49.3 mL/kg, respectively).

Each animal received a single intravenous injection via a tail vein, aiming for a flow rate of 2 mL/min. The group allocation and treatment regimen were carried out as set out in Table 1 below:

TABLE 1

Group Allocation and Treatment Regimens

| Group | | | |
|---|---|---|---|
| short term (1 day) | long term (14 days) | Compound | Dose/Volume |
| A | K | rVWF buffer + ADVATE ® | 31.7 mL/kg + 17.6 mL kg; 49.3 mL/kg |
| B | L | rVWF + rFVIII | 4000 RCoU/kg + 3077 IU/kg |
| C | M | rVWF + rFVIII | 1000 RCoU/kg + 769 IU/kg |
| D | N | rVWF | 1000 RCoU/kg |
| E | O | rVWF + rFVIII | 2000 RCoU/kg + 1538 IU/kg |
| F | P | rVWF buffer | 31.7 mL/kg |
| G | Q | HAEMATE ® P | 2000 RCoU/kg |
| H | R | Saline | 49.3 mL/kg |
| I | S | rVWF | 2000 RCoU/kg |
| J | T | rVWF | 4000 RCoU/kg |
| U | Y | rVWF + rFVIII | 500 RCoU/kg + 385 IU/kg |
| V | Z | rVWF | 500 RCoU/kg |
| W | AA | rVWF + rFVIII | 250 RCoU/kg + 192 IU/kg |
| X | BB | rVWF | 250 RCoU/kg |

The study was divided into a short-term part and a long-term part to evaluate possible immediate and delayed effects. Each part consisted of 14 groups, each comprising 10 animals (5 male and 5 female). The short-term part was terminated one day after treatment and the long-term part was terminated after 14 days of observation. Blood samples were withdrawn from the mice under anesthesia (Ketamine and Xylazine) by cardiac puncture at day one (study part 1) or day 14 (study part 2). All surviving animals were weighed at the end of each study part and blood samples were withdrawn for analysis of hematocrit, platelet count, lactate dehydrogenase (LDH) level, and creatinine kinase (CK) level. A necropsy was performed, and selected organs (adrenal glands, brain, heart, kidneys, liver, lungs, spleen, and eyes) were preserved and evaluated histopathologically.

The primary end-point was mortality. Activity level and physical conditions were closely monitored for the first six hours after injection and checked daily thereafter up to 14 days for signs indicative of toxicity. All animals were weighed on day 0 and day 1 (short-term part) and day 1, day 7 (8) and day 14 (long-term part) to provide an indication of general health.

Secondary endpoints for statistical evaluations were body mass development (as a percentage of body mass at day 0) and changes in hematological and serological variables. Changes in hematological and serological variables were analyzed using descriptive statistics. The variables analyzed were hematocrit, platelet count, LDH and CK.

Under the conditions of this study, the intravenous administration of rVWF alone at doses of 4000, 2000, 1000, 500, and 250 RCoU/kg BW alone, or in combination with rFVIII at doses of 3077, 1538, 769, 385, and 192 IU/kg BW was not associated with any spontaneous deaths. There were no clear dose-related changes in body mass. The comparison with HAEMATE® P revealed no statistically significant differences.

Clinical symptoms indicative of toxicity in the mice were observed in the high-dose groups, those treated with rVWF at 4000 or 2000 RCoU/kg BW with or without rFVIII. Thrombocytopenia was evident with rVWF at doses of 2000 RCoU/kg BW or greater, alone or combined with rFVIII at day 1 with recovery after 14 days. Other variables showed no biologically relevant changes. Comparing the data of the selected hematological and serum chemistry variables, a drop in platelet-count was observed at day 1 after administration of rVWF at doses of 2000 RCoU/kg and greater administered alone or in combination with rFVIII. An increase in lactate dehydrogenase concentration in the blood was seen in groups treated with rVWF at 2000 RCoU/kg BW or greater doses combined with rFVIII after 1 day. All variables returned to normal levels after 14 days.

The histopathological changes revealed the picture of a low grade "ischemic heart disease" after administration of rVWF at a dose of 500 RCoU/kg BW or greater alone or in combination with rFVIII. These changes consisted of coronary microthrombi, myocardial necrosis, myocardial degeneration/reparation (all of minimal to moderate severity), and slightly increased coronary perivasculitis. Most of these changes showed a slight dose-dependent increase in incidence (and partly also severity), especially in animals treated with a combination of rVWF and rFVIII. They indicated that rVWF has thrombogenic potential in C57BL/6J mice at doses of 500 RCoU/kg and higher, either administered alone or combined with rFVIII.

In animals, which underwent scheduled necropsy on day 1, thromboembolic changes were recorded in the heart, which is highly sensitive to hypoxia. The vascular occlusion by coronary microthrombi led to reduced blood flow to the heart, which causes ischemic myocardial necrosis (cell starvation second to a lack of oxygen) and reactive coronary perivasculitis (early effects).

In animals, which underwent scheduled necropsy on day 14, predominately degenerative and/or reparative changes were recorded in the heart (inflammation, fibrosis, calcification, hemosiderin deposition). These cardiac infarct-like changes were deemed to be the consequences of a previous vascular occlusion by microthrombi (delayed effects).

No toxic effect could be demonstrated for HAEMATE® P treatment (used here as a positive control). This lack of toxic effect with HAEMATE® P is most likely due to a different composition of VWF multimers with the absence of ultra-large molecular weight forms and is because the VWF subunit present in HAEMATE® P is cleaved by ADAMTS13. In addition, HAEMATE® P contains a variety of contaminating plasma proteins, as well as citrate in the final composition, which also might influence results.

Because human rVWF is resistant to murine ADAMTS13, mice are not able to sufficiently cleave the human rVWF subunit and decrease the ultra-large molecular weight multimers of rVWF by murine ADAMTS13. In addition, it was found by Western blot analysis that C57BL/6J normal mice have VWF with ultra-large molecular weight multimers in the circulation because ADAMTS13 activity is reduced in these mice. Therefore, the administration of human rVWF results in supraphysiological circulating levels of VWF and in particular in a substantial increase in the presence of ultra-large VWF multimers. Consequently, the observed symptoms of microthrombosis may be interpreted as an exaggerated pharmacological effect.

The "no observable adverse effect level dose (NOAEL)" for rVWF in the C57BL/6J mouse was 250 RCoU/kg BW. Thus, C57BL/6J mice can be used as a model of TTP if they are administered doses of rVWF at concentrations greater than 250 RCoU/kg BW.

Regarding strain-specific differences of the toxicological profile of rVWF, normal C57BL/6J mice are clearly less susceptible than ADAMTS13-deficient mice to rVWF, but slightly more susceptible to rVWF than VWF-deficient mice (see Examples 2 and 3).

Example 2

Acute Toxicity of Human Recombinant Von Willebrand Factor (RVWF) Alone or in Combination with Human Recombinant Factor VIII (RFVIII) in VWF-Deficient Mice The aim of the study was to determine the acute toxicity of rVWF alone or in combination with rFVIII (ADVATE®, Baxter) after a single intravenous injection (clinical application route) in VWF-deficient mice. VWF-deficient mice (Baxter) were chosen for the study because this transgenic strain mimics conditions in patients who lack VWF.

One lot of rVWF, administered alone or in combination with rFVIII (ADVATE®), was compared with a plasma-derived VWF-FVIII preparation (HAEMATE® P), the corresponding solution buffers (vehicle control), and isotonic saline (negative control). Recombinant VWF was tested alone at five dose levels: 4000, 2000, 1000, 500, and 250 ristocetin cofactor (RCo) U/kg body weight (BW), or in combination with rFVIII also at five doses. In the combined administration, the doses of rVWF were the same as in the single administration and those of rFVIII were 3077, 1538, 769, 385 and 192 IU/kg rFVIII in descending order, i.e., 4000 RCoU/kg BW rVWF was co-administered with 3077 111/kg rFVIII, 2000 RCoU/kg IBW rVWF was co-administered with 1538 IU/kg rFVIII, and the like. HAEMATE® P was tested at 2000 RCoU/kg BW (+1347 IU/kg BW FVIII). The corresponding buffers for rVWF alone, the mixed buffer, and isotonic saline were administered according to the highest dose volume given.

Each animal received a single intravenous injection via a tail vein, aiming for a flow rate of 2 mL/min. For the group allocation and treatment regimens, see Table 2 below:

TABLE 2

Group Allocation and Treatment Regimens

| Group short term (1 day) | Group long term (14 days) | Compound | Dose/Volume |
| --- | --- | --- | --- |
| A | K | rVWF + rFVI11 | 1000 RCoU/kg + 769 IU/kg |
| B | L | rVWF | 1000 RCoU/kg |
| C | M | rVWF + rFVIII | 4000 RCoU/kg + 3077 IU/kg |
| D | N | rVWF buffer + ADVATE ® buffer | 31.7 mL/kg + 17.6 mL/kg; 49.3 mL/kg |
| E | O | HAEMATE ® P | 2000 RCoU/kg |
| F | P | rVWF + rFVIII | 2000 RCoU/kg + 1538 IU/kg |
| G | O | rVWF buffer | 31.7 mL/kg |
| H | R | rVWF | 4000 RCoU/kg |
| I | S | Saline | 49.3 mL/kg |
| J | T | rVWF | 2000 RCoU/kg |
| U | Y | rVWF + rFVIII | 500 RCoU/kg + 385 IU/kg |
| V | Z | rVWF | 500 RCoU/kg |
| W | AA | rVWF + rFVIII | 250 RCoU/kg + 192 IU/kg |
| X | BB | rVWF | 250 RCoU/kg |

The study was divided into a short-term part and a long-term part to evaluate possible immediate and delayed effects. Each part consisted of 14 groups, each comprising 10 animals (5 male and 5 female). The short-term part was terminated one day after treatment and the long-term part was terminated after 14 days of observation. All surviving animals were weighed at the end of each study part and blood samples were withdrawn for analysis of hematocrit, platelet count, lactate dehydrogenase (LDH) level and creatinine kinase (CK) level. A necropsy was performed, and selected organs (adrenal glands, brain, heart, kidneys, liver, lungs, spleen, and eyes) were preserved and evaluated histopathologically.

Under the conditions set out above, the intravenous administration of rVWF alone at doses of 4000, 2000. 1000, 500. and 250 RCoU/kg BW alone, or in combination with rFVIII at doses of 3077 1538, 769, 385 and 192 IU/kg BW was not associated with any spontaneous deaths.

Body mass development was not affected by treatment with either rVWF alone or rVWF+rFVIII at a dose of 500 or 4000 RCoU/kg BW, respectively. There was no statistically significant difference between mean body mass development (day 0 to 1 and day 0 to 14) of animals treated with HAEMATE® P and those treated with the corresponding dose of rVWF+rFVIII.

Clinical symptoms were observed in animals of the high-dose groups, those treated with rVWF at 4000 RCoU/kg BW with or without rFVIII. Thrombocytopenia was evident at doses of rVWF of 2000 RCoU/kg BW or greater, with or without rFVIII at day 1 with recovery after 14 days. Other variables showed no biologically relevant changes.

The histopathological changes revealed the picture of a low grade "ischemic heart disease" after administration of rVWF at doses of 1000 RCoU/kg BW or greater alone or in combination with rFVIII. No toxic effect could be demonstrated for HAEMATE® P. As discussed herein in Example 1, mice are not able to sufficiently cleave the rVWF subunit and decrease the ultra-large molecular weight multimers of rVWF by murine ADAMTS13, because human rVWF is resistant to murine ADAMTS13. Therefore, the observed symptoms of microthrombosis may be interpreted as an exaggerated pharmacological effect.

The NOAEL for rVWF in the VWF-deficient mouse was 500 RCoU/kg BW. Thus, VWF-deficient mice can be used as a model of TTP for people deficient in VWF if the mice are administered doses of rVWF at concentrations greater than 500 RCoU/kg BW.

In addition, this study shows that the presence of endogenous murine VWF (as evident in the mice in Example 1) had an influence on toxicity, because the control mice (C57BL/6J) were more sensitive to rVWF with a NOAEL of 250 RCoU/kg BW.

Example 3

Acute Toxicity of Human Recombinant Von Willebrand Factor (RVWF) Alone or in Combination with Human Recombinant Factor VIII (RFVIII) in ADAMTS13-Deficient Mice The aim of the study was to determine the acute toxicity of rVWF alone or in combination with rFVIII (ADVATE®, Baxter) after a single intravenous injection (clinical application route) in ADAMTS13-deficient mice (Baxter). ADAMTS13 is a protease that cleaves VWF to reduce high-molecular-weight multimers. Thus, ADAMTS13 knock-out mice are not able to cleave the rVWF subunit at Tyr1605-MET1606 because of their lack of ADAMTS13. Consequently, these mice cannot break down the ultra-large VWF multimers, resulting in microvascular thrombosis in multiple organs. Thus, they should be susceptible to harmful effects of rVWF at a much lower dose than their counterpart controls. ADAMTS13-deficient mice were chosen for the study because this transgenic strain mimics the condition in patients who lack the ADAMTS13-cleavage protease for VWF.

Recombinant VWF, administered either alone or in combination with ADVATE®, was compared with a plasma-derived VWF-FVIII preparation (HAEMATE® P), corresponding solution buffers (vehicle control), and isotonic saline (negative control). Recombinant VWF was tested alone at five dose levels: 4000, 2000, 1000, 500, and 250 ristocetin cofactor (RCo) U/kg body weight (BW), or in combination with rFVIII also at five doses. In the combined administration, the doses of rVWF were the same as in the single administration and those of rFVIII were 3077, 1538, 769, 385, and 192 IU/kg rFVIII in descending order, i.e., 4000 RCoU/kg BW rVWF was co-administered with 3077 IU/kg rFVIII, 2000 RCoU/kg BW rVWF was co-administered with 1538 IU/kg rFVIII, and the like. HAEMATE® P was tested at 4000 RCoU/kg BW VWF (+3322 IU/kg BW FVIII) and 2000 RCoU/kg BW VWF (+1664 IU/kg BW FVIII) (Table 3). The corresponding buffers for rVWF alone, the mixed buffer, and isotonic saline were administered according to the highest dose volume given. For example, the corresponding buffer for rVWF alone was administered at a volume of 31.7 mL/kg (according to the highest dose volume of rVWF), the mixed buffer (according to highest volume of the combined administration of rVWF+rFVIII) at 49.3 mL/kg and isotonic saline at 51.1 mL/kg (according to highest volume of HAEMATE® P).

Each animal received a single intravenous injection via a tail vein, aiming for a flow rate of 2 mL/min. For the group allocation and treatment regimens, see Table 3 below:

TABLE 3

Group Allocation and Treatment Regimens

| Group short term (1 day) | Group long term (14 days) | Compound | Dose/Volume |
| --- | --- | --- | --- |
| A | K | rVWF + rFVIII | 4000 RCoU/kg + 3077 IU/kg |
| B | L | rVWF | 2000 RCoU/kg |
| C | M | rVWF buffer + ADVATE® buffer | 31.7 mL/kg + 17.6 mL/kg; 49.3 mL/kg |
| D | N | rVWF + rFVIII | 1000 RCoU/kg + 769 RCoU/kg |
| E | O | rVWF | 4000 RCoU/kg |
| F | P | Saline | 51.1 mL/kg |
| G | Q | rVWF | 1000 RCoU/kg |
| H | R | rVWF buffer | 31.7 mL/kg |
| I | S | rVWF + rFVIII | 2000 RCoU/kg + 1538 IU/kg |
| J | U | HAEMATE® P | 2000 RCoU/kg |
| V | Z | rVWF + rFVIII | 500 RCoU/kg + 385 IU/kg |
| W | AA | rVWF | 500 RCoU/kg |
| X | BB | rVWF + rFVIII | 250 RCoU/kg + 192 IU/kg |
| Y | CC | rVWF | 250 RCoU/kg |
|   | T | HAEMATE® P | 4000 RCoU/kg |

The study was divided into a short-term and a long-term part to evaluate possible immediate and delayed effects. Each part consisted of groups of 10 animals (5 male and 5 female). The short-term part was terminated one day after treatment and the long-term part was terminated after 14 days of observation. All surviving animals were weighed at the end of each study part and blood samples were withdrawn for analysis of hematocrit, platelet count, and lactate dehydrogenase (LDH) level. A necropsy was performed, and selected organs (adrenal glands, brain, heart, kidneys, liver, lungs, spleen and eyes) were preserved and evaluated histopathologically.

Slides of all tissue samples collected at necropsy from every animal in the test-compound treated high-dose groups, the reference-compound-treated groups, the control groups as well as tissue samples of all macroscopic findings were processed, embedded in paraffin, cut at a nominal thickness of 2-4 micrometers, stained with hematoxylin and eosin (H&E) and examined by light microscope by the study pathologist. The same applied to tissue samples from several organs (heart, brain, eyes, kidneys, adrenals and lungs) of every animal in all other test-compound treated groups.

The highest mortality in this study was observed in the group treated with HAEMATE® P at the 4000 RCoU/kg dose level; 80% (8 of 10) died immediately after administration showing unequivocal signs of sodium citrate overload (281 mg/kg citrate were injected with the administered volume of 51.1 mL/kg). As the $LD_{50}$ of sodium citrate after intravenous application in mice is 231 mg/kg (Sax's Dangerous Properties of Industrial Materials, $8^{th}$ edition, 1992), the dose of HAEMATE® P was shifted to 2000 RCoU/kg VWF. No further mortality was observed at this dose level with HAEMATE® P.

40% (8 of 20) of the animals that received 4000 RCoU/kg of rVWF alone died, whereas the mortality decreased to 20% (4 of 20) in those that received 2000 RCoU/kg. There was no further mortality in the lower dose groups. 25% (5 of 20) of the animals that received 4000 RCoU/kg rVWF combined with 3077 IU/kg rFVIII died. There was no further mortality in the lower dose groups, even in the group that received 2000 RCoU/kg combined with rFVIII. As there were 141 mg/kg sodium citrate in the injected volume of the 4000 RCoU/kg dose groups, this may also be a reason for some sudden deaths in these groups. This cause of death can be excluded for the delayed cases in the high-dose groups as well as for the sudden deaths in the 2000 RCoU/kg dose groups.

The statistically ad hoc performed test for a trend demonstrated that the probability of death increased as the dose of rVWF increases (two-sided p-value<0.0001).

There was no mortality (0 of 20) with HAEMATE® P administered at a dose of 2000 RCoU/kg VWF+1664 IU/kg FVIII, and there was no mortality (0 of 20) with 2000 RCoU/kg rVWF+1538 IU/kg rFVIII.

The clinical observations revealed a broad spectrum of abnormalities. Short-term symptoms were obviously also caused by the injected sodium citrate amount, because symptoms typical for sodium citrate toxicity (e.g. short-term behavioral depression, convulsions, dyspnea) were recorded in 20% (4 of 20) of the animals of the buffer group.

However, there was a clear correlation between the incidence and severity of symptoms of the dose administered. 85% (17 of 20) of the animals were affected after receiving 4000 RCoU/kg rVWF, whereas 45% (9 of 20) of the animals were affected after receiving of 2000 RCoU/kg rVWF.

Clinical abnormalities were observed in 75% (15 of 20) of the animals that received 4000 RCoU/kg combined with 3077 IU/kg rFVIII, whereas 35% (7 of 20) were affected after receiving 2000 RCoU/kg rVWF combined with 1538 IU/kg rFVIII. No clinical abnormalities were recorded in any of the other groups treated with rVWF alone or combined with rFVIII.

The symptoms observed in the group treated with HAEMATE® P at the 4000 RCoU/kg dose level (90%, 9 of 10 animals) were clearly caused by the citrate overload (281 mg/kg) and led to immediate death. All affected animals (40%, 8 of 20 animals) in the groups treated with 2000 RCoU/kg HAEMATE® P also showed only short-term abnormalities, indicative of sodium citrate toxicity (140.5 mg/kg; e.g. short-term behavioral depression, convulsions, dyspnea). No further long-term symptoms were recorded.

The minimum detectable dose (MDD) for changes in body mass from day 0 to day 1 was estimated to be 1000 RCoU/kg rVWF+769 IU/kg rFVIII. The dose of 500 RCoU/kg rVWF+385 IU/kg rFVIII could therefore be regarded as the NOAEL dose in terms of body mass development from day 0 to day 1. There was no minimum detectable dose for changes in body mass from day 0 to day 14, and the highest dose of rVWF+rFVIII investigated (4000 RCoU/kg+3077 IU/kg) could therefore be regarded as the NOAEL dose in terms of body mass development from day 0 to day 14.

The minimum detectable dose (MDD) for changes in body mass from day 0 to day 1 for rVWF administered alone was estimated to be 2000 RCoU/kg. The dose of 1000 RCoU/kg could therefore be regarded as the no observed adverse effect level (NOAEL) dose in terms of body mass development from day 0 to day 1. The minimum detectable dose for changes in body mass from day 0 to day 14 was estimated to be the lowest dose of rVWF investigated (250 RCoU/kg). No dose among the doses of rVWF investigated could therefore be regarded as the NOAEL dose in terms of body mass development from day 0 to day 14. This estimated difference can be considered unpredictable because the increase in body mass (2.3% vs. 4.8% for the buffer group) is higher than that of saline (1.8%) and HAEMATE® P (1.5%) and similar to that of the group treated with 250 RCoU/kg rVWF+rFVIII (2.7%). Mean body mass development from day 0 to day 1 was 0.6% with HAEMATE® P administered at a dose of 2000 RCoU/kg+1664 IU/kg FVIII and −7.4% with the corresponding dose of rVWF+rFVIII administered. This difference was statistically significant at the 5% level (two-sided p-value<0.0001). No statistically significant differences were found from day 0 to day 14.

Comparing the data of the selected hematological and serum chemistry variables in surviving animals, a drop in platelet-count was observed at day 1 after administration of 1000 RCoU/kg rVWF and higher doses, administered alone or combined with rFVIII. Additionally, hematocrit dropped after administration of 2000 RCoU/kg rVWF and higher doses administered alone or combined with rFVIII.

Compared with control groups, lactate dehydrogenase was increased on day 1 after treatment with 2000 RCoU/kg rVWF and higher doses administered alone or combined with rFVIII.

Only a drop in platelet count could be measured 1 day after application of 2000 RCoU/kg VWF in HAEMATE® P (+1664 IU/kg FVIII). The measured variables returned to normal in all affected groups after the 14 days of observation.

The histopathological examination revealed many affected organs: Heart (coronary microthrombi, myocardial necrosis, increased coronary perivasculitis, myocardial degeneration/reparation), brain (microthrombi, glia cell foci), eyes (microthrombi), kidneys (microthrombi, cortical necrosis), adrenals (microthrombi, hemorrhage), and lungs (increased incidence or mean severity of microthrombi). These pathohistological changes may be summarized as a disseminated intravascular coagulopathy (DIC). At high doses 2000 RCoU rVWF), the animals resemble the picture of a thrombotic thrombocytopenic purpura (TTP) in humans to some extent. At lower doses (500-1000 RCoU), the heart was mainly affected with pathohistological changes resembling the picture of a low grade "ischemic heart disease". In contrast to test-compound-treated animals receiving recombinant product(s), such findings were not recorded in reference-compound-treated animals receiving the human plasma-derived VWF-FVIII preparation (HAEMATE® P). Here, only low grade pulmonary microthrombi were recorded at incidences similar to those in control animals.

Thromboembolic changes were recorded for one or several organs in test-compound-treated animals which were killed on the scheduled day 1 (or which died spontaneously shortly after administration). The heart, which is highly sensitive to hypoxia, was the most severely affected organ. The vascular occlusion by coronary microthrombi led to reduced blood flow to the heart which causes ischemic myocardial necrosis (cell starvation secondary to a lack of oxygen) and reactive coronary perivasculitis (early effects).

Predominately degenerative and/or reparative changes were recorded in the hearts (inflammation, fibrosis, hemosiderin deposition, calcification) of test-compound-treated animals which were killed on the scheduled day 14 (or which died spontaneously with some delay after administration). These cardiac infarct-like changes were deemed to be the consequences of a previous vascular occlusion by microthrombi (delayed effects). The renal cortical necrosis recorded in one animal of the group treated with 2000 RCoU/kg rVWF alone, which died spontaneously, can be interpreted in the same way. Here, the vascular occlusion of kidney vessels by microthrombi led to a renal infarction.

Low incidences of microthrombi (minimal to slight grade) without accompanying organ destruction were recorded for several organs (lungs, kidneys, brain) of saline-, buffer- and also HAEMATE® P-treated control animals.

The pathological changes recorded consisted of an adverse microthrombosis in one or several organs. They indicated an thrombogenic potential of the test compound, rVWF, in this animal model with a lack of VWF cleavage protease (ADAMTS13-deficient mouse) at doses of 500 RCoU/kg rVWF and higher, either administered alone or combined with rFVIII. As no adverse histopathological changes were recorded in the low-dose groups (rVWF alone and combined with rVWF) a NOAEL could be established at 250 RCoU/kg.

Because of their inability to cleave rVWF, ADAMTS13-knock out mice were very sensitive to treatment with rVWF. In fact, ADAMTS13 knock-out mice represent the most sensitive murine strain tested in this study. The results may be interpreted as an exaggerated pharmacological effect of rVWF at high doses caused by both the absence of endogenous murine ADAMTS13 and also by the presence of endogenous murine VWF having ultra-large VWF multimers. The NOAEL for rVWF in the ADAMTS13 knock-out mouse was 250 RCoU/kg BW. Thus, ADAMTS13-deficient mice can be used as a model of TTP for people deficient in ADAMTS13 if the mice are administered doses of rVWF at concentrations greater than 250 RCoU/kg BW.

The absence of ADAMTS13 (ADAMTS13 knock-outs) in the presence of endogenous murine VWF has the most severe effect on mortality and toxicity, resulting in microvascular thrombosis in multiple organs.

Example 4

The Acute Toxicity of Human Recombinant Von Willebrand Factor (RVWF) in ADAMTS13-Deficient Mice can be Attenuated with the Co-Administration of ADAMTS13

The objective of this study was to evaluate whether or not acute toxicity of rVWF can be attenuated by the co-administration (i.e. replacement) of recombinant ADAMTS13 in ADAMTS13-deficient mice (Baxter).

As set out in Example 3, there were no substantial effects in ADAMTS13-deficient mice treated with HAEMATE® P, which was used as a positive control, compared to mice treated with human rVWF. This difference was due to a different composition of VWF multimers in the different compounds, with the absence of ultra-large molecular weight forms in HAEMATE® P, because the VWF subunit present in HAEMATE® P is cleaved by ADAMTS13. In addition, HAEMATE® P contains a variety of contaminating plasma proteins as well as citrate and ADAMTS13, which also might influence the results.

In the present study, human rVWF (BAXTER) was administered at a dosage of 2000 RCoU/kg+human rADAMTS13 (from CHO cells, clone 938, BAXTER) at a dosage of 19.4 µg/kg (according to a ratio analyzed in the human plasma-derived preparation, HAEMATE® P). The compounds were injected either premixed in the syringe immediately before application (group A, 10 mice) or injected consecutively as a first injection of rADAMTS13, followed immediately by the rVWF injection (group B, 10 mice).

Animals were observed for signs indicative of toxicity after injection until termination at day 1. As in previous studies set out herein above, blood samples were drawn under anesthesia, tissues were prepared for histological analysis, and necropsies were performed.

No deaths and no signs of clinical toxicity were observed in any of the animals, independent of the treatment regimen, clearly demonstrating a role of ADAMTS13 in reducing the toxicity of rVWF.

Comparing the analytical data, a drop in platelet count was measured 1 day after the consecutive administration of rADAMTS13 and rVWF, in contrast to the administration of the premixed compounds. There were no necropsy findings which gave an indication of a possible test-compound-related association. Histopathological changes were recorded for the heart consisting of coronary microthrombi (minimal to slight grade), myocardial necrosis (minimal to moderate grade), and slightly increased coronary perivasculitis in test-compound-treated animals groups A and B.

Furthermore, a slight grade fibrosis was recorded in a single test-compound-treated animal of group B. This finding, which was clearly characterized by signs of chronicity, was deemed to be pre-existing and therefore not related to the test compound as it was recorded in an animal killed 1 day after administration.

Comparing the two groups (A vs. B), and considering the drop in platelet count after the consecutive administration of rADAMTS13 and rVWF, no pronounced difference in the severity or incidence of the histopathological changes were recorded. However, in contrast to the study set out in Example 3 (without rADAMTS13 co-administration), no mortality and no test compound-related macroscopic findings were recorded at necropsy in this study. The incidence and severity of the myocardial necrosis was similar in both studies (Examples 3 and 4). However, the coronary microthrombosis and the coronary perivasculitis was less pronounced with rADAMTS13 co-administration. Furthermore, with rADAMTS13 co-administration, treatment-related effects were only recorded for the heart, whereas in the study without ADAMTS13 co-administration (Example 3), microthrombi were also recorded for the brain, kidneys, and lungs.

The reduction of procoagulative activity of rVWF after co-administration with the cleaving enzyme ADAMTS13 reflects the importance of ADAMTS13 for the pharmacological effects of rVWF in this animal model and also partially explains the lack of observed toxicity of HAEMATE® P in Example 3.

Example 5

Murine ADAMTS13 does not React with RVWF

ADAMTS13 is a protease that cleaves VWF to reduce high molecular weight multimers. Murine ADAMTS13 does not react with human recombinant VWF as demonstrated in in vitro tests as well as ex vivo.

Mice have a decreased ADAMTS13 activity, therefore murine plasma contains ultra-large VWF multimers. Administration of rVWF will result in supraphysiological levels and an exaggerated pharmacological effect.

Human rVWF is resistant to the proteolytic activity of murine ADAMTS13. The data demonstrated this in vitro by exposing human rVWF to plasmas of various species, including mice, and either measuring residual VWF activity or visualizing the multimeric composition. The data also demonstrated the resistance of human VWF to murine ADAMTS13 ex vivo after infusion of rVWF into mice. Plasma samples obtained at various time points after infusions did not show any VWF fragments derived from the action of ADAMTS13 cleavage at $Tyr^{1605}$-$Met^{1606}$ (the C-terminal 176 kD and the N-terminal 140 kD), consistent with the resistance of rVWF to murine ADAMTS13 in vivo. In contrast, administration of rVWF into a rabbit resulted in the expected cleavage pattern of the VWF subunit with the appearance of the fragments on immunoblots that used monoclonal antibodies. See FIG. 1.

rVWF consists of intact VWF subunits because rVWF has never been exposed to ADAMTS13 specific proteolysis. Plasma-derived VWF consists of subunits which are cleaved at Tyr1605-Met1606 in the A2 domain of VWF. rVWF is not processed to lower molecular weight VWF multimers in mice, resulting in an exaggerated pharmacological effect and potentially thrombogenic multimers.

Experimental Overview of Examples 6-9

An animal model for TTP was established by exposing mice to various conditions and observing TTP symptoms and toxicity. Data sets were gathered from wild type (C57BL/6J) mice, VWF-deficient mice, and ADAMTS13 knock-out mice. The mice were treated with a single injection of: rVWF alone (at one of 5 dosages), rVWF in combination with rFVIII (Advate) (each at one of 5 dosages), HAEMATE® P (a commercial preparation of VWF and FVIII isolated from human serum), or the corresponding buffers. Mice were observed at 1 day and 14 days post-injection, after which, necropsy analyses were performed.

More specifically, the conditions studied were as follows. rVWF was tested alone at five dose levels: 4000, 2000, 1000, 500, and 250 ristocetin cofactor (RCo) U/kg body weight (BW), and combined with rFVIII also at five doses. In the combined administration the doses of rVWF were the same as in the single administration and those of rFVIII were 3077, 1538, 769, 385 and 192 IU/kg rFVIII in descending order, i.e., 4000 RCoU/kg BW rVWF was co-administered with 3077 IU/kg rFVIII, 2000 RCoU/kg BW rVWF was co-administered with 1538 IU/kg rFVIII etc. HAEMATE® P was tested at 2000 RCoU/kg BW (+1347 IU/kg BW FVIII). The corresponding buffers for rVWF alone, the mixed buffer, and isotonic saline were administered according to the highest dose volume given.

The study was divided into a short-term and a long-term part to evaluate possible immediate and delayed effects. Each part consisted of 14 groups each comprising 10 animals (5 male and 5 female). The short-term part was terminated one day after application and the long-term part was terminated after 14 days of observation. All surviving animals were weighed at the end of each study part and blood samples were withdrawn for analysis of hematocrit, platelet count, lactate dehydrogenase (LDH), and creatinine kinase (CK). A necropsy was performed, and selected organs (adrenal glands, brain, heart, kidneys, liver, lungs, spleen and eyes) were preserved and evaluated histopathologically.

1. Materials

The following materials were used for the experiments.

Freeze-dried human recombinant von Willebrand factor (rVWF) (630.85 IU VWF:RCo/vial (actual value)) was reconstituted in 5 ml water for injection (WFI). Upon reconstitution, rVWF was present at 126 IU VWF: RCo/ml. The VWF buffer consisted of a hepes/citrate buffer with a bulking agent, a surfactant, a stabilizing agent and an amino acid.

Advate rAHF-PFM (antihemophilic factor (recombinant) plasma albumin-free method; FVIII) was present at 876 IU/vial. Upon reconstitution in WFI, the solution consisted of a Tris buffer, with appropriate salts, a bulking agent, a surfactant, a stabilizing agent, an amino acid, and an antioxidant. The solution was stored at 2-8 C.

The mixture of rVWF and Advate was at a ratio of 1.3 parts rVWF:RCo (IU) to 1 part rFVIII(IU).

Vehicle controls consisted of the Citrate buffer for rVWF and the Combination buffer, which was a mixture of the rVWF buffer and Advate buffer. The combination buffer was prepared by mixing the same volume ratio for the rVWF and Advate buffers as were mixed for the high-dose combined rVWF and Advate group. Isotonic saline was used as a negative control (0.9% NaCl).

HAEMATE® P (human plasma-derived, antihemophilic factor-von Willebrand factor complex) was used as an active control. The composition was 1143.4 IU VWF:RCo/vial, 770 IU FVIII/vial as obtained from ZLB Behring GmbH, Germany. Upon reconstitution in WFI, the composition was as follows: 114.34 IU VWF:RCo/mL, 77 IU FVIII/mL in a buffer of NaCl, sodium citrate, human albumin, and glycine.

2. Procedures a. Treatment of Animals

Mice were caged in Macrolon II cages. Animals were kept at a temperature (mean±SEM) of 20.8±0.44° C. and 21.6±0.36° C. (targeted range: 20-24° C.), at a relative humidity (mean±SEM) of 52.8±3.51% and 53.5±2.77% (targeted range: 45-65%) in room 3/1-83 (18 air changes per hour) and at a light:dark ratio of 1:1 (12 h light: 12 h dark; artificial lighting).

The mice were assigned to 28 groups (A-J and U-X for the 1-day study part, and K-T and Y-BB for the 14-day study part) of 10 animals (5 males and 5 females) per group. Each group received one of the following treatments:

Recombinant von Willebrand factor (rVWF) alone at five dose levels rVWF combined with Advate (RCoU:IUFVIII in a ratio of 1.3:1) at five dose levels

HAEMATE® P

The corresponding formulation buffer for rVWF alone

The combined formulation buffers for rVWF and Advate in the same volume ratio as for the high-dose rVWF and Advate combination Isotonic Saline The primary end-point was mortality. Activity level and physical conditions were closely monitored for the first 6 hours after injection and checked daily thereafter up to 14 days for signs indicative of toxicity. All animals were weighed on day 0 and day 1 (short-term part) and day 1, day 7 (8) and day 14 (long-term part) to provide an indication of general health.

Each animal received a single intravenous injection via a tail vein, aiming for a flow rate of 2 mL/min. For the group allocation and treatment regimen see Table 4 below:

TABLE 4

Allocation and treatment regimen of groups

| Group | | Item | Dose/Volume |
|---|---|---|---|
| short term (1 day) | long term (14 days) | | |
| A | K | rVWF buffer + Advate buffer | 31.7 mL/kg + 17.6 mL kg; 49.3 mL/kg |
| B | L | rVWF + rFVIII | 4000 RCoU/kg + 3077 IU/kg |
| C | M | rVWF + rFVIII | 1000 RCoU/kg + 769 IU/kg |
| D | N | rVWF | 1000 RCoU/kg |
| E | O | rVWF + rFVIII | 2000 RCoU/kg + 1538 IU/kg |
| F | P | rVWF buffer | 31.7 mL/kg |
| G | Q | HAEMATE® P | 2000 RCoU/kg |
| H | R | Saline | 49.3 mL/kg |
| I | S | rVWF | 2000 RCoU/kg |
| J | T | rVWF | 4000 RCoU/kg |
| U | Y | rVWF + rFVIII | 500 RCoU/kg + 385 IU/kg |
| V | Z | rVWF | 500 RCoU/kg |
| W | AA | rVWF + rFVIII | 250 RCoU/kg + 192 IU/kg |
| X | BB | rVWF | 250 RCoU/kg | b. Body Mass Analysis

The change in body mass between study day 0 and study days 1, 7 and 14 (as Δ% of body mass at day 0) were visualized using box plots grouped by item and dose. Male and female animals were combined for these box plots. (See FIGS. 2-4, 13-15, 24-26)

The box plots are designed as follows. The lower edge of the box represented the 25th percentile (or 1st quartile), the upper edge of the box represented the 75th percentile (or 3rd quartile) and the line within the lower edge and the upper edge of the box indicated the median. The plus indicated the mean. The distance from the lower edge to the upper edge of the box represented the interquartile range (IQR). A whisker was drawn above the 75th percentile to the largest data value that was less or equal to the value that was 1.5*IQR above the 75th percentile. Any data value larger than that was marked. A whisker was drawn below the 25th percentile to the smallest data value that was less or equal to the value that was 1.5*IQR below the 25th percentile. Any data value smaller than that was marked.

Means and corresponding two-sided 95% bootstrap-t confidence intervals (Efron B and Tibshirani R J, An Introduction to the Bootstrap, Chapman and Hall/CRC, Boca Raton, London, N.Y., Washington D.C., page 160-167 (1993)) were presented for changes in body mass between study day 0 and study days 1, 7 and 14 (as Δ% of body mass at day 0) grouped by item and dose. These analyses were performed for changes from day 0 to day 1 (pooled STADS and LTADS, for changes from day 0 to day 7 (LTADS) and for changes from day 0 to day 14 (LTADS) for male and female animals separately as well as for male and female animals combined. Bootstrap-t confidence intervals were calculated based on 100,000 bootstrap replications stratified by sex and data set.

Differences in body mass development between different doses of rVWF and rVWF+rFVIII with the corresponding buffer were assessed for changes from day 0 to day 1 (pooled STADS and LTADS) and for changes from day 0 to day 14 (LTADS) separately.

Body mass development was compared for the contrasts specified by a two-sided permutation test (by SAS procedure PROC MULTTEST, option=PERMUTATION, statement=TEST MEAN) stratified by sex with 1,000,000 permutation replications.

Adjustment for multiplicity for comparison of two dose groups with the corresponding buffer simultaneously was applied using the Holm method (1979) (Holm S., Scandinavian Journal of Statistics, 6:65-70 (1979)). Unadjusted and multiplicity adjusted two-sided p-values were presented. No adjustment for multiplicity was applied for investigation of different items or for investigation of different study days.

Differences in body mass development between HAE-MATE® P and the corresponding dose of rVWF+rFVIII were assessed for changes from day 0 to day 1 (pooled STADS and LTADS) and for changes from day 0 to day 14 (LTADS) separately. Two-sided p-values were calculated by permutation tests [by SAS procedure PROC MULTTEST, option=PERMUTATION, statement=TEST MEAN] stratified by sex with 1,000,000 permutation replications. No adjustment for multiplicity was applied for investigation of two different study days.

The minimum detectable dose (MDD), defined as the minimum dose which is shifted from the corresponding buffer, was estimated using contrasts which were tested a step-down manner as suggested by Tamhane et al. (Biometrics, 52:21-37 (1996)). As this analysis was exploratory, linear and reverse helmert contrasts were considered for estimation where the contrast that resulted in the lowest MDD was reported.

The minimum detectable dose so determined is one dose level higher than the no observed adverse effect level dose (NOAEL). The minimum detectable dose was estimated for rVWF+rFVIII and for rVWF for changes in body mass from day 0 to day 1 (pooled STADS and LTADS) as well as for changes in body mass from day 0 to day 14 (LTADS) separately.

Two-sided p-values for linear contrasts were calculated using permutation tests [by SAS procedure PROC MULT-TEST, option=PERMUTATION, statement=TEST MEAN] stratified by sex with 1,000,000 permutation replications. No adjustment for multiplicity was applied for investigation of different items or for investigation of different study days.

c. Blood Sampling, Preparation and Measurement of Hematology and Serum Chemistry Variables Blood samples were withdrawn under anesthesia (Ketamine+Xylazin i.m.) by cardiac puncture at day one (study part 1) or day 14 (study part 2). Approximately 300 µL blood was collected in EDTA tubes for hematological investigation and approximately 300 µL of blood was prepared for serum preparation, filled in sample cups and sent at room temperature to the laboratory for analysis. The following variables were investigated using the Haematologiesystem ADVIA 120 and Serumchemieanalysegerät Konelab 20i.

Hematological investigation comprised hematocrit, hemoglobulin concentration, erythrocyte count, reticulocytes, total leucocyte count, differential leucocyte count, abnormalities of the blood morphology, platelet count, mean cell hemoglobulin, mean cell volume, and mean cell hemoglobulin concentration. Blood chemistry investigation comprised lactate dehydrogenase (LDH) and creatinine kinase (CK).

Only the variables hematocrit, platelet count, LDH and CK were further considered for statistical analysis.

Hematological and serological variables (hematocrit, platelet count, LDH, CK) at study day 1 and study day 14 were visualized using box plots grouped by item and dose. Male and female animals were combined for these figures.

Hematological and serological variables at study day 1 and study day 14 were summarized using means and coefficient of variations (CV) grouped by item and dose. These statistics were provided for male and female animals separately as well as for male and female animals combined.

d. Necropsy and Histology

Necropsy was performed in all surviving animals at day 1 (study part 1) and day 14 (study part 2). All macroscopically changed tissues and the following tissues were collected for further histopathological examination:

Adrenal Glands
Brain (with medulla oblongata)
Heart
Kidneys
Liver
Lungs (perfused, without trachea)
Spleen
Eyes All organs and tissues were fixed in 4% buffered formaldehyde (eyes in modified Davidson's solution) and sent to the histological laboratory at room temperature for histological preparation.

Slides of all tissue samples collected at necropsy from every animal in the test-item treated high-dose groups, the reference-item-treated groups, the control groups as well as tissue samples of all macroscopic findings were processed, embedded in paraffin, cut at a nominal thickness of 2 to 4 micrometers, stained with hematoxylin and eosin (H&E) and examined by light microscope by the study pathologist. The same applied to tissue samples from the heart of every animal in all other test-item-treated groups.

The microscopic findings were recorded by the pathologist during histopathological examination. In a separate pathology report, histological changes were described, wherever possible, according to distribution, severity and morphologic character. Severity scores were assigned as given under "Explanation of Codes and Symbols."

Microscopic findings were recorded, and incidence tables derived from these data were generated.

e. Statistical Methods and Data Sets

The minimum detectable dose (MDD), defined as the minimum dose which is shifted from the corresponding buffer, was estimated for rVWF+rFVIII as well as for rVWF by using contrasts that were tested in a step-down manner. Different doses of rVWF+rFVIII and rVWF were also compared with the corresponding buffer.

Additionally, HAEMATE® P at a dose of 2000 RCoU/kg VWF+1347 IU/kg FVIII was compared with rVWF+rFVIII at a dose of 2000 RCoU/kg rVWF+1538 IU/kg rFVIII.

All statistical calculations were performed with SAS version 8.2 for Linux (SAS Institute Inc. (2000). SAS OnlineDoco, Version 8, February 2000, Cary, N.C., USA: SAS Institute Inc.; SAS Institute Inc. (2001). SAS/STAT® Software: Changes and Enhancements, Release 8.2, Cary, N.C., USA: SAS Institute Inc.). The level of statistical significance was set to 5%. The null hypotheses of no differences were tested against their two-sided alternatives.

The short-term analysis data set (STADS) consisted of animals that received treatment at study day 0 and were killed at study day 1. The long-term analysis data set (LTADS) consisted of animals that received treatment at study day 0 and were killed at study day 14.

The primary endpoint for statistical evaluation was mortality. Secondary endpoints for statistical evaluations were body mass development (as Δ% of body mass at day 0) and changes in hematological and serological variables. Changes in hematological and serological variables were analyzed using descriptive statistics. The variables analyzed were hematocrit, platelet count, LDH and CK.

Example 6

Intravenous Application of Human RVWF Alone or in Combination with Human RFVIII in C57BL/6J MICE 1. Mice C57BL/6J mice were chosen for the study because this strain is the genetic background strain to VWF-deficient and ADAMTS13 deficient mice used in parallel studies. In general, mice are widely used in acute toxicity studies and are recognized as suitable for this purpose by regulatory authorities.

2. Protocol Used in this Study

There were no mortalities with any of the items investigated. Statistical analysis of mortality was therefore not performed. Comparisons of body mass development had been planned on ranks where animals that died before body mass measurement were to receive the lowest rank (Lachin J M, Controlled Clinical Trials, 20(5) 408-422 (1999)). There were no mortalities and comparisons of body mass development were therefore performed on relative changes (Δ% of body mass at day 0) and not on corresponding ranks.

Six different doses of rVWF and rVWF+rFVIII were investigated. For this reason, the minimum detectable dose (MDD), defined as the minimum dose which is shifted from the corresponding buffer, was estimated in a step-down manner using contrasts.

Hematological and serological variables grouped by item and study day were summarized using means and coefficient of variations instead of medians and ranges because coefficient of variations are scale independent and allow assessment of differences in variability of doses in laboratory variables.

3. Clinical Abnormalities

Clinical abnormalities indicative of toxicity were observed after administration of 4000 RCoU/kg rVWF in 75% (15 of 20, groups J and T) of the animals, and in 85% (17 of 20, groups B and L) of the animals after the combined administration of 4000 RCoU/kg rVWF and 3077 IU/kg rFVIII.

Short-term symptoms were also seen in 20% (4 of 20, groups A and K) of the animals treated with the combined buffer solutions (total volume of 49.3 mL/kg). All other treated groups were normal during the observation period.

A summary of clinical abnormalities of the animals per group is given in Table 5.

TABLE 5

| Clinical abnormalities in animals | | | | |
|---|---|---|---|---|
| Item | dose | group | Animal No. | Symptoms |
| rVWF | 4000 RCoU/kg | J | 46 | behavioral depression up to 6 hours |
| | | | 48 | prone position, dyspnea 3 min; behavioral depression up to 6 hours |
| | | | 50 | behavioral depression up to 6 hours |
| | | | 146 | prone position, dyspnea; behavioral depression up to 6 hours |
| | | | 147 | behavioral depression up to 6 hours |
| | | | 148 | behavioral depression up to 6 hours |
| | | | 149 | behavioral depression up to 6 hours |
| rVWF | 4000 RCoU/kg | T | 96 | ataxia, behavioral depression up to 6 hours |
| | | | 97 | behavioral depression, piloerection up to 6 hours |
| | | | 98 | behavioral depression, piloerection up to 6 hours |
| | | | 99 | piloerection up to 6 hours |
| | | | 197 | side position, dyspnea; behavioral depression, piloerection up to 6 hours |
| | | | 198 | behavioral depression short |
| | | | 199 | behavioral depression up to 6 hours |
| | | | 200 | behavioral depression, piloerection up to 6 hours |
| rVWF + rFVIII | 4000 RCoU/kg + 3077 IU/kg | B | 6 | behavioral depression, piloerection up to 6 hours |
| | | | 7 | behavioral depression, piloerection up to 6 hours |
| | | | 8 | side position, dyspnea 2 min; behavioral depression, piloerection up to 6 hours |
| | | | 9 | behavioral depression, piloerection up to 6 hours |
| | | | 10 | behavioral depression, piloerection up to 6 hours |
| | | | 106 | behavioral depression, piloerection up to 6 hours |
| | | | 107 | behavioral depression up to 6 hours |
| | | | 109 | behavioral depression, piloerection up to 6 hours |
| | | | 110 | behavioral depression, piloerection up to 6 hours |

TABLE 5-continued

Clinical abnormalities in animals

| Item | dose | Animal group | No. | Symptoms |
|---|---|---|---|---|
| rVWF + rFVIII | 4000 RCoU/kg + 3077 IU/kg | L | 56 | behavioral depression, piloerection up to 6 hours |
| | | | 57 | piloerection up to 6 hours |
| | | | 58 | behavioral depression, piloerection up to 6 hours |
| | | | 59 | behavioral depression (short) |
| | | | 60 | dyspnea, behavioral depression, piloerection up to 6 hours |
| | | | 157 | behavioral depression, piloerection up to 6 hours |
| | | | 158 | behavioral depression up to 6 hours |
| | | | 159 | behavioral depression up to 6 hours |
| rVWF buffer + Advate buffer | 49.3 mL/kg | A | 4 | short behavioral depression |
| | | | 102 | side position, convulsions, dyspnea; 0.5 min |
| | | | 104 | short behavioral depression |
| | | K | 51 | dyspnea 1 min |

4. Body Mass Analysis

Figure 2:
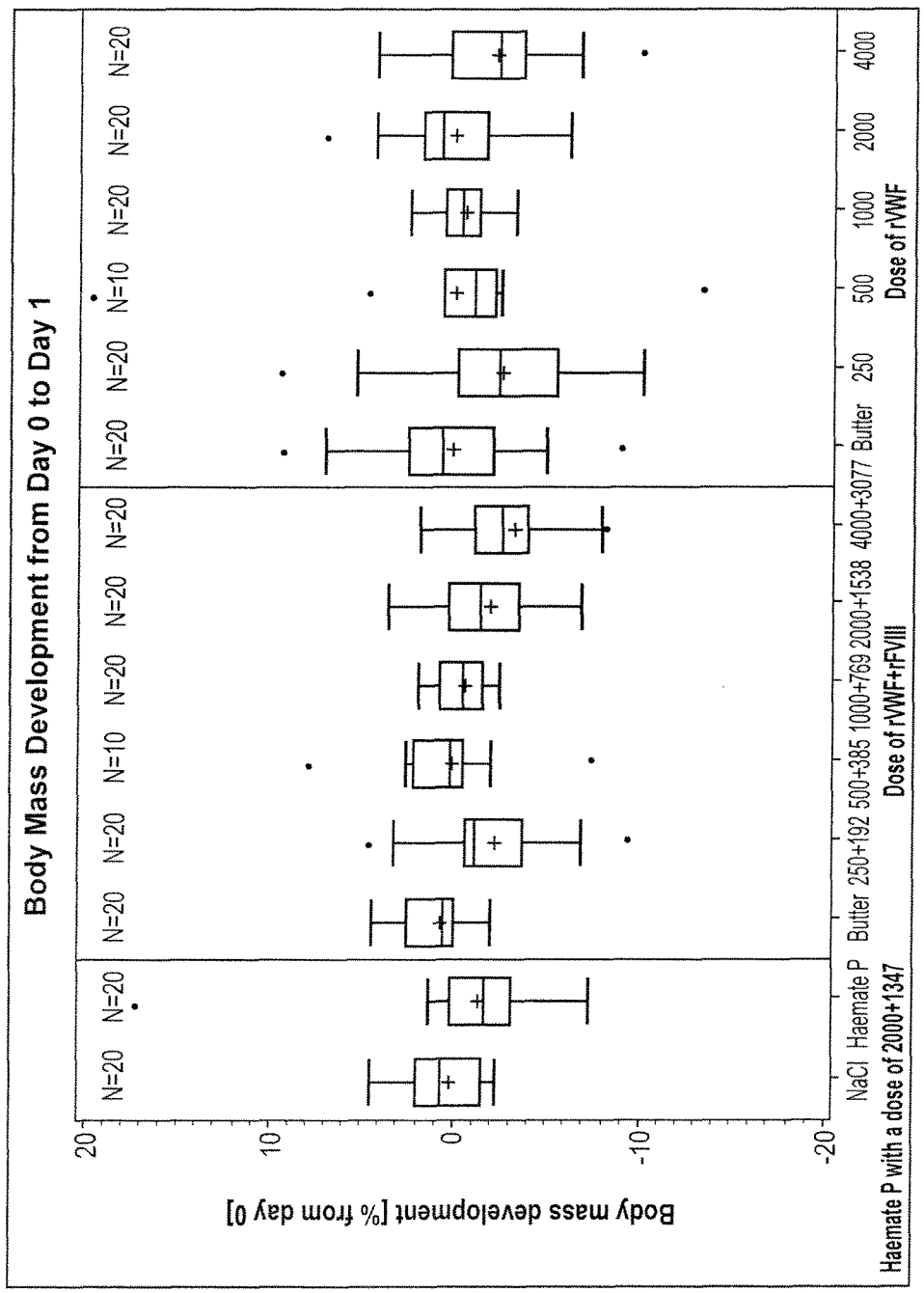
FIGS. 2-4 illustrate changes in body mass over the term of the study for C57BL/6J mice. Details of the analysis are described in more detail in the Examples.
Figure 3:
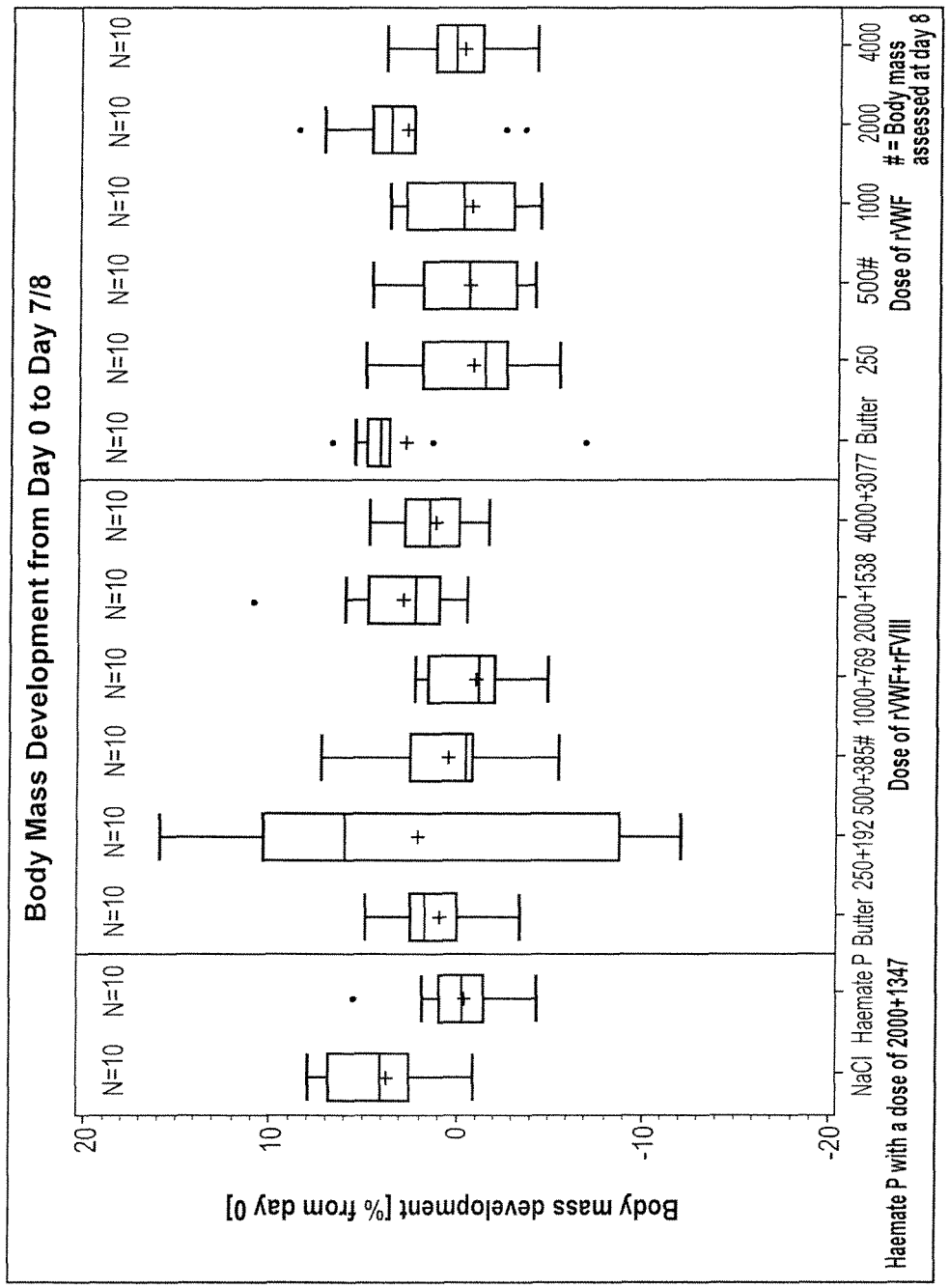
Figure 4:
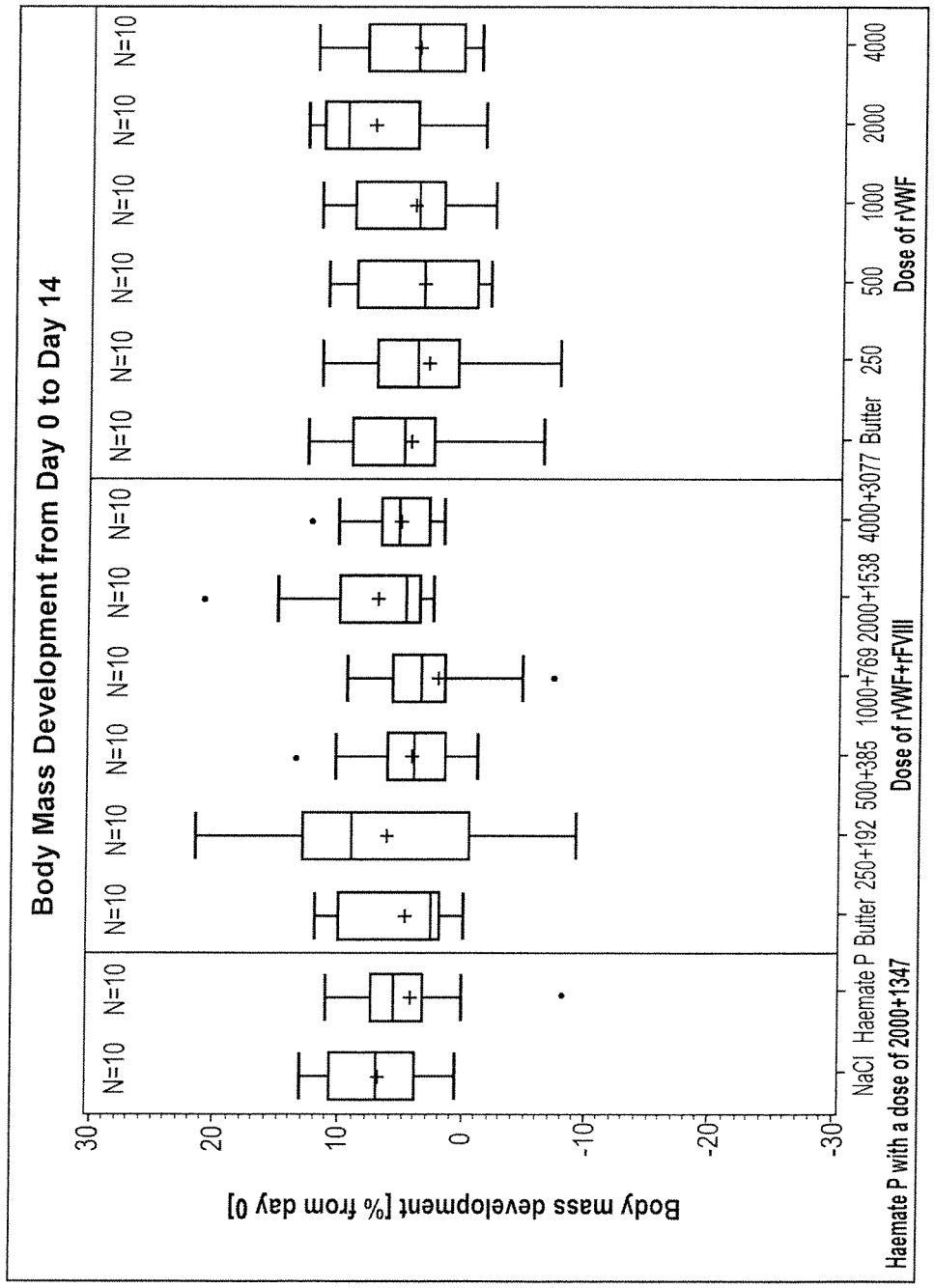
Figure 5:
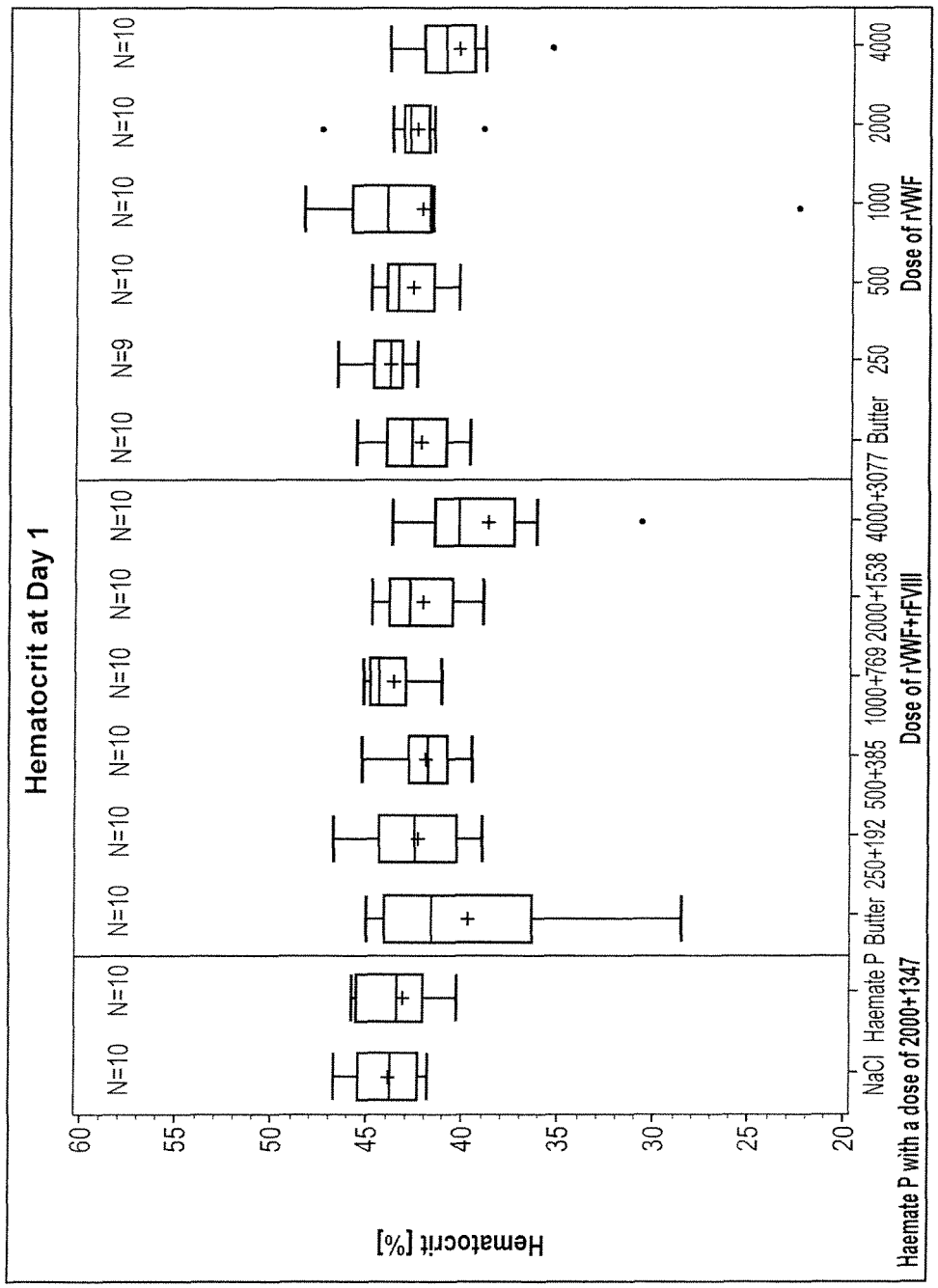
FIGS. 5-12 show data for hematocrit, platelet count, creatinine kinase (CK), and lactose dehydrogenase (LDH) over the term of the study for C57BL/6J mice. Details of the analysis are described in more detail in the Examples.
Figure 6:
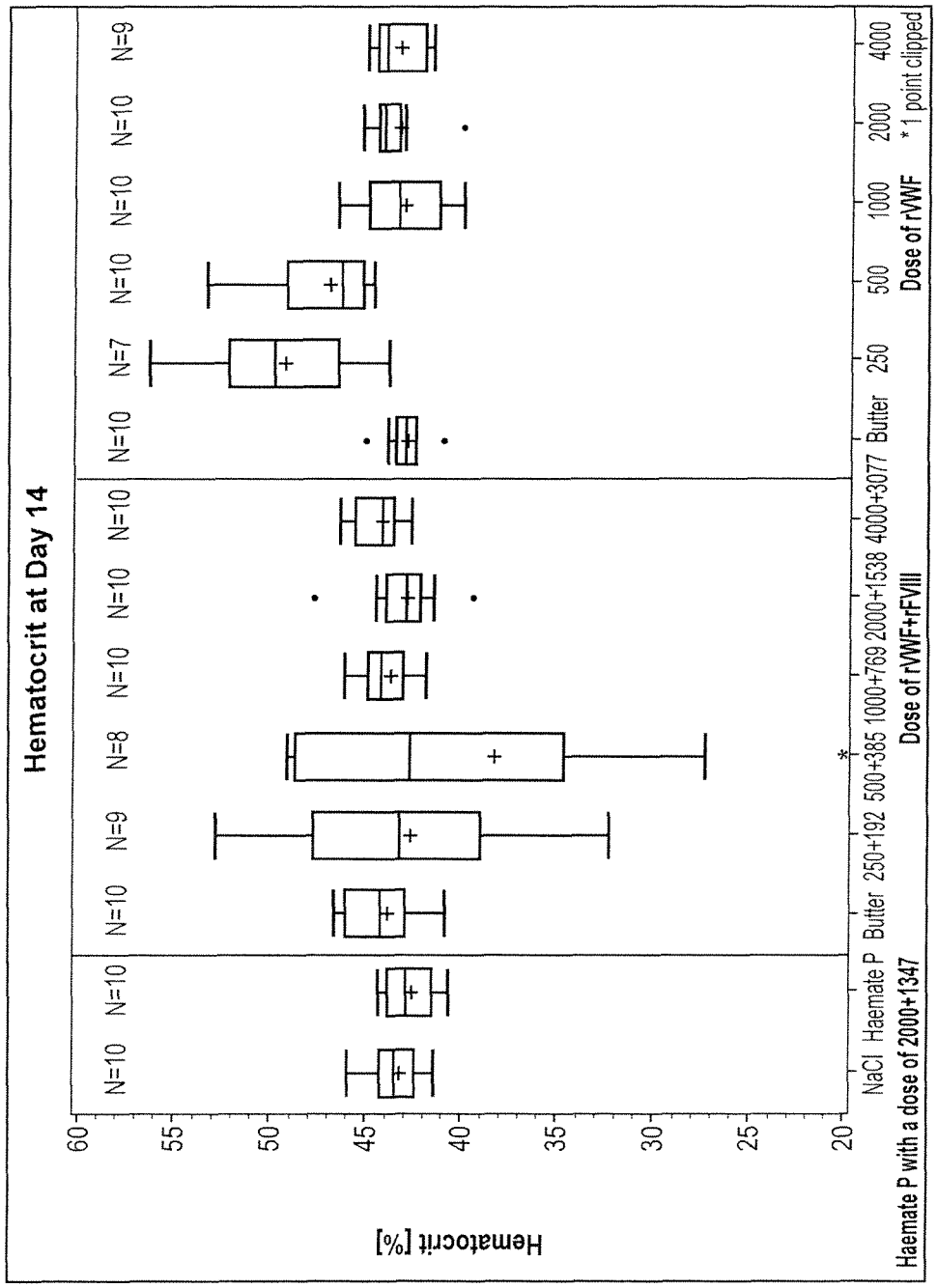
Figure 7:
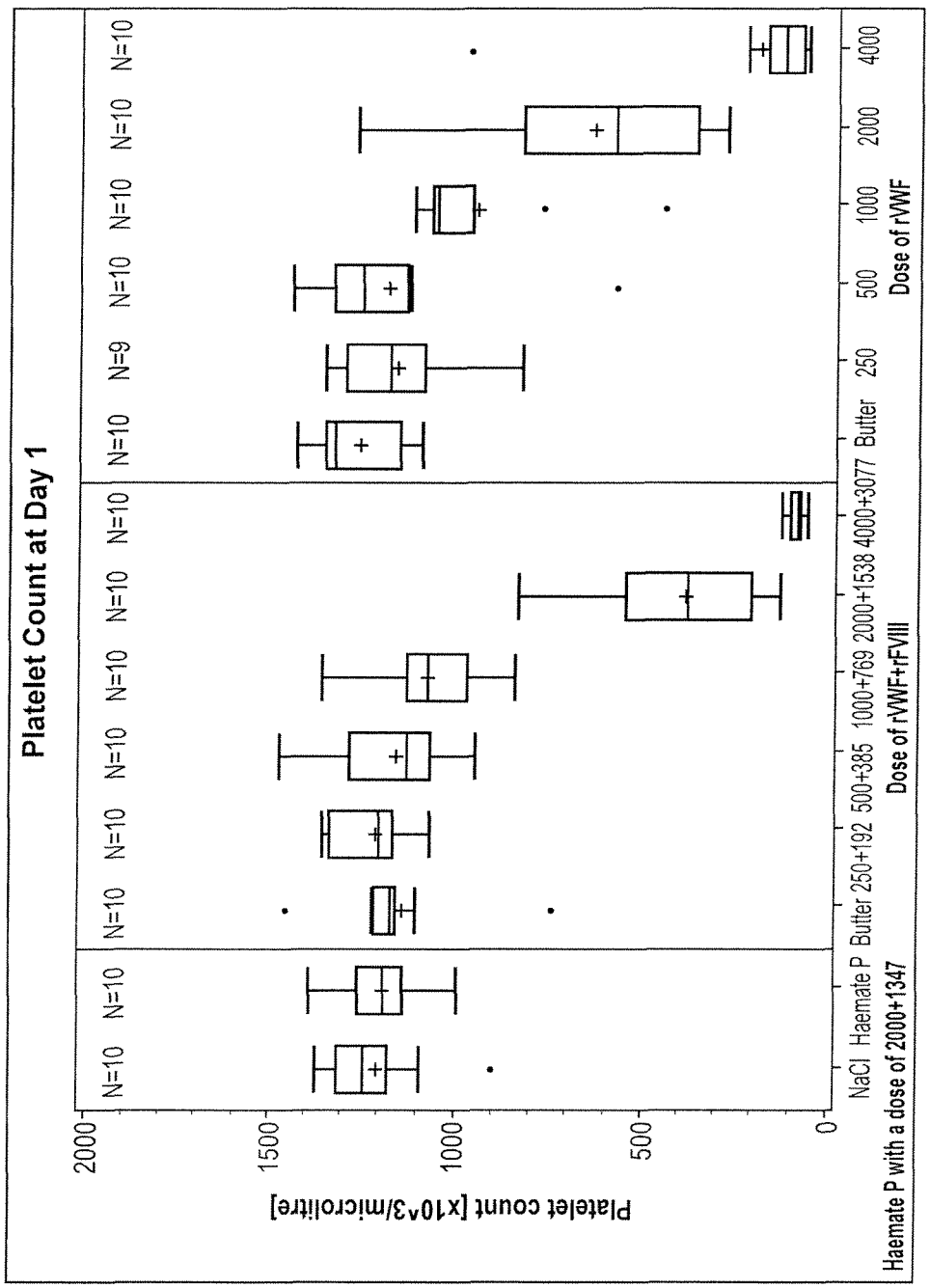
Figure 8:
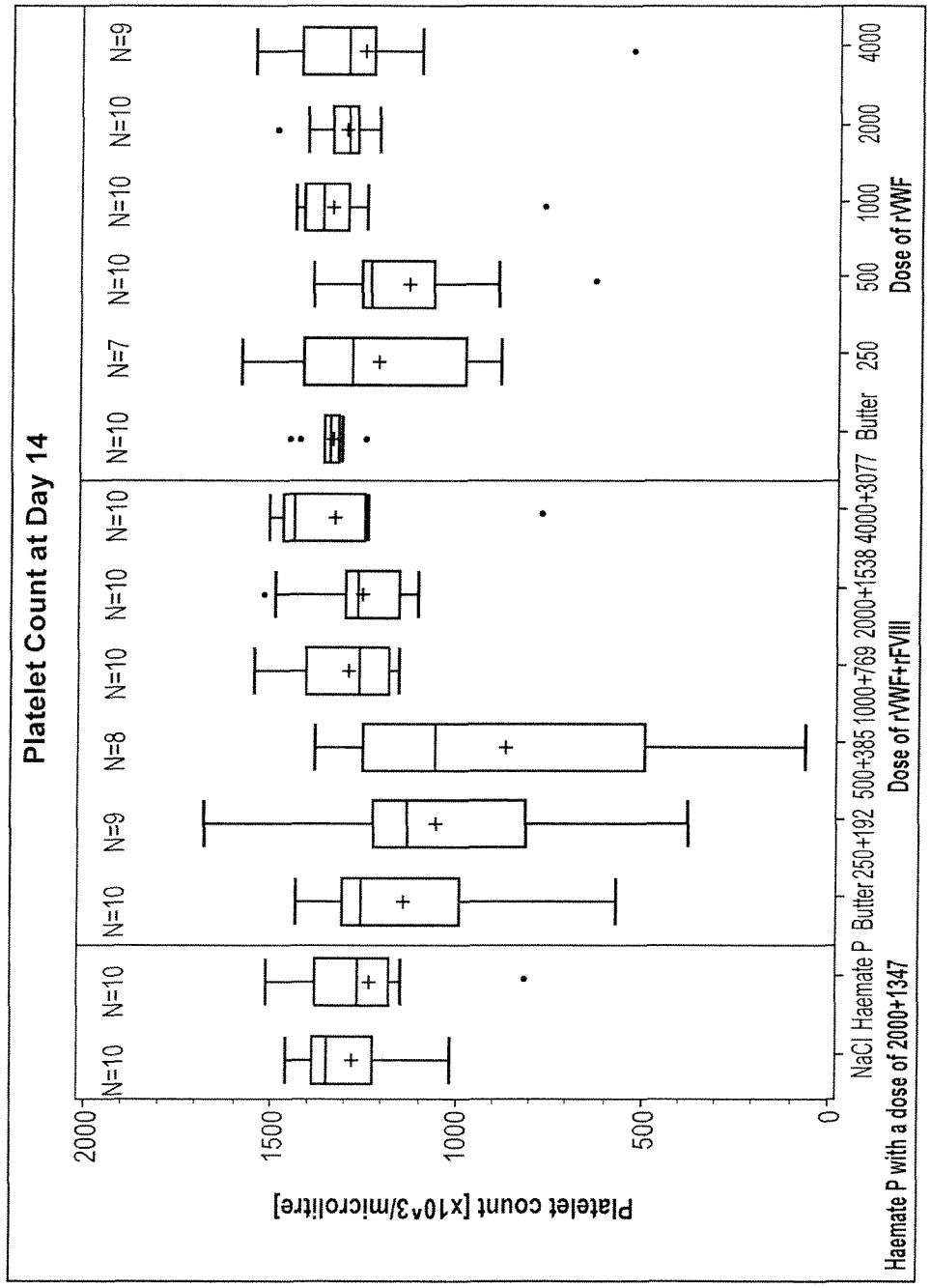
Figure 9:
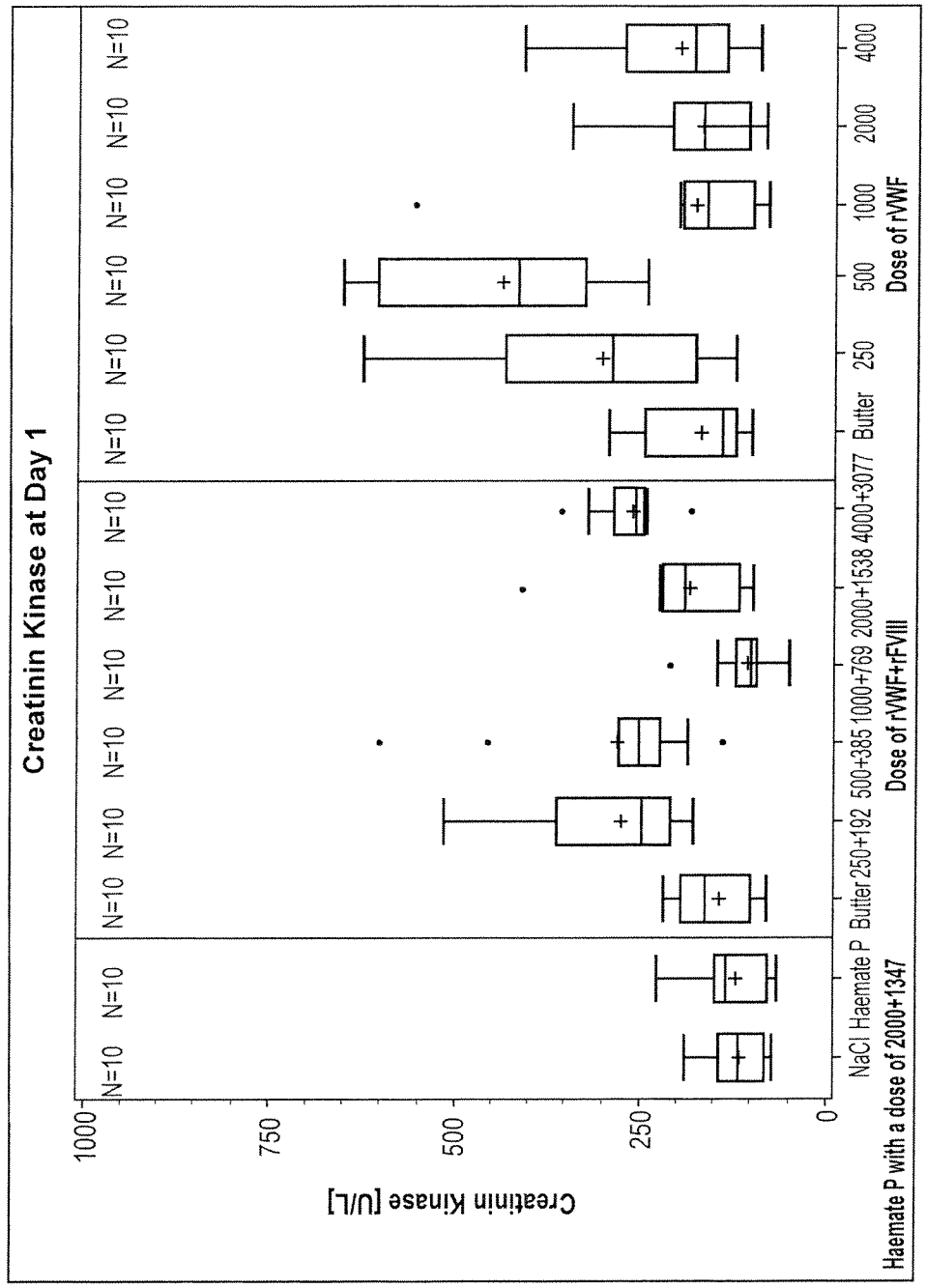
Figure 10:
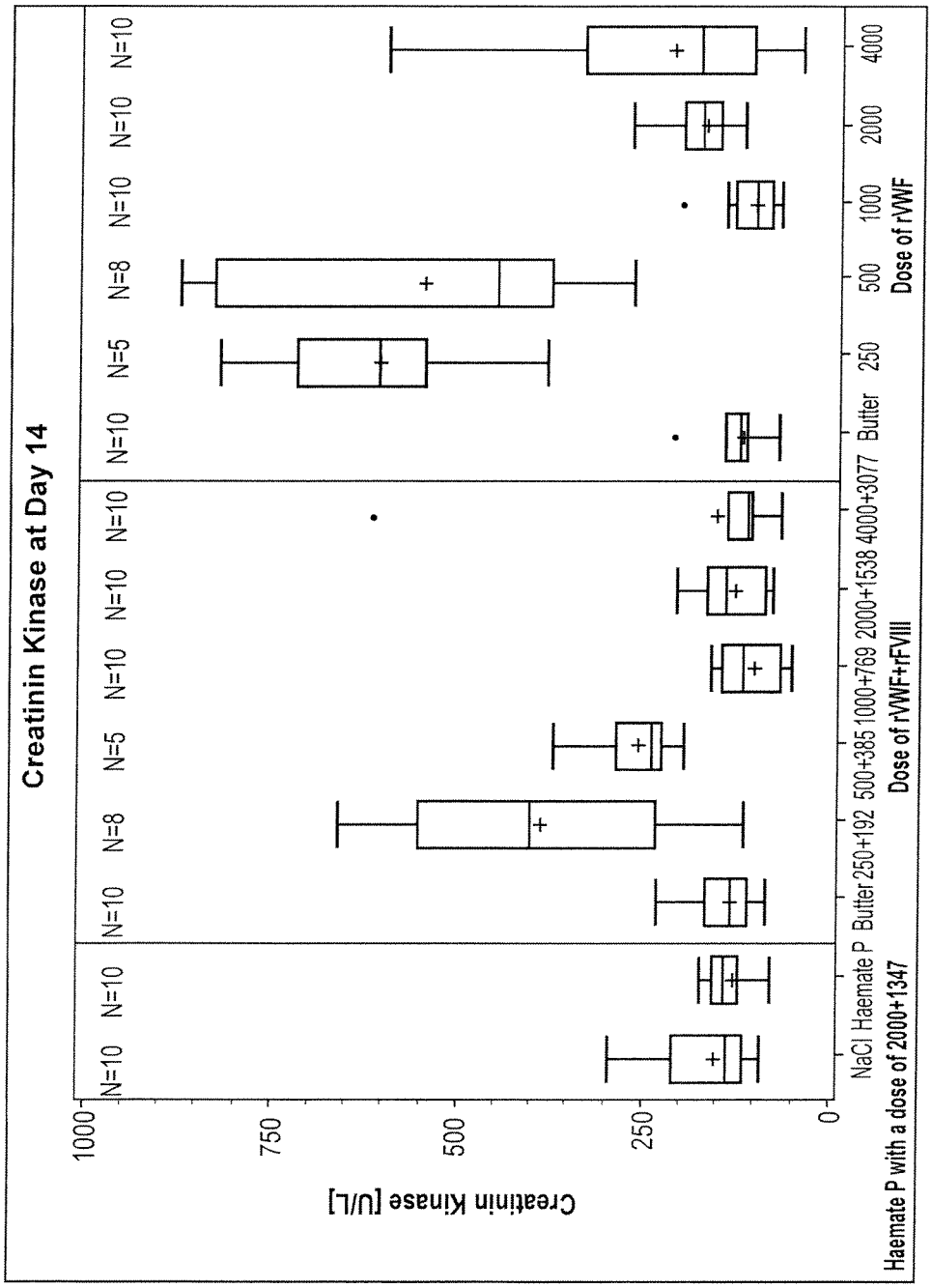
Figure 11:
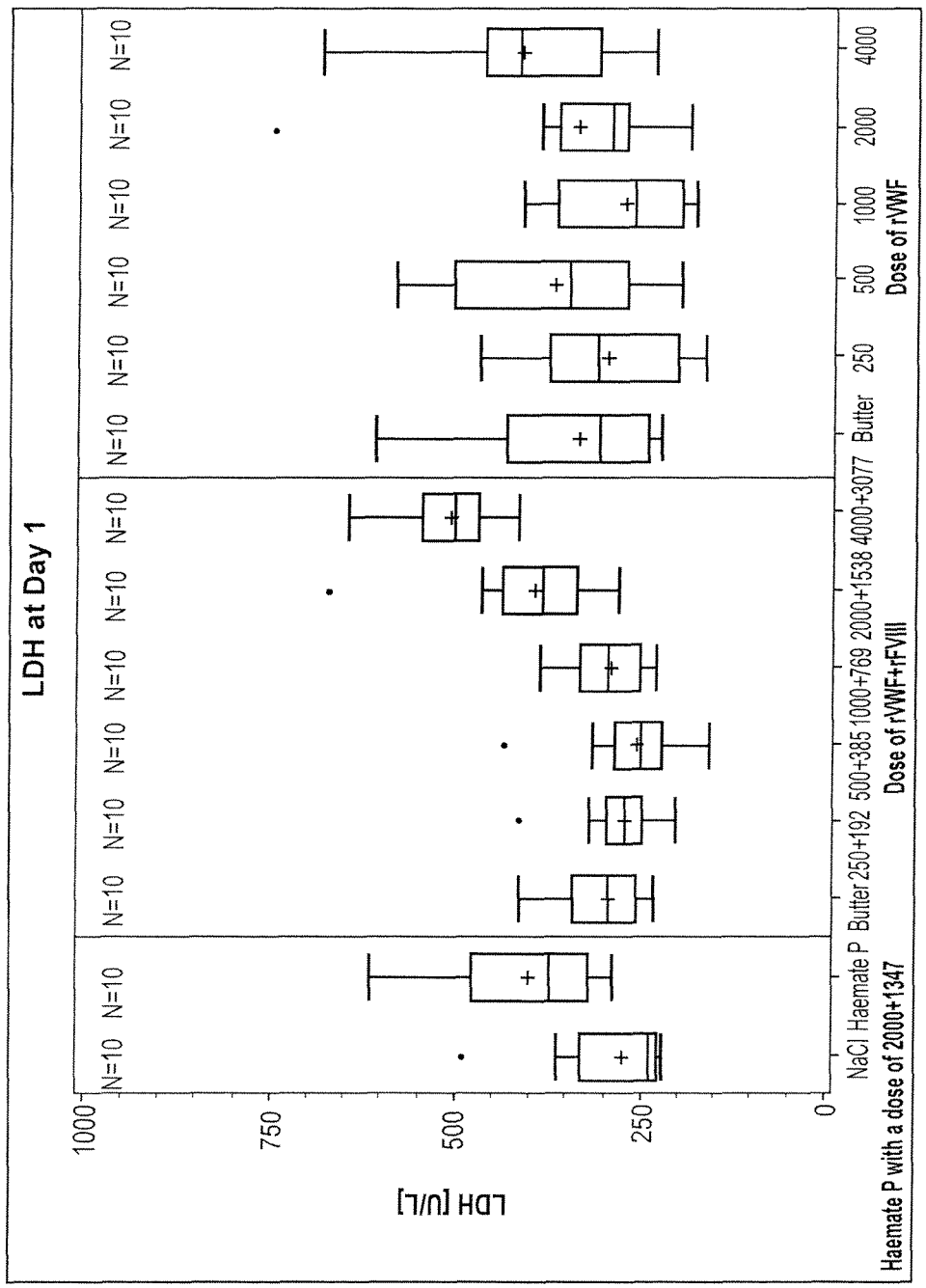
Figure 12:
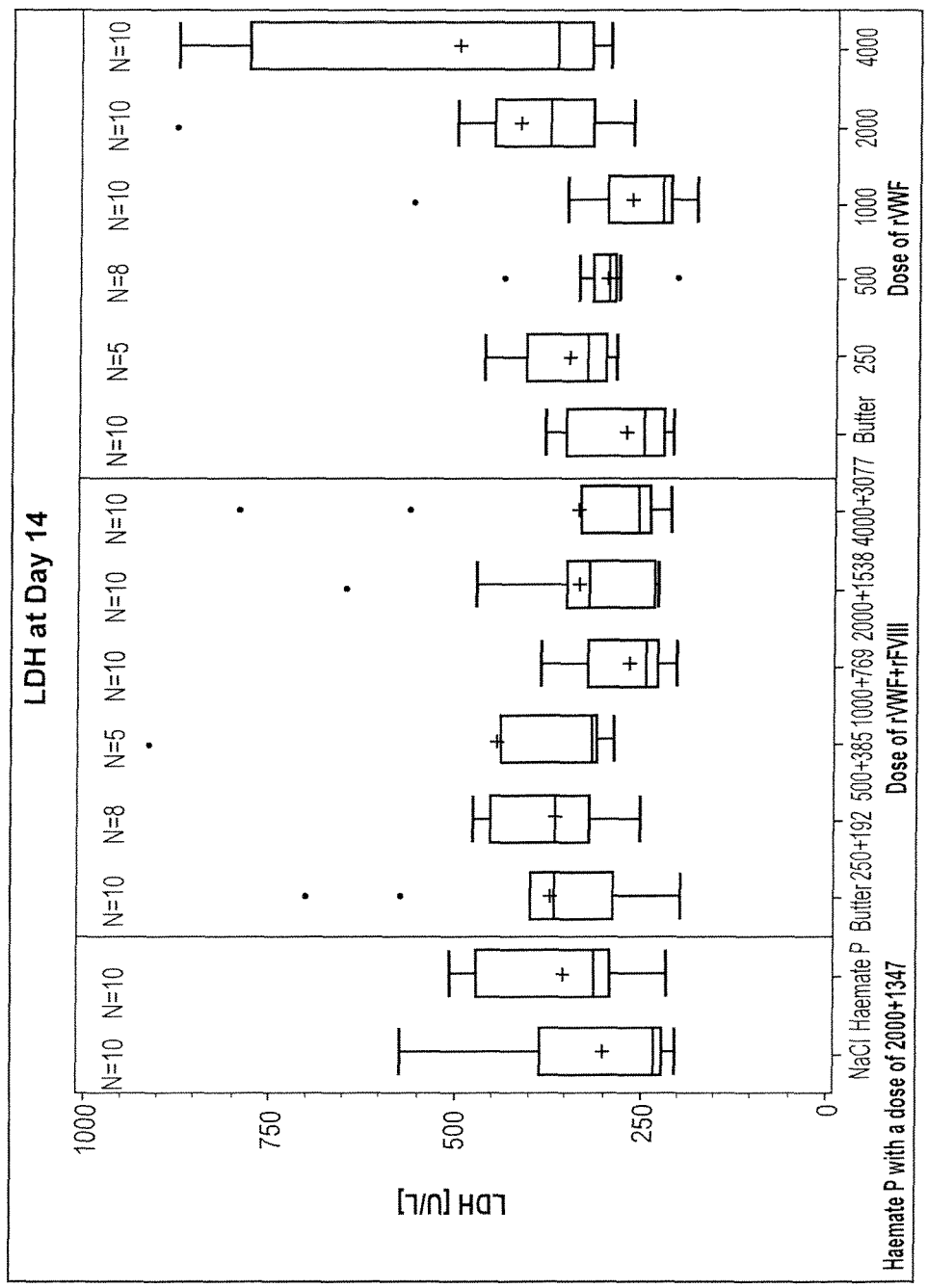
Figure 13:
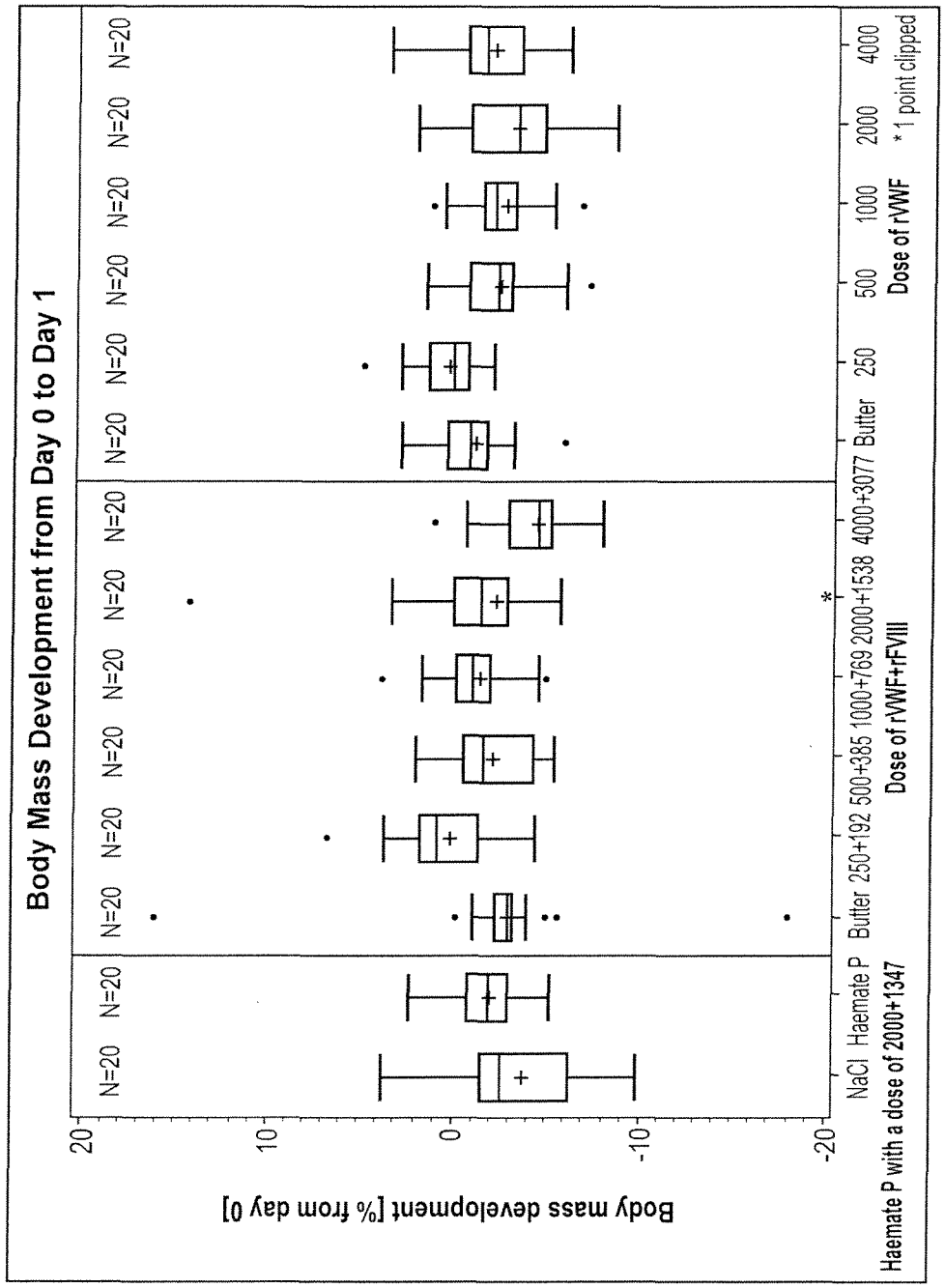
FIGS. 13-15 illustrate changes in body mass over the term of the study for VWF-deficient mice. Details of the analysis are described in more detail in the Examples.
Figure 14:
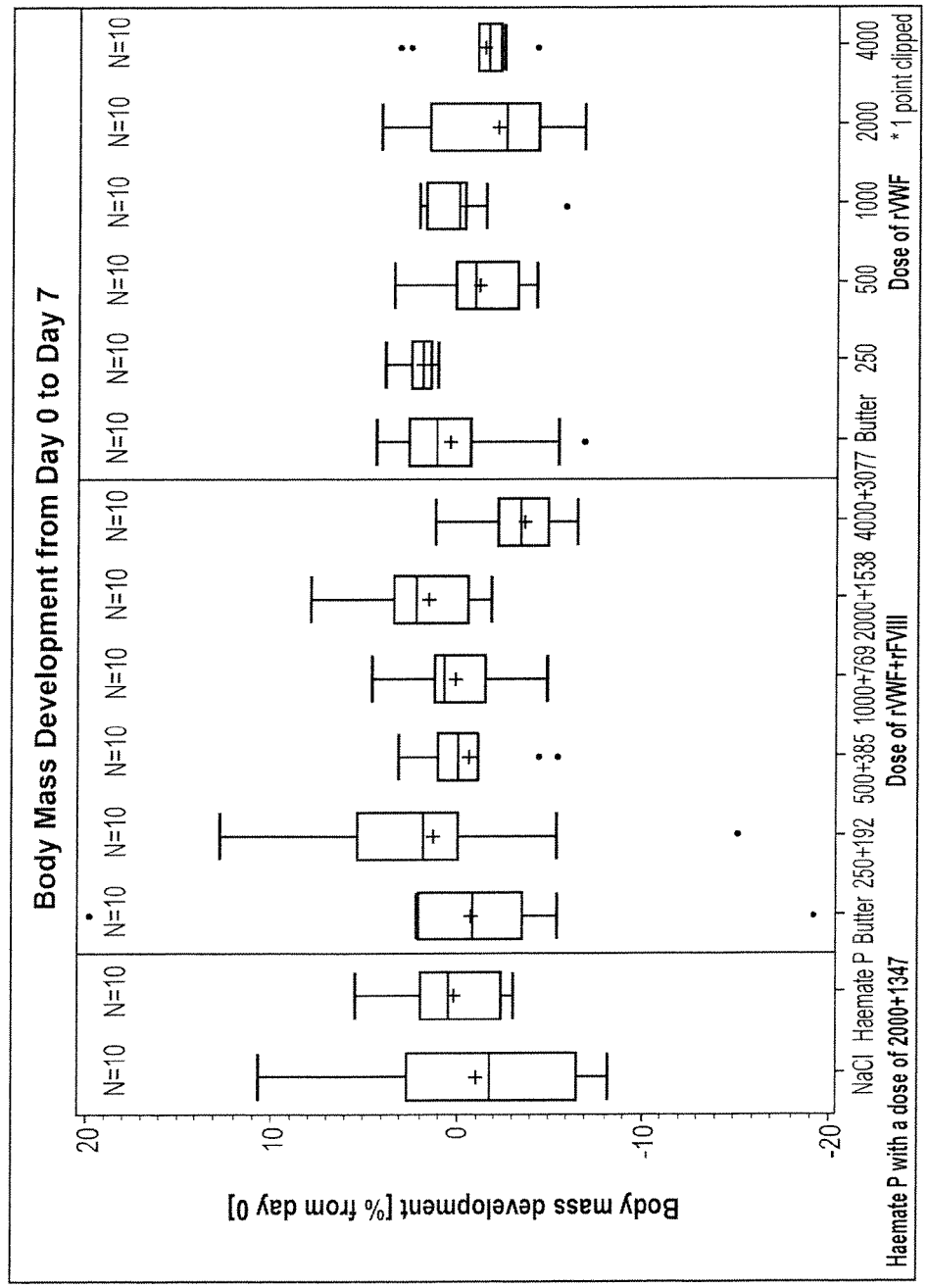
Figure 15:
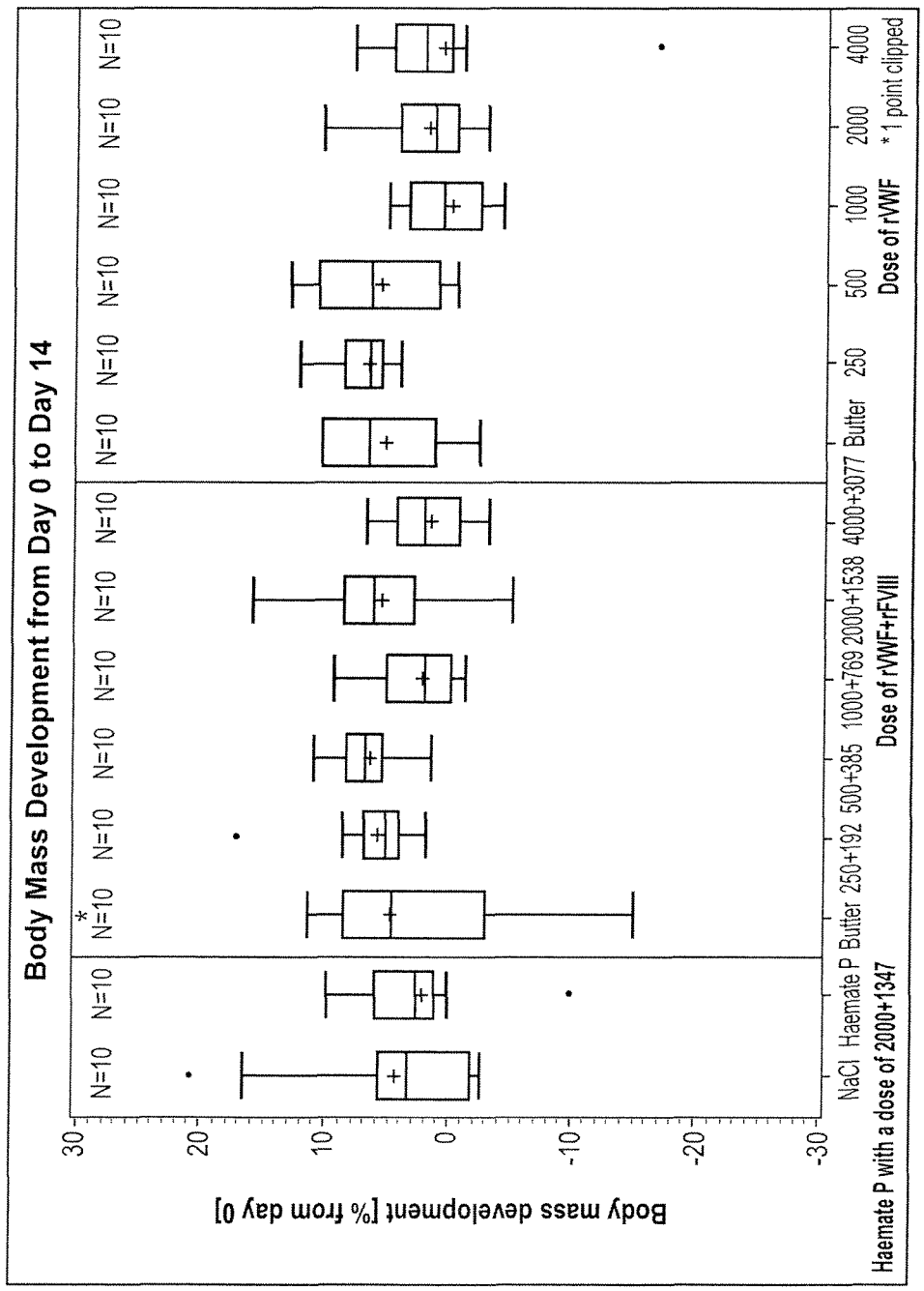
Figure 16:
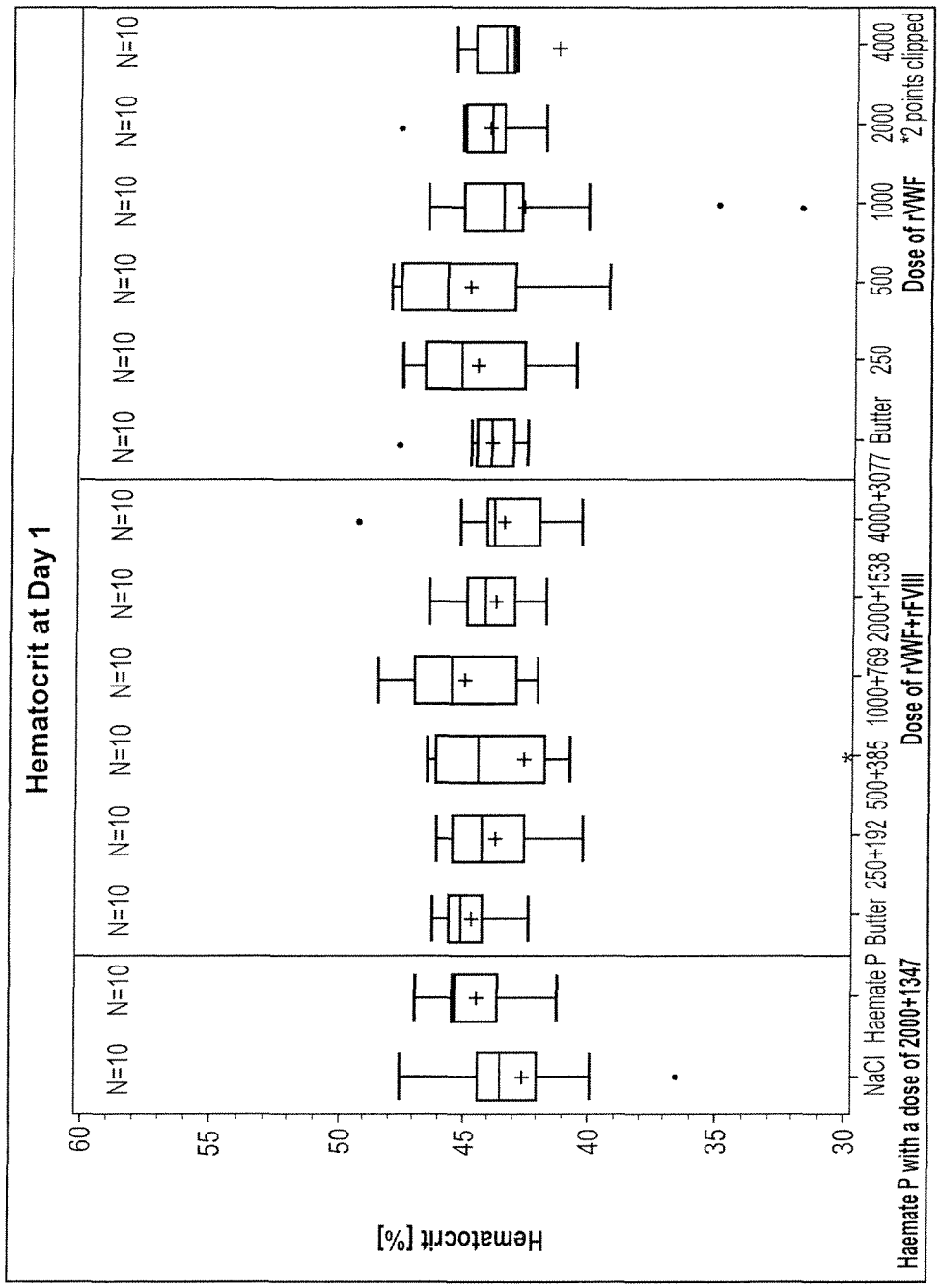
FIGS. 16-23 show data for hematocrit, platelet count, creatinine kinase (CK), and lactose dehydrogenase (LDH) over the term of the study for VWF-deficient mice. Details of the analysis are described in more detail in the Examples.
Figure 17:
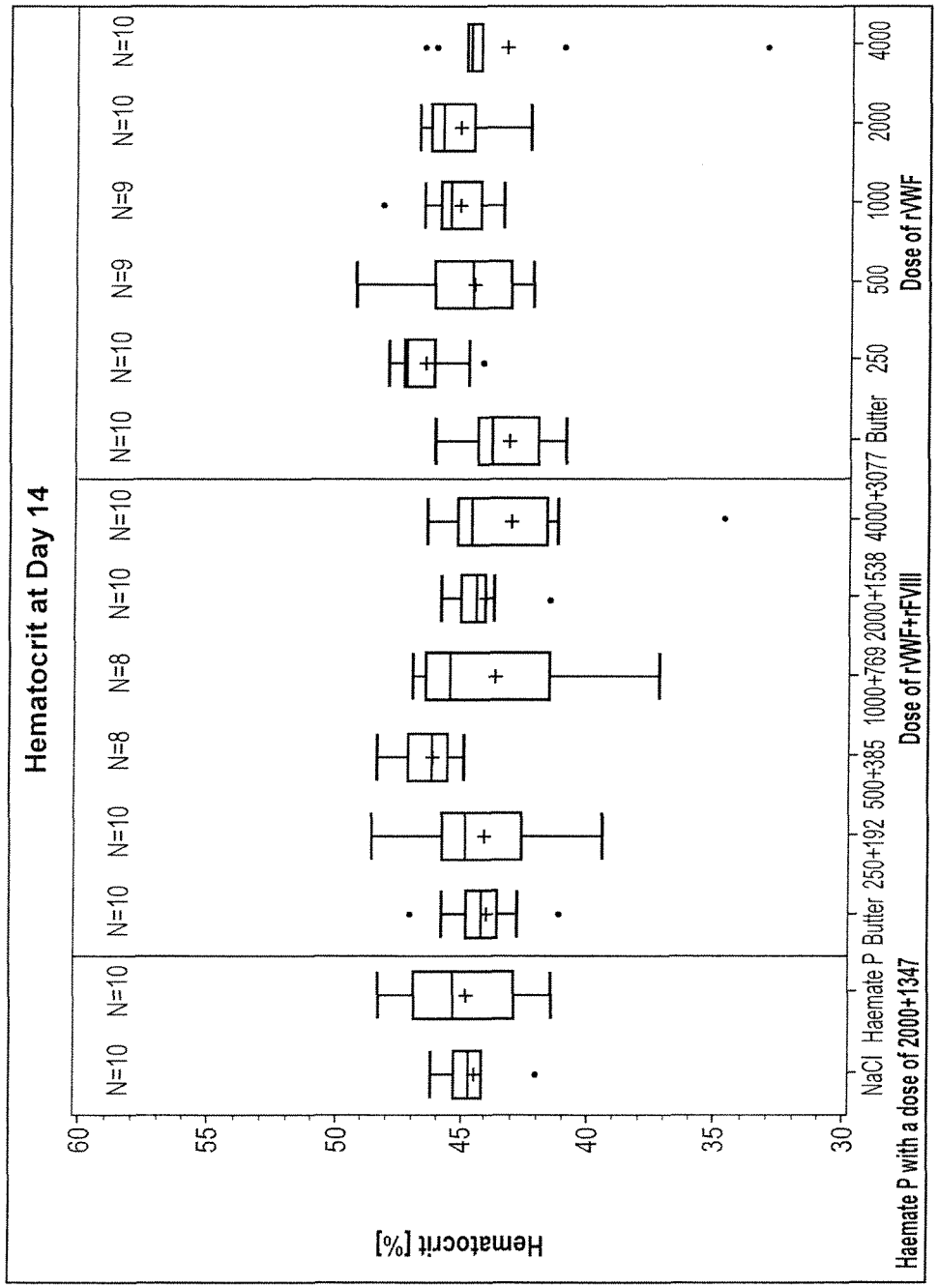
Figure 18:
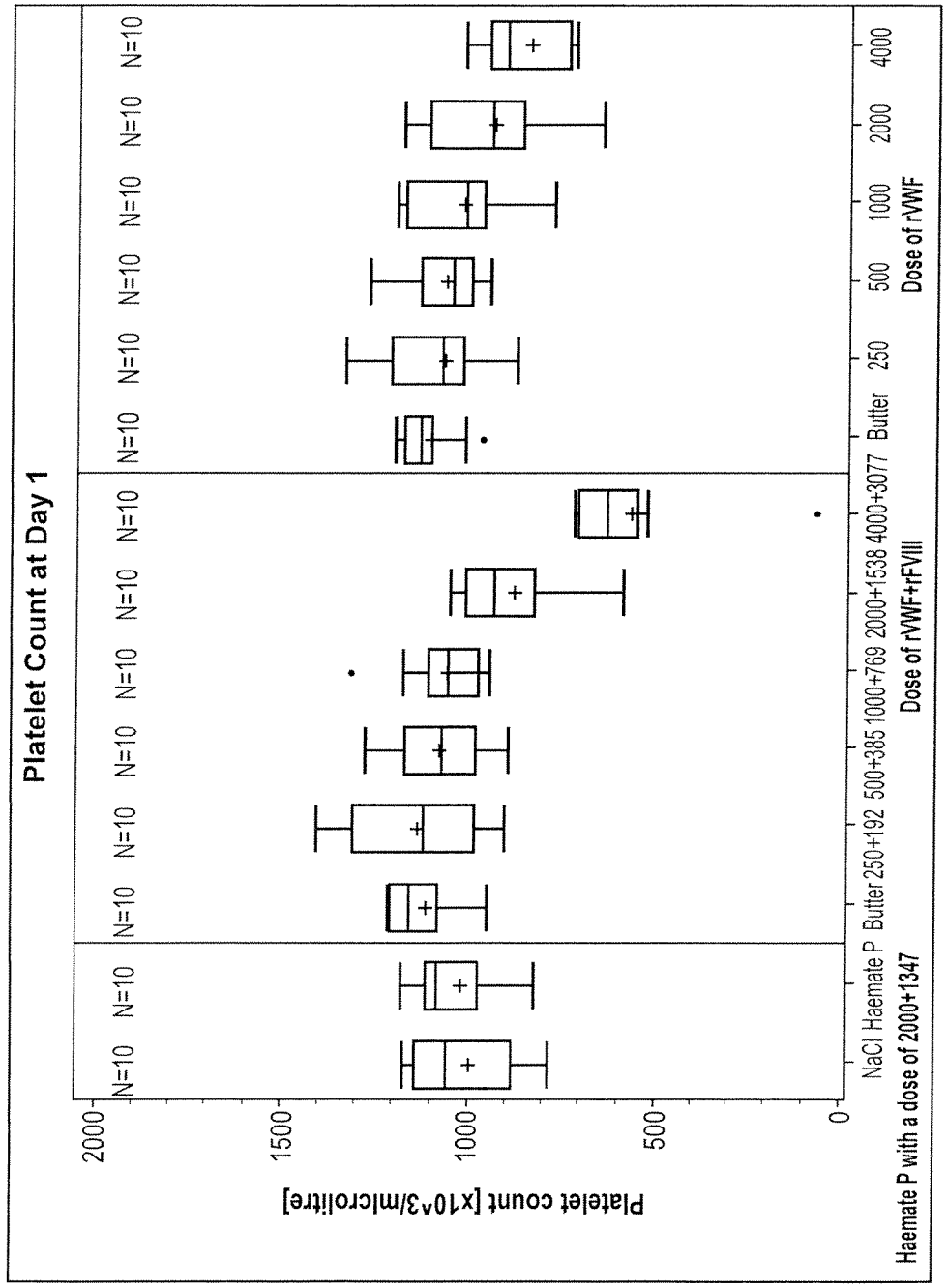
Figure 19:
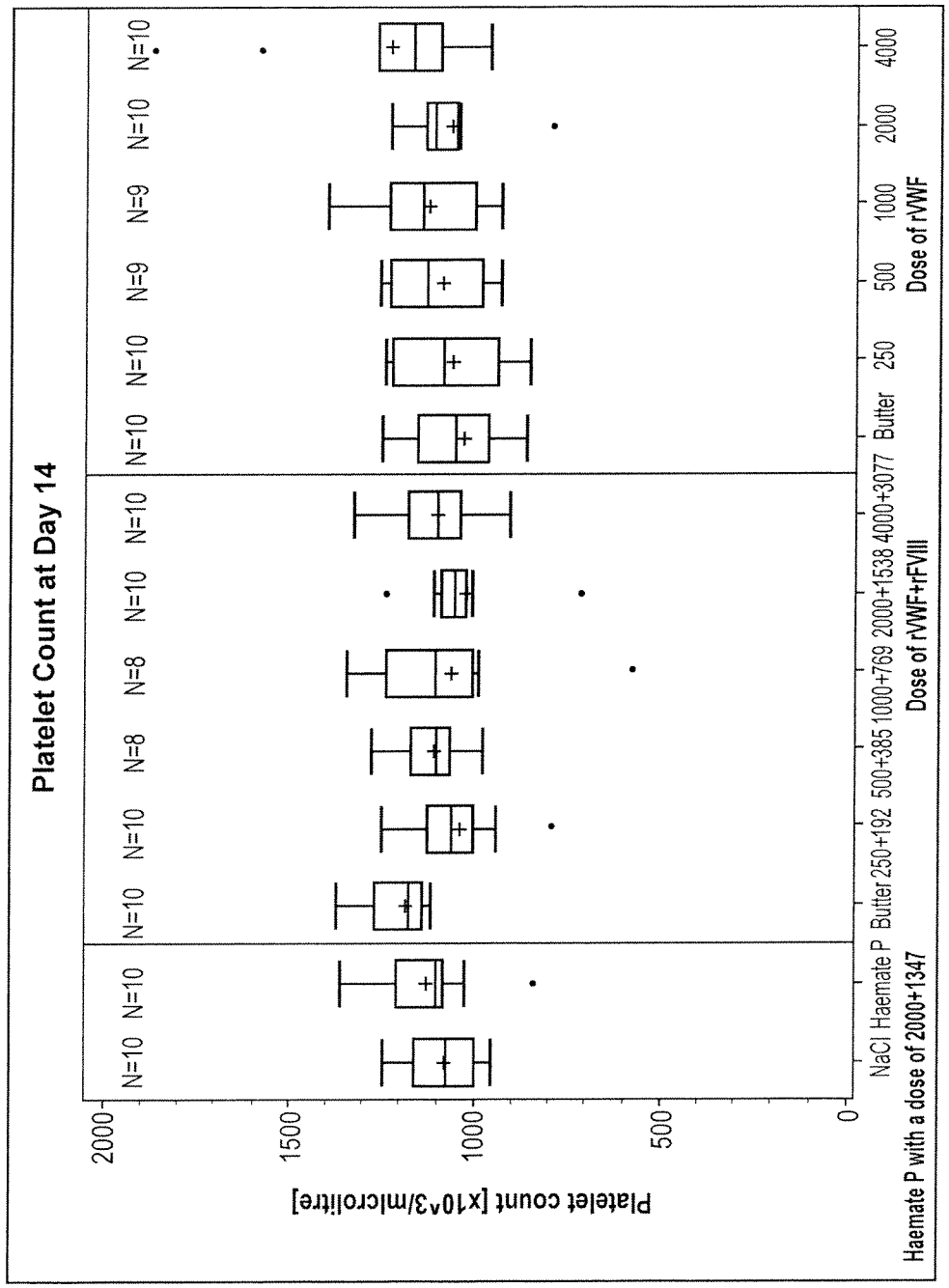
Figure 20:
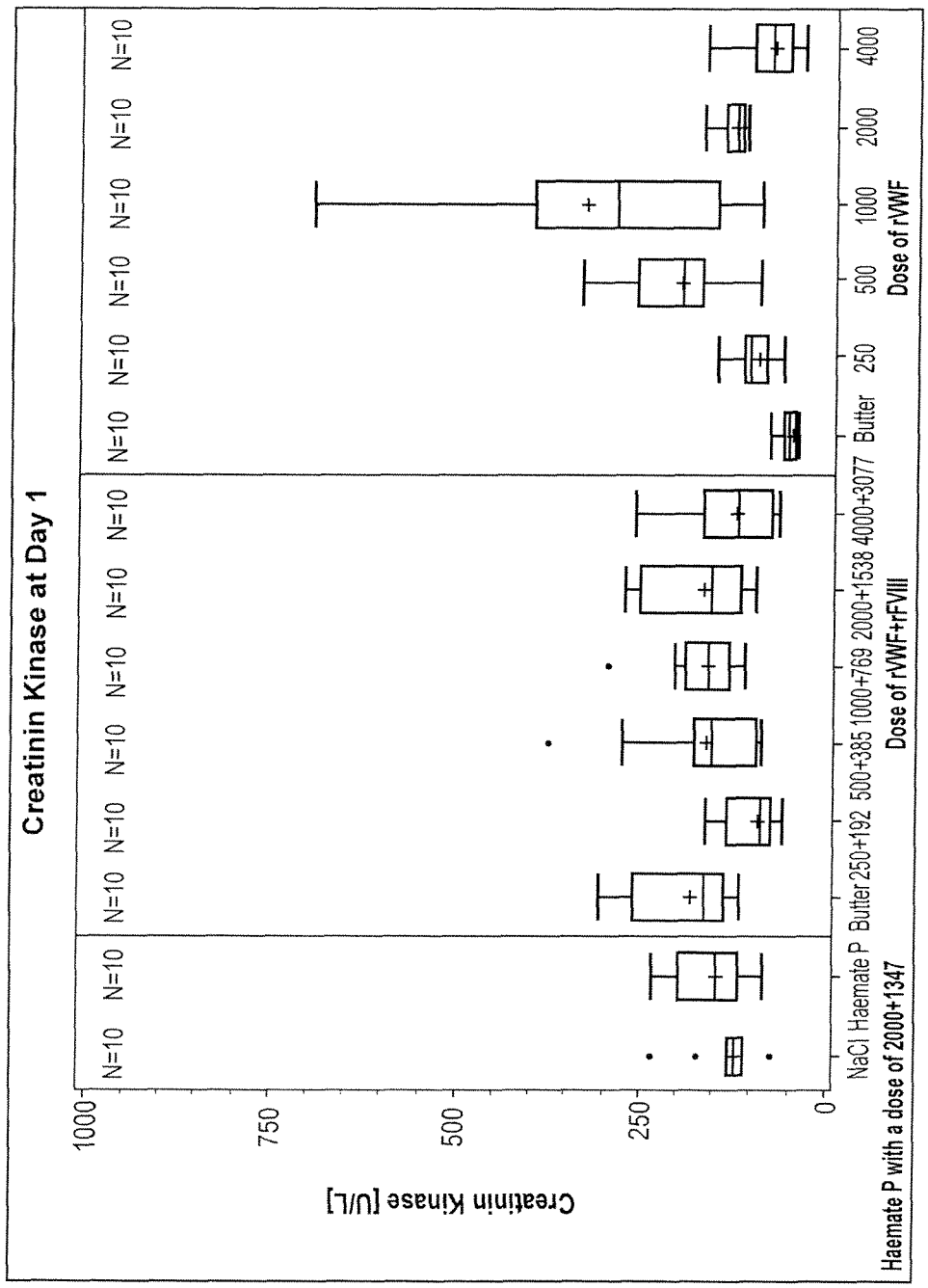
Figure 21:
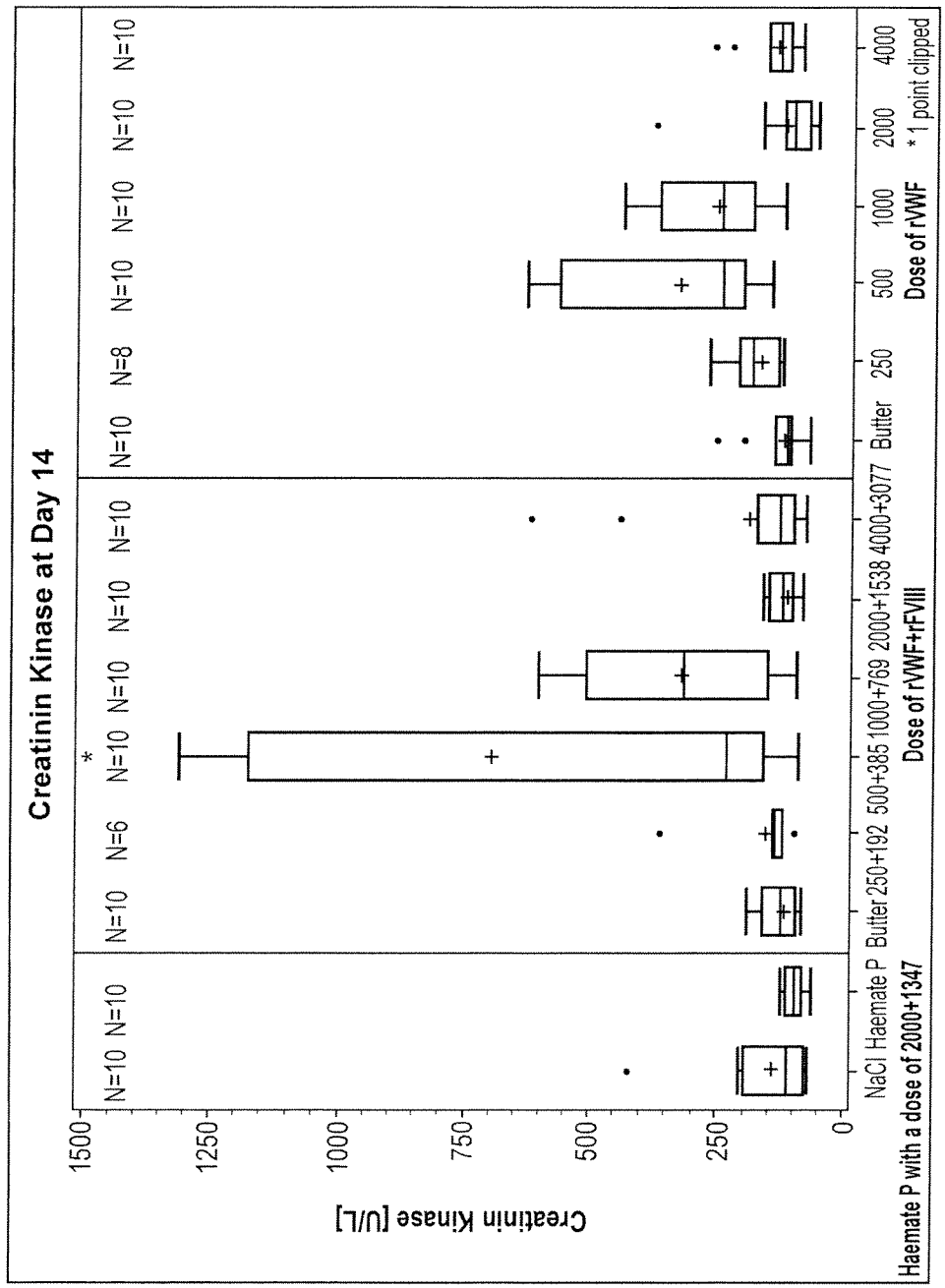
Figure 22:
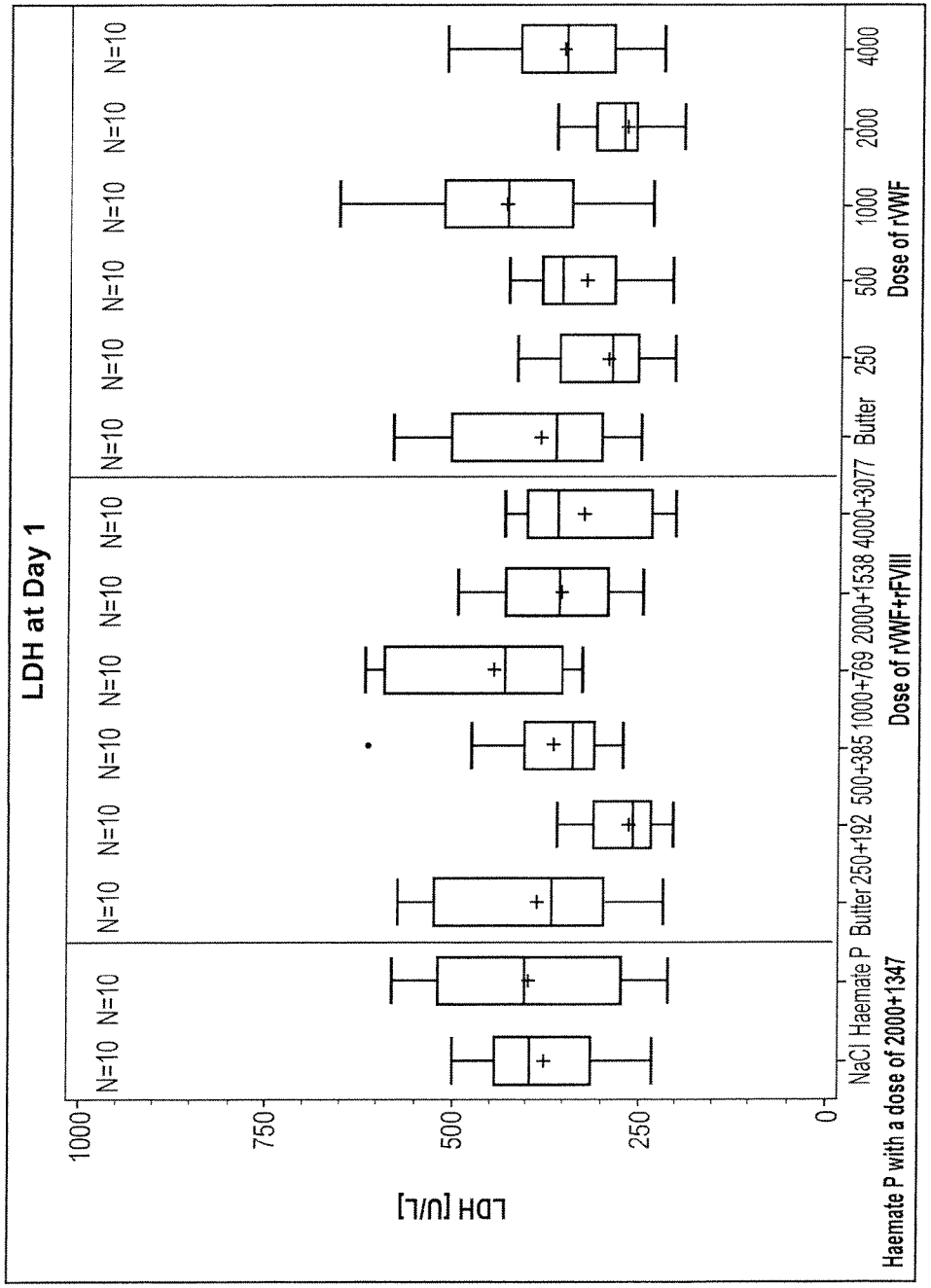
Figure 23:
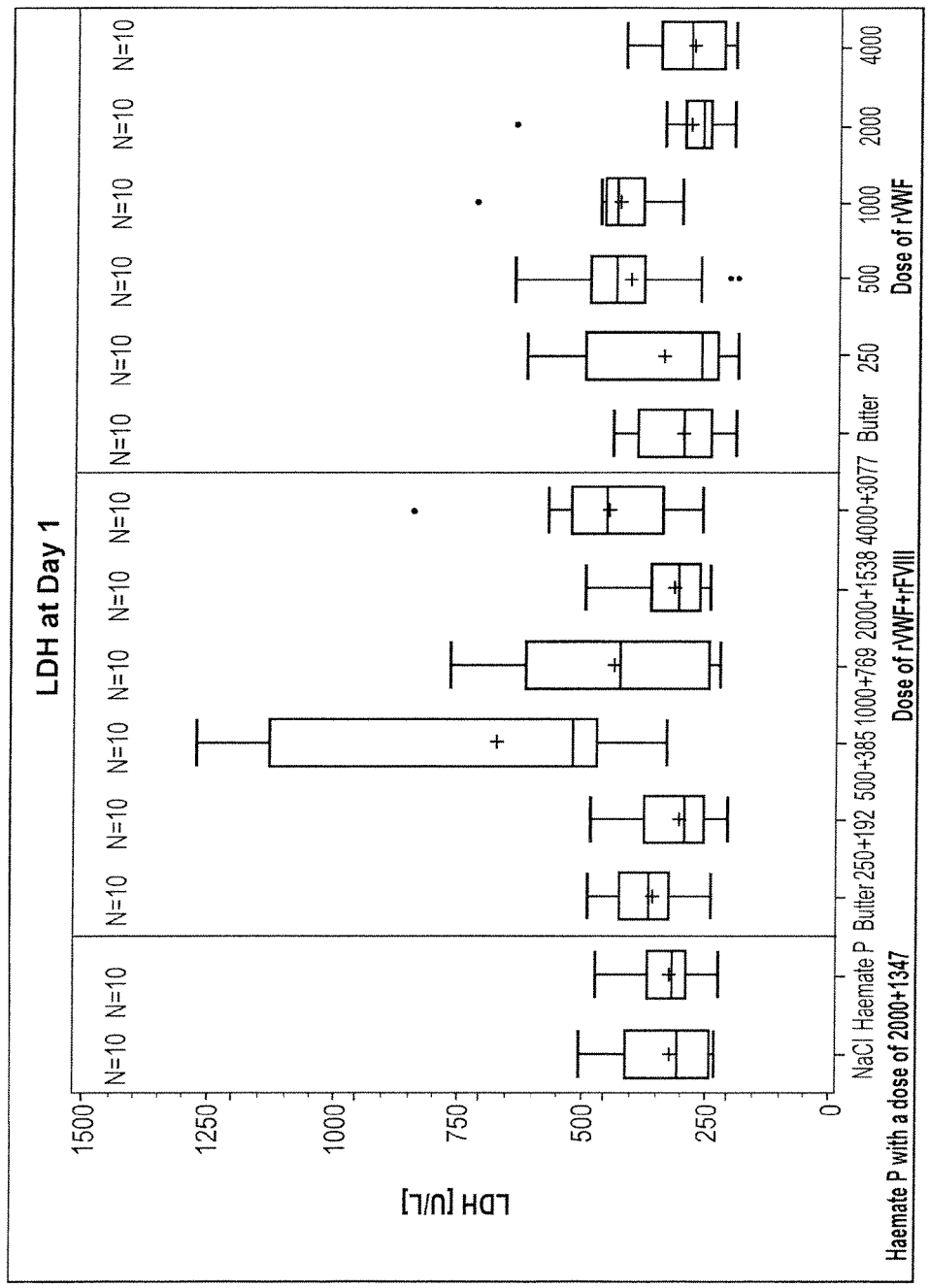
Figure 24:
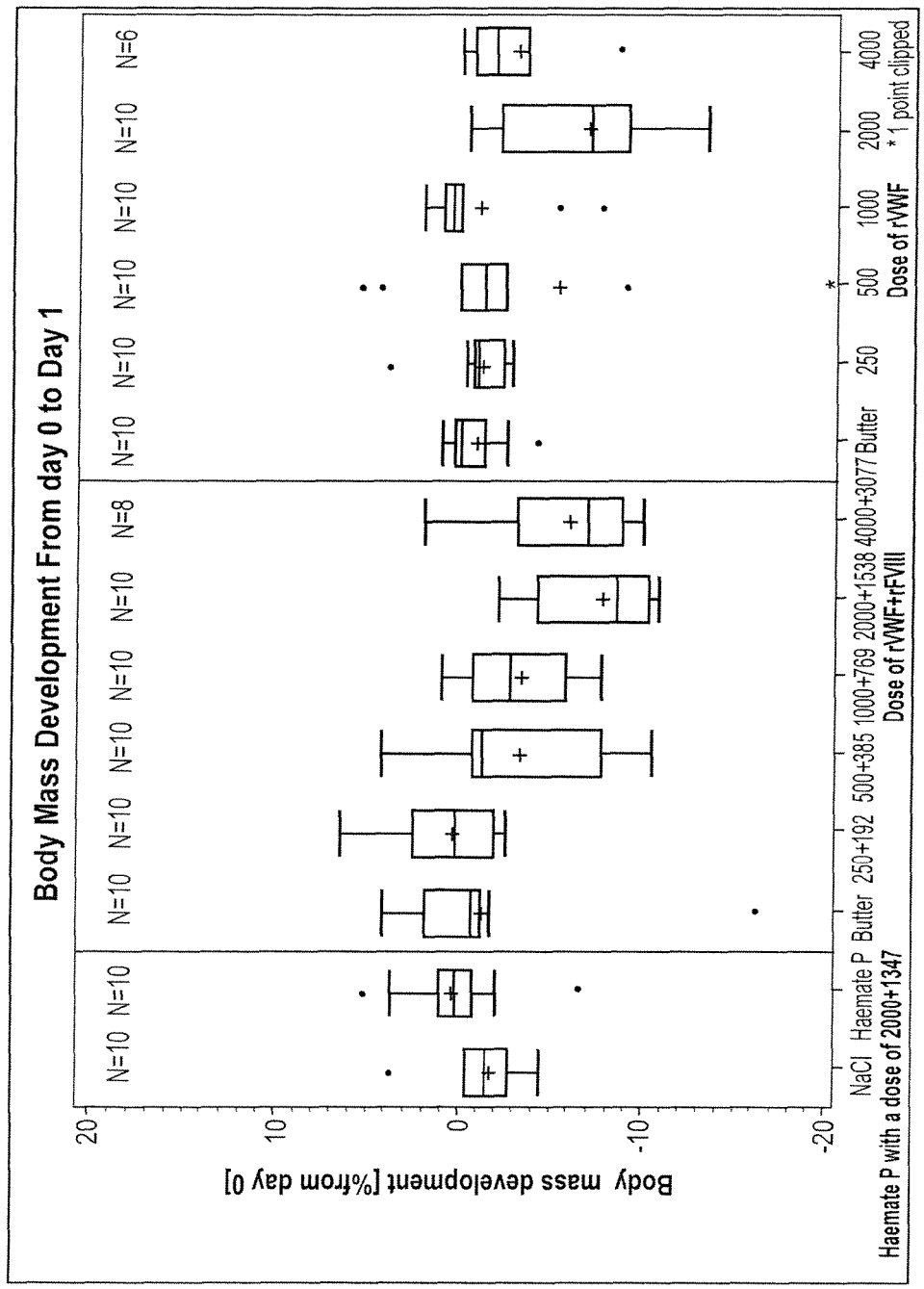
FIGS. 24-26 illustrate changes in body mass over the term of the study for ADAMTS13 deficient mice. Details of the analysis are described in more detail in the Examples.
Figure 25:
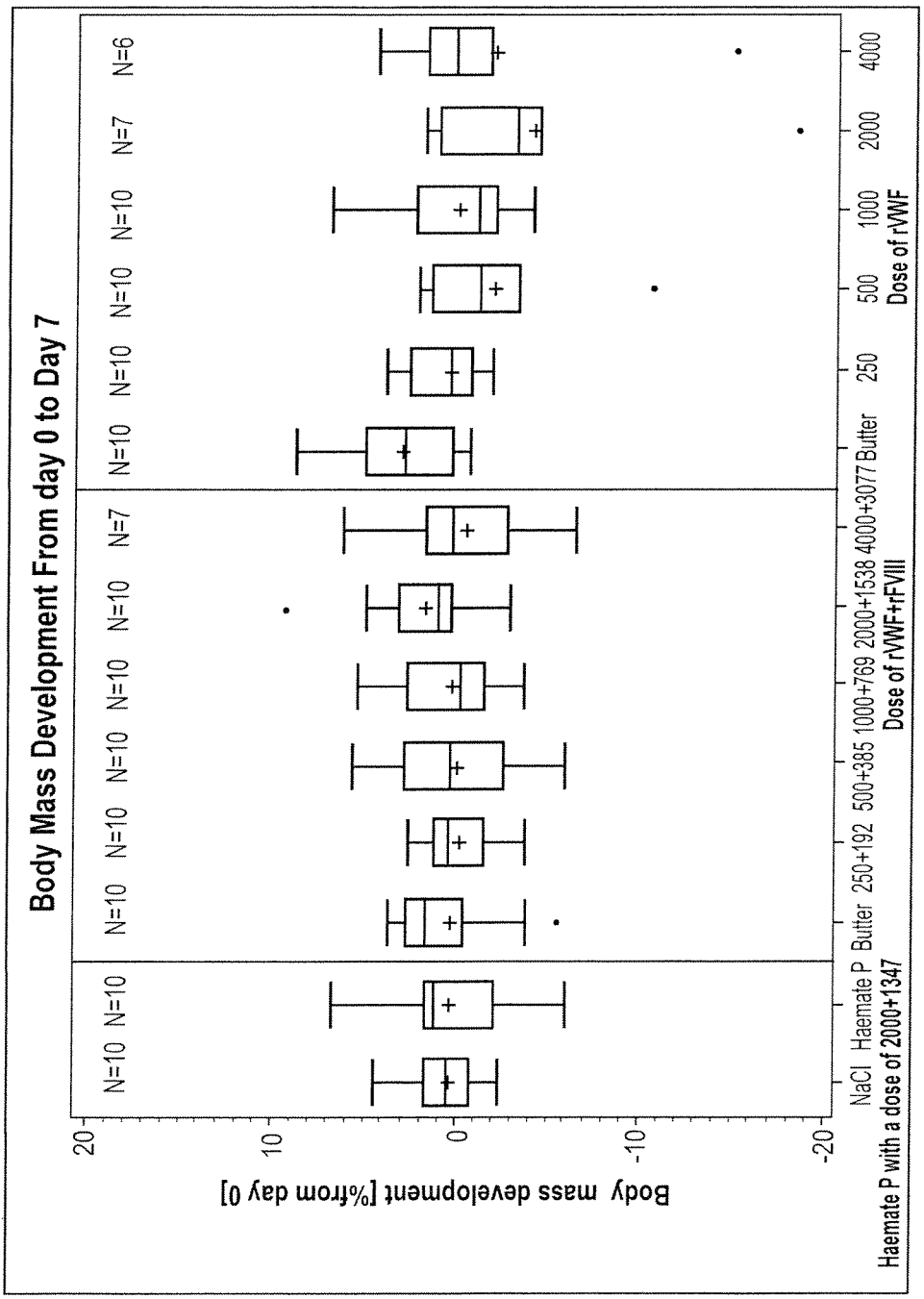
Figure 26:
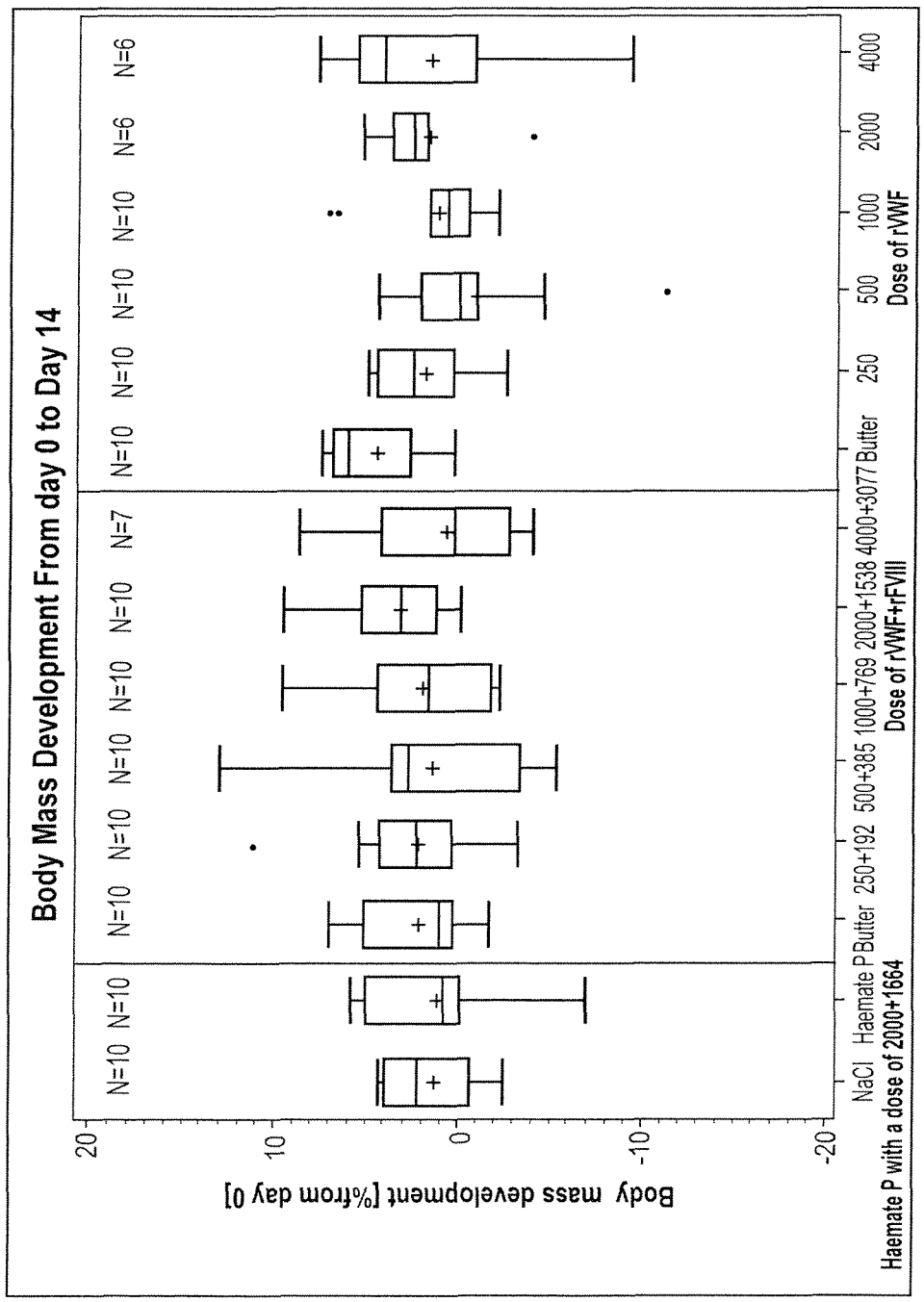
Figure 27:
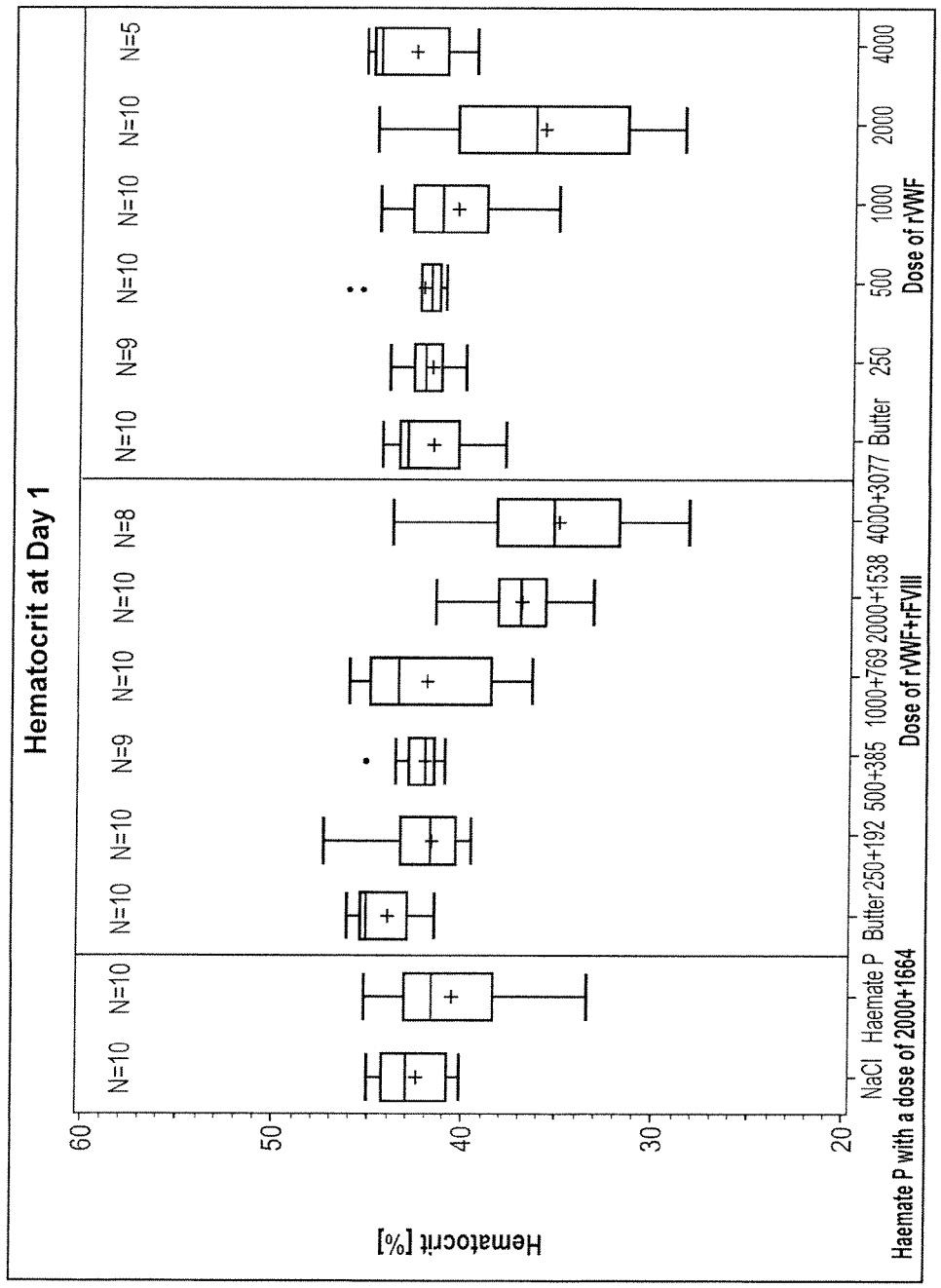
FIGS. 27-32 show data for hematocrit, platelet count, and lactose dehydrogenase (LDH) over the term of the study for ADAMTS13 deficient mice. Details of the analysis are described in more detail in the Examples.
Figure 28:
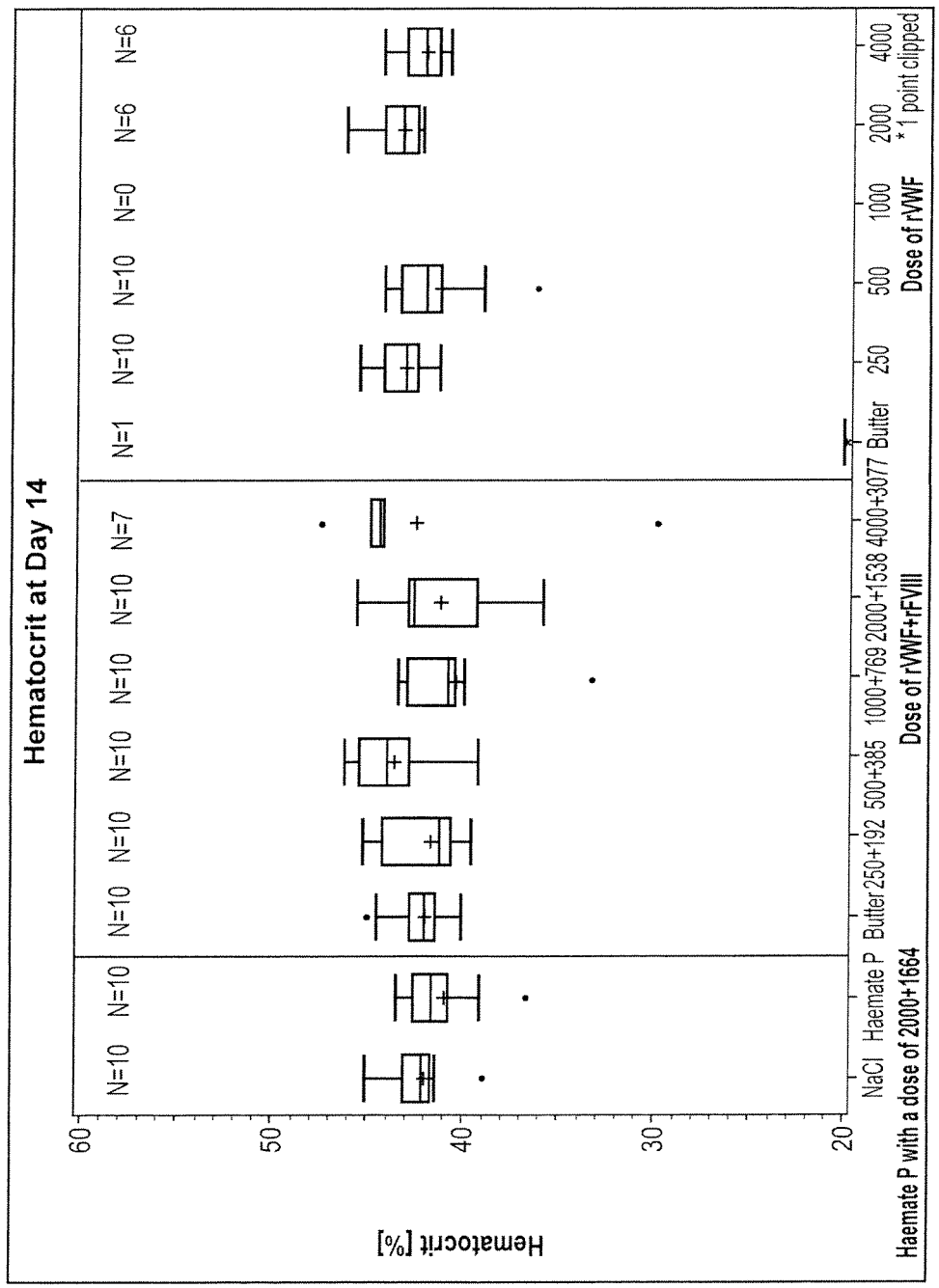
Figure 29:
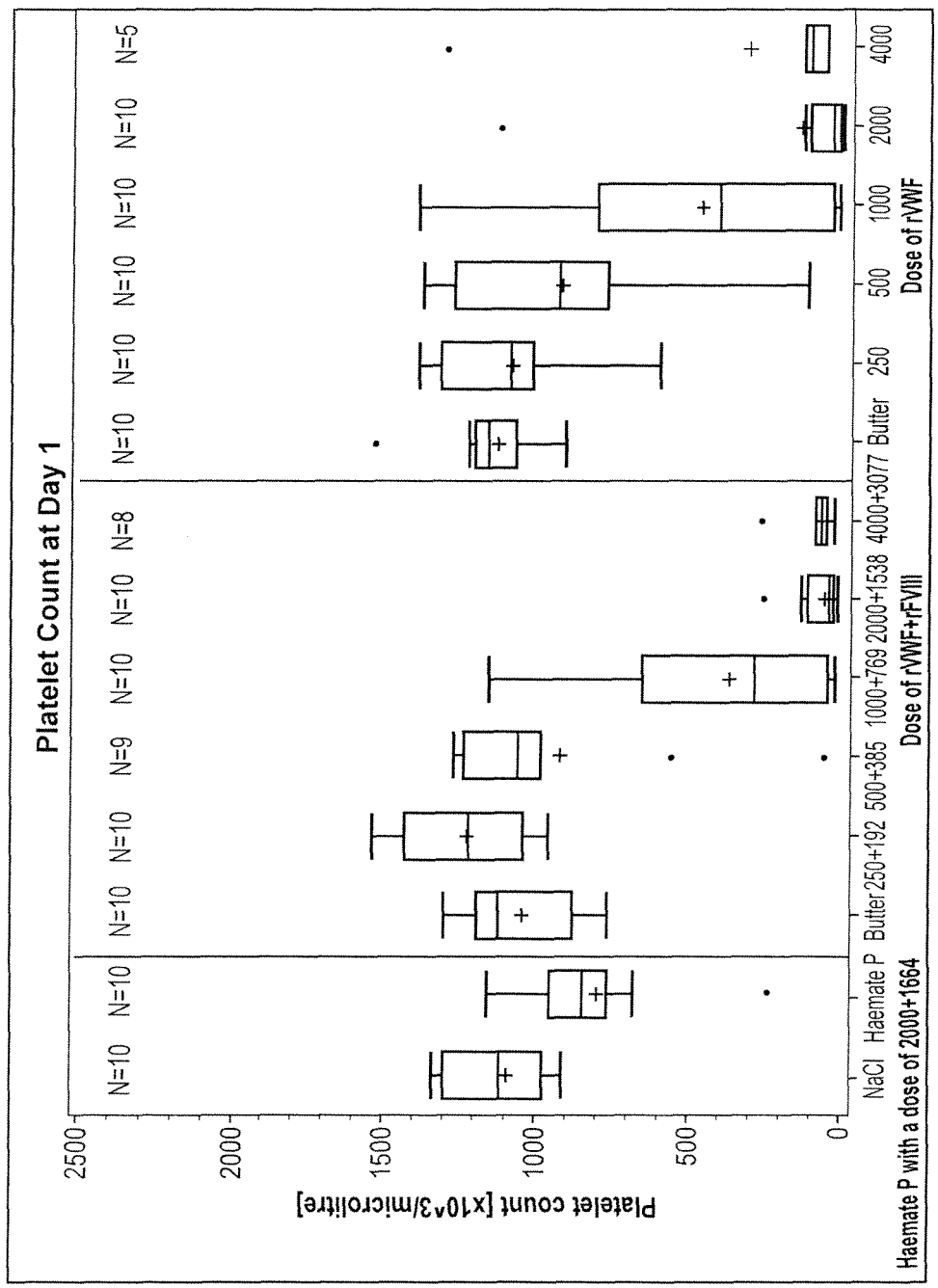
Figure 30:
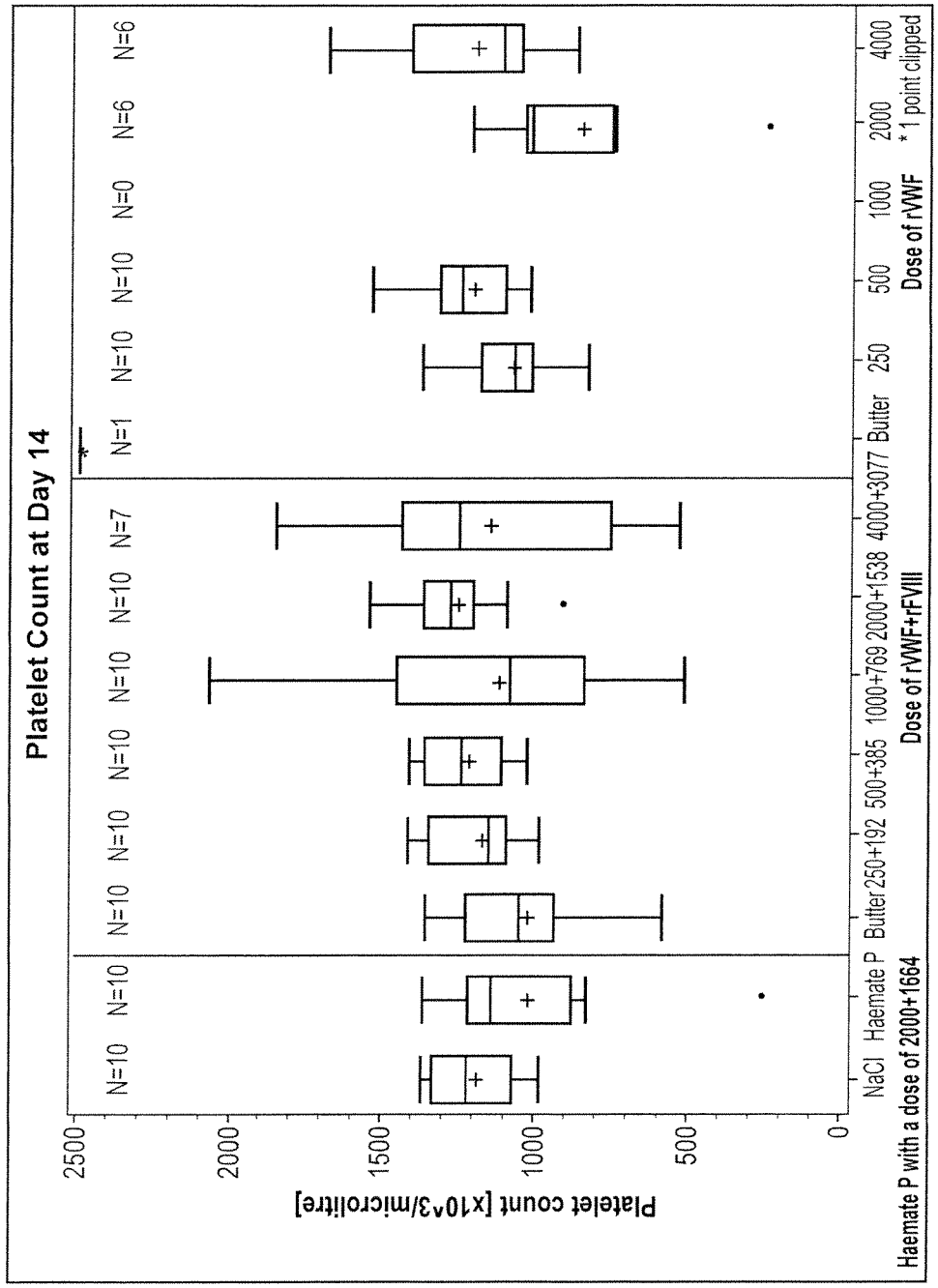
Figure 31:
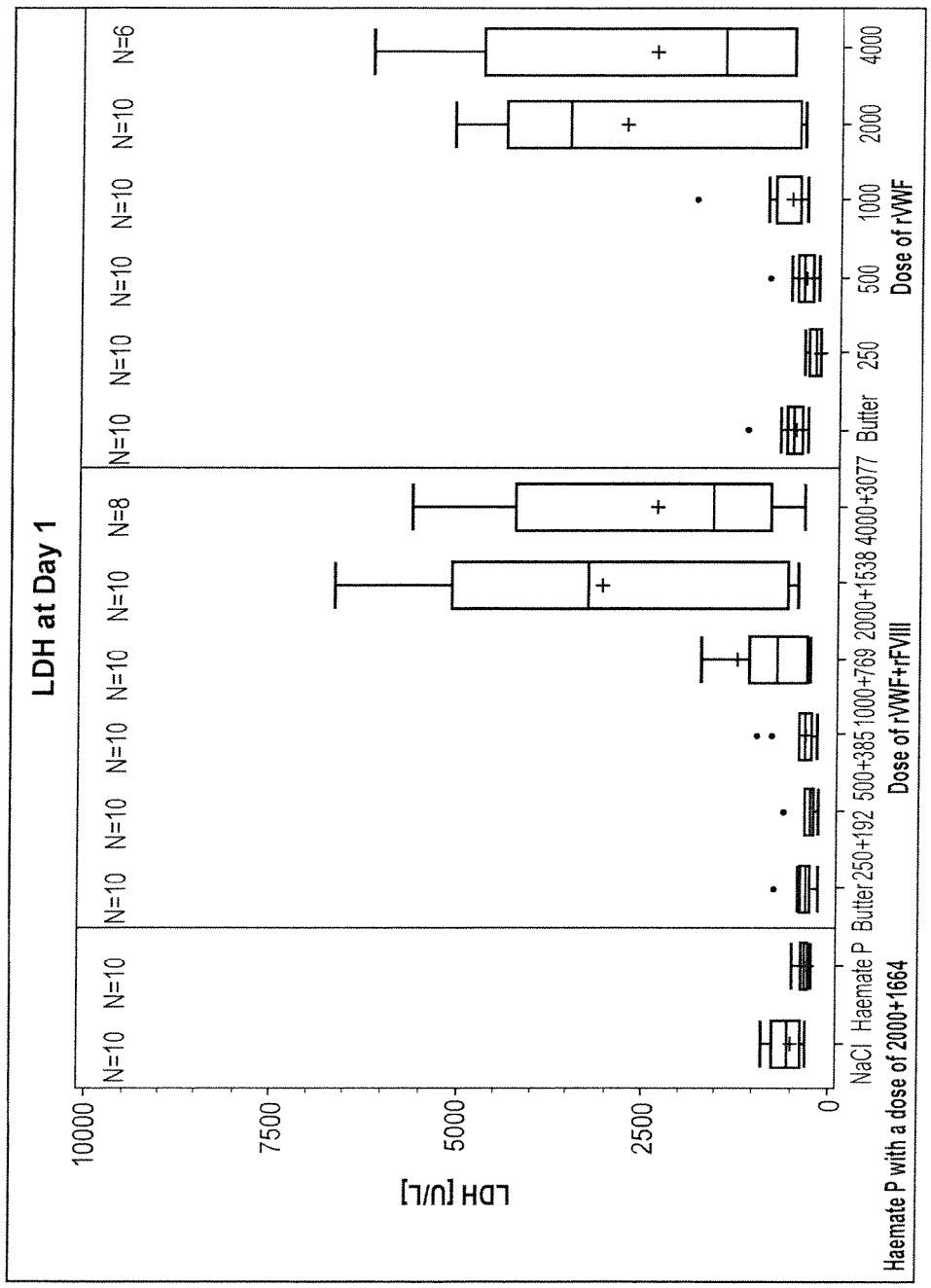
Figure 32:
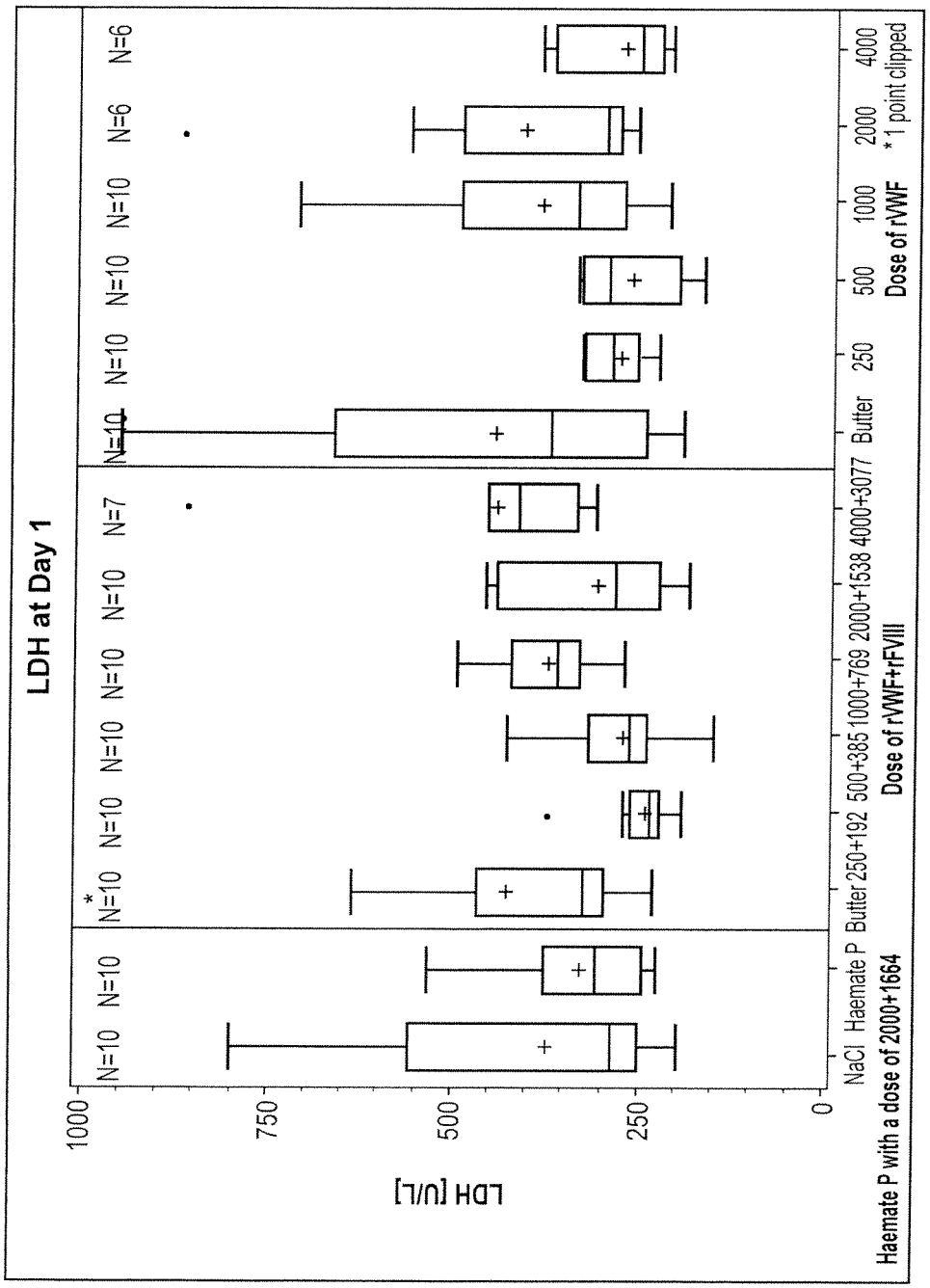

The change in body mass between study day 0 and study days 1, 7 and 14 (as Δ% of body mass at day 0) were visualized using box plots grouped by item and dose. Male and female animals were combined for these box plots (FIGS. 2-4). A comparison of body mass development is also shown in Table 6.

TABLE 6

Summary of body mass analysis

| Item | Dose of VWF:RCo [U/kg] | Dose of FVIII [IU/kg] | Sex | Day 0 to Day 1 | | | Day 0 to Day 7/8 | | | Day 0 to Day 14 | | |
|---|---|---|---|---|---|---|---|---|---|---|---|---|
| | | | | N | Mean | 95% CI for mean | N | Mean | 95% CI for mean | N | Mean | 95% CI for mean |
| NaCl | 0 | 0 | Female | 10 | 1.3% | −0.7% to 2.9% | 5 | 2.8% | −2.2% to 6.5% | 5 | 4.5% | −5.4% to 7.6% |
| | | | Male | 10 | −0.2% | −1.1% to 0.9% | 5 | 5.4% | 2.7% to 8.9% | 5 | 10.2% | 1.6% to 12.9% |
| | | | Pooled | 20 | 0.6% | −0.3% to 1.5% | 10 | 4.1% | 2.0% to 5.7% | 10 | 7.3% | 5.1% to 9.5% |
| HAEMATE ® P | 2000 | 1347 | Female | 10 | −3.1% | −4.1% to −2.1% | 5 | −1.2% | −7.1% to 0.5% | 5 | 3.3% | −15.4% to 10.5% |
| | | | Male | 10 | 1.0% | −1.5% to 12.3% | 5 | 1.1% | −1.7% to 6.1% | 5 | 6.0% | 3.7% to 13.0% |
| | | | Pooled | 20 | −1.1% | −2.3% to 1.8% | 10 | −0.0% | −1.5% to 2.0% | 10 | 4.7% | −1.1% to 9.5% |
| rVWF buffer | 0 | 0 | Female | 10 | 2.8% | 0.8% to 5.8% | 5 | 4.4% | 2.1% to 6.3% | 5 | 4.6% | 2.1% to 10.4% |
| | | | Male | 10 | −1.8% | −5.1% to −0.2% | 5 | 2.3% | −40.4% to 6.3% | 5 | 6.0% | −7.6% to 12.1% |
| | | | Pooled | 20 | 0.5% | −0.9% to 1.9% | 10 | 3.3% | −4.0% to 5.1% | 10 | 5.3% | 1.1% to 8.4% |
| rVWF + rFVIII buffer | 0 | 0 | Female | 10 | 1.6% | −0.2% to 2.6% | 5 | 0.0% | −15.1% to 2.7% | 5 | 1.5% | −2.3% to 2.9% |
| | | | Male | 10 | 0.4% | −0.2% to 1.3% | 5 | 2.5% | 0.4% to 4.5% | 5 | 8.9% | −5.1% to 12.1% |
| | | | Pooled | 20 | 1.0% | −0.3% to 1.6% | 10 | 1.3% | −1.2% to 2.5% | 10 | 5.2% | 3.8% to 7.5% |
| rVWF | 250 | 0 | Female | 10 | −2.1% | −5.2% to 3.3% | 5 | −2.3% | −5.5% to −0.5% | 5 | 2.3% | −14.0% to 12.4% |
| | | | Male | 10 | −2.2% | −3.7% to −0.7% | 5 | 1.4% | −8.0% to 6.2% | 5 | 5.6% | 1.4% to 16.8% |
| | | | Pooled | 20 | −2.2% | −3.8% to 0.0% | 10 | −0.4% | −2.3% to 2.2% | 10 | 3.9% | −1.5% to 7.8% |
| | 500 | 0 | Female | 5 | −0.1% | −2.5% to 9.1% | 5 | −2.3% | −4.0% to 3.7% | 5 | 0.4% | −1.9% to 9.2% |
| | | | Male | 5 | 0.6% | −10.2% to 28.3% | 5 | 1.9% | −1.7% to 5.5% | 5 | 8.3% | −2.6% to 12.7% |
| | | | Pooled | 10 | 0.2% | −4.1% to 8.0% | 10 | −0.2% | −1.4% to 1.3% | 10 | 4.3% | 2.7% to 6.6% |
| | 1000 | 0 | Female | 10 | −0.2% | −1.5% to 0.9% | 5 | −1.3% | −4.8% to 12.4% | 5 | 2.1% | −1.1% to 4.7% |
| | | | Male | 10 | −0.5% | −1.3% to 0.2% | 5 | 1.0% | −3.4% to 5.2% | 5 | 8.1% | 0.5% to 12.1% |
| | | | Pooled | 20 | −0.3% | −1.0% to 0.3% | 10 | −0.2% | −2.2% to 1.9% | 10 | 5.1% | 3.3% to 7.4% |
| | 2000 | 0 | Female | 10 | 0.4% | −2.1% to 3.2% | 5 | 1.5% | −5.3% to 7.1% | 5 | 6.5% | −0.7% to 17.2% |
| | | | Male | 10 | 0.2% | −0.6% to 0.8% | 5 | 5.3% | 3.7% to 10.1% | 5 | 10.8% | 8.3% to 13.1% |
| | | | Pooled | 20 | 0.3% | −0.8% to 1.5% | 10 | 3.4% | 0.5% to 5.3% | 10 | 8.7% | 4.5% to 11.0% |
| | 4000 | 0 | Female | 10 | 0.3% | −1.1% to 1.7% | 5 | −0.1% | −3.2% to 4.0% | 5 | 5.6% | −3.6% to 13.5% |
| | | | Male | 10 | −4.1% | −6.5% to −2.6% | 5 | 1.0% | −0.7% to 3.7% | 5 | 4.4% | 1.0% to 19.2% |
| | | | Pooled | 20 | −1.9% | −3.1% to −1.0% | 10 | 0.4% | −1.1% to 2.0% | 10 | 5.0% | 2.0% to 8.6% |
| rVWF + rFVIII | 250 | 192 | Female | 10 | −2.5% | −3.5% to −1.0% | 5 | −0.8% | −13.0% to 29.3% | 5 | 3.1% | −8.6% to 32.4% |
| | | | Male | 10 | −1.3% | −4.0% to 0.7% | 5 | 5.7% | −20.3% to 12.5% | 5 | 10.3% | −3.5% to 15.9% |
| | | | Pooled | 20 | −1.9% | −3.1% to −0.7% | 10 | 2.4% | −5.2% to 8.9% | 10 | 6.7% | −0.2% to 12.8% |
| | 500 | 385 | Female | 5 | 0.4% | −5.8% to 6.3% | 5 | 0.4% | −4.6% to 6.8% | 5 | 3.5% | −0.6% to 13.2% |
| | | | Male | 5 | 0.1% | −1.6% to 1.9% | 5 | 1.1% | −1.3% to 33.2% | 5 | 6.0% | 2.1% to 14.5% |
| | | | Pooled | 10 | 0.4% | −2.2% to 2.9% | 10 | 0.7% | −1.7% to 4.0% | 10 | 4.8% | 2.2% to 9.2% |
| | 1000 | 769 | Female | 10 | −0.3% | −1.3% to 0.8% | 5 | −1.7% | −4.6% to 2.7% | 5 | 0.3% | −17.5% to 7.0% |
| | | | Male | 10 | −0.4% | −1.3% to 0.6% | 5 | 0.2% | −4.9% to 2.6% | 5 | 5.0% | 1.7% to 11.4% |
| | | | Pooled | 20 | −0.3% | −0.9% to 0.3% | 10 | −0.7% | −2.4% to 0.8% | 10 | 2.6% | −2.8% to 5.2% |

TABLE 6-continued

Summary of body mass analysis

| Item | Dose of VWF:RCo [U/kg] | Dose of FVIII [IU/kg] | Sex | Day 0 to Day 1 | | | Day 0 to Day 7/8 | | | Day 0 to Day 14 | | |
|---|---|---|---|---|---|---|---|---|---|---|---|---|
| | | | | N | Mean | 95% CI for mean | N | Mean | 95% CI for mean | N | Mean | 95% CI for mean |
| | 2000 | 1538 | Female | 10 | −2.0% | −3.2% to −1.1% | 5 | 1.5% | −0.3% to 6.8% | 5 | 4.2% | 3.4% to 6.6% |
| | | | Male | 10 | −1.2% | −3.2% to 0.6% | 5 | 5.2% | 2.2% to 13.6% | 5 | 11.2% | 2.7% to 23.6% |
| | | | Pooled | 20 | −1.6% | −2.6% to −0.6% | 10 | 3.4% | 1.8% to 6.3% | 10 | 7.7% | 5.4% to 14.4% |
| | 4000 | 3077 | Female | 10 | −2.7% | −4.6% to −1.0% | 5 | 0.7% | −1.2% to 3.1% | 5 | 3.5% | 2.2% to 5.9% |
| | | | Male | 10 | −3.2% | −5.5% to −1.9% | 5 | 2.5% | 0.3% to 5.6% | 5 | 8.4% | 5.4% to 19.6% |
| | | | Pooled | 20 | −2.9% | −4.1% to −1.9% | 10 | 1.6% | 0.4% to 2.9% | 10 | 6.0% | 4.8% to 8.3% |

There were statistically significant (at the multiplicity adjusted 5% level) larger decreases in body mass from day 0 to day 1 with doses of 4000+3077 (mean Δ% of −2.9%) and with 2000+1538 (mean Δ% of −1.6%) than with the corresponding buffer (mean Δ% of 1.0%). There was also a statistically significant larger decrease in body mass development with a dose of 250+192 (mean Δ% of −1.9%) than with the corresponding buffer (multiplicity adjusted two-sided p-value=0.0033).

There were no statistically significant differences (at the multiplicity adjusted 5% level) in body mass development from day 0 to day 14 between different doses of rVWF+rFVIII and the corresponding buffer because all two-sided p-values adjusted for multiplicity were greater than 5%.

Estimation of the minimum detectable dose for changes in body mass from day 0 to day 1 in a step-down manner stopped at the contrast for the lowest dose investigated where the two-sided p-value was still below 5%. The minimum detectable dose was therefore 250 U/kg VWF:RCo+192 IU/kg FVIII.

Estimation of the minimum detectable dose for changes in body mass from day 0 to day 14 in a step-down manner stopped at the contrast for the highest dose. The two-sided p-value for the highest dose was 0.8476, which was above 5%, and no further contrasts were investigated. There was no minimum detectable dose for changes in body mass from day 0 to day 14 with rVWF+rFVIII and the highest dose investigated could be regarded as the NOAEL dose.

There were no statistically significant differences (at the multiplicity adjusted 5% level) in body mass development from day 0 to day 1 (as Δ% from day 0) between different doses of rVWF and the corresponding buffer because all two-sided p-values adjusted for multiplicity were greater than 5%. Comparison of the highest dose (mean Δ % of −1.9%) and the lowest dose (mean Δ% of −2.2) of rVWF with the corresponding buffer (mean Δ% of 0.5%) resulted in unadjusted two-sided p-values below 5% whereas the multiplicity-adjusted two-sided p-values were above 5%. These significant results could therefore have occurred by chance with a probability of more than 5% if the null hypotheses were true.

There were no statistically significant differences (at the multiplicity adjusted 5% level) in body mass development from day 0 to day 14 (as Δ% from day 0) between different doses of rVWF and the corresponding buffer because all two-sided p-values adjusted for multiplicity were greater than 5%.

Estimation of the minimum detectable dose for changes in body mass from day 0 to day 1 as well as for changes from day 0 to day 14 in a step-down manner stopped at the contrast for the highest dose. The two-sided p-values for the highest dose were above 5% and no further contrasts were investigated. There was no minimum detectable dose for changes in body mass from day 0 to day 1 or for changes from day 0 to day 14 with rVWF and the highest dose investigated could be regarded as the NOAEL dose.

Mean body mass development from day 0 to day 1 was −1.1% (95% CI: −2.3% to 1.8%) with HAEMATE® P and −1.6% (95% CI: −2.6% to −0.6%) with the corresponding dose of rVWF+rFVIII. This difference was not statistically significant at the 5% level (two-sided p-value=0.6931).

Mean body mass development from day 0 to day 14 was 4.7% (95% CI: −1.1% to 7.7%) with HAEMATE® P and 7.7% (95% CI: 5.4% to 14.4%) with the corresponding dose of rVWF+rFVIII. This difference was not statistically significant at the 5% level (two-sided p-value=0.2289).

5. Hematological and Serological Variables

Hematological and serological variables (hematocrit, platelet count, LDH, CK) at study day 1 and study day 14 were visualized using box plots grouped by item and dose. Male and female animals were combined for these figures.

Hematological and serological variables at study day 1 and study day 14 were summarized using means and coefficient of variations (CV) grouped by item and dose. These statistics were provided for male and female animals separately as well as for male and female animals combined.

A comparison of hematocrit, platelet count, LDH and CK indicated as box plots is given in FIGS. 5-12 and Tables 7-10.

TABLE 7

Summary of hematocrit data

| Item | Dose of VWF:RCo [U/kg] | Dose of FVIII [IU/kg] | Sex | Hematocrit (%) | | | | | |
|---|---|---|---|---|---|---|---|---|---|
| | | | | Study day | | | | | |
| | | | | 1 | | | 14 | | |
| | | | | N | Mean | CV [%] | N | Mean | CV [%] |
| NaCl | 0 | 0 | Male | 5 | 45.3 | 3.6 | 5 | 43.6 | 3.9 |
| | | | Female | 5 | 42.6 | 2.9 | 5 | 43.8 | 2.1 |
| | | | Pooled | 10 | 44.0 | 4.4 | 10 | 43.7 | 3.0 |

TABLE 7-continued

Summary of hematocrit data

| Hematocrit (%) | | | | Study day | | | | | |
|---|---|---|---|---|---|---|---|---|---|
| | | | | 1 | | | 14 | | |
| Item | Dose of VWF:RCo [U/kg] | Dose of FVIII [IU/kg] | Sex | N | Mean | CV [%] | N | Mean | CV [%] |
| HAEMATE ® P | 2000 | 1347 | Male | 5 | 44.1 | 4.6 | 5 | 43.0 | 3.1 |
| | | | Female | 5 | 42.5 | 4.9 | 5 | 42.8 | 3.3 |
| | | | Pooled | 10 | 43.3 | 4.9 | 10 | 42.9 | 3.1 |
| rVWF buffer | 0 | 0 | Male | 5 | 44.2 | 2.2 | 5 | 43.7 | 2.3 |
| | | | Female | 5 | 40.8 | 2.7 | 5 | 42.7 | 2.2 |
| | | | Pooled | 10 | 42.5 | 4.8 | 10 | 43.2 | 2.5 |
| rVWF + rFVIII buffer | 0 | 0 | Male | 5 | 39.7 | 16.5 | 5 | 44.8 | 4.2 |
| | | | Female | 5 | 39.9 | 10.8 | 5 | 43.9 | 4.4 |
| | | | Pooled | 10 | 39.8 | 13.2 | 10 | 44.4 | 4.2 |
| rVWF | 250 | 0 | Male | 5 | 44.4 | 3.4 | 3 | 45.9 | 3.9 |
| | | | Female | 4 | 43.6 | 2.5 | 4 | 52.5 | 5.4 |
| | | | Pooled | 9 | 44.1 | 3.1 | 7 | 49.7 | 8.4 |
| | 500 | 0 | Male | 5 | 41.7 | 3.7 | 5 | 46.4 | 3.9 |
| | | | Female | 5 | 44.0 | 1.4 | 5 | 48.3 | 7.0 |
| | | | Pooled | 10 | 42.8 | 3.8 | 10 | 47.4 | 5.8 |
| | 1000 | 0 | Male | 5 | 41.8 | 26.1 | 5 | 42.9 | 5.5 |
| | | | Female | 5 | 42.7 | 3.1 | 5 | 43.7 | 4.4 |
| | | | Pooled | 10 | 42.2 | 17.4 | 10 | 43.3 | 4.8 |
| | 2000 | 0 | Male | 5 | 43.6 | 5.3 | 5 | 43.1 | 4.3 |
| | | | Female | 5 | 41.9 | 4.0 | 5 | 44.3 | 1.5 |
| | | | Pooled | 10 | 42.8 | 4.9 | 10 | 43.7 | 3.3 |
| | 4000 | 0 | Male | 5 | 40.5 | 7.3 | 4 | 43.6 | 3.5 |
| | | | Female | 5 | 40.7 | 4.9 | 5 | 43.4 | 3.3 |
| | | | Pooled | 10 | 40.6 | 5.8 | 9 | 43.5 | 3.2 |
| rVWF + rFVIII | 250 | 192 | Male | 5 | 43.0 | 5.9 | 4 | 38.7 | 13.9 |
| | | | Female | 5 | 42.0 | 5.9 | 5 | 46.6 | 11.0 |
| | | | Pooled | 10 | 42.5 | 5.7 | 9 | 43.1 | 14.9 |
| | 500 | 385 | Male | 5 | 41.6 | 5.3 | 4 | 33.8 | 51.9 |
| | | | Female | 5 | 42.4 | 4.1 | 4 | 43.6 | 24.9 |
| | | | Pooled | 10 | 42.0 | 4.6 | 8 | 38.7 | 37.4 |
| | 1000 | 769 | Male | 5 | 44.5 | 2.4 | 5 | 44.5 | 4.0 |
| | | | Female | 5 | 43.2 | 3.3 | 5 | 43.9 | 2.8 |
| | | | Pooled | 10 | 43.9 | 3.1 | 10 | 44.2 | 3.4 |
| | 2000 | 1538 | Male | 5 | 42.9 | 5.5 | 5 | 43.3 | 7.3 |
| | | | Female | 5 | 41.6 | 4.0 | 5 | 43.2 | 1.7 |
| | | | Pooled | 10 | 42.3 | 4.9 | 10 | 43.2 | 5.0 |
| | 4000 | 3077 | Male | 5 | 41.5 | 3.4 | 5 | 45.0 | 3.5 |
| | | | Female | 5 | 36.7 | 10.7 | 5 | 44.1 | 1.8 |
| | | | Pooled | 10 | 39.1 | 9.6 | 10 | 44.6 | 2.9 |

TABLE 8

Summary of platelet counts

| Platelet count (×10^3/μL) | | | | Study day | | | | | |
|---|---|---|---|---|---|---|---|---|---|
| | | | | 1 | | | 14 | | |
| Item | Dose of VWF:RCo [U/kg] | Dose of FVIII [IU/kg] | Sex | N | Mean | CV [%] | N | Mean | CV [%] |
| NaCl | 0 | 0 | Male | 5 | 1203 | 15 | 5 | 1302 | 14 |
| | | | Female | 5 | 1252 | 8 | 5 | 1323 | 5 |
| | | | Pooled | 10 | 1227 | 11 | 10 | 1312 | 10 |
| HAEMATE ® P | 2000 | 1347 | Male | 5 | 1280 | 6 | 5 | 1380 | 9 |
| | | | Female | 5 | 1136 | 7 | 5 | 1146 | 17 |
| | | | Pooled | 10 | 1208 | 9 | 10 | 1263 | 15 |
| rVWF buffer | 0 | 0 | Male | 5 | 1367 | 3 | 5 | 1361 | 3 |
| | | | Female | 5 | 1174 | 8 | 5 | 1347 | 5 |
| | | | Pooled | 10 | 1270 | 10 | 10 | 1354 | 4 |
| rVWF + rFVIII buffer | 0 | 0 | Male | 5 | 1242 | 10 | 5 | 1257 | 13 |
| | | | Female | 5 | 1088 | 17 | 5 | 1067 | 32 |
| | | | Pooled | 10 | 1165 | 15 | 10 | 1162 | 24 |
| rVWF | 250 | 0 | Male | 5 | 1202 | 18 | 3 | 1433 | 10 |
| | | | Female | 4 | 1114 | 6 | 4 | 1080 | 17 |
| | | | Pooled | 9 | 1163 | 14 | 7 | 1231 | 20 |
| | 500 | 0 | Male | 5 | 1202 | 29 | 5 | 1210 | 16 |
| | | | Female | 5 | 1189 | 5 | 5 | 1084 | 25 |
| | | | Pooled | 10 | 1196 | 20 | 10 | 1147 | 20 |

TABLE 8-continued

Summary of platelet counts

| Platelet count (x10^3/μL) | | | | Study day | | | | |
|---|---|---|---|---|---|---|---|---|
| | Dose of | Dose of | | 1 | | | 14 | |
| Item | VWF:RCo [U/kg] | FVIII [IU/kg] | Sex | N | Mean | CV [%] | N | Mean | CV [%] |
| | 1000 | 0 | Male | 5 | 1059 | 1 | 5 | 1356 | 5 |
| | | | Female | 5 | 876 | 30 | 5 | 1365 | 5 |
| | | | Pooled | 10 | 967 | 21 | 10 | 1361 | 5 |
| | 2000 | 0 | Male | 5 | 511 | 47 | 5 | 1314 | 2 |
| | | | Female | 5 | 801 | 42 | 5 | 1336 | 8 |
| | | | Pooled | 10 | 656 | 48 | 10 | 1325 | 6 |
| | 4000 | 0 | Male | 5 | 93 | 21 | 4 | 1404 | 15 |
| | | | Female | 5 | 334 | 107 | 5 | 1154 | 31 |
| | | | Pooled | 10 | 214 | 127 | 9 | 1265 | 25 |
| rVWF + rFVIII | 250 | 192 | Male | 5 | 1279 | 9 | 4 | 1202 | 50 |
| | | | Female | 5 | 1180 | 3 | 5 | 963 | 23 |
| | | | Pooled | 10 | 1229 | 8 | 9 | 1069 | 39 |
| | 500 | 385 | Male | 5 | 1270 | 11 | 4 | 818 | 68 |
| | | | Female | 5 | 1081 | 9 | 4 | 951 | 53 |
| | | | Pooled | 10 | 1175 | 13 | 8 | 884 | 56 |
| | 1000 | 769 | Male | 5 | 1054 | 18 | 5 | 1427 | 8 |
| | | | Female | 5 | 1132 | 11 | 5 | 1197 | 4 |
| | | | Pooled | 10 | 1093 | 15 | 10 | 1312 | 11 |
| | 2000 | 1538 | Male | 5 | 284 | 57 | 5 | 1377 | 9 |
| | | | Female | 5 | 545 | 41 | 5 | 1171 | 6 |
| | | | Pooled | 10 | 414 | 55 | 10 | 1274 | 11 |
| | 4000 | 3077 | Male | 5 | 93 | 11 | 5 | 1335 | 24 |
| | | | Female | 5 | 123 | 14 | 5 | 1366 | 8 |
| | | | Pooled | 10 | 108 | 19 | 10 | 1350 | 16 |

TABLE 9

Summary of creatinine kinase

| Creatinine Kinase (U/L) | | | | Study day | | | | |
|---|---|---|---|---|---|---|---|---|
| | Dose of | Dose of | | 1 | | | 14 | |
| Item | VWF:RCo [U/kg] | FVIII [IU/kg] | Sex | N | Mean | CV [%] | N | Mean | CV [%] |
| NaCl | 0 | 0 | Male | 5 | 144 | 21 | 5 | 183 | 27 |
| | | | Female | 5 | 106 | 40 | 5 | 153 | 53 |
| | | | Pooled | 10 | 125 | 32 | 10 | 168 | 39 |
| HAEMATE ® P | 2000 | 1347 | Male | 5 | 159 | 28 | 5 | 147 | 8.5 |
| | | | Female | 5 | 99 | 36 | 5 | 134 | 30 |
| | | | Pooled | 10 | 129 | 38 | 10 | 141 | 21 |
| rVWF buffer | 0 | 0 | Male | 5 | 164 | 35 | 5 | 144 | 28 |
| | | | Female | 5 | 196 | 45 | 5 | 116 | 29 |
| | | | Pooled | 10 | 180 | 40 | 10 | 130 | 29 |
| rVWF + rFVIII buffer | 0 | 0 | Male | 5 | 186 | 16 | 5 | 156 | 20 |
| | | | Female | 5 | 126 | 39 | 5 | 136 | 42 |
| | | | Pooled | 10 | 156 | 32 | 10 | 146 | 31 |
| rVWF | 250 | | Male | 5 | 443 | 26 | 3 | 512 | 23 |
| | | | Female | 5 | 181 | 27 | 2 | 768 | 9.2 |
| | | | Pooled | 10 | 312 | 52 | 5 | 614 | 27 |
| | 500 | | Male | 5 | 538 | 23 | 5 | 573 | 42 |
| | | | Female | 5 | 354 | 27 | 3 | 527 | 59 |
| | | | Pooled | 10 | 446 | 32 | 8 | 556 | 44 |
| | 1000 | | Male | 5 | 250 | 68 | 5 | 123 | 19 |
| | | | Female | 5 | 116 | 39 | 5 | 110 | 50 |
| | | | Pooled | 10 | 183 | 75 | 10 | 116 | 35 |
| | 2000 | | Male | 5 | 239 | 29 | 5 | 169 | 22 |
| | | | Female | 5 | 112 | 29 | 5 | 195 | 26 |
| | | | Pooled | 10 | 176 | 48 | 10 | 182 | 24 |
| | 4000 | | Male | 5 | 261 | 36 | 5 | 344 | 45 |
| | | | Female | 5 | 153 | 45 | 5 | 108 | 42 |
| | | | Pooled | 10 | 207 | 46 | 10 | 226 | 73 |
| rVWF + rFVIII | 250 | 192 | Male | 5 | 323 | 38 | 5 | 364 | 65 |
| | | | Female | 5 | 248 | 30 | 3 | 448 | 33 |
| | | | Pooled | 10 | 285 | 36 | 8 | 395 | 51 |
| | 500 | 385 | Male | 5 | 306 | 56 | 3 | 244 | 18 |
| | | | Female | 5 | 273 | 42 | 2 | 301 | 34 |
| | | | Pooled | 10 | 289 | 47 | 5 | 267 | 25 |

TABLE 9-continued

Summary of creatinine kinase

| Creatinine Kinase (U/L) | | | | Study day | | | | |
| --- | --- | --- | --- | --- | --- | --- | --- | --- |
| | Dose of | Dose of | | 1 | | | 14 | |
| Item | VWF:RCo [U/kg] | FVIII [IU/kg] | Sex | N | Mean | CV [%] | N | Mean | CV [%] |
| --- | --- | --- | --- | --- | --- | --- | --- | --- | --- |
| | 1000 | 769 | Male | 5 | 137 | 35 | 5 | 139 | 11 |
| | | | Female | 5 | 92 | 23 | 5 | 90 | 49 |
| | | | Pooled | 10 | 115 | 37 | 10 | 114 | 35 |
| | 2000 | 1538 | Male | 5 | 234 | 44 | 5 | 178 | 14 |
| | | | Female | 5 | 154 | 39 | 5 | 104 | 24 |
| | | | Pooled | 10 | 194 | 46 | 10 | 141 | 32 |
| | 4000 | 3077 | Male | 5 | 293 | 16 | 5 | 224 | 98 |
| | | | Female | 5 | 248 | 15 | 5 | 108 | 19 |
| | | | Pooled | 10 | 271 | 17 | 10 | 166 | 96 |

TABLE 10

Summary of LDH data

| LDH [U/L] | | | | Study day | | | | |
| --- | --- | --- | --- | --- | --- | --- | --- | --- |
| | Dose of | Dose of | | 1 | | | 14 | |
| Item | VWF:RCo [U/kg] | FVIII [IU/kg] | Sex | N | Mean | CV [%] | N | Mean | CV [%] |
| --- | --- | --- | --- | --- | --- | --- | --- | --- | --- |
| NaCl | 0 | 0 | Male | 5 | 257 | 17 | 5 | 329 | 42 |
| | | | Female | 5 | 314 | 37 | 5 | 287 | 56 |
| | | | Pooled | 10 | 285 | 31 | 10 | 308 | 46 |
| HAEMATE ® P | 2000 | 1347 | Male | 5 | 394 | 17 | 5 | 365 | 23 |
| | | | Female | 5 | 427 | 36 | 5 | 357 | 35 |
| | | | Pooled | 10 | 411 | 27 | 10 | 361 | 28 |
| rVWF buffer | 0 | 0 | Male | 5 | 340 | 47 | 5 | 277 | 23 |
| | | | Female | 5 | 353 | 28 | 5 | 280 | 27 |
| | | | Pooled | 10 | 346 | 36 | 10 | 279 | 24 |
| rVWF + rFVIII buffer | 0 | 0 | Male | 5 | 317 | 20 | 5 | 341 | 24 |
| | | | Female | 5 | 298 | 17 | 5 | 418 | 50 |
| | | | Pooled | 10 | 308 | 18 | 10 | 380 | 41 |
| rVWF | 250 | 0 | Male | 5 | 374 | 18 | 3 | 388 | 21 |
| | | | Female | 5 | 239 | 35 | 2 | 306 | 9 |
| | | | Pooled | 10 | 307 | 33 | 5 | 355 | 21 |
| | 500 | 0 | Male | 5 | 432 | 28 | 5 | 329 | 19 |
| | | | Female | 5 | 321 | 41 | 3 | 265 | 20 |
| | | | Pooled | 10 | 377 | 35 | 8 | 305 | 21 |
| | 1000 | 0 | Male | 5 | 266 | 35 | 5 | 232 | 21 |
| | | | Female | 5 | 305 | 30 | 5 | 315 | 47 |
| | | | Pooled | 10 | 286 | 31 | 10 | 273 | 41 |
| | 2000 | 0 | Male | 5 | 434 | 41 | 5 | 315 | 11 |
| | | | Female | 5 | 263 | 15 | 5 | 530 | 37 |
| | | | Pooled | 10 | 348 | 44 | 10 | 422 | 42 |
| | 4000 | 0 | Male | 5 | 498 | 25 | 5 | 584 | 45 |
| | | | Female | 5 | 346 | 28 | 5 | 426 | 47 |
| | | | Pooled | 10 | 422 | 31 | 10 | 505 | 46 |
| rVWF + rFVIII | 250 | 192 | Male | 5 | 313 | 20 | 5 | 391 | 16 |
| | | | Female | 5 | 251 | 14 | 3 | 344 | 33 |
| | | | Pooled | 10 | 282 | 21 | 8 | 373 | 22 |
| | 500 | 385 | Male | 5 | 281 | 34 | 3 | 353 | 20 |
| | | | Female | 5 | 248 | 23 | 2 | 598 | 74 |
| | | | Pooled | 10 | 265 | 29 | 5 | 451 | 58 |
| | 1000 | 769 | Male | 5 | 273 | 10 | 5 | 289 | 20 |
| | | | Female | 5 | 331 | 19 | 5 | 256 | 28 |
| | | | Pooled | 10 | 302 | 18 | 10 | 273 | 23 |
| | 2000 | 1538 | Male | 5 | 455 | 28 | 5 | 402 | 41 |
| | | | Female | 5 | 355 | 20 | 5 | 282 | 18 |
| | | | Pooled | 10 | 405 | 27 | 10 | 342 | 38 |
| | 4000 | 3077 | Male | 5 | 486 | 15 | 5 | 357 | 69 |
| | | | Female | 5 | 547 | 11 | 5 | 329 | 41 |
| | | | Pooled | 10 | 517 | 14 | 10 | 343 | 55 |

6. Necropsy

There were no necropsy findings that indicated a possible test item-related association. However, a variety of incidental changes were found and recorded.

7. Histopathology

In the short-term study (1 day), myocardial necrosis (minimal to moderate grade) was recorded in the hearts of test item-treated animals of the 500 RCoU/kg, 1000 RCoU/kg and 2000 RCoU/kg and high-dose groups, which were either treated with rVWF alone or with a combination of rVWF and rFVIII. Additionally, microthrombi (minimal to moderate grade) were recorded in test-item-treated animals of the 2000 RCoU/kg and high-dose groups which were treated with rVWF alone, as well as in the 1000 RCoU/kg and 2000 RCoU/kg and high-dose animals which were treated with a combination of rVWF and rFVIII. Both changes showed a clear dose-dependent increase in incidence (and partly also severity), especially in animals treated with a combination of rVWF and rFVIII.

Additionally, a slightly increased coronary perivasculitis was recorded in animals of the 2000 RCoU/kg dose group which were treated with rVWF alone, as well as in animals of the 1000 RCoU/kg and 2000 RCoU/kg and high-dose groups which were treated with a combination of rVWF and rFVIII.

In the brain, a single microthrombus (minimal grade) was recorded in a citrate-buffer-treated control animal. This finding was not recorded in any test item-treated animal of the short-term study part (1 day) or in any animal of the long-term study part (14 days). Therefore, this organ was not investigated in lower dose groups.

In lungs, low incidences of microthrombi (all of minimal grade) were recorded in test-item-treated as well as in control animals treated with HAEMATE® P, saline or citrate buffer (incidence: 2/10; mean severity: 1.0). However, no differences were recorded between test-item-treated animals and controls. Therefore, this organ was not investigated in lower dose groups.

In the long-term study part (14 days), myocardial degeneration/reparation (minimal to moderate grade) was recorded in the hearts of test item-treated animals of the 1000 RCoU/kg and 2000 RCoU/kg and high-dose groups which were treated with rVWF alone as well as in animals of the 500 RCoU/kg, 1000 RCoU/kg, 2000 RCoU/kg and high-dose groups which were treated with a combination of rVWF and rFVIII. This change showed a slight dose-dependent increase in incidence (and partly also severity) and was characterized by inflammation (mainly mononuclear) and fibrosis, accompanied by hemosiderin deposition and sometimes also by myocardial calcification.

In the lungs, low incidences of microthrombi (all of minimal grade) were recorded in test-item-treated as well as in control animals treated with HAEMATE® P, saline, citrate buffer or combination buffer (incidence: ≤1/10; mean severity: ≤1.0). However, no differences were recorded between test item-treated animals and controls. Therefore, this organ was not investigated in low- and mid-dose groups.

At the injection site, a moderate grade thrombosis of tail vessels was recorded in a single test-item-treated animal (low-dose group) and led to a black discoloration of the distal end of the tail recorded at necropsy. As this finding was not recorded in any other animal of this study its incidence and morphologic appearance gave no indication of a test-item-related association. It was deemed to be caused by the technical procedure of the intravenous application.

8. Discussion

As set forth above, rVWF was tested alone at five dose levels: 4000, 2000, 1000, 500, and 250 ristocetin cofactor (RCo) U/kg body weight (BW), and combined with rFVIII also at five doses. In the combined administration the doses of rVWF were the same as in the single administration and those of rFVIII were 3077, 1538, 769, 385 and 192 IU/kg rFVIII in descending order, i.e. 4000 RCoU/kg BW rVWF was co-administered with 3077 IU/kg rFVIII, 2000 RCoU/kg BW rVWF was co-administered with 1538 IU/kg rFVIII etc. HAEMATE® P, a plasma-derived VWF-FVIII preparation, was tested at 2000 RCoU/kg (+1347 IU/kg FVIII). Buffer alone and isotonic saline were included as controls.

Symptoms indicative of toxicity were seen during clinical observation up to 6 hours in the high-dose groups treated with 4000 RCoU/kg rVWF alone (in 15 of 20 animals) and combined with rFVIII (in 17 of 20 animals) and in the groups treated with the combination buffer (in 4 of 20 animals). Short-term symptoms, as seen in the buffer groups, were indicative of sodium citrate toxicity (e.g. dyspnea, convulsions, short-time behavioral depression) because the administered sodium citrate dose in the corresponding volume of 49.3 mL/kg was 143 mg/kg. Similar symptoms were also observed in 2 of the 32 affected animals of the high-dose groups, also indicating sodium citrate toxicity effects. In contrast, 30 of the 32 animals in the groups treated with 4000 RCoU/kg rVWF alone or combined with rFVIII showed long-term symptoms (e.g. behavioral depression, ataxia, piloerection) up to 6 hours after administration. These symptoms were obviously indicative of a direct toxic effect of the high dose, because no symptoms were observed in any of the other groups.

There was no minimum detectable dose (MDD), defined as the minimum dose which is shifted from the corresponding buffer, with rVWF in changes in body mass from day 0 to day 1 as well as for changes from day 0 to day 14. The highest dose of rVWF investigated (4000 RCoU/kg) could therefore be regarded as the no observed adverse effect level (NOAEL) dose.

The minimum detectable dose (MDD) with rVWF+rFVIII for changes in body mass from day 0 to day 1 was estimated to be the lowest dose of rVWF+rFVIII investigated (250 RCoU/kg+192 IU/kg rFVIII). No dose among the doses investigated with rVWF+rFVIII could therefore be regarded as the NOAEL dose in terms of body mass development from day 0 to day 1. This estimated effect can be considered as having occurred by chance because there is a weight increase at the next higher dose level of 500 RCoU/kg rVWF+385 IU/kg rFVIII and the weight decrease is moderate compared directly with the group treated with 250 RCoU/kg rVWF alone (−1.9% vs. −2.2%). There was no minimum detectable dose for changes in body mass from day 0 to day 14, and the highest dose of rVWF+rFVIII investigated (4000 RCoU/kg+3077 IU/kg rFVIII) could therefore be regarded as the NOAEL dose in terms of body mass development from day 0 to day 14.

Mean body mass development (as Δ% of body mass from day 0) from day 0 to day 1 was −1.1% with HAEMATE® P and −1.6% with the corresponding dose of rVWF+rFVIII. This difference was not statistically significant at the 5% level (two-sided p-value=0.6931). Mean body mass development from day 0 to day 14 was 4.7% with HAEMATE® P and 7.7% with the corresponding dose of rVWF+rFVIII. This difference was not statistically significant at the 5% level (two-sided p-value=0.2289).

Comparing the data of the selected hematological and serum chemistry variables, a drop in platelet-count was observed at day 1 after administration of 2000 RCoU/kg rVWF and higher administered alone or combined with rFVIII. No changes were seen after administration of HAEMATE® P.

Creatinine kinase was increased at days 1 and 14 after administration of 250 RCoU/kg and 500 RCoU/kg rVWF alone or combined with rFVIII. A dose dependency can be excluded because the increase of these variables was seen only in the lower dose groups. Furthermore, no histopathological correlation at the lowest dose could be found.

An increase of lactate dehydrogenase was seen for the group treated with a dose of 2000 RCoU/kg BW rVWF or higher combined with rFVIII after 1 day.

There were no necropsy findings that indicated a possible rVWF-related association.

Histopathological changes were recorded for the heart in test item-treated animals treated with doses of 500 RCoU rVWF or higher (alone or combined with rFVIII). These changes consisted of coronary microthrombi, myocardial necrosis, myocardial degeneration/reparation (all of minimal to moderate severity), and slightly increased coronary perivasculitis. Most of these changes showed a slight dose-dependent increase in incidence (and partly also severity), especially in animals treated with a combination of rVWF and rFVIII. The pathohistological changes resemble the picture of a low grade "ischemic heart disease". In contrast to test item-treated animals receiving recombinant product(s), such findings were not recorded in reference-item-treated animals receiving a human plasma-derived VWF-FVIII preparation (HAEMATE® P).

In test item-treated animals which were killed at scheduled necropsy on day 1 thrombembolic changes were recorded in the heart, which is highly sensitive to hypoxia. The vascular occlusion by coronary microthrombi led to reduced blood flow to the heart, which causes ischemic myocardial necrosis (cell starvation secondary to a lack of oxygen) and reactive coronary perivasculitis (early effects).

In test item-treated animals which were killed at scheduled necropsy on day 14 predominately degenerative and/or reparative changes were recorded in the heart (inflammation, fibrosis, calcification, hemosiderin deposition). These cardiac infarct-like changes were deemed to be the consequences of a previous vascular occlusion by microthrombi (delayed effects).

Additionally, low incidences of microthrombi (all of minimal grade) without accompanying organ destruction were recorded for the lungs (and partly for the brain) of test item-treated animals as well as control animals treated with saline, buffers and HAEMATE® P. Furthermore, a thrombosis of the tail vessels was recorded in one test-item-treated animal in the study. These "background changes" were deemed to be caused by technical procedures (sham i.v. treatment, intra-cardial blood sampling) and were therefore not related to the test item.

Summarized, clinical symptoms indicative of toxicity were observed up to 6 hours in the high-dose groups treated with 4000 RCoU/kg BW rVWF alone or combined with rFVIII. Acute thrombocytopenia was induced after administration of 2000 RCoU/kg BW rVWF and higher doses, administered alone or combined with rFVIII. The pathological changes resembled the picture of a low grade "ischemic heart disease". They indicated an thrombogenic potential of the test item, rVWF, in the C57BL/6J mouse at doses of 500 RCoU/kg and higher, either administered alone or combined with rFVIII.

Regarding strain-specific differences of the toxicological profile of rVWF, normal C57BL/6J mice are less susceptible than ADAMTS13 deficient mice (Example 8), but slightly more susceptible than VWF-deficient mice (Example 7).

No substantial observations were made in C57BL/6J mice treated with HAEMATE® P, which was used here as a positive control. HAEMATE® P has a different composition of VWF multimers, and lacks ultra-large molecular weight forms due to cleavage by endogenous human ADAMTS13. In addition, HAEMATE® P contains a variety of contaminating plasma proteins as well as citrate, which may also influence results.

Considering all results, the overall NOAEL in C57BL/6J mice can be set at 250 RCoU/kg.

Example 7

Intravenous Application of Human RVWF Alone or in Combination with Human RFVIII in VWF-Deficient Mice 1. Mice VWF-deficient mice were chosen for the study because this transgenic strain mimics the condition in patients who lack VWF. Mice are widely used in acute toxicity studies and are generally recognized as suitable for this purpose by regulatory authorities.

2. Protocol used in this study

There were no mortalities with any of the items investigated. Statistical analysis of mortality was therefore not performed. Comparisons of body mass development had been planned on ranks where animals that died before body mass measurement were to receive the lowest rank. There were no mortalities and comparisons of body mass development were therefore performed on relative changes (Δ% of body mass at day 0) and not on corresponding ranks.

A study with four different doses of rVWF and rVWF+rFVIII (including corresponding buffer as zero dose) had been planned but finally six different doses of rVWF and rVWF+rFVIII were investigated. For this reason, the minimum detectable dose (MDD), defined as the minimum dose which is shifted from the corresponding buffer, was estimated in a step-down manner using contrasts.

Hematological and serological variables grouped by item and study day were summarized using means and coefficient of variations instead of medians and ranges because coefficient of variations are scale independent and allow assessment of differences in variability of doses in laboratory variables.

3. Clinical abnormalities

No Deaths were Observed in this Study.

Clinical signs of toxicity were observed in 3 of 20 (15%) animals after administration of 4000 RCoU/kg rVWF alone (groups H, R), in 4 of 20 (20%) animals after administration of 4000 RCoU/kg rVWF combined with 3077 IU/kg rFVIII (Advate, groups C, M), in 4 of 20 animals (20%) after administration of 31.7 mL/kg of the corresponding formulation buffer of rVWF (groups G, Q) and also in 4 of 20 animals (20%) after administration of 49.3 mL/kg of the combined formulation buffers (groups D, N).

The symptoms recorded were short-term behavior depression (lasting up to 2 minutes) after injection, independent of the treatment regimen.

4. Body Mass Analysis

The change in body mass between study day 0 and study days 1, 7 and 14 (as Δ% of body mass at day 0) were visualized using box plots grouped by item and dose. Male and female animals were combined for these box plots. The body mass analysis is provided in Table 11 and FIGS. 13-15.

TABLE 11

Summary of body mass analysis

| Item | Dose of VWF:RCo [U/kg] | Dose of FVIII [IU/kg] | Sex | Day 0 to Day 1 | | | Day 0 to Day 7/8 | | | Day 0 to Day 14 | | |
|---|---|---|---|---|---|---|---|---|---|---|---|---|
| | | | | N | Mean | 95% Cl for mean | N | Mean | 95% Cl for mean | N | Mean | 95% Cl for mean |
| NaCl | 0 | 0 | Female | 10 | −3.2% | −7.2% to −1.0% | 5 | 1.7% | −10.8% to 18.2% | 5 | 9.1% | −1/8% to 26.5% |
| | | | Male | 10 | −3.7% | −5.1% to −2.0% | 5 | −3.2% | −9.5% to 3.4% | 5 | 0.5% | −2.2% to 10.7% |
| | | | Pooled | 20 | −3.4% | −4.8 to −2.1% | 10 | −0.8% | −4.5% to 5.4% | 10 | 4.8% | 1.4% to 13.0% |
| HAEMATE ® P | 2000 | 1347 | Female | 10 | −1.4% | −3.0% to 0.8% | 5 | 0.1% | −2.7% to 6.9% | 5 | 1.1% | −11.1% to 7.5% |
| | | | Male | 10 | −1.9% | −2.9% to −0.9% | 5 | 0.8% | −4.4% to 5.4% | 5 | 4.4% | 1.0% to 13.0% |
| | | | Pooled | 20 | −1.7% | −2.5% to −0.7% | 10 | 0.4% | −1.6% to 3.0% | 10 | 2.8% | −2.1% to 5.8% |
| rVWF buffer | 0 | 0 | Female | 10 | −1.1% | −2.6% to 0.0% | 5 | −0.2% | −8.6% to 2.6% | 5 | 3.3% | −2.3% to 17.1% |
| | | | Male | 10 | 0.0% | −0.8% to 0.9% | 5 | 2.1% | −1.1% to 4.5% | 5 | 9.0% | −169% to 11.5% |
| | | | Pooled | 20 | −0.5% | −1.3% to 0.1% | 10 | 1.0% | −1.6% to 2.4% | 10 | 6.2% | 2.9% to 8.4% |
| rVWF + rFVIII buffer | 0 | 0 | Female | 10 | −3.4% | −5.9% to −2.8% | 5 | −2.3% | −5.5% to 1.7% | 5 | 2.2% | −6.4% to 9.9% |
| | | | Male | 10 | −1.8% | −6.4 to 3.7% | 5 | 1.3% | −14.6% to 17.2% | 5 | 8.4% | −9.2% to 33.6% |
| | | | Pooled | 20 | −2.6% | −4.7% to −0.0% | 10 | −0.5% | −6.0% to 6.4% | 10 | 5.3% | −1.5% to 15.7% |
| rVWF | 250 | 0 | Female | 10 | 1.9% | 0.3% to 3.6% | 5 | 2.3% | 1.4% to 7.8% | 5 | 8.4% | 4.9% to 12.5% |
| | | | Male | 10 | 0.0% | −0.6% to 0.6% | 5 | 2.6% | 1.8% to 5.0% | 5 | 6.9% | 4.9% to 9.5% |
| | | | Pooled | 20 | 0.9% | 0.3% to 1.9% | 10 | 2.4% | 1.9% to 3.7% | 10 | 7.6% | 6.3% to 9.7% |
| | 500 | 0 | Female | 10 | −2.3% | −4.4% to −0.5% | 5 | −1.1% | −4.2% to 8.3% | 5 | 6.6% | −2.8% to 17.0% |
| | | | Male | 10 | −1.3% | −2.1% to −0.1% | 5 | −0.0% | −2.3% to 3.2% | 5 | 7.1% | 0.7% to 11.1% |
| | | | Pooled | 20 | −1.8% | −2.9% to −0.9% | 10 | −0.6% | −2.3% to 1.8% | 10 | 6.9% | 3.2% to 10.1% |
| | 1000 | 0 | Female | 10 | −3.0% | −4.3% to −1.7% | 5 | 0.5% | −41.2% to 3.1% | 5 | 0.5% | −3.7% to 15.5% |
| | | | Male | 10 | −1.1% | −1.9% to 0.0% | 5 | −0.1% | −Infinity to 0.4% | 5 | 2.0% | 0.5% to 7.1% |
| | | | Pooled | 20 | −2.1% | −2.9% to −1.3% | 10 | 0.2% | −2.0% to 1.4% | 10 | 1.3% | −1.0% to 3.3% |
| | 2000 | 0 | Female | 10 | −3.1% | −4.6% to −0.2% | 5 | −1.2% | −5.5% to 13.9% | 5 | 3.9% | −1.2% to 36.6% |
| | | | Male | 10 | −2.1% | −5.0% to −0.4% | 5 | −1.8% | −5.7% to 1.7% | 5 | 1.9% | −2.7% to 4.5% |
| | | | Pooled | 20 | −2.6% | −3.8% to −1.4% | 10 | −1.5% | −3.9% to 1.5% | 10 | 2.9% | 0.6% to 7.6% |
| | 4000 | 0 | Female | 10 | −1.1% | −2.0% to 0.4% | 5 | −0.5% | −2.3% to 14.0% | 5 | 5.6% | 0.5% to 9.7% |
| | | | Male | 10 | −1.5% | −3.6% to 0.6% | 5 | −0.8% | −3.9% to 2.6% | 5 | −2.0% | −34.5% to 4.2% |
| | | | Pooled | 20 | −1.3% | −2.3% to −0.3% | 10 | 0.7% | −2.0% to 2.1% | 10 | 1.8% | −4.4% to 4.5% |
| rVWF + FVIII | 250 | 192 | Female | 10 | 0.7% | −0.6% to 2.7% | 5 | 2.0% | −32.4% to 15.1% | 5 | 7.6% | 2.8% to 19.8% |
| | | | Male | 10 | 0.3% | −1.3% to 1.3% | 5 | 1.3% | −0.9% to 3.1% | 5 | 5.2% | 2.9% to 8.4% |
| | | | Pooled | 20 | 0.5% | −0.4% to 1.4% | 10 | 1.7% | −5.0% to 6.9% | 10 | 6.4% | 4.2% to 11.4% |
| | 500 | 385 | Female | 10 | −3.0% | −4.2% to −1.5% | 5 | −0.1% | −4.5% to 2.2% | 5 | 6.2% | 2.5% to 11.1% |
| | | | Male | 10 | −0.5% | −2.5% to 0.7% | 5 | −0.5% | −5.0% to 2.6% | 5 | 7.8% | 4.2% to 8.9% |
| | | | Pooled | 20 | −1.8% | −2.7% to −0.9% | 10 | −0.3% | −3.1% to 1.4% | 10 | 7.0% | 5.1% to 8.4% |

TABLE 11-continued

Summary of body mass analysis

| Item | Dose of VWF:RCo [U/kg] | Dose of FVIII [IU/kg] | Sex | Day 0 to Day 1 | | | Day 0 to Day 7/8 | | | Day 0 to Day 14 | | |
|---|---|---|---|---|---|---|---|---|---|---|---|---|
| | | | | N | Mean | 95% CI for mean | N | Mean | 95% CI for mean | N | Mean | 95% CI for mean |
| | 1000 | 769 | Female | 10 | −1.6% | −3.3% to −0.1% | 5 | −0.7% | −3.5% to 4.2% | 5 | 3.0% | −0.9% to 15.9% |
| | | | Male | 10 | −0.2% | −1.0% to 1.9% | 5 | 1.8% | 0.5% to 7.9% | 5 | 2.8% | −2.8% to 7.1% |
| | | | Pooled | 20 | −0.9% | −1.7% to −0.1% | 10 | 0.5% | −1.2% to 2.1% | 10 | 2.9% | 0.8% to 6.0% |
| | 2000 | 1538 | Female | 10 | −2.9% | −12.9% to 2.6% | 5 | 1.6% | −2.0% to 18.1% | 5 | 6.6% | −6.4% to 13.3% |
| | | | Male | 10 | −0.7% | −3.0% to 0.9% | 5 | 2.5% | −1.4% to 3.8% | 5 | 6.4% | 2.0% to 12.9% |
| | | | Pooled | 20 | −1.8% | −6.1% to 0.8% | 10 | 2.1% | 0.4% to 4.3% | 10 | 6.5% | 2.2% to 10.4% |
| | 4000 | 3077 | Female | 10 | −3.8% | −5.0% to 0.9% | 5 | −3.8% | −6.2% to 4.4% | 5 | 1.4% | −2.7% to 14.1% |
| | | | Male | 10 | −4.1% | −6.3% to −2.9% | 5 | −2.6% | −4.4% to −2.0% | 5 | 3.2% | −0.6% to 7.0% |
| | | | Pooled | 20 | −4.0% | −4.8% to −2.8% | 10 | −3.2% | −4.4% to −1.8% | 10 | 2.3% | −0.0% to 4.6% |

There were no statistically significant differences (at the multiplicity adjusted 5% level) in body mass development from day 0 to day 1 (as Δ% from day 0) between different doses of rVWF+rFVIII and the corresponding buffer because all two-sided p-values adjusted for multiplicity were greater than 5%. There was one unadjusted two-sided p-value of 0.0299 for the comparison of the lowest dose of rVWF+rFVIII (mean Δ% of 0.5%) with the corresponding buffer (mean Δ% of −2.6%) whereas the multiplicity adjusted two-sided p-value was 0.1496. This significantly larger decrease in body mass development with buffer than with the lowest dose of rVWF+rFVIII could have therefore occurred by chance of more than 5% if the null hypothesis were true.

There were no statistically significant differences (at the multiplicity adjusted 5% level) in body mass development from day 0 to day 14 between different doses of rVWF+rFVIII and the corresponding buffer because all two-sided p-values adjusted for multiplicity were greater than 5%.

Estimation of the minimum detectable dose for changes in body mass from day 0 to day 1 in a step-down manner stopped at the contrast for the highest dose. The two-sided p-value for the highest dose was 0.1195, which was above 5%, and no further contrasts were investigated. There was no minimum detectable dose for changes in body mass from day 0 to day 1 with rVWF+rFVIII and the highest dose investigated could be regarded as the NOAEL dose.

Estimation of the minimum detectable dose for changes in body mass from day 0 to day 14 in a step-down manner stopped at the contrast for the highest dose. The two-sided p-value for the highest dose was 0.3031, which was above 5%, and no further contrasts were investigated. There was no minimum detectable dose for changes in body mass from day 0 to day 14 with rVWF+rFVIII and the highest dose investigated could be regarded as the NOAEL dose.

There was a statistically significant (at the multiplicity adjusted 5% level) larger decrease in body mass with a rVWF dose of 2000 (mean Δ% of −2.6%) than with the corresponding buffer (mean Δ% of −0.5%) from day 0 to day 1. There were two unadjusted two-sided p-values below 5% whereas the multiplicity adjusted two-sided p-values were above 5%. These significant differences with a dose of 1000 (mean Δ% of −2.1%) and with a dose of 250 (mean Δ% of 0.9%) compared with the buffer (mean Δ% of −0.5%) could have therefore occurred with a chance of more than 5% if the null hypothesis were true.

There was a statistical trend (multiplicity adjusted two-sided p-value of 0.0693) for smaller increase in body mass with a rVWF dose of 1000 (mean Δ% of 1.3%) than with the corresponding buffer (mean Δ% of 6.2%) from day 0 to day 14. There was one unadjusted two-sided p-value of 0.0279 for the comparison of the highest dose of rVWF (mean Δ% of 1.8%) with the corresponding buffer (mean Δ% of 6.2%) whereas the multiplicity adjusted two-sided p-value was 0.1117. This significant smaller body mass development with the highest dose of rVWF than with the corresponding buffer could have therefore occurred by chance of more than 5% if the null hypothesis were true.

Estimation of the minimum detectable dose for changes in body mass from day 0 to day 1 in a step-down manner stopped at the contrast for 500 U/kg, which was the first two-sided p-value above 5% (two-sided p-value=0.0741). The minimum detectable dose was therefore 1000 U/kg rVWF.

Estimation of the minimum detectable dose for changes in body mass from day 0 to day 14 in a step-down manner stopped at the contrast for 500 U/kg, which was the first two-sided p-value above 5% (two-sided p-value=0.7267). The minimum detectable dose was therefore 1000 U/kg rVWF.

Mean body mass development from day 0 to day 1 was −1.7% (95% CI: −2.5% to −0.7%) with HAEMATE® P and −1.8% (95% CI: −6.1% to 0.8%) with the corresponding dose of rVWF+rFVIII. This difference was not statistically significant at the 5% level (two-sided p-value=0.9499).

Mean body mass development from day 0 to day 14 was 2.8% (95% CI: −2.1% to 5.8%) with HAEMATE® P and 6.5% (95% CI: 2.2% to 10.4%) with the corresponding dose of rVWF+rFVIII. This difference was not statistically significant at the 5% level (two-sided p-value=0.1855).

5. Hematological and Serological Variables

A comparison of the selected variables hematocrit, platelet count, CK and LDH is shown in the following FIGS. 16-23 and Tables 12-15.

TABLE 12

Summary of hematocrit data

| Item | Dose of VWF:RCo [U/kg] | Dose of FVIII [IU/kg] | Sex | Study day 1 | | | Study day 14 | | |
|---|---|---|---|---|---|---|---|---|---|
| | | | | N | Mean | CV [%] | N | Mean | CV [%] |
| NaCl | 0 | 0 | Male | 5 | 41.8 | 7.4 | 5 | 45.3 | 1.8 |
| | | | Female | 5 | 44.0 | 6.4 | 5 | 44.0 | 2.6 |
| | | | Pooled | 10 | 42.9 | 7.0 | 10 | 44.7 | 2.6 |
| HAEMATE ® P | 2000 | 1347 | Male | 5 | 45.8 | 1.7 | 5 | 45.8 | 4.1 |
| | | | Female | 5 | 43.7 | 4.1 | 5 | 44.3 | 6.0 |
| | | | Pooled | 10 | 44.8 | 3.8 | 10 | 45.1 | 5.1 |
| rVWF buffer | 0 | 0 | Male | 5 | 44.9 | 4.1 | 5 | 44.0 | 3.2 |
| | | | Female | 5 | 43.7 | 1.2 | 5 | 42.7 | 3.9 |
| | | | Pooled | 10 | 44.3 | 3.2 | 10 | 43.4 | 3.7 |
| rVWF + rFVIII buffer | 0 | 0 | Male | 5 | 44.1 | 3.0 | 5 | 44.3 | 2.5 |
| | | | Female | 5 | 45.6 | 1.4 | 5 | 44.2 | 4.9 |
| | | | Pooled | 10 | 44.9 | 2.8 | 10 | 44.2 | 3.7 |
| rVWF | 250 | 0 | Male | 5 | 45.2 | 4.7 | 5 | 46.4 | 3.7 |
| | | | Female | 5 | 44.5 | 6.4 | 5 | 47.2 | 1.4 |
| | | | Pooled | 10 | 44.9 | 5.4 | 10 | 46.8 | 2.8 |
| | 500 | 0 | Male | 5 | 46.6 | 3.8 | 5 | 46.5 | 3.6 |
| | | | Female | 5 | 43.7 | 7.1 | 4 | 42.9 | 1.1 |
| | | | Pooled | 10 | 45.2 | 6.3 | 9 | 44.9 | 5.1 |
| | 1000 | 0 | Male | 5 | 43.7 | 5.3 | 5 | 45.9 | 3.6 |
| | | | Female | 5 | 42.6 | 10.1 | 4 | 44.8 | 2.3 |
| | | | Pooled | 10 | 43.1 | 7.6 | 9 | 45.4 | 3.2 |
| | 2000 | 0 | Male | 5 | 43.8 | 2.7 | 5 | 45.7 | 2.6 |
| | | | Female | 5 | 45.2 | 3.5 | 5 | 45.1 | 3.6 |
| | | | Pooled | 10 | 44.5 | 3.4 | 10 | 45.4 | 3.1 |
| | 4000 | 0 | Male | 5 | 39.2 | 28.0 | 5 | 42.0 | 12.7 |
| | | | Female | 5 | 44.3 | 2.6 | 5 | 45.1 | 1.9 |
| | | | Pooled | 10 | 41.8 | 18.8 | 10 | 43.6 | 9.1 |
| rVWF + rFVIII | 250 | 192 | Male | 5 | 44.8 | 2.4 | 5 | 43.0 | 6.4 |
| | | | Female | 5 | 43.2 | 5.1 | 5 | 45.6 | 4.5 |
| | | | Pooled | 10 | 44.0 | 4.2 | 10 | 44.3 | 6.1 |
| | 500 | 385 | Male | 5 | 41.6 | 16.3 | 3 | 46.4 | 2.9 |
| | | | Female | 5 | 44.0 | 5.5 | 5 | 46.4 | 2.5 |
| | | | Pooled | 10 | 42.8 | 11.6 | 8 | 46.4 | 2.5 |
| | 1000 | 769 | Male | 5 | 44.5 | 4.1 | 5 | 45.0 | 7.0 |
| | | | Female | 5 | 46.0 | 5.4 | 3 | 42.1 | 10.3 |
| | | | Pooled | 10 | 45.3 | 4.9 | 8 | 43.9 | 8.3 |
| | 2000 | 1538 | Male | 5 | 44.5 | 1.9 | 5 | 44.3 | 1.1 |
| | | | Female | 5 | 43.7 | 4.3 | 5 | 44.4 | 3.9 |
| | | | Pooled | 10 | 44.1 | 3.3 | 10 | 44.4 | 2.7 |
| | 4000 | 3077 | Male | 5 | 45.0 | 6.0 | 5 | 45.0 | 1.9 |
| | | | Female | 5 | 42.5 | 3.6 | 5 | 41.6 | 10.5 |
| | | | Pooled | 10 | 43.8 | 5.6 | 10 | 43.3 | 8.0 |

TABLE 13

Summary of platelet counts

| Item | Dose of VWF:RCo [U/kg] | Dose of FVIII [IU/kg] | Sex | Study day 1 | | | Study day 14 | | |
|---|---|---|---|---|---|---|---|---|---|
| | | | | N | Mean | CV [%] | N | Mean | CV [%] |
| NaCl | 0 | 0 | Male | 5 | 1112 | 4 | 5 | 1121 | 10 |
| | | | Female | 5 | 874 | 12 | 5 | 1029 | 8 |
| | | | Pooled | 10 | 993 | 15 | 10 | 1075 | 10 |
| HAEMATE ® P | 2000 | 1347 | Male | 5 | 1102 | 4 | 5 | 1192 | 10 |
| | | | Female | 5 | 934 | 12 | 5 | 1028 | 13 |
| | | | Pooled | 10 | 1018 | 12 | 10 | 1110 | 13 |
| rVWF buffer | 0 | 0 | Male | 5 | 1140 | 4 | 5 | 1133 | 7 |
| | | | Female | 5 | 1064 | 8 | 5 | 940 | 9 |
| | | | Pooled | 10 | 1102 | 7 | 10 | 1037 | 12 |
| rVWF + rFVIII buffer | 0 | 0 | Male | 5 | 1158 | 5 | 5 | 1213 | 8 |
| | | | Female | 5 | 1050 | 9 | 5 | 1160 | 5 |
| | | | Pooled | 10 | 1104 | 9 | 10 | 1186 | 7 |
| rVWF | 250 | 0 | Male | 5 | 1157 | 11 | 5 | 1186 | 4 |
| | | | Female | 5 | 982 | 9 | 5 | 934 | 8 |
| | | | Pooled | 10 | 1070 | 13 | 10 | 1060 | 14 |

TABLE 13-continued

Summary of platelet counts

| Plate count (×10^3/μL) | | | | Study day | | | | | |
|---|---|---|---|---|---|---|---|---|---|
| | | | | | 1 | | | 14 | |
| Item | Dose of VWF:RCo [U/kg] | Dose of FVIII [IU/kg] | Sex | N | Mean | CV [%] | N | Mean | CV [%] |
| | 500 | 0 | Male | 5 | 1149 | 7 | 5 | 1161 | 9 |
| | | | Female | 5 | 970 | 3 | 4 | 996 | 9 |
| | | | Pooled | 10 | 1060 | 10 | 9 | 1088 | 12 |
| | 1000 | 0 | Male | 5 | 1132 | 6 | 5 | 1230 | 9 |
| | | | Female | 5 | 908 | 10 | 4 | 998 | 9 |
| | | | Pooled | 10 | 1020 | 14 | 9 | 1127 | 14 |
| | 2000 | 0 | Male | 5 | 1003 | 22 | 5 | 1130 | 6 |
| | | | Female | 5 | 874 | 13 | 5 | 1012 | 13 |
| | | | Pooled | 10 | 939 | 19 | 10 | 1071 | 11 |
| | 4000 | 0 | Male | 5 | 897 | 12 | 5 | 1427 | 20 |
| | | | Female | 5 | 796 | 13 | 5 | 1051 | 6 |
| | | | Pooled | 10 | 847 | 13 | 10 | 1239 | 22 |
| rVWF + rFVIII | 250 | 192 | Male | 5 | 1272 | 9 | 5 | 1073 | 17 |
| | | | Female | 5 | 985 | 11 | 5 | 1005 | 6 |
| | | | Pooled | 10 | 1129 | 16 | 10 | 1039 | 13 |
| | 500 | 385 | Male | 5 | 1159 | 6 | 3 | 1150 | 8 |
| | | | Female | 5 | 970 | 6 | 5 | 1067 | 7 |
| | | | Pooled | 10 | 1065 | 11 | 8 | 1098 | 8 |
| | 1000 | 769 | Male | 5 | 1118 | 10 | 5 | 1187 | 10 |
| | | | Female | 5 | 984 | 7 | 3 | 848 | 29 |
| | | | Pooled | 10 | 1051 | 11 | 8 | 1060 | 23 |
| | 2000 | 1538 | Male | 5 | 973 | 5 | 5 | 1087 | 7 |
| | | | Female | 5 | 779 | 18 | 5 | 960 | 15 |
| | | | Pooled | 10 | 876 | 16 | 10 | 1023 | 13 |
| | 4000 | 3077 | Male | 5 | 502 | 51 | 5 | 1200 | 6 |
| | | | Female | 5 | 635 | 13 | 5 | 1005 | 6 |
| | | | Pooled | 10 | 569 | 34 | 10 | 1103 | 11 |

TABLE 14

Summary of creatinine kinase

| Creatinine Kinase (U/L) | | | | Study day | | | | | |
|---|---|---|---|---|---|---|---|---|---|
| | | | | | 1 | | | 14 | |
| Item | Dose of VWF:RCo [U/kg] | Dose of FVIII [IU/kg] | Sex | N | Mean | CV [%] | N | Mean | CV [%] |
| NaCl | 0 | 0 | Male | 5 | 153 | 32 | 5 | 195 | 73 |
| | | | Female | 5 | 100 | 26 | 5 | 108 | 31 |
| | | | Pooled | 10 | 126 | 37 | 10 | 151 | 71 |
| HAEMATE ® P | 2000 | 1347 | Male | 5 | 152 | 19 | 5 | 102 | 13 |
| | | | Female | 5 | 150 | 43 | 5 | 88 | 31 |
| | | | Pooled | 10 | 151 | 31 | 10 | 95 | 23 |
| rVWF buffer | 0 | 0 | Male | 5 | 70 | 20 | 5 | 172 | 36 |
| | | | Female | 5 | 54 | 11 | 5 | 103 | 18 |
| | | | Pooled | 10 | 62 | 21 | 10 | 137 | 41 |
| rVWF + rFVIII buffer | 0 | 0 | Male | 5 | 236 | 25 | 5 | 123 | 21 |
| | | | Female | 5 | 138 | 12 | 5 | 136 | 34 |
| | | | Pooled | 10 | 187 | 35 | 10 | 129 | 28 |
| rVWF | 250 | | Male | 5 | 116 | 23 | 3 | 237 | 18 |
| | | | Female | 5 | 103 | 25 | 5 | 156 | 21 |
| | | | Pooled | 10 | 110 | 23 | 8 | 186 | 29 |
| | 500 | | Male | 5 | 229 | 29 | 5 | 315 | 57 |
| | | | Female | 5 | 199 | 47 | 5 | 379 | 57 |
| | | | Pooled | 10 | 214 | 26 | 10 | 347 | 55 |
| | 1000 | | Male | 5 | 223 | 51 | 5 | 260 | 30 |
| | | | Female | 5 | 464 | 52 | 5 | 290 | 47 |
| | | | Pooled | 10 | 344 | 63 | 10 | 275 | 38 |
| | 2000 | | Male | 5 | 131 | 13 | 5 | 162 | 77 |
| | | | Female | 5 | 145 | 14 | 5 | 112 | 38 |
| | | | Pooled | 10 | 138 | 14 | 10 | 137 | 67 |
| | 4000 | | Male | 5 | 118 | 29 | 5 | 187 | 35 |
| | | | Female | 5 | 67 | 24 | 5 | 130 | 16 |
| | | | Pooled | 10 | 92 | 40 | 10 | 159 | 35 |

TABLE 14-continued

Summary of creatinine kinase

| | Creatinine Kinase (U/L) | | | Study day | | | | |
| --- | --- | --- | --- | --- | --- | --- | --- | --- |
| | Dose of | Dose of | | 1 | | | 14 | |
| Item | VWF:RCo [U/kg] | FVIII [IU/kg] | Sex | N | Mean | CV [%] | N | Mean | CV [%] |
| --- | --- | --- | --- | --- | --- | --- | --- | --- |
| rVWF + rFVIII | 250 | 192 | Male | 5 | 112 | 35 | 5 | 174 | 61 |
| | | | Female | 5 | 88 | 33 | 1 | 127 | NA |
| | | | Pooled | 10 | 100 | 35 | 6 | 166 | 58 |
| | 500 | 385 | Male | 5 | 176 | 33 | 5 | 816 | 167 |
| | | | Female | 5 | 164 | 75 | 5 | 601 | 98 |
| | | | Pooled | 10 | 170 | 54 | 10 | 709 | 141 |
| | 1000 | 769 | Male | 5 | 180 | 39 | 5 | 421 | 43 |
| | | | Female | 5 | 157 | 18 | 5 | 248 | 71 |
| | | | Pooled | 10 | 168 | 31 | 10 | 335 | 26 |
| | 2000 | 1538 | Male | 5 | 176 | 29 | 5 | 123 | 26 |
| | | | Female | 5 | 175 | 51 | 5 | 137 | 15 |
| | | | Pooled | 10 | 176 | 39 | 10 | 130 | 20 |
| | 4000 | 3077 | Male | 5 | 163 | 42 | 5 | 133 | 29 |
| | | | Female | 5 | 106 | 40 | 5 | 285 | 83 |
| | | | Pooled | 10 | 135 | 46 | 10 | 209 | 86 |

TABLE 15

Summary of LDH data

| | LDH [U/L] | | | Study day | | | | |
| --- | --- | --- | --- | --- | --- | --- | --- | --- |
| | Dose of | Dose of | | 1 | | | 14 | |
| Item | VWF:RCo [U/kg] | FVIII [IU/kg] | Sex | N | Mean | CV [%] | N | Mean | CV [%] |
| --- | --- | --- | --- | --- | --- | --- | --- | --- |
| NaCl | 0 | 0 | Male | 5 | 427 | 11 | 5 | 364 | 25 |
| | | | Female | 5 | 330 | 25 | 5 | 304 | 32 |
| | | | Pooled | 10 | 378 | 21 | 10 | 334 | 28 |
| HAEMATE ® P | 2000 | 1347 | Male | 5 | 504 | 12 | 5 | 368 | 19 |
| | | | Female | 5 | 302 | 26 | 5 | 296 | 15 |
| | | | Pooled | 10 | 403 | 31 | 10 | 332 | 20 |
| rVWF buffer | 0 | 0 | Male | 5 | 478 | 27 | 5 | 371 | 21 |
| | | | Female | 5 | 326 | 19 | 5 | 259 | 22 |
| | | | Pooled | 10 | 402 | 31 | 10 | 315 | 27 |
| rVWF + rFVIII buffer | 0 | 0 | Male | 5 | 518 | 11 | 5 | 416 | 12 |
| | | | Female | 5 | 274 | 15 | 5 | 318 | 22 |
| | | | Pooled | 10 | 396 | 35 | 10 | 367 | 21 |
| rVWF | 250 | 0 | Male | 5 | 363 | 13 | 5 | 475 | 27 |
| | | | Female | 5 | 254 | 15 | 5 | 229 | 12 |
| | | | Pooled | 10 | 309 | 23 | 10 | 352 | 44 |
| | 500 | 0 | Male | 5 | 375 | 15 | 5 | 415 | 31 |
| | | | Female | 5 | 305 | 27 | 5 | 428 | 38 |
| | | | Pooled | 10 | 340 | 22 | 10 | 422 | 33 |
| | 1000 | 0 | Male | 5 | 472 | 28 | 5 | 423 | 11 |
| | | | Female | 5 | 428 | 32 | 5 | 463 | 34 |
| | | | Pooled | 10 | 450 | 29 | 10 | 443 | 25 |
| | 2000 | 0 | Male | 5 | 304 | 8 | 5 | 365 | 43 |
| | | | Female | 5 | 276 | 23 | 5 | 239 | 14 |
| | | | Pooled | 10 | 290 | 17 | 10 | 302 | 42 |
| | 4000 | 0 | Male | 5 | 439 | 16 | 5 | 371 | 10 |
| | | | Female | 5 | 315 | 17 | 5 | 220 | 7 |
| | | | Pooled | 10 | 377 | 24 | 10 | 296 | 28 |
| rVWF + rFVIII | 250 | 192 | Male | 5 | 286 | 18 | 5 | 368 | 25 |
| | | | Female | 5 | 258 | 19 | 5 | 270 | 21 |
| | | | Pooled | 10 | 272 | 18 | 10 | 319 | 28 |
| | 500 | 385 | Male | 5 | 372 | 19 | 5 | 656 | 54 |
| | | | Female | 5 | 378 | 37 | 5 | 712 | 56 |
| | | | Pooled | 10 | 375 | 28 | 10 | 684 | 52 |
| | 1000 | 769 | Male | 5 | 460 | 30 | 5 | 545 | 34 |
| | | | Female | 5 | 452 | 23 | 5 | 349 | 47 |
| | | | Pooled | 10 | 456 | 25 | 10 | 447 | 44 |
| | 2000 | 1538 | Male | 5 | 415 | 18 | 5 | 345 | 11 |
| | | | Female | 5 | 318 | 23 | 5 | 308 | 34 |
| | | | Pooled | 10 | 366 | 24 | 10 | 327 | 24 |

TABLE 15-continued

Summary of LDH data

| | LDH [U/L] | | | Study day | | | | |
|---|---|---|---|---|---|---|---|---|
| | Dose of VWF:RCo [U/kg] | Dose of FVIII [IU/kg] | Sex | 1 | | | 14 | |
| Item | | | | N | Mean | CV [%] | N | Mean | CV [%] |
| | 4000 | 3077 | Male | 5 | 381 | 21 | 5 | 450 | 15 |
| | | | Female | 5 | 294 | 27 | 5 | 472 | 51 |
| | | | Pooled | 10 | 338 | 26 | 10 | 461 | 36 |

6. Necropsy

There were no necropsy findings whose incidences, distribution or morphologic appearance indicated a possible rVWF-related association.

7. Histopathology

In the short-term study (1 day), myocardial necrosis (minimal to slight grade) was recorded in test-item-treated animals of the 1000 RCoU/kg and higher dose groups, which were treated with either rVWF alone or with a combination of rVWF and rFVIII. This change showed a slight dose relation, especially in animals treated with a combination of rVWF and rFVIII. A single microthrombus (slight grade) was recorded in a single animal of the high-dose group treated with a combination of rVWF and rFVIII. Additionally, a slightly increased incidence of coronary perivasculitis was recorded in rVWF-treated animals of the high-dose groups, which were either treated with rVWF alone or with a combination of rVWF and rFVIII.

In the long-term study (14 days), minimal myocardial degeneration/reparation was recorded in a few test-item-treated animals of 2000 RCoU/kg and higher dose groups, which were treated with either rVWF alone or with a combination of rVWF and rFVIII. This change was of very low grade and characterized by minimal inflammation (mainly mononuclear) and fibrosis, partly accompanied by hemosiderin deposition. Additionally, minimal myocardial degeneration/reparation was also recorded in a single animal treated with HAEMATE® P.

A variety of other changes were also found in this study. These commonly occur with intravenous application. Microthrombi (of minimal to slight grade) in the lungs were among these findings. Furthermore, a moderate grade myocardial degeneration/reparation was recorded in a single animal at day 1 (1000 RCoU/kg combined with rFVIII). The incidences, distribution and morphologic appearance of these changes gave no indication of a rVWF-related association.

8. Discussion

As explained above, rVWF was tested alone at five dose levels: 4000, 2000, 1000, 500 and 250 RCoU/kg BW, and combined with rFVIII, also at five doses. In the combined administration, the doses of rVWF were the same as in the single administration and those of rFVIII were 3077, 1538, 769, 385 and 192 IU/kg rFVIII in descending order, i.e., 4000 RCoU/kg BW rVWF was co-administered with 3077 IU/kg rFVIII, 2000 RCoU/kg BW rVWF was co-administered with 1538 IU/kg rFVIII, and the like. HAEMATE® P was tested at 2000 RCoU/kg BW+1347 IU/kg BW FVIII. The corresponding buffer for rVWF alone was administered at a volume of 31.7 mL/kg (according to the highest dose volume), the mixed buffer at 49.3 mL/kg, and isotonic saline at 49.3 mL/kg.

Short-term symptoms (mainly behavioral depression, lasting for a few minutes) were observed after administration of the high dose of rVWF alone or combined with rFVIII and the corresponding buffer volumes, indicative of sodium citrate toxicity. The incidence and severity was similar in all affected groups.

The minimum detectable dose (MDD), defined as the minimum dose which is shifted from the corresponding buffer, was estimated to be 1000 RCoU/kg rVWF for changes in body mass from day 0 to day 1 as well as for changes in body mass from day 0 to day 14. The dose of 500 RCoU/kg could therefore be regarded as the no observed adverse effect level (NOAEL) dose in terms of body mass development from day 0 to day 1 as well as for body mass development from day 0 to day 14.

There was no minimum detectable dose for rVWF+rFVIII in changes in body mass from day 0 to day 1 as well as for changes from day 0 to day 14. The highest dose of rVWF+rFVIII investigated (4000 RCoU/kg VWF+3077 IU/kg rFVIII) could therefore be regarded as the NOAEL dose in terms of body mass development from day 0 to day 1 as well as for body mass development from day 0 to day 14.

Mean body mass development (as Δ% of body mass at day 0) from day 0 to day 1 was −1.7% with HAEMATE® P and −1.8% with the corresponding dose of rVWF+rFVIII investigated. This difference was not statistically significant at the 5% level (two-sided p-value=0.9499). Mean body mass development from day 0 to day 14 was 2.8% with HAEMATE® P and 6.5% with the corresponding dose of rVWF+rFVIII. This difference was not statistically significant at the 5% level (two-sided p-value=0.1855).

Comparing the data of the selected hematological and serum chemistry variables, a drop in platelet count compared to buffer treated controls was observed at day 1 after administration of 4000 RCoU/kg rVWF (−23%) and 2000 RCoU/kg rVWF (−15%) administered alone or combined with rFVIII (−48% and −21%, respectively). No changes were seen after administration of HAEMATE® P.

Creatinine kinase was increased compared with control groups at day 1 after administration of 1000 RCoU/kg rVWF alone. Increased levels were measured after the 14 days of observation in the groups treated with 500 and 1000 RCoU/kg rVWF alone and combined with rFVIII. An increase of lactate dehydrogenase was seen after the 14 days of observation in the group treated with 500 RCoU/kg rVWF combined with rFVIII. A dose dependency can be excluded and a test item relation is very unlikely because the increase of these variables was seen only in the lower dose groups.

Histopathological changes were recorded for the heart in rVWF-treated animals at doses of 1000 RCoU rVWF or higher (alone or combined with rFVIII). Coronary microthrombi, myocardial necrosis (both of minimal to slight grade) and slightly increased coronary perivasculitis was found 1 day after application (early effects). Myocardial degeneration/reparation (minimal grade) was found after 14 days, and can be assessed as delayed effects. Some of these changes showed a slight dose dependency, especially in animals treated with a combination of rVWF and rFVIII. The pathohistological changes resemble the picture of a low grade "ischemic heart disease". In contrast to test-item-treated animals receiving recombinant product(s), most of these findings were not recorded in reference-item-treated animals receiving a commercially available human plasma-derived VWF-FVIII preparation (HAEMATE® P). However, a minimal myocardial degeneration/reparation was also recorded in one animal treated with HAEMATE® P (14 days). The reference-item relation of this finding is unclear.

Additionally, very low incidences of microthrombi of minimal to slight severity without accompanying organ destruction were recorded for the lungs of rVWF-treated animals as well as of saline-treated control animals. These microthrombi, which were all in an early state showing no signs of fibrin condensation, were not recorded in animals killed at day 1. Therefore, this change was deemed not to be related to the test item. This background change may be caused by a spontaneous disposition, which may be further enhanced by technical procedures (e.g. intra-cardial blood sampling).

Murine ADAMTS13 does not react with human recombinant VWF. Thus, it can be assumed that the hematological and pathohistological findings during this study are caused by the uncleaved recombinant VWF, including thrombogenicity and symptoms of disseminated intravascular coagulopathy (thrombocytopenia, microthrombosis). As this animal model has no endogenous VWF, however, it was less sensitive than other mouse strains. The NOAEL for rVWF in the VWF-deficient mouse was 500 RCoU/kg BW.

Comparing the three different mouse strains, the results indicated the following. The presence of endogenous murine rVWF has an influence on toxicity, as C57BL/6J mice had increased severity of symptoms and histopathological findings compared to VWF deficient mice. The absence of ADAMTS13 in the presence of endogenous murine VWF has the most severe effect on mortality and toxicity.

Example 8

Intravenous Application of Human RVWF Alone or in Combination with Human RFVIII IN ADAMTS13 Deficient Mice 1. Mice ADAMTS13 deficient mice were chosen for the study because this transgenic strain mimics the condition of patients who lack the ADAMTS13 protease for VWF.

2. Protocol Used in this Study

An additional analysis was performed to test the null hypothesis of no trend in mortality with increasing doses of rVWF (with or without rFVIII) against the two-sided alternative using the Cochran-Armitage trend test as an exact test (SAS procedure PROC FREQ, statement=EXACT TREND).

Six different doses of rVWF and rVWF+rFVIII were investigated. For this reason, the minimum detectable dose (MDD) in body mass development, defined as the minimum dose which is shifted from the corresponding buffer, was estimated in a step-down manner using contrasts.

A comparison of HAEMATE® P with rVWF+rFVIII at a dose of 4000 RCoU/kg had been planned but this dose proved not to be feasible with HAEMATE® P (citrate toxicity) and a dose of 2000 RCoU/kg of HAEMATE® P was included. Therefore, rVWF+rFVIII, at a dose of 2000 RCoU/kg+1538 IU/kg, was compared with HAEMATE® P at a dose of 2000 RCoU/kg VWF.

Body mass data from HAEMATE® P, at a dose of 4000 RCoU/kg, were excluded from the calculation of ranks of body mass development, which were used to compare items, and laboratory variables because data from only 2 animals were available.

Hematological and serological variables grouped by item and study day were summarized using means and coefficient of variations instead of medians and ranges because coefficient of variations are scale independent and allow assessment of differences in variability of doses in laboratory variables.

3. Analysis of Mortality

The proportion of animals that died during the observational period and corresponding two-sided 95% confidence intervals were calculated per item and dose. Two-sided 95% confidence intervals were calculated by the Wilson score method (Altman et al., *Brit. Med. J. Books,* 2nd ed., J W Arrowsmith Ltd., Bristol, p 46-48 (2000)). These analyses were performed for the STADS, LTADS and for the pooled STADS and LTADS separately. These analyses were also provided for male and female animals separately and for male and female animals combined.

Differences in mortality between different doses of rVWF and rVWF+rFVIII with the corresponding buffer were assessed for male and female animals combined by the two-sided Fisher exact test (by SAS procedure PROC MULTTEST). This analysis was performed for the pooled STADS and LTADS. Adjustment for multiplicity for comparison of five dose groups with the corresponding buffer simultaneously was applied using the Holm method. Unadjusted and multiplicity adjusted two-sided p values were calculated. No adjustment for multiplicity was applied for investigation of different items.

An additional analysis was performed to test the null hypothesis of no trend in mortality with increasing doses of rVWF (with or without rFVIII) against the two-sided alternative using the Cochran-Armitage trend test as an exact test (by SAS procedure PROC FREQ, statement=EXACT TREND). This analysis was performed for the pooled STADS and LTADS and for male and females combined.

After administration of 4000 RCoU/kg rVWF, 40% of the animals died immediately or up to 4 days after treatment (8 of 20, in groups E and O). After administration of 2000 RCoU/kg rVWF, 20% of animals died immediately or up to 9 days after treatment (4 of 20, in groups B and L). A mortality of 25% was registered after administration of 4000 RCoU/kg rVWF+3077 IU/kg rFVIII (5 of 20, in groups A and K), immediately after treatment or up to 1 day after treatment. There was no mortality in groups I and S (2000 RCoU/kg rVWF+1538 IU/kg rFVIII), or in any of the other lower-dose or negative control groups.

80% (8 of 10) of animals in the group treated with HAEMATE® P at 4000 RCoU/kg VWF (group T) died immediately after administration. No animal died in the groups treated with the lower dose level of 2000 RCoU/kg VWF (groups J and U).

A summary of mortality is shown in the following Table 16.

TABLE 16

Summary of mortality

| Item | Dose VWF | Dose FVIII | Sex | N | STADS Percent | STADS 95% Cl | N | LTADS Percent | LTADS 95% Cl | N | STADS + LTADS Percent | STADS + LTADS 95% Cl |
|---|---|---|---|---|---|---|---|---|---|---|---|---|
| NaCl | 0 | 0 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| HAEMATE ® P | 2000 | 1664 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| | 4000 | 3322 | F | NA | NA | NA | 5 | 80% | 38% to 96% | 5 | 80% | 38% to 96% |
| | | | M | NA | NA | NA | 5 | 80% | 38% to 96% | 5 | 80% | 38% to 96% |
| | | | P | NA | NA | NA | 10 | 80% | 49% to 94% | 10 | 80% | 49% to 94% |
| rVWF buffer | 0 | 0 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| rVWF | 250 | 0 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| | 500 | 0 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 0 | 0% | 0% to 28% | 10 | 0% | 0% to 28% | 20 | 0% | 0% to 16% |
| | 1000 | 0 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| | 2000 | 0 | F | 5 | 0% | 0% to 43% | 5 | 0% | 0% to 43% | 10 | 0% | 0% to 28% |
| | | | M | 5 | 0% | 0% to 43% | 5 | 80% | 38% to 96% | 10 | 40% | 17% to 69% |
| | | | Pool | 10 | 0% | 0% to 28% | 10 | 40% | 17% to 69% | 20 | 20% | 8% to 42% |
| | 4000 | 0 | F | 5 | 60% | 23% to 88% | 5 | 20% | 4% to 62% | 10 | 40% | 17% to 69% |
| | | | M | 5 | 20% | 4% to 62% | 5 | 60% | 23% to 88% | 10 | 40% | 17% to 69% |
| | | | Pool | 10 | 40% | 17% to 69% | 10 | 40% | 17% to 69% | 20 | 40% | 22% to 61% |
| rVWF + rFVIII buffer | 0 | 0 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| rVWF + rFVIII | 250 | 192 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| | 500 | 385 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |

TABLE 16-continued

Summary of mortality

| Item | Dose VWF | Dose FVIII | Sex | N | STADS Percent | STADS 95% Cl | N | LTADS Percent | LTADS 95% Cl | N | STADS + LTADS Percent | STADS + LTADS 95% Cl |
|---|---|---|---|---|---|---|---|---|---|---|---|---|
| | 1000 | 769 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| | 2000 | 1538 | F | 5 | 0% | 0% to 43% | 5 | 0% | 0% to 43% | 10 | 0% | 0% to 28% |
| | | | M | 5 | 0% | 0% to 43% | 5 | 0% | 0% to 43% | 10 | 0% | 0% to 28% |
| | | | Pool | 10 | 0% | 0% to 28% | 10 | 0% | 0% to 28% | 20 | 0% | 0% to 16% |
| | 4000 | 3077 | F | 5 | 40% | 12% to 77% | 5 | 40% | 12% to 77% | 10 | 40% | 17% to 69% |
| | | | M | 5 | 0% | 0% to 43% | 5 | 20% | 4% to 62% | 10 | 10% | 2% to 40% |
| | | | Pool | 10 | 20% | 6% to 51% | 10 | 30% | 11% to 60% | 20 | 25% | 11% to 47% |

There was a mortality of 20% (4 of 20) with the 2000 RCoU/kg dose and a mortality of 40% (8 of 20) with the 4000 RCoU/kg dose of rVWF. There was no mortality with the remaining doses investigated.

With rVWF+rFVIII, there was a mortality of 25% (5 of 20) with the highest dose investigated. There were no mortality with the remaining doses investigated.

There was a mortality of 80% (8 of 10) with a dose of 4000 RCoU/kg HAEMATE® P (+3322 IU/kg FVIII). There was no mortality (0 of 20) with a dose of 2000 RCoU/kg HAEMATE® P (+1664 IU/kg FVIII).

There was a mortality of 25% (5 of 20) with the highest dose of rVWF+rFVIII. There was no mortality (0 of 20) with the remaining doses or with the corresponding buffer.

There were no statistically significant (at the multiplicity adjusted 5% level) differences in mortality between different doses of rVWF+rFVIII and the corresponding buffer because all two-sided p-values adjusted for multiplicity were above 5%.

The observed difference in mortality of 25% between the highest dose of rVWF+rFVIII and the corresponding buffer was not statistically significant at the multiplicity adjusted 5% level. However, the unadjusted two-sided p-value was 0.0471. This raw two-sided p-value was not adjusted for comparing five different dose groups with the corresponding buffer simultaneously. The significant result could therefore occurred by chance with a probability of more than 5% if the overall null hypothesis of no difference between the five different doses and buffer were true.

The observed difference in mortality of 40% between the highest dose of rVWF and the corresponding buffer was statistically significant (multiplicity adjusted two-sided p-value=0.0164).

There were no statistically significant differences (at the multiplicity adjusted 5% level) in mortality between the buffer of rVWF and doses of 2000, 1000, 500 and 250 RCoU/kg.

The Cochran-Armitage trend test supports the dose-trend hypothesis in mortality with rVWF+rFVIII, as well as with rVWF alone. Both two-sided p-values were below 1% and demonstrated that the probability of death increased as dose increases.

There was no mortality (0 of 20) with HAEMATE® P at a dose of 2000 RCoU/kg (+1664 1 U/kg FVIII) or (0 of 20) with rVWF+rFVIII at a dose of 2000 RCoU/kg+1538 IU/kg rFVIII (two-sided p-value=1.0000).

4. Clinical Abnormalities

Clinical abnormalities indicative of toxicity were observed in 85% of the animals treated with 4000 RCoU/kg rVWF (17 of 20 in groups E and O), and in 75% treated with 4000 RCoU/kg rVWF+3077 IU/kg rFVIII (15 of 20 in groups A and K). Symptoms were seen in 45% of the animals treated with 2000 RCoU/kg rVWF alone (9 of 20, in groups B and L), and in 35% of the animals treated with 2000 RCoU/kg rVWF+1538 IU/kg rFVIII (7 of 20, in groups I and S). Symptoms indicative of toxicity were seen in 90% of the animals treated with 4000 RCoU/kg HAEMATE® P (9 of 10 in group T), and 40% of the animals treated with 2000 RCoU/kg HAEMATE® P (8 of 20, in groups J and U).

Clinical symptoms were also observed in 20% of the animals treated with the combined buffer solutions (4 of 20, in groups C and M).

All other treatment groups were clinically normal. A summary is provided in the following Table 17.

TABLE 17

Clinical abnormalities in animals

| Item | dose | group | Animal No. | Symptoms |
|---|---|---|---|---|
| rVWF | 4000 RCoU/kg | E | 21 | behavioral depression, prone position, 3 min |
| | | | 22 | behavioral depression, dyspnea, prone position, 3 min |
| | | | 24 | ataxia, prone position, behavioral depression, immobile, death after 2.5 hours |

TABLE 17-continued

Clinical abnormalities in animals

| Item | dose | Animal group | No. | Symptoms |
|---|---|---|---|---|
| | | | 25 | dyspnea, prone position, piloerection, behavioral depression, copper-colored urine |
| | | | 121 | convulsions, side position, dyspnea, behavioral depression, death after 2.5 hours |
| | | | 122 | prone position, immobile, blood urine |
| | | | 123 | side position, cramps, dyspnea, death after 2 min |
| | | | 124 | side position, convulsions, death after 2 min |
| rVWF | 4000 RCoU/kg | O | 125 | ataxia, prone position, behavioral depression |
| | | | 71 | side position, convulsions, dyspnea, behavioral depression, immobile, death after 4 days |
| | | | 72 | dyspnea, behavioral depression, piloerection, immobile, death after 4 days |
| | | | 73 | behavioral depression, immobile, death after 1 day |
| | | | 74 | dyspnea, behavioral depression, piloerection for 7 days |
| | | | 75 | prone position, behavioral depression, immobile, piloerection for 4 days |
| | | | 172 | side position, dyspnea, immobile, behavioral depression up to 3 days |
| | | | 173 | side position, convulsions, sudden death |
| rVWF + rFVIII | 4000 RCoU/kg + 3077 IU/kg | A | 175 | side position, dyspnea, immobile, piloerection up to 6 hours |
| | | | 2 | prone position, dyspnea, behavioral depression |
| | | | 3 | prone position, behavioral depression |
| | | | 4 | behavioral depression up to 6 hours |
| | | | 101 | prone position, behavioral depression for 3 min |
| | | | 102 | dyspnea, behavioral depression, immobile |
| | | | 103 | side position, convulsions, dyspnea, death |
| | | | 104 | behavioral depression, dyspnea for 6 hours |
| | | | 105 | side position, dyspnea for 5 min behavioral depression for 6 hours |
| rVWF + rFVIII | 4000 RCoU/kg + 3077 IU/kg | K | 52 | dyspnea, ataxia, behavioral depression, death after 1 hour |
| | | | 53 | prone position, dyspnea, behavioral depression for 1 day |
| | | | 54 | prone position, dyspnea for 5 min |
| | | | 55 | convulsions, dyspnea, prone position for 5 min |
| | | | 151 | prone position, dyspnea, behavioral depression for 3 min |
| | | | 153 | behavioral depression, dyspnea for 6 hours |
| | | | 154 | behavioral depression, dyspnea for 6 hours |
| rVWF | 2000 RCoU/kg | B | 6 | behavioral depression short |
| | | | 8 | behavioral depression, dyspnea, immobile |
| | | | 9 | behavioral depression, piloerection |
| | | | 10 | behavioral depression, piloerection |
| | | | 106 | behavioral depression, piloerection |
| | | | 56 | prone position, dyspnea, behavioral depression, death after 1.5 hours |
| rVWF | 2000 RCoU/kg | L | 57 | behavioral depression for 2 min |
| | | | 58 | behavioral depression, piloerection, death after 5 days |
| | | | 59 | behavioral depression, piloerection, immobile, death after 9 days |
| rVWF + rFVIII | 2000 RCoU/kg + 1538 IU/kg | I | 42 | behavioral depression up to 6 hours |
| | | | 91 | behavioral depression, piloerection up to 6 hours |
| | | | 92 | behavioral depression up to 6 hours |
| rVWF + rFVIII | 2000 RCoU/kg + 1538 IU/kg | S | 94 | behavioral depression up to 6 hours |
| | | | 95 | behavioral depression up to 6 hours |
| | | | 191 | behavioral depression up to 6 hours |
| | | | 195 | behavioral depression up to 6 hours |
| | | | 96 | side position, immediate death |
| | | | 97 | side position, dyspnoe, immediate death |
| | | | 98 | side position, convulsions, immediate death |
| | | | 99 | side position, convulsions 3 min |
| HAEMATE ® P | 4000 RCoU/kg | T | 196 | side position, convulsions, immediate death |
| | | | 197 | side position, dyspnea, immediate death |
| | | | 198 | side position, convulsions, dyspnea for 3 min |
| | | | 199 | convulsions, immediate death |
| | | | 200 | convulsions, immediate death |
| | | | 48 | prone position, dyspnea for 1 min |

TABLE 17-continued

Clinical abnormalities in animals

| Item | dose | group | Animal No. | Symptoms |
|---|---|---|---|---|
| HAEMATE ® P | 2000 RCoU/kg | J | 146 | prone position, convulsions, dyspnea for 1 min |
| | | | 148 | ataxia short |
| | | | 150 | ataxia short |
| | | | 201 | dyspnea, side position for 1 min |
| | | U | 203 | side position, convulsions, dyspnea for 2 min |
| HAEMATE ® P | 2000 RCoU/kg | | 208 | ataxia for 1 min |
| | | | 209 | ataxia short |
| rVWF buffer + Advate buffer | 31.7 + 17.6 mL/kg; 49.3 mL/kg | C | 14 | prone position, dyspnea, ataxia (2 min) |
| | | | 15 | behavioral depression, ataxia (2 min) |
| rVWF buffer + Advate buffer | 31.7 + 17.6 mL/kg; 49.3 mL/kg | H | 161 | prone position, ataxia, dyspnea (3 min) |
| | | | 165 | side-prone position, dyspnea (2 min) |

5. Body Mass Analysis

The change in body mass between study day 0 and study days 1, 7 and 14 (as Δ% of body mass at day 0) were visualized using box plots grouped by item and dose. Male and female animals were combined for these box plots. The body mass analysis is provided in Table 18 and FIGS. 24-26.

TABLE 18

Summary of body mass analysis

| Item | Dose of VWF:RCo [U/kg] | Dose of FVIII [IU/kg] | Sex | Day 0 to Day 1 | | | Day 0 to Day 7/8 | | | Day 0 to Day 14 | | |
|---|---|---|---|---|---|---|---|---|---|---|---|---|
| | | | | N | Mean | 95% CI for mean | N | Mean | 95% CI for mean | N | Mean | 95% CI for mean |
| NaCl | 0 | 0 | Female | 5 | −1.1% | −4.8% to 3.9% | 5 | 1.7% | 0.3% to 4.5% | 5 | 1.7% | −11.3% to 4.3% |
| | | | Male | 5 | −1.8% | −3.1% to −0.1% | 5 | −0.8% | −2.6% to 0.8% | 5 | 1.9% | −2.5% to 6.1% |
| | | | Pooled | 10 | −1.5% | −2.7% to 0.6% | 10 | 0.5% | −0.4% to 1.5% | 10 | 1.8% | −0.3% to 3.4% |
| HAEMATE ® P | 2000 | 1664 | Female | 5 | 1.9% | −1.1% to 6.5% | 5 | 2.6% | 0.4% to 15.0% | 5 | 3.4% | −16.5% to 6.1% |
| | | | Male | 5 | −0.6% | −2.6% to 0.2% | 5 | −1.7% | −5.9% to 2.6% | 5 | −0.4% | −8.9% to 3.3% |
| | | | Pooled | 10 | 0.6% | −0.3% to 2.7% | 10 | 0.5% | −1.5% to 2.1% | 10 | 1.5% | −1.3% to 3.5% |
| | 4000 | 3322 | Female | 0 | NA | NA | 1 | 3.6% | NA | 1 | 7.6% | NA |
| | | | Male | 0 | NA | NA | 1 | −3.6% | NA | 1 | 0.7% | NA |
| | | | Pooled | 0 | NA | NA | 2 | −0.0% | NA | 2 | 4.2% | NA |
| rVWF buffer | 0 | 0 | Female | 5 | −0.8% | −2.4% to 1.3% | 5 | 3.9% | −1.9% to 9.7% | 5 | 6.1% | 3.5% to 7.3% |
| | | | Male | 5 | −0.6% | −10.0% to 1.1% | 5 | 1.9% | −0.7% to 19.4% | 5 | 3.5% | −0.4% to 10.3% |
| | | | Pooled | 10 | −0.7% | −2.5% to 0.2% | 10 | 2.9% | 0.9% to 5.4% | 10 | 4.8% | 2.8% to 6.0% |
| rVWF + rFVIII buffer | 0 | 0 | Female | 5 | −0.1% | −1.9% to 8.4% | 5 | 0.9% | −13.2% to 3.6% | 5 | 2.7% | 0.1% to 29.6% |
| | | | Male | 5 | −2.1% | −23.3% to 4.0% | 5 | −0.1% | −9.8% to 2.5% | 5 | 2.2% | −1.7% to 7.8% |
| | | | Pooled | 10 | −1.1% | −8.4% to 1.5% | 10 | 0.4% | −3.6% to 2.2% | 10 | 2.5% | 0.6% to 5.0% |
| rVWF | 250 | 0 | Female | 5 | −0.8% | −2.9% to 7.7% | 5 | 0.9% | −1.4% to 5.0% | 5 | 2.0% | −4.6% to 5.2% |
| | | | Male | 5 | −1.0% | −3.2% to −0.4% | 5 | 0.4% | −2.4% to 5.5% | 5 | 2.7% | −0.4% to 4.6% |
| | | | Pooled | 10 | −0.9% | −1.9% to 1.1% | 10 | 0.6% | −0.7% to 2.2% | 10 | 2.3% | 0.0% to 3.7% |
| | 500 | 0 | Female | 5 | 1.6% | −1.6% to 15.1% | 5 | −3.1% | −13.5% to 0.6% | 5 | −0.8% | −15.7% to 3.7% |
| | | | Male | 5 | −11.5% | −372.2% to 2.7% | 5 | −0.7% | −3.9% to 3.0% | 5 | −0.3% | −4.9% to 2.2% |
| | | | Pooled | 10 | −5.0% | −32.4% to 0.6% | 10 | −1.9% | −5.7% to −0.1% | 10 | −0.6% | −6.2% to 1.8% |

TABLE 18-continued

Summary of body mass analysis

| | | | | | Day 0 to Day 1 | | | Day 0 to Day 7/8 | | | Day 0 to Day 14 | |
|---|---|---|---|---|---|---|---|---|---|---|---|---|
| Item | Dose of VWF:RCo [U/kg] | Dose of FVIII [IU/kg] | Sex | N | Mean | 95% Cl for mean | N | Mean | 95% Cl for mean | N | Mean | 95% Cl for mean |
| | 1000 | 0 | Female | 5 | −0.6% | −16.0% to 1.3% | 5 | 0.7% | −4.1% to 14.2% | 5 | 2.8% | −1.3% to 15.3% |
| | | | Male | 5 | −0.7% | −21.8% to 2.3% | 5 | −0.5% | −3.4% to 5.0% | 5 | 0.3% | −3.3% to 1.6% |
| | | | Pooled | 10 | −0.6% | −10.4% to 0.9% | 10 | 0.1% | −2.0% to 3.9% | 10 | 1.5% | 0.1% to 5.6% |
| | 2000 | 0 | Female | 5 | −8.3% | −13.5% to 0.5% | 5 | −1.0% | −5.0% to 3.0% | 5 | 3.3% | 2.0% to 6.6% |
| | | | Male | 5 | −4.8% | −10.4% to 4.0% | 2 | −11.5% | NA | 1 | −3.7% | NA |
| | | | Pooled | 10 | −6.5% | −9.3% to −3.5% | 7 | −4.0% | −10.8% to −1.6% | 6 | 2.1% | 1.3% to 3.1% |
| | 4000 | 0 | Female | 2 | −5.0% | NA | 4 | 1.4% | −0.5% to 8.4% | 4 | 5.5% | 3.7% to 26.3% |
| | | | Male | 4 | −1.6% | −8.1% to 1.2% | 2 | −8.5% | NA | 2 | −4.9% | NA |
| | | | Pooled | 6 | −2.7% | −9.3% to −1.1% | 6 | −1.9% | −10.2% to 0.6% | 6 | 2.0% | −1.2% to 3.7% |
| rVWF + FVIII | 250 | 192 | Female | 5 | 2.2% | −2.0% to 5.2% | 5 | 1.2% | 0.3% to 4.4% | 5 | 4.6% | 0.6% to 12.0% |
| | | | Male | 5 | −1.1% | −2.4% to 1.6% | 5 | −1.6% | −4.2% to 0.5% | 5 | 0.7% | −16.5% to 3.3% |
| | | | Pooled | 10 | 0.5% | −0.8% to 2.5% | 10 | −0.2% | −1.2% to 0.5% | 10 | 2.7% | 0.7% to 5.4% |
| | 500 | 385 | Female | 5 | −6.1% | −11.1% to 8.1% | 5 | −0.7% | −3.5% to 9.4% | 5 | 0.7% | −5.9% to 51.9% |
| | | | Male | 5 | 0.1% | −1.8% to 41.7% | 5 | 0.8% | −9.2% to 4.8% | 5 | 3.0% | −1.4% to 5.4% |
| | | | Pooled | 10 | −3.0% | −5.9% to −1.1% | 10 | 0.1% | −2.6% to 2.5% | 10 | 1.9% | −1.4% to 6.0% |
| | 1000 | 769 | Female | 5 | −2.6% | −17.5% to 1.9% | 5 | −0.4% | −4.6% to 3.1% | 5 | 1.3% | −1.6% to 6.6% |
| | | | Male | 5 | −3.8% | −7.7% to 0.5% | 5 | 1.1% | −1.7% to 11.4% | 5 | 3.2% | −5.0% to 11.8% |
| | | | Pooled | 10 | −3.2% | −5.8% to −1.0% | 10 | 0.4% | −1.4% to 2.5% | 10 | 2.3% | −0.0% to 5.7% |
| | 2000 | 1538 | Female | 5 | −8.0% | −11.1% to 2.6% | 5 | 2.9% | −0.4% to 26.8% | 5 | 4.8% | 0.0% to 8.9% |
| | | | Male | 5 | −6.8% | −10.8% to 1.4% | 5 | 0.5% | −3.3% to 2.4% | 5 | 2.5% | −0.5% to 5.4% |
| | | | Pooled | 10 | −7.4% | −9.4% to −4.6% | 10 | 1.7% | 0.0% to 5.2% | 10 | 3.6% | 2.0% to 5.8% |
| | 4000 | 3077 | Female | 3 | −2.8% | NA | 3 | −0.2% | NA | 3 | −0.5% | NA |
| | | | Male | 5 | −7.5% | −9.9% to −2.1% | 4 | −0.6% | −9.3% to 10.1% | 4 | 2.4% | −6.4% to 11.4% |
| | | | Pooled | 8 | −5.7% | −7.9% to −0.8% | 7 | −0.5% | −4.2% to 3.2% | 7 | 1.2% | −1.9% to 6.1% |

There were statistically significant (at the multiplicity adjusted 5% level) decreases in body mass from day 0 to day 1 with the highest dose (mean Δ% of −5.7%) and with the second highest dose (mean Δ% of −7.4%) than with the corresponding buffer (mean Δ% of −1.1%).

There were no statistically significant differences (at the multiplicity adjusted 5% level) in body mass development from day 0 to day 14 between different doses of rVWF+rFVIII and the corresponding buffer because all two-sided p-values adjusted for multiplicity were greater than 5%.

Estimation of the minimum detectable dose for changes in body mass from day 0 to day 1 in a step-down manner stopped at the contrast for 500 RCoU/kg+385 IU/kg which was the first two-sided p-value above 5% (two-sided p-value=0.1069). The minimum detectable dose was therefore 1000 RCoU/kg+769 IU/kg rFVIII.

Estimation of the minimum detectable dose for changes in body mass from day 0 to day 14 in a step-down manner stopped at the contrast for the highest dose. The two-sided p-value for the highest dose was 0.2276, which was above 5% and no further contrasts were investigated. There was no minimum detectable dose for changes in body mass from day 0 to day 14 with rVWF+rFVIII and the highest dose investigated could be regarded as the NOAEL dose.

There were statistically significant (at the multiplicity adjusted 5% level) larger decreases in body mass from day 0 to day 1 with the highest dose (mean Δ% of −2.7%) and with the second highest dose (mean Δ% of −6.5%) than with the corresponding buffer (mean Δ% of −0.7%).

There were statistically significant (at the multiplicity adjusted 5% level) larger differences in body mass from day 0 to day 14 with all doses investigated than with the corresponding buffer because all two-sided p-values adjusted for multiplicity were below 5%.

Estimation of the minimum detectable dose for changes in body mass from day 0 to day 1 in a step-down manner stopped at the contrast for 1000 RCoU/kg, which was the first two-sided p-values above 5% (two-sided p-value=0.6932). The minimum detectable dose was therefore 2000 RCoU/kg.

Estimation of the minimum detectable dose for changes in body mass from day 0 to day 14 in a step-down manner stopped at the contrast for the lowest dose investigated where the two-sided p-value was still above 5%. The minimum detectable dose was therefore 250 RCoU/kg.

Mean body mass development from day 0 to day 1 was 0.6% (95% CI: −0.3% to 2.7%) with HAEMATE® P (2000 RCoU/kg+1664 IU/kg FVIII) and −7.4% (95% CI: −9.4% to −4.6%) with the corresponding dose of rVWF+rFVIII administered. This difference was statistically significant at the 5% level (two-sided p-value<0.0001).

Mean body mass development from day 0 to day 14 was 1.5% (95% CI: −1.3% to 3.5%) with HAEMATE® P (2000 RCoU/kg+1664 IU/kg FVIII) and 3.6% (95% CI: 2.0% to 5.8%) with the corresponding dose of rVWF+rFVIII administered. This difference was not statistically significant at the 5% level (two-sided p-value=0.2079).

6. Hematological and Serological Variables

A comparison of hematocrit, platelet count, and LDH are given in Tables 19-21 and FIGS. 27-32.

Data for hematocrit and platelet count at day 14 in the groups treated with 1000 RCoU/kg rVWF and buffer are missing because of sample damage.

TABLE 19

Summary of hematocrit data

| | Hematocrit (%) | | | | Study day | | | | |
| | | | | | 1 | | | 14 | |
| Item | Dose of VWF:RCo [U/kg] | Dose of FVIII [IU/kg] | Sex | N | Mean | CV [%] | N | Mean | CV [%] |
|---|---|---|---|---|---|---|---|---|---|
| NaCl | 0 | 0 | Male | 5 | 42.4 | 4.0 | 5 | 42.3 | 5.4 |
| | | | Female | 5 | 43.2 | 4.8 | 5 | 42.5 | 1.9 |
| | | | Pooled | 10 | 42.8 | 4.3 | 10 | 42.4 | 3.8 |
| HAEMATE ® P | 2000 | 1347 | Male | 5 | 42.1 | 6.2 | 5 | 40.2 | 6.0 |
| | | | Female | 5 | 39.7 | 10.6 | 5 | 42.3 | 2.3 |
| | | | Pooled | 10 | 40.9 | 8.6 | 10 | 41.3 | 4.9 |
| | 4000 | 3322 | Male | 0 | NA | NA | 1 | 35.8 | NA |
| | | | Female | 0 | NA | NA | 1 | 43.5 | NA |
| | | | Pooled | 0 | NA | NA | 2 | 39.7 | 13.7 |
| rVWF buffer | 0 | 0 | Male | 5 | 40.6 | 4.9 | 1 | 7.6 | NA |
| | | | Female | 5 | 43.8 | 1.3 | 0 | NA | NA |
| | | | Pooled | 10 | 42.2 | 5.2 | 1 | 7.6 | NA |
| rVWF + rFVIII buffer | 0 | 0 | Male | 5 | 44.0 | 4.4 | 5 | 43.1 | 4.3 |
| | | | Female | 5 | 44.7 | 3.4 | 5 | 41.7 | 2.1 |
| | | | Pooled | 10 | 44.3 | 3.8 | 10 | 42.4 | 3.7 |
| rVWF | 250 | 0 | Male | 5 | 43.0 | 2.3 | 5 | 43.8 | 2.8 |
| | | | Female | 4 | 41.5 | 2.6 | 5 | 43.1 | 2.8 |
| | | | Pooled | 9 | 42.2 | 3.0 | 10 | 43.5 | 2.8 |
| | 500 | 0 | Male | 5 | 43.6 | 5.1 | 5 | 42.0 | 4.6 |
| | | | Female | 5 | 41.8 | 1.2 | 5 | 41.6 | 7.6 |
| | | | Pooled | 10 | 42.7 | 4.2 | 10 | 41.8 | 5.9 |
| | 1000 | 0 | Male | 5 | 39.6 | 7.2 | 0 | NA | NA |
| | | | Female | 5 | 42.2 | 5.7 | 0 | NA | NA |
| | | | Pooled | 10 | 40.9 | 6.9 | 0 | NA | NA |
| | 2000 | 0 | Male | 5 | 37.7 | 18.5 | 1 | 46.5 | NA |
| | | | Female | 5 | 34.7 | 13.7 | 5 | 43.3 | 2.0 |
| | | | Pooled | 10 | 36.2 | 16.2 | 6 | 43.9 | 3.5 |
| | 4000 | 0 | Male | 5 | 42.8 | 6.5 | 2 | 41.8 | 2.7 |
| | | | Female | 5 | 45.1 | NA | 4 | 42.9 | 3.0 |
| | | | Pooled | 10 | 43.3 | 6.0 | 6 | 42.5 | 3.0 |
| rVWF + rFVIII | 250 | 192 | Male | 5 | 41.4 | 4.0 | 5 | 41.2 | 4.6 |
| | | | Female | 5 | 42.9 | 6.5 | 5 | 42.9 | 4.3 |
| | | | Pooled | 10 | 42.2 | 5.5 | 10 | 42.1 | 4.7 |
| | 500 | 385 | Male | 5 | 42.8 | 4.1 | 5 | 43.7 | 6.4 |
| | | | Female | 4 | 42.2 | 1.4 | 5 | 44.3 | 3.0 |
| | | | Pooled | 9 | 42.5 | 3.1 | 10 | 44.0 | 4.8 |
| | 1000 | 769 | Male | 5 | 42.1 | 7.5 | 5 | 39.3 | 8.5 |
| | | | Female | 5 | 42.6 | 9.8 | 5 | 42.4 | 3.7 |
| | | | Pooled | 10 | 42.3 | 8.3 | 10 | 40.8 | 7.2 |
| | 2000 | 1538 | Male | 5 | 36.6 | 3.6 | 5 | 39.7 | 10.5 |
| | | | Female | 5 | 37.9 | 9.1 | 5 | 43.5 | 2.9 |
| | | | Pooled | 10 | 37.2 | 6.9 | 10 | 41.6 | 8.4 |
| | 4000 | 3077 | Male | 5 | 35.0 | 12.4 | 4 | 40.9 | 18.0 |
| | | | Female | 3 | 36.1 | 19.6 | 3 | 45.7 | 3.7 |
| | | | Pooled | 8 | 35.4 | 14.2 | 7 | 43.0 | 13.7 |

TABLE 20

Summary of platelet count

| Platelet count (×10^3/μL) | | | | Study day | | | | | |
|---|---|---|---|---|---|---|---|---|---|
| | Dose of | Dose of | | 1 | | | 14 | | |
| Item | VWF:RCo [U/kg] | FVIII [IU/kg] | Sex | N | Mean | CV [%] | N | Mean | CV [%] |
| NaCl | 0 | 0 | Male | 5 | 1199 | 15 | 5 | 1338 | 3 |
| | | | Female | 5 | 1044 | 10 | 5 | 1083 | 7 |
| | | | Pooled | 10 | 1122 | 14 | 10 | 1211 | 12 |
| HAEMATE ® P | 2000 | 1664 | Male | 5 | 940 | 17 | 5 | 998 | 45 |
| | | | Female | 5 | 710 | 40 | 5 | 1084 | 14 |
| | | | Pooled | 10 | 825 | 30 | 10 | 1041 | 31 |
| | 4000 | 3322 | Male | 0 | NA | NA | 1 | 1273 | NA |
| | | | Female | 0 | NA | NA | 1 | 1204 | NA |
| | | | Pooled | 0 | NA | NA | 2 | 1239 | 4 |
| rVWF buffer | 0 | 0 | Male | 5 | 1220 | 18 | 1 | 3971 | NA |
| | | | Female | 5 | 1103 | 10 | 0 | NA | NA |
| | | | Pooled | 10 | 1161 | 15 | 1 | 3971 | NA |
| rVWF + rFVIII buffer | 0 | 0 | Male | 5 | 1143 | 14 | 5 | 1180 | 14 |
| | | | Female | 5 | 999 | 17 | 5 | 898 | 22 |
| | | | Pooled | 10 | 1071 | 16 | 10 | 1039 | 22 |
| rVWF | 250 | 0 | Male | 5 | 1291 | 10 | 5 | 1184 | 11 |
| | | | Female | 5 | 933 | 23 | 5 | 994 | 11 |
| | | | Pooled | 10 | 1112 | 23 | 10 | 1089 | 14 |
| | 500 | 0 | Male | 5 | 1141 | 25 | 5 | 1348 | 9 |
| | | | Female | 5 | 783 | 49 | 5 | 1112 | 8 |
| | | | Pooled | 10 | 962 | 38 | 10 | 1230 | 13 |
| | 1000 | 0 | Male | 5 | 615 | 86 | 0 | NA | NA |
| | | | Female | 5 | 393 | 98 | 0 | NA | NA |
| | | | Pooled | 10 | 504 | 90 | 0 | NA | NA |
| | 2000 | 0 | Male | 5 | 307 | 154 | 1 | 754 | NA |
| | | | Female | 5 | 51 | 88 | 5 | 909 | 42 |
| | | | Pooled | 10 | 179 | 193 | 6 | 883 | 39 |
| | 4000 | 0 | Male | 4 | 423 | 143 | 2 | 1375 | 33 |
| | | | Female | 1 | 84 | NA | 4 | 1137 | 20 |
| | | | Pooled | 5 | 355 | 153 | 6 | 1216 | 24 |
| rVWF + rFVIII | 250 | 192 | Male | 5 | 1358 | 13 | 5 | 1280 | 13 |
| | | | Female | 5 | 1145 | 20 | 5 | 1095 | 6 |
| | | | Pooled | 10 | 1252 | 18 | 10 | 1188 | 13 |
| | 500 | 385 | Male | 5 | 844 | 62 | 5 | 1356 | 4 |
| | | | Female | 4 | 1090 | 10 | 5 | 1127 | 7 |
| | | | Pooled | 9 | 954 | 42 | 10 | 1241 | 11 |
| | 1000 | 769 | Male | 5 | 412 | 107 | 5 | 1408 | 32 |
| | | | Female | 5 | 378 | 98 | 5 | 876 | 29 |
| | | | Pooled | 10 | 395 | 97 | 10 | 1142 | 39 |
| | 2000 | 1538 | Male | 5 | 57 | 67 | 5 | 1327 | 19 |
| | | | Female | 5 | 113 | 84 | 5 | 1226 | 7 |
| | | | Pooled | 10 | 85 | 87 | 10 | 1277 | 15 |
| | 4000 | 3077 | Male | 5 | 78 | 21 | 4 | 1329 | 34 |
| | | | Female | 3 | 131 | 98 | 3 | 966 | 41 |
| | | | Pooled | 8 | 98 | 77 | 7 | 1173 | 37 |

TABLE 21

Summary of LDH data

| LDH [U/L] | | | | Study day | | | | | |
|---|---|---|---|---|---|---|---|---|---|
| | Dose of | Dose of | | 1 | | | 14 | | |
| Item | VWF:RCo [U/kg] | FVIII [IU/kg] | Sex | N | Mean | CV [%] | N | Mean | CV [%] |
| NaCl | 0 | 0 | Male | 5 | 425 | 8 | 5 | 490 | 51 |
| | | | Female | 5 | 821 | 11 | 5 | 278 | 20 |
| | | | Pooled | 10 | 623 | 35 | 10 | 384 | 53 |
| HAEMATE ® P | 2000 | 1664 | Male | 5 | 376 | 18 | 5 | 334 | 36 |
| | | | Female | 5 | 370 | 24 | 5 | 346 | 35 |
| | | | Pooled | 10 | 373 | 20 | 10 | 340 | 33 |
| | 4000 | 3322 | Male | 0 | NA | NA | 1 | 267 | NA |
| | | | Female | 0 | NA | NA | 1 | 261 | NA |
| | | | Pooled | 0 | NA | NA | 2 | 264 | 2 |
| rVWF buffer | 0 | 0 | Male | 5 | 662 | 43 | 5 | 610 | 49 |
| | | | Female | 5 | 451 | 25 | 5 | 297 | 29 |
| | | | Pooled | 10 | 557 | 42 | 10 | 453 | 58 |

TABLE 21-continued

Summary of LDH data

| | LDH [U/L] | | | Study day | | | | |
| | | | | 1 | | | 14 | |
| Item | Dose of VWF:RCo [U/kg] | Dose of FVIII [IU/kg] | Sex | N | Mean | CV [%] | N | Mean | CV [%] |
|---|---|---|---|---|---|---|---|---|---|
| rVWF + rFVIII buffer | 0 | 0 | Male | 5 | 386 | 16 | 5 | 543 | 65 |
| | | | Female | 5 | 385 | 61 | 5 | 330 | 29 |
| | | | Pooled | 10 | 385 | 42 | 10 | 437 | 62 |
| rVWF | 250 | 0 | Male | 5 | 228 | 25 | 5 | 296 | 10 |
| | | | Female | 5 | 238 | 35 | 5 | 277 | 17 |
| | | | Pooled | 10 | 233 | 29 | 10 | 287 | 13 |
| | 500 | 0 | Male | 5 | 402 | 32 | 5 | 292 | 25 |
| | | | Female | 5 | 399 | 62 | 5 | 246 | 26 |
| | | | Pooled | 10 | 401 | 47 | 10 | 269 | 26 |
| | 1000 | 0 | Male | 5 | 669 | 96 | 5 | 380 | 29 |
| | | | Female | 5 | 577 | 37 | 5 | 405 | 50 |
| | | | Pooled | 10 | 623 | 73 | 10 | 392 | 39 |
| | 2000 | 0 | Male | 5 | 1662 | 123 | 1 | 297 | NA |
| | | | Female | 5 | 3990 | 13 | 5 | 438 | 59 |
| | | | Pooled | 10 | 2826 | 66 | 6 | 415 | 58 |
| | 4000 | 0 | Male | 4 | 962 | 95 | 2 | 251 | 12 |
| | | | Female | 2 | 5450 | 19 | 4 | 297 | 31 |
| | | | Pooled | 6 | 2458 | 100 | 6 | 282 | 27 |
| rVWF + rFVIII | 250 | 192 | Male | 5 | 352 | 50 | 5 | 266 | 24 |
| | | | Female | 5 | 227 | 31 | 5 | 232 | 12 |
| | | | Pooled | 10 | 290 | 49 | 10 | 249 | 20 |
| | 500 | 385 | Male | 5 | 504 | 74 | 5 | 298 | 19 |
| | | | Female | 5 | 370 | 21 | 5 | 264 | 43 |
| | | | Pooled | 10 | 437 | 60 | 10 | 281 | 31 |
| | 1000 | 769 | Male | 5 | 2265 | 158 | 5 | 349 | 16 |
| | | | Female | 5 | 465 | 78 | 5 | 413 | 20 |
| | | | Pooled | 10 | 1365 | 189 | 10 | 381 | 20 |
| | 2000 | 1538 | Male | 5 | 3790 | 67 | 5 | 354 | 30 |
| | | | Female | 5 | 2572 | 93 | 5 | 280 | 36 |
| | | | Pooled | 10 | 3181 | 76 | 10 | 317 | 33 |
| | 4000 | 3077 | Male | 5 | 1614 | 62 | 4 | 517 | 46 |
| | | | Female | 3 | 3790 | 78 | 3 | 359 | 16 |
| | | | Pooled | 8 | 2430 | 86 | 7 | 450 | 42 |

7. Necropsy

The necropsy findings indicated an association of rVWF with animals that died spontaneously.

8. Histopathology

For the short term study, heart myocardial necrosis (minimal to moderate grade, focal or multifocal) was recorded in rVWF-treated groups treated with 500 RCoU/kg rVWF, and higher doses, alone or combined with rFVIII. Microthrombi (minimal to moderate grade) were recorded in rVWF-treated animals with 1000 RCoU/kg and higher doses, alone or combined with rFVIII. Both of these changes showed a slight dose-dependent increase in severity and/or incidence.

Additionally, an increased incidence for coronary perivasculitis was recorded in test-item-treated animals with doses of 1000 RCoU/kg rVWF and higher doses alone or combined with rFVIII.

Microthrombi (minimal grade) combined with glial cell foci (minimal grade) were recorded in the brains of the high-dose group treated with rVWF alone. A slightly increased incidence of microthrombi (all of minimal grade) was recorded in animals in the 2000 RCoU/kg dose group treated with rVWF alone, and in animals of the 1000 RCoU/kg dose group treated with a combination of rVWF and rFVIII.

Microthrombi of minimal incidence and grade without accompanying degenerative lesions were recorded in single rVWF-treated animals of different groups as well as in one control animal treated with isotonic saline.

Microthrombi (minimal grade) were recorded in the eyes of one rVWF-treated animal of the high-dose group, which died spontaneously. This finding was not observed in animals treated with a combination of rVWF and rFVIII.

Microthrombi (minimal to slight grade) were recorded in the kidneys of a rVWF-treated animal of the high-dose group (which died spontaneously) and in a rVWF-treated animal of the 500 RCoU/kg dose group (both treated with rVWF alone), and in animals in the 1000 RCoU/kg and high-dose groups which were treated with a combination of rVWF and rFVIII.

Low incidences of microthrombi (minimal to slight grade) were recorded in the lungs of test-item-treated animals, as well as in control animals, which were treated with HAEMATE® P, isotonic saline or combined buffers (incidence: ≤4/10; mean severity: ≤1.5). All microthrombi were at an early stage, showed no signs of fibrin condensation and were not accompanied by necrosis or infarction.

Additionally, minimally increased mean severity of microthrombi were recorded in test-item-treated animals of the high-dose group which were treated with rVWF alone. This increase was caused by two animals of this group, which both had a moderate severity of pulmonary microthrombi (grade 3). No clear dose relation could be recorded.

For the long term study, myocardial degeneration/reparation (minimal to marked grade) was recorded in the hearts of test-item-treated animals treated with doses of 500 RCoU/kg rVWF and higher doses, alone or combined with rFVIII. This change showed a dose-dependent increase in severity and/or incidence and was characterized by inflammation (mainly mononuclear) and fibrosis, often accompanied by hemosiderin deposition and sometimes also by myocardial calcification.

Additionally, microthrombi and myocardial necrosis were recorded at a low incidence, especially in animals which died spontaneously.

Microthrombi (minimal grade) combined with glial cell foci (minimal grade) were recorded in the brains of the high-dose group treated with rVWF alone, as well as in the group treated with a combination of 2000 RCoU/kg rVWF and rFVIII.

Additionally, a slightly increased incidence of microthrombi (all of minimal grade) was recorded in animals treated with 2000 RCoU/kg rVWF alone. Microthrombi of minimal incidence and grade, without accompanying degenerative lesions, were recorded in single test-item-treated animals of different groups, as well as in a one control animal treated with the combined buffers.

Microthrombi (minimal to slight grade) were recorded in the kidneys of test-item-treated animals of groups that were treated with 1000 RCoU/kg rVWF and higher doses alone, as well as in animals of groups treated with 500 RCoU/kg rVWF and higher doses combined with rFVIII. This finding was also recorded in minimal grade in one control animal treated with the combined buffers.

The microthrombi (slight grade) were accompanied by a cortical necrosis (moderate grade) in one test-item-treated animal in the 2000 RCoU/kg dose group treated with rVWF alone (died spontaneously).

A microthrombus (minimal grade) was recorded in the adrenal cortices of one test-item-treated animal of the high-dose group, which was treated with rVWF alone (died spontaneously). This finding was not observed in animals treated with rVWF combined with rFVIII.

Additionally, slight to moderate hemorrhage was recorded in three test-item-treated animals of the high-dose group which were treated with rVWF alone (died spontaneously). This finding was not observed in animals treated with rVWF combined with rFVIII.

Low incidences of microthrombi (minimal to slight grade) were recorded in the lungs of test-item-treated animals as well as in control animals treated with HAEMATE® P, isotonic saline, citrate buffer or combined buffers (incidence: ≤3/10; mean severity: ≤1.5). All microthrombi (except the one described below) were at an early state, showed no signs of fibrin condensation, and were not accompanied by necrosis or infarction.

Additionally, a slightly increased mean severity of microthrombi was recorded in test-item-treated animals of the 2000 RCoU/kg dose group which were treated with rVWF alone. This increase was caused by a single animal of this group which had the only hyaline pulmonary thrombus in this study. This thrombosis led to a macroscopically visible blue-red discoloration of the lungs recorded at necropsy (see "Table of Macroscopic Findings" in the pathology report). No clear dose relation could be recorded.

Furthermore, a slightly increased incidence of microthrombi (all of minimal grade) was recorded in test-item-treated animals of the high-dose group which were treated with a combination of rVWF and rFVIII. No clear dose relation could be recorded.

9. Discussion

As explained above, rVWF was tested alone at five dose levels: 4000, 2000, 1000, 500, and 250 RCoU/kg BW), and combined with rFVIII, also at five doses. In the combined administration the doses of rVWF were the same as in the single administration and those of rFVIII were 3077, 1538, 769, 385 and 192 IU/kg rFVIII in descending order, i.e., 4000 RCoU/kg BW rVWF was co-administered with 3077 IU/kg rFVIII, 2000 RCoU/kg BW rVWF was co-administered with 1538 IU/kg rFVIII, etc. HAEMATE® P was tested at 4000 RCoU/kg BW (+3322 IU/kg BW FVIII) and 2000 RCoU/kg BW (+1664 IU/kg BW FVIII).

The corresponding buffer for rVWF alone was administered at a volume of 31.7 mL/kg (according to the highest dose volume of rVWF), the mixed buffer at 49.3 mL/kg, and isotonic saline at 51.1 mL/kg.

The highest mortality in this study was observed in the group treated with HAEMATE® P at the 4000 RCoU/kg dose level, 80% (8 of 10) died immediately after administration showing unequivocal signs of sodium citrate overload (281 mg/kg citrate were injected with the administered volume of 51.1 mL/kg). As the LD50 of sodium citrate after intravenous application in mice is 231 mg/kg (Sax's Dangerous Properties of Industrial Materials, 1992), the dose of HAEMATE® P was shifted to 2000 RCoU/kg VWF. No further mortality was observed at this dose level with HAEMATE® P.

40% (8 of 20) of the animals that received 4000 RCoU/kg of rVWF alone died, whereas the mortality decreased to 20% (4 of 20) in those that received 2000 RCoU/kg. There was no further mortality in the lower dose groups. 25% (5 of 20) of the animals that received 4000 RCoU/kg rVWF combined with 3077 IU/kg rFVIII died. There was no further mortality in the lower-dose groups, even in the group that received 2000 RCoU/kg combined with rFVIII. As there were 141 mg/kg sodium citrate in the injected volume of the 4000 RCoU/kg dose groups, this may also be a reason for some sudden deaths in these groups. This cause of death can be excluded for the delayed cases in the high-dose groups as well as for the sudden deaths in the 2000 RCoU/kg dose groups.

The statistically ad hoc performed test for a trend demonstrated that the probability of death increased as the dose of rVWF increases (two-sided p-value<0.0001).

There was no mortality (0 of 20) with HAEMATE® P administered with a dose of 2000 RCoU/kg VWF+1664 IU/kg FVIII and no mortality (0 of 20) with 2000 RCoU/kg rVWF+1538 IU/kg rFVIII.

The clinical observation revealed a broad spectrum of abnormalities. Short-term symptoms were obviously also caused by the injected sodium citrate amount because symptoms typical for sodium citrate toxicity (e.g., short-term behavioral depression, convulsions, dyspnea) were recorded in 20% (4 of 20) of the animals of the buffer group.

However, there was a clear correlation between the incidence and severity of symptoms of the dose administered. 85% (17 of 20) of the animals were affected after receiving 4000 RCoU/kg rVWF whereas 45% (9 of 20) of the animals were affected after receiving of 2000 RCoU/kg rVWF.

Clinical abnormalities were observed in 75% (15 of 20) of the animals that received 4000 RCoU/kg combined with 3077 IU/kg rFVIII whereas 35% (7 of 20) were affected after receiving 2000 RCoU/kg rVWF combined with 1538 IU/kg rFVIII. No clinical abnormalities were recorded in any of the other groups treated with rVWF alone or combined with rFVIII.

The symptoms observed in the group treated with HAEMATE® P at the 4000 RCoU/kg dose level (90%, 9 of 10 animals) were clearly caused by the citrate overload (281 mg/kg) and led to immediate death. All affected animals (40%, 8 of 20 animals) in the groups treated with 2000 RCoU/kg HAEMATE® P also showed only short-term abnormalities, indicative of sodium citrate toxicity (140.5 mg/kg; e.g., short-term behavioral depression, convulsions, dyspnea). No further long-term symptoms were recorded.

The minimum detectable dose (MDD) for changes in body mass from day 0 to day 1 was estimated to be 1000 RCoU/kg rVWF+769 IU/kg rFVIII. The dose of 500 RCoU/kg rVWF+385 IU/kg rFVIII could therefore be regarded as the "no observed adverse effect level" (NOAEL) dose in terms of body mass development from day 0 to day 1. There was no minimum detectable dose for changes in body mass from day 0 to day 14, and the highest dose of rVWF+rFVIII investigated (4000 RCoU/kg+3077 IU/kg) could therefore be regarded as the NOAEL dose in terms of body mass development from day 0 to day 14.

The minimum detectable dose (MDD) for changes in body mass from day 0 to day 1 for rVWF administered alone was estimated to be 2000 RCoU/kg. The dose of 1000 RCoU/kg could therefore be regarded as the no observed adverse effect level (NOAEL) dose in terms of body mass development from day 0 to day 1. The minimum detectable dose for changes in body mass from day 0 to day 14 was estimated to be the lowest dose of rVWF investigated (250 RCoU/kg). No dose among the doses of rVWF investigated could therefore be regarded as the NOAEL dose in terms of body mass development from day 0 to day 14. This estimated difference can be considered unpredictable because the increase in body mass (2.3% vs. 4.8% for the buffer group) is higher than that of saline (1.8%) and HAEMATE® P (1.5%) and similar to that of the group treated with 250 RCoU/kg rVWF+rFVIII (2.7%). Mean body mass development from day 0 to day 1 was 0.6% with HAEMATE® P administered at a dose of 2000 RCoU/kg+1664 IU/kg FVIII and −7.4% with the corresponding dose of rVWF+rFVIII administered. This difference was statistically significant at the 5% level (two-sided p-value<0.0001). No statistically significant differences were found from day 0 to day 14.

Comparing the data of the selected hematological and serum chemistry variables in surviving animals, a drop in platelet count was observed at day 1 after administration of 1000 RCoU/kg rVWF and higher doses, administered alone or combined with rFVIII. Additionally, hematocrit dropped after administration of 2000 RCoU/kg rVWF and higher doses administered alone or combined with rFVIII.

Compared with control groups, lactate dehydrogenase was increased on day 1 after treatment with 2000 RCoU/kg rVWF and higher doses administered alone or combined with rFVIII.

Only a drop in platelet count could be measured 1 day after application of 2000 RCoU/kg VWF in HAEMATE® P (+1664 IU/kg FVIII). The measured variables returned to normal in all affected groups after the 14 days of observation.

The histopathological examination revealed many affected organs: Heart (coronary microthrombi, myocardial necrosis, increased coronary perivasculitis, myocardial degeneration/reparation), brain (microthrombi, glia cell foci), eyes (microthrombi), kidneys (microthrombi, cortical necrosis), adrenals (microthrombi, hemorrhage), and lungs (increased incidence or mean severity of microthrombi). These pathohistological changes may be summarized as a disseminated intravascular coagulopathy (DIC). At high doses (≥2000 RCoU rVWF) they resemble the picture of a thrombotic thrombocytopenic purpura (TTP) in humans to some extent. At lower doses (500-1000 RCoU) the heart was mainly affected with pathohistological changes resembling the picture of a low grade "ischemic heart disease." In contrast to test-item-treated animals receiving recombinant product(s), such findings were not recorded in reference-item-treated animals receiving the human plasma-derived VWF-FVIII preparation (HAEMATE® P). Here, only low grade pulmonary microthrombi were recorded at incidences similar to those in control animals.

Thromboembolic changes were recorded for one or several organs in test-item-treated animals which were killed on the scheduled day 1 (or which died spontaneously shortly after administration). The heart, which is highly sensitive to hypoxia, was the most severely affected organ. The vascular occlusion by coronary microthrombi led to reduced blood flow to the heart which causes ischemic myocardial necrosis (cell starvation secondary to a lack of oxygen) and reactive coronary perivasculitis (early effects).

Predominately degenerative and/or reparative changes were recorded in the hearts (inflammation, fibrosis, hemosiderin deposition, calcification) of test-item-treated animals which were killed on the scheduled day 14 (or which died spontaneously with some delay after administration). These cardiac infarct-like changes were deemed to be the consequences of a previous vascular occlusion by microthrombi (delayed effects). The renal cortical necrosis recorded in one animal of the group treated with 2000 RCoU/kg rVWF alone, which died spontaneously, can be interpreted in the same way. Here, the vascular occlusion of kidney vessels by microthrombi led to a renal infarction.

Low incidences of microthrombi (minimal to slight grade) without accompanying organ destruction were recorded for several organs (lungs, kidneys, brain) of saline, buffer, and also HAEMATE® P-treated control animals.

The pathological changes recorded consisted of an adverse microthrombosis in one or several organs. They indicated an thrombogenic potential of the test item, rVWF, in this animal model with a lack of VWF cleavage protease (ADAMTS13-deficient mouse) at doses of 500 RCoU/kg rVWF and higher, either administered alone or combined with rFVIII. As no adverse histopathological changes were recorded in the low-dose groups (rVWF alone and combined with rVWF) a NOAEL could be established at 250 RCoU/kg.

Regarding strain-specific differences of the toxicological profile of rVWF, ADAMTS13-deficient mice represent the most susceptible of the murine strains tested. In contrast to the ADAMTS13-deficient mice, no mortality was observed even with the highest dose of rVWF both in VWF-deficient and in C57BL/6J mice. The NOAEL for rVWF in the ADAMTS13 knock-out mouse was 250 RCoU/kg BW.

Example 9

Coadministration of Human Recombinant ADAMTS13 with Human RVWF in ADAMTS13 Deficient Mice The objective of this study was to evaluate the effect of coadministration of rVWF with recombinant human ADAMTS13 (rADAMTS13) in ADAMTS13-deficient mice. rVWF was administered at 2000 RCoU/kg, and rADAMTS13 at 19.44/kg, in accordance with the ratio found in the human plasma-derived preparation, HAEMATE® P. 2000 RCoU of rVWF was chosen because this dose resulted in a 20% mortality in ADAMTS13-deficient mice (study no. PV1940601). rVWF and rADAMTS13 were either injected premixed in the syringe immediately before application (group A) or consecutively, as an injection of rADAMTS13 followed immediately by rVWF (group B).

HAEMATE® P not only lacks ultra-large VWF multimers, but it also contains ADAMTS13. As demonstrated in Example 8, ADAMTS13 deficient mice did not show signs of thrombogenicity after treatment with HAEMATE® P.

1. Protocol for Coadministration of ADAMTS13 and rVWF

Doses of 2000 RCoU/kg rVWF (equivalent to 15.9 mL/kg) and 19.4 μg/kg rADAMTS13 (equivalent to 5 mL/kg) were used. Both items were mixed in the syringe immediately before tail vein injection in treatment group A. rADAMTS13 was injected immediately before injection of rVWF in treatment group B.

Similar to the protocols for examples above, the animals were observed for signs indicative of toxicity after injection until termination at day 1. Blood samples were withdrawn under anesthesia (ketamine+xylazine i.m.) by cardiac puncture 1 day after administration for analysis of hematological (hematocrit, platelet count) and serological variables (LDH, CK).

A necropsy was performed and selected organs (lungs [perfused, without trachea], heart, kidneys, adrenal glands, liver, brain [without medulla oblongata], spleen, eyes), were preserved in 4% formaldehyde solution for histopathological evaluation after a standard hemotoxylin-eosin staining procedure.

Slides of all tissue samples collected at necropsy from every animal (as well as tissue samples of all macroscopic findings) were processed, embedded in paraffin, cut at a nominal thickness of 2 to 4 micrometers, stained with hematoxylin and eosin (H&E) and examined by light microscope.

2. Results

No deaths occurred and no clinical signs indicative of toxicity were recorded in any of the animals.

Clinical and analytical data of hematological and serological variables are summarized below.

Furthermore, a slight grade fibrosis was recorded in a single test-item-treated animal of group B. The fibrosis appeared to be a chronic, pre-existing condition, as it was recorded in an animal sacrificed one day after administration. It was therefore deemed to be unrelated to the test item.

Comparing the two groups (A vs. B), no pronounced difference in the severity or incidence of the histopathological changes were recorded. In contrast to the previous study without rADAMTS13 co-administration, no mortality or macroscopic findings were recorded at necropsy in this study. The incidence and severity of the myocardial necrosis was similar in both studies. However, the coronary microthrombosis and the coronary perivasculitis was less pronounced in ADAMTS13 treated mice. In addition, mice receiving ADAMTS13 only displayed microthrombi in the heart, while microthrombi were recorded for the heart, brain, kidneys, and lungs of mice in the previous study.

The results of the present study demonstrate that cleavage by ADAMTS13 can prevent rVWF toxicity.

The invention has been described in terms of particular embodiments found or proposed to comprise specific modes for the practice of then invention. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A mouse model for testing the efficacy of a therapeutic agent in the treatment of a blood clotting disorder characterized by histopathological changes indicative of disseminated intravascular coagulopathy (DIC) or thrombotic thrombocytopenic purpura (TTP), said mouse comprising a circulating level of recombinant human von Willebrand factor (VWF) polypeptide comprising ultra-large VWF multimers in an amount sufficient to induce DIC or microthrombosis caused by administering a non-lethal dosage greater than or equal to 1000 RCoU/kg body weight of recombinant human VWF polypeptide, wherein said mouse has inability to break down recombinant human VWF polypeptide, and wherein said mouse exhibits histopathological changes indicative of DIC and/or TTP.

TABLE 22

| Treatment Groups | Mortality (%) | Clinical abnormalities (%) | Analysis 1 Day (Mean ± SEM) | | | |
|---|---|---|---|---|---|---|
| | | | Hematocrit (%) | Platelets (×1000/μL) | CK (U/L) | LDH (U/L) |
| A | 0 | 0 | 41.3 ± 0.7 | 1065.6 ± 52.4 | 193.0 ± 16.4 | 255.9 ± 13.8 |
| B | 0 | 0 | 41.2 ± 0.5 | 716.2 ± 87.0 | 196.4 ± 15.2 | 346.7 ± 25.9 |

3. Discussion

The objective of this study was to evaluate whether or not acute toxicity of rVWF can be attenuated by co-administration with recombinant ADAMTS13 in ADAMTS13 deficient mice.

The toxicity of rVWF was clearly observed in ADAMTS13 deficient mice in Example 8. Example 8 also illustrates that HAEMATE® P did not have a significant effect on ADAMTS13 deficient mice (positive control).

In the present study, no deaths or signs of toxicity were observed, demonstrating that cleavage by ADAMTS13 can prevent rVWF toxicity.

Comparing the analytical data, a drop in platelet count was measured 1 day after the consecutive administration of rADAMTS13 and rVWF, in contrast to the administration of the premixed items. There were no necropsy findings. Histopathological changes were recorded for the heart consisting of coronary microthrombi (minimal to slight grade), myocardial necrosis, (minimal to moderate grade), and slightly increased coronary perivasculitis in test-item-treated animals groups A and B.

2. The mouse model of claim 1, wherein the mouse is deficient in a disintegrin and metalloprotease with thrombospondin type 1 domains 13 (ADAMTS13) polypeptide.

3. The mouse model of claim 1, wherein the mouse is deficient in VWF polypeptide.

4. The mouse model of claim 1, wherein the mouse is of a C57BL/6J strain.

5. The mouse model of any one of claims 1 and 2-4, wherein the mouse further comprises recombinant Factor VIII (rFVIII).

6. A transgenic mouse whose genome comprises homozygous disruption of endogenous a disintegrin and metalloprotease with thrombospondin type I domains 13 gene (ADAMTS 13−/−), wherein the mouse further comprises a circulating level of recombinant human von Willebrand factor (VWF) polypeptide comprising ultra-large VWF multimers in an amount sufficient to induce disseminated intravascular coagulopathy (DIC) or microthrombosis caused by administering a non-lethal dosage greater than or equal to 500 RCoU/kg body weight of recombinant human VWF polypeptide, wherein said mouse has an inability to break down recombinant human VWF polypeptide, and wherein said mouse exhibits histopathological changes indicative of DIC and/or thrombotic thrombocytopenic purpura (TTP).

7. The mouse of claim 6, wherein the mouse is of a C57BL/6J strain.

8. The mouse of claim 6, wherein the dosage is a non-lethal dosage greater than or equal to 1000 RCoU/kg body weight.

9. The mouse of claim 6, wherein the dosage is a non-lethal dosage greater than or equal to 2000 RCoU/kg body weight.

10. The mouse of claim 6, wherein the mouse further comprises recombinant Factor VIII (rFVIII).

* * * * *